(12) United States Patent
Matsunaga et al.

(10) Patent No.: US 9,023,858 B2
(45) Date of Patent: May 5, 2015

(54) SUBSTITUTED PYRIDO[2,3-D]PYRIMIDINES AS DELTA-5-DESATURASE INHIBITORS

(75) Inventors: Nobuyuki Matsunaga, Kanagawa (JP); Hideo Suzuki, Kanagawa (JP); Kouhei Asano, Kanagawa (JP); Hidekazu Tokuhara, Kanagawa (JP); Takeshi Yamamoto, Kanagawa (JP); Rei Okamoto, Kanagawa (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 13/811,755

(22) PCT Filed: Jul. 22, 2011

(86) PCT No.: PCT/JP2011/066766
§ 371 (c)(1),
(2), (4) Date: Feb. 4, 2013

(87) PCT Pub. No.: WO2012/011591
PCT Pub. Date: Jan. 26, 2012

(65) Prior Publication Data
US 2013/0131050 A1  May 23, 2013

(30) Foreign Application Priority Data

Jul. 23, 2010 (JP) .................................. 2010-166475
May 31, 2011 (JP) .................................. 2011-122796

(51) Int. Cl.
| A61K 31/519 | (2006.01) |
| C07D 487/04 | (2006.01) |
| C07D 471/04 | (2006.01) |
| C07D 475/02 | (2006.01) |
| C07D 513/04 | (2006.01) |

(52) U.S. Cl.
CPC ............ *C07D 471/04* (2013.01); *C07D 475/02* (2013.01); *C07D 513/04* (2013.01); *C07D 487/04* (2013.01)

(58) Field of Classification Search
CPC ........................... A61K 31/519; C07D 487/04
USPC ......................................... 514/264.1; 544/278
See application file for complete search history.

(56) References Cited

U.S. PATENT DOCUMENTS

| 5,925,642 A | 7/1999 | Ulrich |
| 2005/0182045 A1 | 8/2005 | Nagase et al. |
| 2006/0069099 A1 | 3/2006 | Fu et al. |
| 2007/0015773 A1 | 1/2007 | Bergeron et al. |
| 2008/0075297 A1 | 3/2008 | Struthers et al. |
| 2008/0078609 A1 | 4/2008 | Struthers et al. |
| 2008/0078903 A1 | 4/2008 | Struthers et al. |
| 2008/0085887 A1 | 4/2008 | Didiuk et al. |
| 2008/0194557 A1 | 8/2008 | Barbosa et al. |
| 2008/0230266 A1 | 9/2008 | Struthers et al. |
| 2009/0049791 A1 | 2/2009 | Struthers et al. |
| 2009/0064627 A1 | 3/2009 | Struthers et al. |
| 2009/0064629 A1 | 3/2009 | Struthers et al. |
| 2009/0107083 A1 | 4/2009 | Call et al. |
| 2009/0193724 A1 | 8/2009 | Struthers et al. |
| 2009/0209562 A1 | 8/2009 | Nagase et al. |
| 2009/0249705 A1 | 10/2009 | Struthers et al. |
| 2010/0050538 A1 | 3/2010 | Struthers et al. |
| 2010/0190747 A1 | 7/2010 | Suzuki et al. |
| 2011/0000144 A1 | 1/2011 | Struthers et al. |
| 2011/0028452 A1 | 2/2011 | Didiuk et al. |
| 2011/0067320 A1 | 3/2011 | Call et al. |
| 2011/0138739 A1 | 6/2011 | Struthers et al. |
| 2012/0256064 A1 | 10/2012 | Struthers et al. |
| 2013/0000217 A1 | 1/2013 | Struthers et al. |
| 2014/0096054 A1 | 4/2014 | Yang et al. |

FOREIGN PATENT DOCUMENTS

| CN | 101547922 | 9/2009 |
| JP | 2008-504301 | 2/2008 |
| WO | 03/106435 | 12/2003 |
| WO | 2005/077905 | 8/2005 |
| WO | 2005/091711 | 10/2005 |
| WO | 2007/002701 | 1/2007 |
| WO | 2008/089307 | 7/2008 |
| WO | 2010/087467 | 8/2010 |

OTHER PUBLICATIONS

International Search Report issued Sep. 30, 2011 in International (PCT) Application No. PCT/JP2011/066766.

(Continued)

*Primary Examiner* — Douglas M Willis
(74) *Attorney, Agent, or Firm* — Wenderoth, Lind & Ponack, L.L.P.

(57) ABSTRACT

The present invention provides a compound useful for the prophylaxis or treatment of eicosanoid-associated diseases such as atherosclerosis, atherothrombosis, diabetes, obesity, asthma, fever, pain, cancer, rheumatism, osteoarthritis, atopic dermatitis and the like, and having superior pharmacological action, physicochemical properties and the like.

The present invention relates to a compound represented by the following formula:

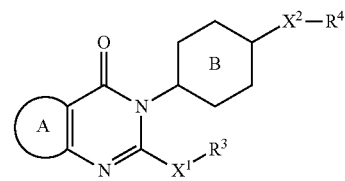

wherein each symbol is as defined in the specification, or a salt thereof.

12 Claims, No Drawings

(56) References Cited

OTHER PUBLICATIONS

X. Du et al. "Imidazo-Pyrazine Derivatives as Potent CXCR3 Antagonists", Bioorganic & Medicinal Chemistry Letters, vol. 19, No. 17, pp. 5200-5204, 2009.

J. Chan et al. "Acetic Acid Mediated Coupling of 2-Aminonicotinamides with Ortho Esters: A Convenient, Scalable Synthesis of 2,3-Substituted Pyrido[2,3-*d*]Pyrimidines", Synthesis, vol. 23, pp. 3678-3682, 2007.

I. S. Rathod et al., "Design, Synthesis and Diuretic Activity of Some Novel 2,4-Diamino-6-aryl-7-arylaminopyrimido[4,5-*d*]Pyrimidin-5(6H)-Ones", Arzneim. Forsch. Drug Res., vol. 56, No. 6, pp. 377-381, 2006.

C. G. Dave et al., "Pyridopyrimidines: Part IX—Synthesis and Antibacterial Activity of 2-Methylthio-6-Phenylazo-5,7-dimethylpyrido[2,3-*d*]Pyrimidin-4(3*H*)-Ones", Indian Journal of Chemistry, vol. 39B, No. 3, pp. 210-214, Mar. 2000.

C. G. Dave et al., "Pyridopyrimidin: Part II—Preparation of Some 2-(Substituted)-Pyrido[2,3-*d*] Pyrimidin-4(3*H*)-Ones", Journal of the Institution of Chemists (India), vol. 57, No. 4, pp. 156-158, Jul. 1985.

Chinese Office Action issued Jul. 2, 2014 in corresponding Chinese Patent Application No. 2011/80045375.4 with statement of relevance.

SUBSTITUTED PYRIDO[2,3-D]PYRIMIDINES AS DELTA-5-DESATURASE INHIBITORS

CROSS-REFERENCE TO RELATED APPLICATIONS

This application is a U.S. national stage of International Application No. PCT/JP2011/066766 filed Jul. 22, 2011.

TECHNICAL FIELD

The present invention relates to a novel fused heterocyclic compound having superior properties as a medicament, and use thereof. To be specific, the present invention relates to a fused heterocyclic compound having a particular structure, which has a delta-5-desaturase inhibitory action, shows various pharmacological actions based on suppression of eicosanoid production, has superior properties such as good crystallinity and stability and the like, and useful for an agent for the prophylaxis or treatment of eicosanoid-associated diseases such as atherosclerosis, atherothrombosis, diabetes, obesity, asthma, fever, pain, cancer, rheumatism, osteoarthritis, atopic dermatitis and the like, or a salt thereof, or a prodrug thereof, and use thereof and the like.

BACKGROUND OF THE INVENTION

Eicosanoids such as prostaglandin, leukotriene, thromboxane and the like are considered to play an important role in various diseases. In the diseases of, for example, inflammatory diseases such as arteriosclerosis, diabetes, obesity, asthma, rheumatism, osteoarthritis, inflammatory pain and the like, the production pathway of inflammatory eicosanoid is considered to be promoted and involved in the onset and aggravation of the diseases.

As therapeutic drugs for eicosanoid-associated diseases, medicaments such as cyclooxygenase inhibitors, thromboxane A2 receptor antagonists and the like, which suppress production of prostanoids, are clinically applied. However, the need for a prophylactic or therapeutic drug for inflammatory diseases and the like still remains high, and the development of a strong therapeutic drug with less side effects is desired.

Bioorganic & Medicinal Chemistry Letters (2009), 19(17), 5200-5204 (non-patent document 1) discloses that the compounds of the following formula:

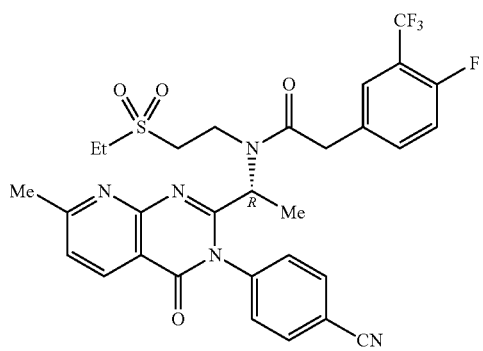

and the like are used for the treatment of diseases such as inflammatory disease, multiple sclerosis, psoriasis, rheumatism, rejection of allogeneic transplantation, inflammatory bowel disease and the like as a CXCR3 antagonist.

Synthesis (2007), (23), 3678-3682 (non-patent document 2) reports that the progress of heterocycle synthesis method is important for forming the basis for many pharmaceutically active substances, and discloses the compounds of the following formulas:

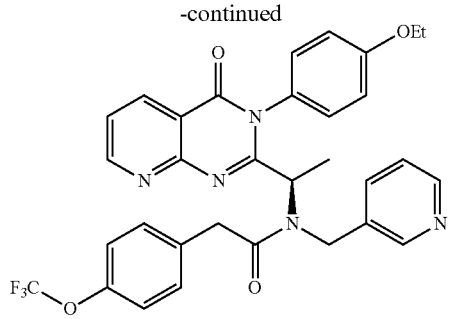

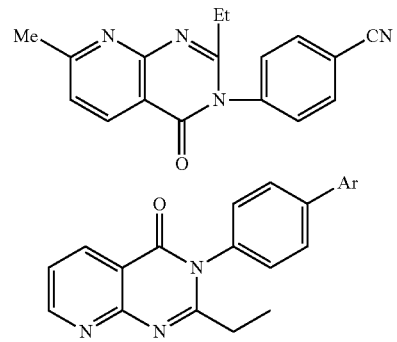

and the like.

WO 2007/002701 (patent document 1) discloses that a compound represented by the following formula:

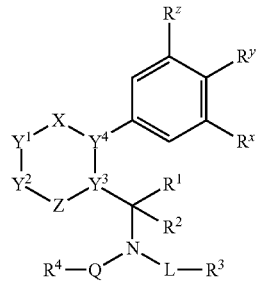

wherein
X is a member selected from the group consisting of a bond, —C(O)—, —C($R^5$)($R^6$)—, —C($R^5$)=—S(O)—, —S(O)$_2$— and —N=;
Z is a member selected from the group consisting of a bond, —N=, —O—, —S—, —C($R^7$)= and —N($R^{14}$)—, with the proviso that X and Z are not both a bond;
L is a member selected from the group consisting of a bond, C(O)—($C_1$-$C_8$)alkylene, ($C_1$-$C_8$)alkylene and ($C_2$-$C_8$)heteroalkylene;
Q is a member selected from the group consisting of ($C_1$-$C_8$) alkylene, —C(O)—, —OC(O)—, —N($R^8$)C(O)—, —CH$_2$CO—, —CH$_2$SO— and —CH$_2$SO$_2$—, or L and Q can be optionally bonded together to form a 5- or 6-membered heterocyclic group having 1 to 3 heteroatoms;

R$^1$ and R$^2$ are independently a member selected from the group consisting of H, (C$_1$-C$_8$)alkyl, (C$_2$-C$_8$)heteroalkyl, aryl and heteroaryl, or R$^1$ and R$^2$ in combination optionally form a 3 to 8-membered ring having 0 to 2 heteroatoms as ring vertices, or R$^2$ can be optionally bonded to L to form a 5- or 6-membered heterocyclic group having 1 to 4 heteroatoms;

R$^3$ is absent or is a member selected from the group consisting of hydroxy, (C$_1$-C$_8$)alkoxy, amino, (C$_1$-C$_8$)alkylamino, di(C$_1$-C$_8$)alkylamino, (C$_1$-C$_{20}$)alkyl, (C$_2$-C$_8$)heteroalkyl, cyclo(C$_3$-C$_9$)heteroalkyl, (C$_1$-C$_8$) acylamino, amidino, guanidino, ureido, cyano, heteroaryl, —CONR$^9$R$^{10}$ and —CO$_2$R$^{11}$, or R$^3$ can be optionally bonded to R$^2$ to form a 4-, 5-, 6-, 7- or 8-membered ring having 1 to 3 heteroatoms selected from the group consisting of N, O and S;

R$^4$ is a member selected from the group consisting of (C$_2$-C$_{20}$)alkyl, (C$_2$-C$_{20}$)heteroalkyl, heteroaryl, aryl, heteroaryl (C$_1$-C$_6$)alkyl, heteroaryl(C$_2$-C$_6$)heteroalkyl, aryl(C$_1$-C$_6$)alkyl and aryl(C$_2$-C$_6$)heteroalkyl;

R$^5$ and R$^6$ are independently a member selected from the group consisting of H, (C$_1$-C$_8$)alkyl, (C$_2$-C$_8$)heteroalkyl, heteroaryl and aryl, or R$^5$ and R$^6$ in combination optionally form a 3- to 7-membered ring;

R$^7$ and R$^8$ are independently a member selected from the group consisting of H, (C$_1$-C$_8$)alkyl, (C$_2$-C$_8$)heteroalkyl, heteroaryl and aryl;

R$^9$, R$^{10}$ and R$^{11}$ are independently a member selected from the group consisting of H, (C$_1$-C$_8$)alkyl, (C$_2$-C$_8$)heteroalkyl, heteroaryl, aryl, heteroary(C$_1$-C$_6$)alkyl, heteroaryl(C$_2$-C$_8$) heteroalkyl, aryl(C$_1$-C$_8$)alkyl and aryl(C$_2$-C$_8$)heteroalkyl;

R$^x$, R$^y$ and R$^z$ are independently H, F or cyano, wherein at least one of R$^x$, R$^y$ and R$^z$ is cyano;

Y$^1$ and Y$^2$ are independently a member selected from the group consisting of —C(R$^{12}$)=, —CH(R$^{12}$)—, —N=, —O—, —S— and —N(R$^{13}$)—;

Y$^3$ is N or C wherein when Y$^3$ is C, then Y$^3$ shares a double bond with Y$^2$, Y$^4$ or Z;

Y$^4$ is N or C wherein when Y$^4$ is C, then Y$^4$ shares a double bond with X, Y$^1$ or Y$^3$;

wherein each R$^{12}$ is a member selected from the group consisting of H, halogen, hydroxy, amino, alkylamino, dialkylamino, (C$_1$-C$_8$) alkyl, cyclo(C$_3$-C$_6$)alkyl, (C$_2$-C$_8$)heteroalkyl, heteroaryl and aryl, or optionally, when Y$^1$ and Y$^2$ are each one of —C(R$^{12}$)= or —CH(R$^{12}$)—, then the two R$^{12}$ groups in combination can be form a substituted or unsubstituted 5- to 6-membered cycloalkyl, cycloheteroalkyl, aryl or heteroaryl ring, or optionally, when Y$^1$ is —O(R$^{12}$)= or —CH(R$^{12}$)— and X is —C(R$^5$)= or —C(R$^5$)(R$^6$)—, then R$^{12}$ and R$^5$ in combination can be form a substituted or unsubstituted 5- to 6-membered cycloalkyl, cycloheteroalkyl, aryl or heteroaryl ring;

each R$^{13}$ is a member selected from the group consisting of H, (C$_1$-C$_8$)alkyl, (C$_2$-C$_8$)heteroalkyl, heteroaryl, aryl, heteroaryl (C$_1$-C$_6$)alkyl, cyclo(C$_3$-C$_6$)alkyl, heteroaryl(C$_2$-C$_8$)heteroalkyl, aryl(C$_1$-C$_8$)alkyl and aryl(C$_2$-C$_8$)heteroalkyl, or optionally, when one of Y$^1$ and Y$^2$ is —C(R$^{12}$)= or —CH (R$^{12}$)— and the other is —N(R$^{13}$)—, then R$^{12}$ and R$^{13}$ in combination can be form a substituted or unsubstituted 5- to 6-membered cycloalkyl, cycloheteroalkyl, aryl or heteroaryl ring, or optionally when Y$^1$ and Y$^2$ are both —N(R$^{13}$)—, then the two R$^{13}$ groups in combination can be form a substituted or unsubstituted 5- to 6-membered cycloalkyl, cycloheteroalkyl, aryl or heteroaryl ring; and R$^{14}$ is a member selected from the group consisting of H, (C$_1$-C$_8$)alkyl, (C$_2$-C$_8$)heteroalkyl, cyclo(C$_3$-C$_6$)alkyl, heteroaryl, aryl, heteroalkyl(C$_1$-C$_6$)alkyl, heteroaryl(C$_2$-C$_8$)heteroalkyl, aryl(C$_1$-C$_8$)alkyl and aryl(C$_2$-C$_8$)heteroalkyl, or optionally, when Y$^2$ is —C(R$^{12}$)=, —CH(R$^{12}$)— or —N(R$^{13}$)—, then R$^{14}$ or R$^7$ can be bonded to R$^{12}$ or R$^{13}$ to form a substituted or unsubstituted 5- to 6-membered cycloalkyl, cycloheteroalkyl, aryl or heteroaryl ring;

the ring containing X, Y$^1$, Y$^2$, Y$^3$, Y$^4$ and Z can be aromatic, as will be understood by those of ordinary skill in the art, a salt, a solvate, a prodrug or an isomer is used for the treatment or prophylaxis of particular inflammatory or immunoregulatory disorder or disease, such as asthma, psoriasis, inflammatory bowel disease, allergic disease, rheumatoid arthritis, multiple sclerosis and the like, which are mediated by CXCR3 chemokine receptor.

Arzneimittel Forschung (2006), 56(6), 377-381 (non-patent document 3) discloses that a compound of the following formula:

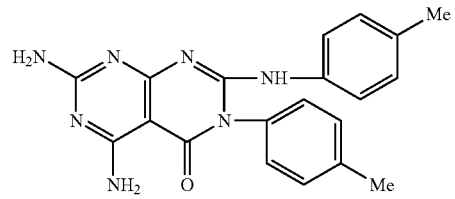 [SMILES: Cc1ccc(Nc2nc3nc(N)nc(N)c3c(=O)n2-c2ccc(C)cc2)cc1]

and the like has a diuretic action.

WO 2005/091711 (patent document 2) discloses that a compound represented by the following formula:

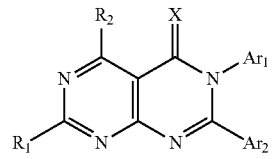

wherein

X is O or S;

Ar$_1$ and Ar$_2$ are same or different and each is substituted or unsubstituted aryl, 5- to 7-membered heteroaryl or heterocyclyl group; and R$_1$ and R$_2$ are same or different and each is hydrogen, hydroxy, thiol, nitro, formyl, azido, cyano, halo, or substituted or unsubstituted alkyl, haloalkyl, alkoxy, aryl, aryloxy, aralkyl, aralkoxy, acyl, acyloxy, amino, hydrazino, monoalkylamino, dialkylamino, acylamino, alkylsulfonyl, arylsulfonyl, alkylsulfinyl, arylsulfinyl, alkylthio, arylthio, alkoxycarbonyl, aryloxycarbonyl, alkoxyalkyl, sulfamoyl or carboxylic acid, or a derivative thereof is used for the treatment of diseases such as rheumatism, osteoporosis, uveitis, acute and chronic myeloid leukemia, atherosclerosis, cancer, pancreatic β cells destruction, osteoarthritis, rheumatoid spondylitis, gouty arthritis, inflammatory bowel disease and the like.

WO 2003/106435 (patent document 3) discloses that a compound represented by the following formula:

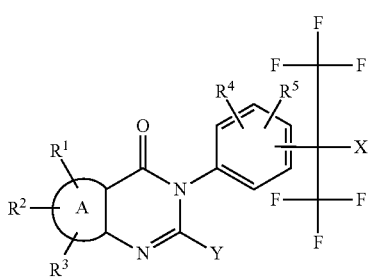

wherein:

A is $C_6$-$C_{14}$ aryl or 5- to 7-membered heteroaryl;

$R^1$, $R^2$ and $R^3$ are the same or different and each is hydrogen, hydroxyl, nitro, cyano, amino, halogen, carboxy, carbamoyl, mercapto, $C_1$-$C_6$ alkyl, $C_1$-$C_6$ alkyl substituted with from 1 to 7 halogen, $C_2$-$C_7$ alkylcarbonyloxy, $C_1$-$C_6$ alkoxy, $C_1$-$C_6$ alkylthio, $C_1$-$C_6$ alkylsulfinyl, $C_1$-$C_6$ alkylsulfonyl, $C_1$-$C_6$ alkylamino, di($C_1$-$C_6$ alkyl)amino (the alkyl groups are the same or different), $C_2$-$C_7$ alkylcarbonylamino, N—($C_2$-$C_7$ alkylcarbonyl)-N—($C_1$-$C_6$ alkyl)amino, $C_2$-$C_7$ alkoxycarbonylamino, N—($C_2$-$C_7$ alkoxycarbonyl)-N—($C_1$-$C_6$ alkyl)amino, $C_1$-$C_6$ alkylsulfonylamino, N—($C_1$-$C_6$ alkylsulfonyl)-N—($C_1$-$C_6$ alkyl)amino, $C_1$-$C_6$ haloalkylsulfonylamino (the $C_1$-$C_6$ haloalkylsulfonylamino is $C_1$-$C_6$ alkylsulfonylamino substituted with from 1 to 7 halogen), N—($C_1$-$C_6$ haloalkylsulfonyl)-N—($C_1$-$C_6$ alkyl)amino (the $C_1$-$C_6$ haloalkylsulfonyl is $C_1$-$C_6$ alkylsulfonyl substituted with from 1 to 7 halogen), $C_2$-$C_7$ alkylcarbonyl, $C_2$-$C_7$ alkoxycarbonyl, $C_2$-$C_7$ alkylaminocarbonyl or di($C_1$-$C_6$ alkyl)aminocarbonyl (the alkyl groups are the same or different), or $R^1$ and $R^2$ are optionally bonded each other to form $C_1$-$C_4$ alkylenedioxy;

$R^4$ and $R^5$ are the same or different and each is hydrogen, hydroxyl, amino, halogen, mercapto, $C_1$-$C_6$ alkyl, $C_1$-$C_6$ alkyl substituted with from 1 to 7 halogen, $C_1$-$C_6$ alkoxy, $C_2$-$C_7$ alkoxycarbonyl or $C_1$-$C_6$ alkylthio;

X is hydrogen, hydroxyl, halogen, $C_1$-$C_6$ alkoxy or $C_1$-$C_6$ alkoxy substituted with from 1 to 7 halogen;

Y is $C_1$-$C_6$ alkyl, $C_1$-$C_6$ alkyl substituted with from 1 to 7 substituents (the substituents are the same or different and are selected from substituent group α), $C_3$-$C_{10}$ cycloalkyl, $C_3$-$C_{10}$ cycloalkyl substituted with from 1 to 7 substituents (the substituents are the same or different and are selected from substituent group α), 5- to 9-membered heterocyclyl, 5- to 9-membered heterocyclyl substituted with from 1 to 7 substituents (the substituents are the same or different and are selected from substituent group α), $C_6$-$C_{10}$ aryl, $C_6$-$C_{10}$ aryl substituted with from 1 to 4 substituents (the substituents are the same or different and are selected from substituent group β), $C_4$-$C_{14}$ cycloalkylalkyl, $C_4$-$C_{14}$ cycloalkylalkyl substituted with from 1 to 7 substituents (the substituents are the same or different and are selected from substituent group α), (5- to 9-membered heterocyclyl)-($C_1$-$C_4$ alkyl), (5- to 9-membered heterocyclyl)-($C_1$-$C_4$ alkyl) substituted with from 1 to 7 substituents (the substituents are the same or different and are selected from substituent group α), $C_7$-$C_{14}$ aralkyl or $C_7$-$C_{14}$ aralkyl substituted with from 1 to 5 substituents (the substituents are the same or different and are selected from substituent group β);

substituent group α is a group consisting of halogen, hydroxyl, cyano, amino, $C_2$-$C_7$ alkylcarbonyloxy, $C_1$-$C_6$ alkyl, $C_1$-$C_6$ alkoxy, $C_1$-$C_6$ alkylthio, $C_1$-$C_6$ alkylsulfinyl, $C_1$-$C_6$ alkylsulfonyl, phenyl, $C_1$-$C_6$ alkylamino, di($C_1$-$C_6$ alkyl)amino (the alkyl groups are the same or different), $C_2$-$C_7$ alkylcarbonylamino, $C_1$-$C_6$ alkylsulfonylamino and $C_1$-$C_6$ haloalkylsulfonylamino (the $C_1$-$C_6$ haloalkylsulfonylamino is $C_1$-$C_6$ alkylsulfonylamino substituted with from 1 to 7 halogen); and substituent group β is a group consisting of halogen, hydroxyl, nitro, cyano, amino, $C_1$-$C_6$ alkyl, $C_1$-$C_6$ alkyl substituted with from 1 to 7 halogen atoms, $C_2$-$C_7$ alkylcarbonyloxy, $C_1$-$C_6$ alkoxy, $C_1$-$C_6$ alkylthio, $C_1$-$C_6$ alkylsulfinyl, $C_1$-$C_6$ alkylsulfonyl, $C_1$-$C_6$ alkylamino, di($C_1$-$C_6$ alkyl)amino (the alkyl groups are the same or different), $C_2$-$C_7$ alkylcarbonylamino, N—($C_2$-$C_7$ alkylcarbonyl)-N—($C_1$-$C_6$ alkyl)amino, $C_2$-$C_7$ alkoxycarbonylamino, N—($C_2$-$C_7$ alkoxycarbonyl)-N—($C_1$-$C_6$ alkyl)amino, $C_1$-$C_6$ alkylsulfonylamino, N—($C_1$-$C_6$ alkylsulfonyl)-N—($C_1$-$C_6$ alkyl)amino, $C_1$-$C_6$ haloalkylsulfonylamino (the haloalkylsulfonylamino is $C_1$-$C_6$ alkylsulfonylamino substituted with from 1 to 7 halogen), N—($C_1$-$C_6$ haloalkylsulfonyl)-N—($C_1$-$C_6$ alkyl)amino (the haloalkylsulfonyl is $C_1$-$C_6$ alkylsulfonyl substituted with from 1 to 7 halogen), $C_6$-$C_{10}$ aryl, $C_7$-$C_{14}$ aralkyloxy, $C_1$-$C_4$ alkylenedioxy, $C_2$-$C_7$ alkylcarbonyl, $C_2$-$C_7$ alkoxycarbonyl, $C_2$-$C_7$ alkylaminocarbonyl and di($C_1$-$C_6$ alkyl)aminocarbonyl (the alkyl are the same or different);

provided that when Y is one of the following (i) to (vii), and A is phenyl, then $R^4$ and $R^5$ are both hydrogen and the —C(CF$_3$)$_2$(X) is —C(CF$_3$)$_2$(OH) bonded to the 3- or 4-position on the phenyl group:

(i) an alkyl substituted at the 1-position thereof with amino, alkylamino, dialkylamino, alkylcarbonylamino, alkylsulfonylamino or haloalkylsulfonylamino and optionally further substituted at the 1-position thereof with alkyl or phenyl;

(ii) cycloalkyl substituted with amino, alkylamino, dialkylamino, alkylcarbonylamino, alkylsulfonylamino or haloalkylsulfonylamino and optionally further substituted with from 1 to 6 substituents selected from substituent group α;

(iii) heterocyclyl having at least one nitrogen atom and optionally substituted with 1 or 2 substituents selected from alkyl, alkylsulfinyl, alkylsulfonyl and phenyl;

(iv) cycloalkylalkyl wherein the alkyl moiety is substituted at the 1-position thereof with amino, alkylamino, dialkylamino, alkylcarbonylamino, alkylsulfonylamino or haloalkylsulfonylamino, the cycloalkylalkyl optionally being further substituted with from 1 to 6 substituents selected from substituent group α;

(v) heterocyclylalkyl wherein the alkyl moiety is substituted at the 1-position thereof with amino, alkylamino, dialkylamino, alkylcarbonylamino, alkylsulfonylamino or haloalkylsulfonylamino, the heterocyclylalkyl optionally being further substituted with from 1 to 6 substituents selected from substituent group α;

(vi) heterocyclylmethyl wherein the heterocyclyl moiety has at least one nitrogen atom and is optionally substituted with from 1 to 7 substituents selected from substituent group α, and the methyl moiety is optionally substituted with alkyl group or phenyl; and (vii) aralkyl group wherein the alkyl moiety is substituted at the 1-position thereof with amino, alkylamino, dialkylamino, alkylcarbonylamino, alkoxycarbonylamino, alkylsulfonylamino, haloalkylsulfonylamino, N-(alkylcarbonyl)-N-(alkyl)amino, N-(alkoxycarbonyl)-N-(alkyl)amino, N-(alkylsulfonyl)-N-(alkyl)amino or N-(haloalkylsulfonyl)-N-(alkyl)amino, the aralkyl group optionally being further substituted with from 1 to 6 substituents selected from substituent group β, or a salt thereof has anti-arteriosclerosis action and an anti-inflammatory action as a LXR modulator.

Indian Journal of Chemistry, Section B: Organic Chemistry Including Medicinal Chemistry (2000), 39B (3), 210-214 (non-patent document 4) discloses that a compound the following formula:

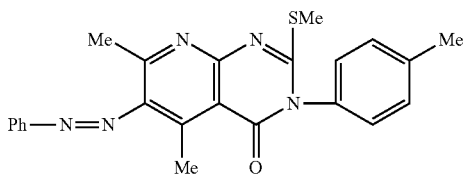 [SMILES: CSc1nc2nc(C)c(N=Nc3ccccc3)c(C)c2c(=O)n1-c1ccc(C)cc1]

and the like has an analgesic action, an antipyretic action, an anti-inflammatory action and a suppressive action of central nervous system.

U.S. Pat. No. 5,925,642 (patent document 4) discloses that a compound represented by the following formula:

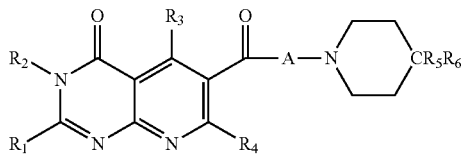

wherein
$R_1$ is hydrogen or 1-7C-alkyl,
$R_2$ is 1-7C-alkyl, phenyl, phenyl-1-4C-alkyl, Ar-1-4C-alkyl, Ar or 1-7C-alkylene substituted by $N(R_7)R_8$, wherein Ar is phenyl substituted by $R_9$, $R_{10}$ and $R_{11}$,
$R_3$ is phenyl or phenyl substituted by $R_{31}$ and $R_{32}$, wherein $R_{31}$ is hydrogen, hydroxyl, halogen, nitro, cyano, carboxyl, trifluoromethyl, 1-4C-alkyl, 1-4C-alkoxy, completely or partly fluorine-substituted 1-4C-alkoxy, 1-4C-alkoxycarbonyl, 1-4C-alkylcarbonyl, amino or mono- or di-1-4C-alkylamino, and $R_{32}$ is hydrogen, hydroxyl, halogen, nitro, trifluoromethyl, 1-4C-alkyl or 1-4C-alkoxy,
$R_4$ is 1-4C-alkyl,
A is 1-20C-alkylene or the group A1-X-A2, wherein A1 is 1-17C-alkylene, X is O (oxygen), A2 is 2-18C-alkylene, and the total of the alkylene carbon atoms of A1 and A2 is 19 or less, $R_5$ is Ar1 and $R_6$ is Ar2, or
$R_5$ and $R_6$ in combination are methylene substituted by Ar1 and Ar2 [=CH(Ar1)Ar2], or
$R_5$ is hydrogen and $R_6$ is methyl substituted by Ar1 and Ar2 [—CH(Ar1)Ar2] or hydroxymethyl substituted by Ar1 and Ar2 [—C(OH)(Ar1)Ar2], wherein Ar1 is phenyl or phenyl substituted by one or two same or different substituents from the group consisting of hydroxyl, halogen, nitro, trifluoromethyl, 1-4C-alkyl and 1-4C-alkoxy, and Ar2 is phenyl or phenyl substituted by one or two same or different substituents from the group consisting of hydroxyl, halogen, 1-4C-alkyl and 1-4C-alkoxy,
$R_7$ is 1-7C-alkyl, 3-8C-cycloalkyl, phenyl-1-4C-alkyl or Ar-1-4C-alkyl, and
$R_8$ is 1-7C-alkyl, 3-8C-cycloalkyl, phenyl-1-4C-alkyl or Ar-1-4C-alkyl,
wherein Ar is phenyl substituted by $R_9$, $R_{10}$ and $R_{11}$, or $R_7$ and $R_8$ in combination and including the nitrogen atom which they are bonded to, are an unsubstituted or substituted heterocycle selected from the group consisting of pyrrolidine, piperidine, piperazine, morpholine, thiomorpholine, indoline, octahydro-1H-indole, 1,2,3,4-tetrahydroquinoline, 1,2,3,4-tetrahydroisoquinoline, decahydroquinoline and decahydroisoquinoline, wherein
the substituted pyrrolidino group is substituted by one or two same or different substituents selected from the group consisting of 1-4C-alkyl, 1-4C-alkoxy, 1-4C-alkoxy-1-4C-alkyl, 1-4C-alkoxycarbonyl, 1-4C-alkylcarbonyloxy, hydroxy-1-4C-alkyl, hydroxyl and carboxyl,
the substituted piperidino group is substituted by one, two or three same or different substituents selected from the group consisting of 1-4C-alkyl, gem-di-1-4C-alkyl, 1-4C-alkoxy, 1-4C-alkoxy-1-4C-alkyl, 1-4C-alkoxycarbonyl, 1-4C-alkylcarbonyl, 1-4C-alkylcarbonyl-1-4C-alkyl, hydroxy-1-4C-alkyl, dihydroxy-1-4C-alkyl, di-1-4C-alkylamino, di-1-4C-alkylamino-1-4C-alkyl, pyrrolidino, piperidino, pyrrolidinyl-1-4C-alkyl, piperidyl-1-4C-alkyl, carbamoyl, di-1-4C-alkylaminocarbonyl, piperidinocarbonyl, morpholinocarbonyl, phenyl, phenyl substituted by $R_9$, $R^{10}$ and $R_{11}$, phenyl-1-4C-alkyl, benzoyl, benzoyl substituted by halogen, formyl, carboxyl, cyano, hydroxyl, halogen and sulfo,
the substituted piperazino group is optionally substituted in the 2-, 3-, 5- or 6-position by a 1-4C-alkyl group, and is substituted in the 4-position by a substituent selected from the group consisting of 1-4C-alkyl, 3-7C-cycloalkyl, 3-7C-cycloalkyl-1-4C-alkyl, 1-4C-alkoxycarbonyl, 1-4C-alkoxycarbonyl-1-4C-alkyl, hydroxy-1-4C-alkyl, di-1-4C-alkylamino-1-4C-alkyl, halo-1-4C-alkyl, carbamoyl, phenyl, phenyl substituted by $R_9$, $R^{10}$ and $R_{11}$, phenyl-1-4C-alkyl, phenyl-1-4C-alkyl wherein the phenyl moiety is substituted by $R_9$, $R_{10}$ and $R_{11}$, naphthyl, benzhydryl and benzhydryl substituted by halogen,
the substituted morpholino group is substituted by one or two same or different 1-4C-alkyl groups,
the substituted indolin-1-yl group is optionally substituted in the 2- and/or 3-position by a carboxyl group or by one or two same or different 1-4C-alkyl groups, and the benzo moiety is optionally substituted by one or two same or different substituents selected from the group consisting of 1-4C-alkyl, halogen and nitro,
the substituted 1,2,3,4-tetrahydroquinoline group is substituted by one or two same or different substituents selected from the group consisting of 1-4C-alkyl, 1-4C-alkoxycarbonyl and halogen,
the substituted 1,2,3,4-tetrahydroisoquinoline group is optionally substituted in the 1-, 3- and/or 4-positions by one or two same or different substituents selected from the group consisting of 1-4C-alkyl, carboxyl, phenyl, phenyl substituted by $R_9$, $R^{10}$ and $R_{11}$, phenyl-1-4C-alkyl and phenyl-1-4C-alkyl wherein the phenyl moiety is substituted by $R_9$, $R_{10}$ and $R_{11}$, and the benzo moiety is optionally substituted by one or two substituents selected from the group consisting of hydroxyl, 1-4C-alkoxy and di-1-4C-alkylamino, wherein $R_9$ is hydrogen, hydroxyl, 1-4C-alkyl, 1-4C-alkoxy, 1-4C-alkylcarbonyl, halogen, 1-4C-alkylamino or nitro, $R_{10}$ is hydrogen, hydroxyl, 1-4C-alkyl, 1-4C-alkoxy, halogen or nitro and $R_{11}$ is hydrogen or trifluoromethyl,
or a salt thereof has a suppressive action of cell proliferation, an antibacterial action and the like.

Journal of the Institution of Chemists (India) (1985), 57(4), 156-158 (non-patent document 5) discloses that a compound of the following formula:

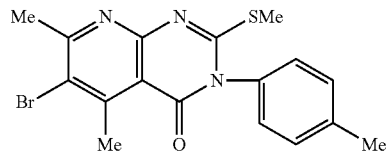 [SMILES: CSc1nc2nc(C)c(Br)c(C)c2c(=O)n1-c1ccc(C)cc1]

and the like is used for the treatment of neoplastic disease.

However, the present compound is distinguished from any of the above-mentioned compound, and none of the documents discloses that the compound has a delta-5-desaturase inhibitory action.

DOCUMENT LIST

Patent Document

Patent Document 1: WO 2007/002701
Patent Document 2: WO 2005/091711
Patent Document 3: WO 2003/106435
Patent Document 4: U.S. Pat. No. 5,925,642

Non-Patent Document

Non-Patent Document 1: Bioorganic & Medicinal Chemistry Letters (2009), 19(17), 5200-5204
Non-Patent Document 2: Synthesis (2007), (23), 3678-3682
Non-Patent Document 3: Arzneimittel Forschung (2006), 56(6), 377-381
Non-Patent Document 4: Indian Journal of Chemistry, Section B: Organic Chemistry Including Medicinal Chemistry (2000), 39B (3), 210-214
Non-Patent Document 5: Journal of the Institution of Chemists (India) (1985), 57(4), 156-158

BRIEF SUMMARY OF THE INVENTION

Problems to be Solved by the Invention

An object of the present invention is to provide a compound useful for the prophylaxis or treatment of eicosanoid-associated diseases such as atherosclerosis, atherothrombosis, diabetes, obesity, asthma, fever, pain, cancer, rheumatism, osteoarthritis, atopic dermatitis and the like, and having a superior pharmacological action, physicochemical properties and the like.

Means of Solving the Problems

The present inventors have first found that a fused heterocyclic compound represented by the following formula (I) has a delta-5-desaturase inhibitory action, shows various pharmacological actions based on suppression of eicosanoid production, has superior properties such as good crystallinity and stability and the like, and useful for the prophylaxis or treatment of eicosanoid-associated diseases such as atherosclerosis, atherothrombosis, diabetes, obesity, asthma, fever, pain, cancer, rheumatism, osteoarthritis, atopic dermatitis and the like. The present inventors have conducted intensive studies based on these findings and completed the present invention.

Accordingly, the present invention relates to
[1] a compound represented by the formula (I):

(I)

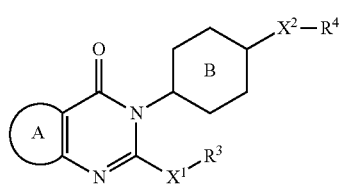

wherein
ring A is a ring represented by the formula:

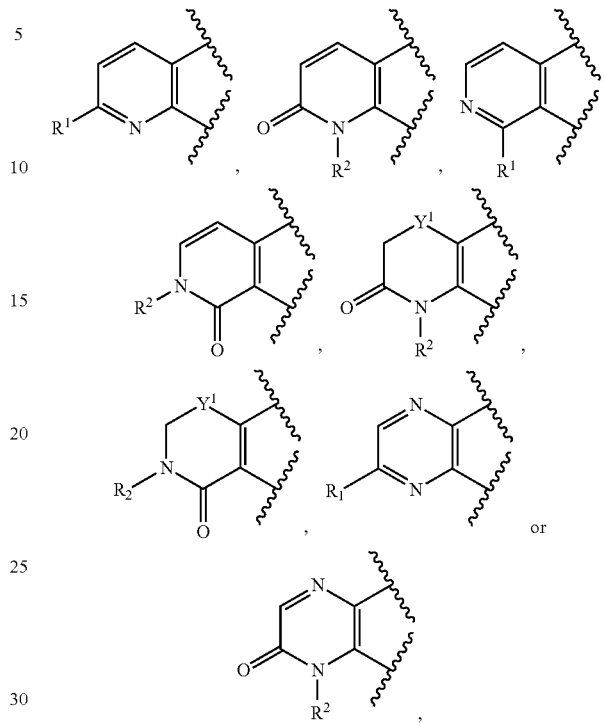

wherein each ring is optionally further substituted by substituent(s) selected from a halogen atom, a $C_{1-6}$ alkyl group and a $C_{1-6}$ alkoxy group, ring B is a 6-membered aromatic ring optionally further substituted by substituent(s) selected from a halogen atom, $C_{1-6}$ alkyl group and a $C_{1-6}$ alkoxy group.

$X^1$ is a bond, S, $SO_2$, O or $NR^5$, $X^2$ is $CR^6R^7$ or O, $Y^1$ is $CR^8R^9$, S, SO, $SO_2$ or O, $R^1$ is an optionally substituted $C_{1-6}$ alkoxy group, an optionally substituted amino group, an optionally substituted carbamoyl group or an optionally substituted $C_{1-6}$ alkylthio group, $R^2$ is a hydrogen atom or an optionally substituted $C_{1-6}$ alkyl group, $R^3$ is an optionally substituted $C_{1-6}$ alkyl group or an optionally substituted 3- to 11-membered cyclic group, $R^4$ is an optionally substituted $C_{1-6}$ alkyl group or an optionally substituted 3- to 11-membered cyclic group, $R^5$ is a hydrogen atom or an optionally substituted $C_{1-6}$ alkyl group, and $R^6$, $R^7$, $R^8$ and $R^9$ are each a hydrogen atom, a halogen atom, a $C_{1-6}$ alkyl group or a $C_{1-6}$ alkoxy group, or a salt thereof (hereinafter sometimes to be referred to as compound (I));

[2] the compound or salt of the above-mentioned [1], wherein $X^2$ is O; and $R^4$ is a $C_{1-6}$ alkyl group optionally substituted by 1 to 3 halogen atoms;

[3] the compound or salt of the above-mentioned [1], wherein ring A is a ring represented by the formula:

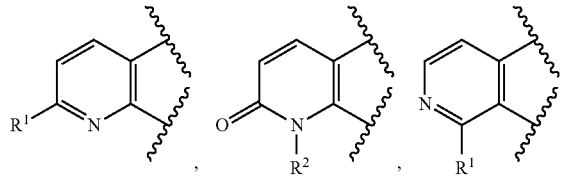

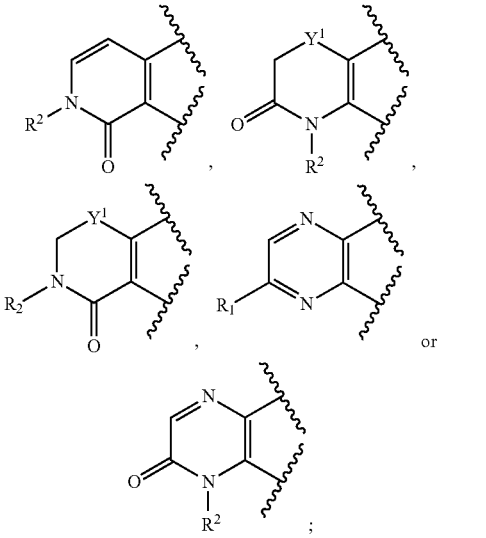

ring B is benzene;
$X^1$ is a bond, S, O or NH;
$X^2$ is O;
$Y^1$ is $CH_2$ or S;
$R^1$ is
(1) a $C_{1-6}$ alkoxy group optionally substituted by 1 to 3 $C_{1-6}$ alkoxy groups;
(2) amino; or
(3) carbamoyl;
$R^2$ is a hydrogen atom or a $C_{1-6}$ alkyl group;
$R^3$ is
(1) a $C_{1-6}$ alkyl group optionally substituted by 1 to 3 substituents selected from
  (A) a $C_{1-6}$ alkylsulfonyl group,
  (B) a hydroxy group,
  (C) a $C_{1-6}$ alkoxy group, and
  (D) a halogen atom, or
(2) a $C_{3-10}$ cycloalkyl group optionally substituted by 1 to 3 halogen atoms; and
$R^4$ is a $C_{1-6}$ alkyl group optionally substituted by 1 to 3 halogen atoms;

[4] the compound or salt of the above-mentioned [1], wherein ring A is a ring represented by the formula:

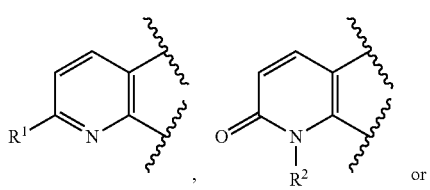

-continued

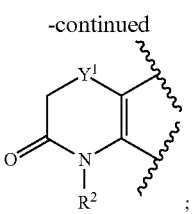

ring B is benzene;
$X^1$ is a bond, S or O;
$X^2$ is O;
$Y^1$ is $CH_2$;
$R^1$ is a $C_{1-6}$ alkoxy group;
$R^2$ is a hydrogen atom;
$R^3$ is
(1) a $C_{1-6}$ alkyl group optionally substituted by 1 to 3 halogen atoms, or
(2) a $C_{3-10}$ cycloalkyl group optionally substituted by 1 to 3 halogen atoms; and
$R^4$ is a $C_{1-6}$ alkyl group optionally substituted by 1 to 3% halogen atoms;

[5] the compound or salt of the above-mentioned [1], wherein ring A is a ring represented by the formula:

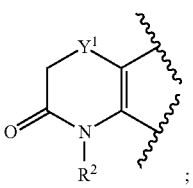

ring B is benzene;
$X^1$ is a bond, S or O;
$X^2$ is O;
$Y^1$ is $CH_2$;
$R^2$ is a hydrogen atom;
$R^3$ is
(1) a $C_{1-6}$ alkyl group optionally substituted by 1 to 3 halogen atoms, or
(2) a $C_{3-10}$ cycloalkyl group optionally substituted by 1 to 3 halogen atoms; and
$R^4$ is a $C_{1-6}$ alkyl group optionally substituted by 1 to 3 halogen atoms;

[6] 2-(2,2,2-trifluoroethoxy)-3-[4-(2,2,2-trifluoroethoxy)phenyl]-5,6-dihydropyrido[2,3-d]pyrimidine-4,7(3H,8H)-dione or a salt thereof;

[7] 2-ethoxy-3-[4-(2,2,2-trifluoroethoxy)phenyl]-5,6-dihydropyrido[2,3-d]pyrimidine-4,7(3H,8H)-dione or a salt thereof;

[8] 3-[4-(2,2,2-trifluoroethoxy)phenyl]-2-(3,3,3-trifluoropropyl)-5,6-dihydropyrido[2,3-d]pyrimidine-4,7(3H,8H)-dione or a salt thereof;

[9] a medicament comprising the compound or salt of any of the above-mentioned [1] to [8];

[10] the medicament of the above-mentioned [9], which is a delta-5-desaturase inhibitor;

[11] the medicament of the above-mentioned [9], which is an agent for the prophylaxis or treatment of eicosanoid-associated diseases;

[12] the medicament of the above-mentioned [9], which is an agent for the prophylaxis or treatment of arteriosclerosis;

[13] the medicament of the above-mentioned [9], which is an agent for the prophylaxis or treatment of diabetes or obesity;

[14] a method for the prophylaxis or treatment of arteriosclerosis in a mammal, comprising administering an effective amount of the compound or salt of any of the above-mentioned [1] to [8] to the mammal;

[15] a method for the prophylaxis or treatment of diabetes or obesity in a mammal, comprising administering an effective amount of the compound or salt of any of the above-mentioned [1] to [8] to the mammal;

[16] use of the compound or salt of any of the above-mentioned [1] to [8] for the production of an agent for the prophylaxis or treatment of arteriosclerosis;

[17] use of the compound or salt of any of the above-mentioned [1] to [8] for the production of an agent for the prophylaxis or treatment of diabetes or obesity;

[18] the compound or salt of any of the above-mentioned [1] to [8] for use in the prophylaxis or treatment of arteriosclerosis;

[19] the compound or salt of any of the above-mentioned [1] to [8] for use in the prophylaxis or treatment of diabetes or obesity; and the like.

DETAILED DESCRIPTION OF THE INVENTION

Compound (I) has a delta-5-desaturase inhibitory action, and is useful for the prophylaxis or treatment of eicosanoid-associated diseases such as atherosclerosis, atherothrombosis, diabetes, obesity, asthma, fever, pain, cancer, rheumatism, osteoarthritis, atopic dermatitis and the like, and has a superior efficacy.

(Detailed Description of the Invention)

The present invention is explained in detail in the following.

In the present specification, examples of the "halogen atom" include a fluorine atom, a chlorine atom, a bromine atom, an iodine atom and the like.

In the present specification, examples of the "$C_{1-6}$ alkyl (group)" include methyl, ethyl, propyl, isopropyl, butyl, isobutyl, sec-butyl, tert-butyl, pentyl, isopentyl, neopentyl, tert-pentyl, hexyl, 2,2-dimethylbutyl, 3,3-dimethylbutyl, 2-ethylbutyl and the like.

In the present specification, examples of the "$C_{1-6}$ alkoxy (group)" include methoxy, ethoxy, propoxy, isopropoxy, butoxy, isobutoxy, sec-butoxy, tert-butoxy, pentyloxy, isopentyloxy, neopentyloxy, tert-pentyloxy, hexyloxy, 2-ethylbutoxy and the like.

In the present specification, examples of the "$C_{3-10}$ cycloalkyl (group)" include cyclopropyl, cyclobutyl, cyclopentyl, cyclohexyl, cycloheptyl and cyclooctyl.

In the present specification, examples of the "$C_{6-14}$ aryl (group)" include phenyl, naphthyl (e.g., 1-naphthyl, 2-naphthyl), anthryl, phenanthryl and the like.

In the present specification, examples of the "$C_{7-13}$ aralkyl (group)" include benzyl, phenethyl, naphthylmethyl, biphenylylmethyl and the like.

In the present specification, examples of the "$C_{2-6}$ alkenyl (group)" include ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl, 5-hexenyl and the like.

Ring A is a ring represented by the formula:

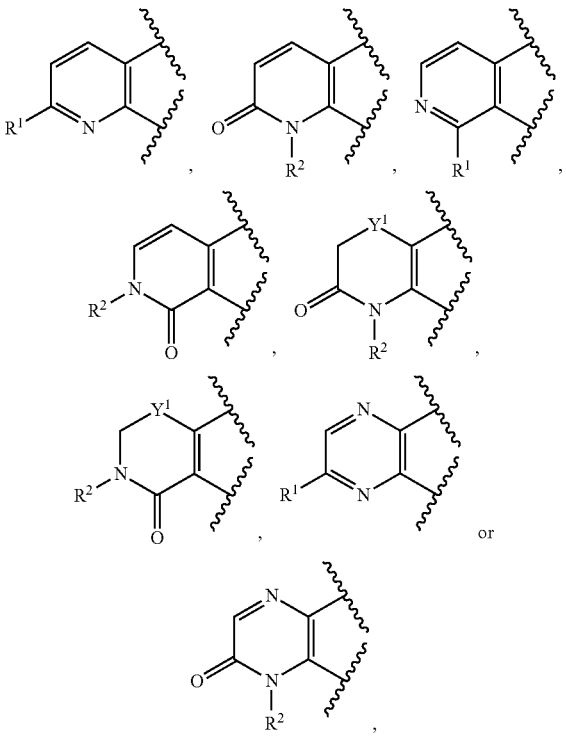

wherein each ring is optionally further substituted by substituent(s) selected from a halogen atom, a $C_{1-6}$ alkyl group and a $C_{1-6}$ alkoxy group.

Ring A is preferably a ring represented by the formula:

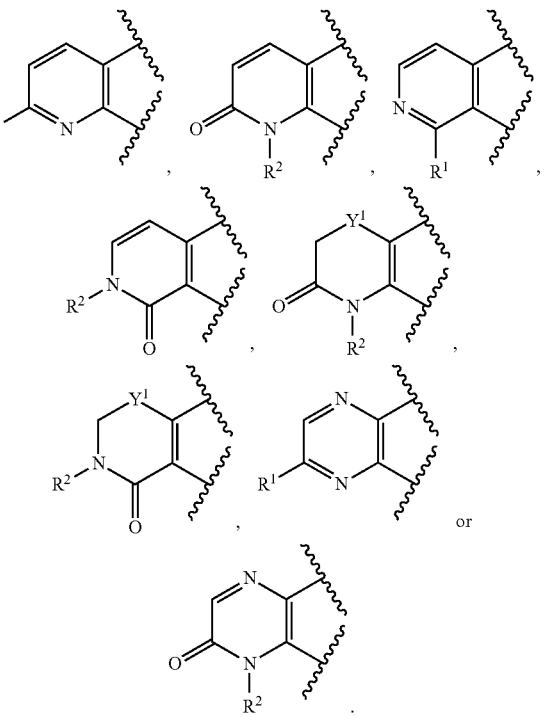

Ring A is more preferably a ring represented by the formula:

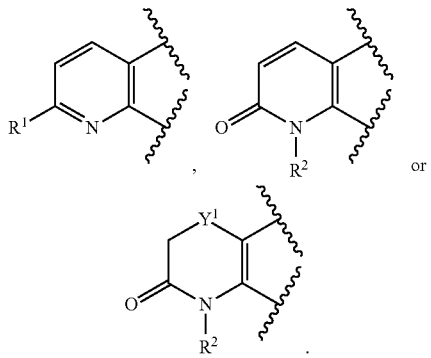

Ring A is still more preferably a ring represented by the formula:

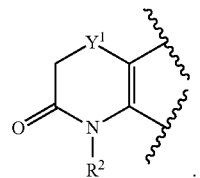

Ring B is a 6-membered aromatic ring optionally further substituted by substituent(s) selected from a halogen atom, a $C_{1-6}$ alkyl group and a $C_{1-6}$ alkoxy group.

Examples of the "6-membered aromatic ring" of the "6-membered aromatic ring optionally further substituted by substituent(s) selected from a halogen atom, a $C_{1-6}$ alkyl group and a $C_{1-6}$ alkoxy group" for ring B include benzene, pyridine, pyridazine, pyrimidine, pyrazine, triazine and the like. Among them, benzene, pyridine, pyridazine, pyrimidine, pyrazine and the like are preferable, and benzene is more preferable.

The "6-membered aromatic ring" of the "6-membered aromatic ring optionally further substituted by substituent(s) selected from a halogen atom, a $C_{1-6}$ alkyl group and a $C_{1-6}$ alkoxy group" for ring B optionally has 1 to 3 substituents selected from a halogen atom, a $C_{1-6}$ alkyl group and a $C_{1-6}$ alkoxy group at substitutable positions. When the number of the substituents is two or more, the respective substituents may be the same or different.

Ring B is preferably benzene.

$X^1$ is a bond, S, $SO_2$, O or $NR^5$.

In one preferable embodiment, $X^1$ is S, O or $NR^5$.

In another preferable embodiment, $X^1$ is a bond, S, O or $NR^5$.

$R^5$ is a hydrogen atom or an optionally substituted $C_{1-6}$ alkyl group.

The "$C_{1-6}$ alkyl group" of the "optionally substituted $C_{1-6}$ alkyl group" for $R^5$ optionally has 1 to 3 substituents at substitutable positions. Examples of the substituent include those similar to the substituent that the "$C_{1-6}$ alkoxy group" of the below-mentioned "optionally substituted $C_{1-6}$ alkoxy group" for $R^1$ optionally has. When the number of the substituents is two or more, the respective substituents may be the same or different.

$R^5$ is preferably a hydrogen atom.

$X^1$ is preferably a bond, S, O or NH.

$X^1$ is more preferably a bond, S or O.

$X^2$ is $CR^6R^7$ or O.

$R^6$ is a hydrogen atom, a halogen atom, a $C_{1-6}$ alkyl group or a $C_{1-6}$ alkoxy group.

$R^6$ is preferably a hydrogen atom.

$R^7$ is a hydrogen atom, a halogen atom, a $C_{1-6}$ alkyl group or a $C_{1-6}$ alkoxy group.

$R^7$ is preferably a hydrogen atom.

$X^2$ is preferably O.

$Y^1$ is $CR^8R^9$, S, SO, $SO_2$ or O.

In one preferable embodiment, $Y^1$ is $CR^8R^9$ or S.

$R^8$ is a hydrogen atom, a halogen atom, a $C_{1-6}$ alkyl group or a $C_{1-6}$ alkoxy group.

$R^8$ is preferably a hydrogen atom.

$R^9$ is a hydrogen atom, a halogen atom, a $C_{1-6}$ alkyl group or a $C_{1-6}$ alkoxy group.

$R^9$ is preferably a hydrogen atom.

$Y^1$ is preferably $CH_2$ or S.

$Y^1$ is more preferably $CH_2$.

$R^1$ is an optionally substituted alkoxy group, an optionally substituted amino group, an optionally substituted carbamoyl group or an optionally substituted $C_{1-6}$ alkylthio group.

The "$C_{1-6}$ alkoxy group" of the "optionally substituted $C_{1-6}$ alkoxy group" for $R^1$ optionally has 1 to 3 substituents at substitutable positions.

Examples of the substituent include (1) a $C_{3-10}$ cycloalkyl group (e.g., cyclopropyl, cyclohexyl);

(2) a $C_{6-14}$ aryl group (e.g., phenyl, naphthyl) optionally substituted by 1 to 3 substituents selected from
    (a) a $C_{1-6}$ alkyl group optionally substituted by 1 to 3 halogen atoms,
    (b) a hydroxy group,
    (c) a $C_{1-6}$ alkoxy group optionally substituted by 1 to 3 halogen atoms, and
    (d) a halogen atom;

(3) a 4- to 7-membered aromatic heterocyclic group (e.g., thienyl, furyl, pyridyl, pyrazolyl, imidazolyl, tetrazolyl, oxazolyl, thiazolyl, oxadiazolyl, thiadiazolyl) optionally substituted by 1 to 3 substituents selected from
    (a) a $C_{1-6}$ alkyl group optionally substituted by 1 to 3 halogen atoms,
    (b) a hydroxy group,
    (c) a $C_{1-6}$ alkoxy group optionally substituted by 1 to 3 halogen atoms, and
    (d) a halogen atom;

(4) a 4- to 7-membered non-aromatic heterocyclic group (e.g., tetrahydrofuryl, morpholinyl, thiomorpholinyl, piperidyl, pyrrolidinyl, piperazinyl) optionally substituted by 1 to 3 substituents selected from
    (a) a $C_{1-6}$ alkyl group optionally substituted by 1 to 3 halogen atoms,
    (b) a hydroxy group,
    (c) a $C_{1-6}$ alkoxy group optionally substituted by 1 to 3 halogen atoms,
    (d) a halogen atom, and
    (e) an oxo group;

(5) an amino group optionally mono- or di-substituted by substituent(s) selected from
    (a) a $C_{1-6}$ alkyl group optionally substituted by 1 to 3 halogen atoms,
    (b) a $C_{1-6}$ alkyl-carbonyl group optionally substituted by 1 to 3 halogen atoms,
    (c) a $C_{1-6}$ alkoxy-carbonyl group optionally substituted by 1 to 3 halogen atoms,
    (d) a $C_{1-6}$ alkylsulfonyl group (e.g., methylsulfonyl) optionally substituted by 1 to 3 halogen atoms, (e) a carbamoyl group optionally mono- or di-substituted by $C_{1-6}$ alkyl group(s) optionally substituted by 1 to 3 halogen atoms, and
(f) a 4- to 7-membered aromatic heterocyclic group (e.g., thienyl, furyl, pyridyl, pyrazolyl, imidazolyl, tetrazolyl, oxazolyl, thiazolyl, oxadiazolyl, thiadiazolyl);
(6) a $C_{1-6}$ alkyl-carbonyl group optionally substituted by 1 to 3 halogen atoms;
(7) a $C_{1-6}$ alkoxy-carbonyl group (e.g., methoxycarbonyl) optionally substituted by 1 to 3 substituents selected from
 (a) a halogen atom,
 (b) a $C_{1-6}$ alkoxy group,
 (c) a $C_{6-14}$ aryl group (e.g., phenyl), and
 (d) a 4- to 7-membered heterocyclic group (e.g., tetrahydrofuryl);
(8) a $C_{1-6}$ alkylsulfonyl group (e.g., methylsulfonyl, ethylsulfonyl, isopropylsulfonyl) optionally substituted by 1 to 3 halogen atoms;
(9) a carbamoyl group optionally mono- or di-substituted by $C_{1-6}$ alkyl group(s) optionally substituted by 1 to 3 halogen atoms;
(10) a thiocarbamoyl group optionally mono- or di-substituted by $C_{1-6}$ alkyl group(s) optionally substituted by 1 to 3 halogen atoms;
(11) a sulfamoyl group optionally mono- or di-substituted by $C_{1-6}$ alkyl group(s) optionally substituted by 1 to 3 halogen atoms;
(12) a carboxy group;
(13) a hydroxy group;
(14) a $C_{1-6}$ alkoxy group optionally substituted by 1 to 3 substituents selected from
 (a) a halogen atom,
 (b) a carboxy group,
 (c) a $C_{1-6}$ alkoxy group,
 (d) a $C_{1-6}$ alkoxy-carbonyl group optionally substituted by 1 to 3 $C_{6-14}$ aryl groups (e.g., phenyl),
 (e) an amino group optionally mono- or di-substituted by substituent(s) selected from a $C_{1-6}$ alkyl group and a $C_{1-6}$ alkoxy-carbonyl group,
 (f) a 4- to 7-membered heterocyclic group (e.g., tetrahydrofuryl), and
 (g) a $C_{3-10}$ cycloalkyl group;
(15) a $C_{2-6}$ alkenyloxy group (e.g., ethenyloxy) optionally substituted by 1 to 3 halogen atoms;
(16) a $C_{7-13}$ aralkyloxy group (e.g., benzyloxy);
(17) a $C_{6-14}$ aryloxy group (e.g., phenyloxy, naphthyloxy);
(18) a $C_{1-6}$ alkyl-carbonyloxy group (e.g., acetyloxy, tert-butylcarbonyloxy);
(19) a $C_{6-14}$ aryl-carbonyl group (e.g., benzoyl) optionally substituted by 1 to 3 substituents selected from
 (a) a halogen atom, and
 (b) a $C_{1-6}$ alkyl group optionally substituted by 1 to 3 halogen atoms;
(20) a 4- to 7-membered non-aromatic heterocyclylcarbonyl group (e.g., pyrrolidinylcarbonyl, morpholinylcarbonyl) optionally substituted by 1 to 3 substituents selected from a $C_{1-6}$ alkyl group optionally substituted by 1 to 3 halogen atoms;
(21) a mercapto group;
(22) a $C_{1-6}$ alkylthio group (e.g., methylthio, ethylthio) optionally substituted by 1 to 3 substituents selected from
 (a) a halogen atom, and
 (b) a $C_{1-6}$ alkoxy-carbonyl group;
(23) a $C_{7-13}$ aralkylthio group (e.g., benzylthio);
(24) a $C_{6-14}$ arylthio group (e.g., phenylthio, naphthylthio);
(25) a cyano group;
(26) a nitro group;
(27) a halogen atom (e.g., a fluorine atom, a chlorine atom, a bromine atom);
(28) a $C_{1-3}$ alkylenedioxy group;
(29) a $C_{1-3}$ alkyleneoxy group (e.g., methyleneoxy, ethyleneoxy);
(30) a 4- to 7-membered aromatic heterocyclylcarbonyl group (e.g., pyrazolylcarbonyl, pyrazinylcarbonyl, isoxazolylcarbonyl, pyridylcarbonyl, thiazolylcarbonyl) optionally substituted by 1 to 3 substituents selected from a $C_{1-6}$ alkyl group optionally substituted by 1 to 3 halogen atoms; and the like. When the number of the substituents is two or more, the respective substituents may be the same or different.

The "optionally substituted $C_{1-6}$ alkoxy group" for $R^1$ is preferably a $C_{1-6}$ alkoxy group (e.g., methoxy, ethoxy) optionally substituted by 1 to 3 $C_{1-6}$ alkoxy groups (e.g., methoxy), or the like.

The "amino group" of the "optionally substituted amino group" for $R^1$ optionally has 1 or 2 substituents at substitutable positions. Examples of the substituent include those similar to the substituent that the "$C_{1-6}$ alkoxy group" of the "optionally substituted $C_{1-6}$ alkoxy group" for $R^1$ optionally has. When the number of the substituents is two or more, the respective substituents may be the same or different.

The "optionally substituted amino group" for $R^1$ is preferably amino or the like.

The "carbamoyl group" of the "optionally substituted carbamoyl group" for $R^1$ optionally has 1 or 2 substituents at substitutable positions. Examples of the substituent include those similar to the substituent that the "$C_{1-6}$ alkoxy group" of the "optionally substituted $C_{1-6}$ alkoxy group" for $R^1$ optionally has. When the number of the substituents is two or more, the respective substituents may be the same or different.

The "optionally substituted carbamoyl group" for $R^1$ is preferably carbamoyl or the like.

Examples of the "$C_{1-6}$ alkylthio group" of the "optionally substituted $C_{1-6}$ alkylthio group" for $R^1$ include methylthio, ethylthio, propylthio, isopropylthio, butylthio, sec-butylthio, tert-butylthio and the like.

The "$C_{1-6}$ alkylthio group" of the "optionally substituted $C_{1-6}$ alkylthio group" for $R^1$ optionally has 1 to 3 substituents at substitutable positions. Examples of the substituent include those similar to the substituent that the "$C_{1-6}$ alkoxy group" of the "optionally substituted $C_{1-6}$ alkoxy group" for $R^1$ optionally has. When the number of the substituents is two or more, the respective substituents may be the same or different.

$R^1$ is preferably
(1) a $C_{1-6}$ alkoxy group (e.g., methoxy, ethoxy) optionally substituted by 1 to 3 $C_{1-6}$ alkoxy groups (e.g., methoxy);
(2) amino;
(3) carbamoyl;
or the like.

$R^1$ is more preferably a $C_{1-6}$ alkoxy group (e.g., methoxy).

$R^2$ is a hydrogen atom or an optionally substituted $C_{1-6}$ alkyl group.

The "$C_{1-6}$ alkyl group" of the "optionally substituted $C_{1-6}$ alkyl group" for $R^2$ optionally has 1 to 3 substituents at substitutable positions. Examples of the substituent include those similar to the substituent that the "$C_{1-6}$ alkoxy group" of the "optionally substituted $C_{1-6}$ alkoxy group" for $R^1$ optionally has. When the number of the substituents is two or more, the respective substituents may be the same or different.

The "optionally substituted $C_{1-6}$ alkyl group" for $R^2$ is preferably methyl or the like.

$R^2$ is preferably a hydrogen atom or a $C_{1-6}$ alkyl group (e.g., methyl).

$R^2$ is more preferably a hydrogen atom.

$R^3$ is an optionally substituted $C_{1-6}$ alkyl group or an optionally substituted 3- to 11-membered cyclic group.

The "$C_{1-6}$ alkyl group" of the "optionally substituted $C_{1-6}$ alkyl group" for $R^3$ optionally has 1 to 3 substituents at substitutable positions. Examples of the substituent include those similar to the substituent that the "$C_{1-6}$ alkoxy group" of the "optionally substituted $C_{1-6}$ alkoxy group" for $R^1$ optionally has. When the number of the substituents is two or more, the respective substituents may be the same or different.

The "optionally substituted $C_{1-6}$ alkyl group" for $R^3$ is preferably a $C_{1-6}$ alkyl group (e.g., methyl, ethyl, propyl, isopropyl) optionally substituted by 1 to 3 substituents selected from (1) a $C_{1-6}$ alkylsulfonyl group (e.g., methylsulfonyl),
(2) a hydroxy group,
(3) a $C_{1-6}$ alkoxy group (e.g., methoxy), and
(4) a halogen atom (e.g., a fluorine atom, a chlorine atom, a bromine atom), or the like.

Examples of the "3- to 11-membered cyclic group" of the "optionally substituted 3- to 11-membered cyclic group" for $R^3$ include a 6- to 10-membered aromatic hydrocarbon group, a 5- to 11-membered aromatic heterocyclic group (e.g., a 5- to 7-membered monocyclic aromatic heterocyclic group, a 8- to 11-membered fused aromatic heterocyclic group), a 3- to 10-membered non-aromatic cyclic hydrocarbon group, a 3- to 8-membered non-aromatic heterocyclic group and the like.

Examples of the 6- to 10-membered aromatic hydrocarbon group include a $C_{6-10}$ aryl group and the like. Specific examples thereof include phenyl, 1-naphthyl, 2-naphthyl and the like.

Examples of the 5- to 7-membered monocyclic aromatic heterocyclic group include a 5- to 7-membered monocyclic aromatic heterocyclic group containing, as a ring constituting atom besides carbon atom, 1 to 4 hetero atoms selected from an oxygen atom, a sulfur atom (the sulfur atom is optionally oxidized) and a nitrogen atom, and the like.

Specific examples of the 5- to 7-membered monocyclic aromatic heterocyclic group include furyl (e.g., 2-furyl, 3-furyl), thienyl (e.g., 2-thienyl, 3-thienyl), pyridyl (e.g., 2-pyridyl, 3-pyridyl, 4-pyridyl), pyrimidinyl (e.g., 2-pyrimidinyl, 4-pyrimidinyl, 5-pyrimidinyl, 6-pyrimidinyl), pyridazinyl (e.g., 3-pyridazinyl, 4-pyridazinyl), pyrazinyl (e.g., 2-pyrazinyl), pyrrolyl (e.g., 1-pyrrolyl, 2-pyrrolyl, 3-pyrrolyl), imidazolyl (e.g., 1-imidazolyl, 2-imidazolyl, 4-imidazolyl, 5-imidazolyl), pyrazolyl (e.g., 1-pyrazolyl, 3-pyrazolyl, 4-pyrazolyl), thiazolyl (e.g., 2-thiazolyl, 4-thiazolyl, 5-thiazolyl), isothiazolyl (e.g., 3-isothiazolyl, 4-isothiazolyl, 5-isothiazolyl), oxazolyl (e.g., 2-oxazolyl, 4-oxazolyl, 5-oxazolyl), isoxazolyl (e.g., 3-isoxazolyl, 4-isoxazolyl, 5-isoxazolyl), oxadiazolyl (e.g., 1,2,4-oxadiazol-5-yl, 1,3,4-oxadiazol-2-yl), thiadiazolyl (e.g., 1,3,4-thiadiazol-2-yl), triazolyl (e.g., 1,2,4-triazol-1-yl, 1,2,4-triazol-3-yl, 1,2,3-triazol-1-yl, 1,2,3-triazol-2-yl, 1,2,3-triazol-4-yl), tetrazolyl (e.g., tetrazol-1-yl, tetrazol-5-yl), triazinyl (e.g., 1,3,5-triazin-2-yl) and the like.

Examples of the 8- to 11-membered fused aromatic heterocyclic group include a group derived from a fused ring formed by fusion of a 5- to 7-membered monocyclic aromatic heterocycle ring containing, as a ring constituting atom besides carbon atom, 1 to 4 hetero atoms selected from an oxygen atom, a sulfur atom (the sulfur atom is optionally oxidized) and a nitrogen atom, and the like with a $C_{6-10}$ aromatic hydrocarbon and the like; a group derived from a fused ring formed by fusion of the above-mentioned 5- to 7-membered monocyclic aromatic heterocycles.

Examples of the 5- to 7-membered monocyclic aromatic heterocycle include a ring corresponding to the above-mentioned 5- to 7-membered monocyclic aromatic heterocyclic group.

Examples of the $C_{6-10}$ aromatic hydrocarbon include a ring corresponding to the above-mentioned $C_{6-10}$ aryl group.

Specific examples of the 8- to 11-membered fused aromatic heterocyclic group include quinolyl (e.g., 2-quinolyl, 3-quinolyl, 4-quinolyl), isoquinolyl (e.g., 1-isoquinolyl, 3-isoquinolyl, 4-isoquinolyl), quinazolyl (e.g., 2-quinazolyl, 4-quinazolyl), quinoxalyl (e.g., 2-quinoxalyl), benzofuryl (e.g., 2-benzofuryl, 3-benzofuryl), benzothienyl (e.g., 2-benzothienyl, 3-benzothienyl), benzoxazolyl (e.g., 2-benzoxazolyl), benzothiazolyl (e.g., 2-benzothiazolyl, 5-benzothiazolyl, 6-benzothiazolyl), benzimidazolyl (e.g., benzimidazol-1-yl, benzimidazol-2-yl, benzimidazol-5-yl), indolyl (e.g., indol-1-yl, indol-3-yl, indol-4-yl, indol-5-yl, indol-6-yl), indazolyl (e.g., 1H-indazol-3-yl), pyrrolopyrazinyl (e.g., 1H-pyrrolo[2,3-b]pyrazin-2-yl, 1H-pyrrolo[2,3-b]pyrazin-6-yl), imidazopyridyl (e.g., 1H-imidazo[4,5-b]pyridin-2-yl, 1H-imidazo[4,5-c]pyridin-2-yl), imidazopyrazinyl (e.g., 1H-imidazo[4,5-b]pyrazin-2-yl), benzisoxazolyl (e.g., 3-benzisoxazolyl), benzotriazolyl (e.g., 1H-1,2,3-benzotriazol-5-yl), pyrazolopyridyl (e.g., 1H-pyrazolo[4,3-c]pyridin-3-yl), pyrazolothienyl (e.g., 2H-pyrazolo[3,4-b]thiophen-2-yl), pyrazolotriazinyl (e.g., pyrazolo[5,1-c][1,2,4]triazin-3-yl) and the like.

Examples of the 3- to 10-membered non-aromatic cyclic hydrocarbon group include a $C_{3-10}$ cycloalkyl group, a $C_{3-10}$ cycloalkenyl group, a $C_{4-10}$ cycloalkadienyl group and the like, each of which is optionally fused with a benzene ring.

Specific examples of the 3- to 10-membered non-aromatic cyclic hydrocarbon group include a $C_{3-10}$ cycloalkyl group (e.g., cyclopropyl, cyclobutyl, cyclopentyl, cyclohexyl, cycloheptyl, cyclooctyl), a $C_{3-10}$ cycloalkenyl group (e.g., cyclopropenyl, cyclobutenyl, cyclopentenyl, cyclohexenyl, cycloheptenyl, cyclooctenyl), a $C_{4-10}$ cycloalkadienyl group (e.g., cyclobutadienyl, cyclopentadienyl, cyclohexadienyl, cycloheptadienyl, cyclooctadienyl, cyclononadienyl, cyclodecadienyl), a fused ring formed by fusion of the group with a benzene ring (e.g., indanyl (e.g., 1-indanyl), tetrahydronaphthyl (e.g., 1,2,3,4-tetrahydronaphthalen-1-yl)), and the like.

Examples of the 3- to 8-membered non-aromatic heterocyclic group include a 3- to 8-membered (preferably 5- or 6-membered) saturated or unsaturated (preferably saturated) non-aromatic heterocyclic group and the like.

Specific examples of the 3- to 8-membered non-aromatic heterocyclic group include oxiranyl (e.g., 2-oxiranyl), azetidinyl (e.g., 2-azetidinyl), oxetanyl (e.g., 2-oxetanyl), thietanyl (e.g., 2-thietanyl), pyrrolidinyl (e.g., 1-pyrrolidinyl, 2-pyrrolidinyl, 3-pyrrolidinyl), tetrahydrofuryl (e.g., 2-tetrahydrofuryl, 3-tetrahydrofuryl), thiolanyl (e.g., 2-thiolanyl), piperidyl (e.g., 1-piperidyl, 2-piperidyl, 3-piperidyl, 4-piperidyl), tetrahydropyranyl (e.g., 2-tetrahydropyranyl, 3-tetrahydropyranyl, 4-tetrahydropyranyl), thianyl (e.g., 2-thianyl), morpholinyl (e.g., 2-morpholinyl, 3-morpholinyl, 4-morpholinyl), thiomorpholinyl (e.g., 2-thiomorpholinyl, 3-thiomorpholinyl, 4-thiomorpholinyl), piperazinyl (e.g., 1-piperazinyl, 2-piperazinyl), azepanyl (e.g., 2-azepanyl), oxepanyl (e.g., 2-oxepanyl), thiepanyl (e.g., 2-thiepanyl), oxazepanyl (e.g., 1,4-oxazepan-5-yl), thiazepanyl (e.g., 1,4-thiazepan-5-yl), azocanyl (e.g., 2-azocanyl), oxocanyl (e.g., 2-oxocanyl), thiocanyl (e.g., 2-thiocanyl), oxazocanyl (e.g., 1,4-oxacan-5-yl), thiazocanyl (e.g., 1,4-thiazocan-5-yl), dioxinyl (e.g., 2-dioxinyl) and the like.

The 6- to 10-membered aromatic hydrocarbon group, 5- to 7-membered monocyclic aromatic heterocyclic group, 8- to 11-membered fused aromatic heterocyclic group, 3- to 10-membered non-aromatic cyclic hydrocarbon group and 3- to 8-membered non-aromatic heterocyclic group, which are exemplified as the "3- to 11-membered cyclic group" of the "optionally substituted 3- to 11-membered cyclic group" for $R^3$, optionally have 1 to 3 substituents at substitutable positions.

Examples of the substituent include (1) a $C_{3-10}$ cycloalkyl group (e.g., cyclopropyl, cyclohexyl);
(2) a $C_{6-14}$ aryl group (e.g., phenyl, naphthyl) optionally substituted by 1 to 3 substituents selected from
    (a) a $C_{1-6}$ alkyl group optionally substituted by 1 to 3 halogen atoms,
    (b) a hydroxy group,
    (c) a $C_{1-6}$ alkoxy group optionally substituted by 1 to 3 halogen atoms, and
    (d) a halogen atom;
(3) a 4- to 7-membered aromatic heterocyclic group (e.g., thienyl, furyl, pyridyl, pyrazolyl, imidazolyl, tetrazolyl, oxazolyl, thiazolyl, oxadiazolyl, thiadiazolyl) optionally substituted by 1 to 3 substituents selected from
    (a) a $C_{1-6}$ alkyl group optionally substituted by 1 to 3 halogen atoms,
    (b) a hydroxy group,
    (c) a $C_{1-6}$ alkoxy group optionally substituted by 1 to 3 halogen atoms, and
    (d) a halogen atom;
(4) a 4- to 7-membered non-aromatic heterocyclic group (e.g., tetrahydrofuryl, morpholinyl, thiomorpholinyl, piperidyl, pyrrolidinyl, piperazinyl) optionally substituted by 1 to 3 substituents selected from
    (a) a $C_{1-6}$ alkyl group optionally substituted by 1 to 3 halogen atoms,
    (b) a hydroxy group,
    (c) a $C_{1-6}$ alkoxy group optionally substituted by 1 to 3 halogen atoms,
    (d) a halogen atom, and
    (e) an oxo group;
(5) an amino group optionally mono- or di-substituted by substituent(s) selected from
    (a) a $C_{1-6}$ alkyl group optionally substituted by 1 to 3 halogen atoms,
    (b) a $C_{1-6}$ alkyl-carbonyl group optionally substituted by 1 to 3 halogen atoms,
    (c) a $C_{1-6}$ alkoxy-carbonyl group optionally substituted by 1 to 3 halogen atoms,
    (d) a $C_{1-6}$ alkylsulfonyl group (e.g., methylsulfonyl) optionally substituted by 1 to 3 halogen atoms,
    (e) a carbamoyl group optionally mono- or di-substituted by $C_{1-6}$ alkyl group(s) optionally substituted by 1 to 3 halogen atoms, and
    (f) a 4- to 7-membered aromatic heterocyclic group (e.g., thienyl, furyl, pyridyl, pyrazolyl, imidazolyl, tetrazolyl, oxazolyl, thiazolyl, oxadiazolyl, thiadiazolyl);
(6) a $C_{1-6}$ alkyl-carbonyl group optionally substituted by 1 to 3 halogen atoms;
(7) a $C_{1-6}$ alkoxy-carbonyl group (e.g., methoxycarbonyl) optionally substituted by 1 to 3 substituents selected from
    (a) a halogen atom,
    (b) a $C_{1-6}$ alkoxy group,
    (c) a $C_{6-14}$ aryl group (e.g., phenyl), and
    (d) a 4- to 7-membered heterocyclic group (e.g., tetrahydrofuryl);
(8) a $C_{1-6}$ alkylsulfonyl group (e.g., methylsulfonyl, ethylsulfonyl, isopropylsulfonyl) optionally substituted by 1 to 3 halogen atoms;
(9) a carbamoyl group optionally mono- or di-substituted by $C_{1-6}$ alkyl group(s) optionally substituted by 1 to 3 halogen atoms;
(10) a thiocarbamoyl group optionally mono- or di-substituted by $C_{1-6}$ alkyl group(s) optionally substituted by 1 to 3 halogen atoms;
(11) a sulfamoyl group optionally mono- or di-substituted by $C_{1-6}$ alkyl group(s) optionally substituted by 1 to 3 halogen atoms;
(12) a carboxy group;
(13) a hydroxy group;
(14) a $C_{1-6}$ alkoxy group optionally substituted by 1 to 3 substituents selected from
    (a) a halogen atom,
    (b) a carboxy group,
    (c) a $C_{1-6}$ alkoxy group,
    (d) a $C_{1-6}$ alkoxy-carbonyl group optionally substituted by 1 to 3 $C_{6-14}$ aryl groups (e.g., phenyl),
    (e) an amino group optionally mono- or di-substituted by substituent(s) selected from a $C_{1-6}$ alkyl group and a $C_{1-6}$ alkoxy-carbonyl group,
    (f) a 4- to 7-membered heterocyclic group (e.g., tetrahydrofuryl), and
    (g) a $C_{3-10}$ cycloalkyl group;
(15) a $C_{2-6}$ alkenyloxy group (e.g., ethenyloxy) optionally substituted by 1 to 3 halogen atoms;
(16) a $C_{7-13}$ aralkyloxy group (e.g., benzyloxy);
(17) a $C_{6-14}$ aryloxy group (e.g., phenyloxy, naphthyloxy);
(18) a $C_{1-6}$ alkyl-carbonyloxy group (e.g., acetyloxy, tert-butylcarbonyloxy);
(19) a $C_{6-14}$ aryl-carbonyl group (e.g., benzoyl) optionally substituted by 1 to 3 substituents selected from
    (a) a halogen atom, and
    (b) a $C_{1-6}$ alkyl group optionally substituted by 1 to 3 halogen atoms;
(20) a 4- to 7-membered non-aromatic heterocyclylcarbonyl group (e.g., pyrrolidinylcarbonyl, morpholinylcarbonyl) optionally substituted by 1 to 3 substituents selected from a $C_{1-6}$ alkyl group optionally substituted by 1 to 3 halogen atoms;
(21) a mercapto group;
(22) a $C_{1-6}$ alkylthio group (e.g., methylthio, ethylthio) optionally substituted by 1 to 3 substituents selected from
    (a) a halogen atom, and
    (b) a $C_{1-6}$ alkoxy-carbonyl group;
(23) a $C_{7-13}$ aralkylthio group (e.g., benzylthio);
(24) a $C_{6-14}$ arylthio group (e.g., phenylthio, naphthylthio);
(25) a cyano group;
(26) a nitro group;
(27) a halogen atom (e.g., a fluorine atom, a chlorine atom, a bromine atom);
(28) a $C_{1-3}$ alkylenedioxy group;
(29) a $C_{1-3}$ alkyleneoxy group (e.g., methyleneoxy, ethyleneoxy);
(30) a 4- to 7-membered aromatic heterocyclylcarbonyl group (e.g., pyrazolylcarbonyl, pyrazinylcarbonyl, isoxazolylcarbonyl, pyridylcarbonyl, thiazolylcarbonyl) optionally substituted by 1 to 3 substituents selected from a $C_{1-6}$ alkyl group optionally substituted by 1 to 3 halogen atoms;
(31) a $C_{3-10}$ cycloalkoxy group (e.g., cyclopropoxy, cyclopentyloxy) optionally substituted by 1 to 3 substituents selected from
    (a) a halogen atom (e.g., a fluorine atom), and
    (b) a $C_{1-6}$ alkoxy group (e.g., methoxy);

(32) a $C_{1-6}$ alkyl group optionally substituted by 1 to 3 substituents selected from
   (a) a halogen atom,
   (b) a carboxy group,
   (c) a hydroxy group,
   (d) a $C_{1-6}$ alkoxy-carbonyl group,
   (e) a $C_{1-6}$ alkoxy group, and
   (f) an amino group optionally mono- or di-substituted by $C_{1-6}$ alkyl group(s);
(33) a $C_{2-6}$ alkenyl group (e.g., ethenyl, 1-propenyl) optionally substituted by 1 to 3 substituents selected from
   (a) a halogen atom,
   (b) a carboxy group,
   (c) a hydroxy group,
   (d) a $C_{1-6}$ alkoxy-carbonyl group,
   (e) a $C_{1-6}$ alkoxy group, and
   (f) an amino group optionally mono- or di-substituted by $C_{1-6}$ alkyl group(s);
(34) a $C_{7-13}$ aralkyl group (e.g., benzyl) optionally substituted by 1 to 3 substituents selected from
   (a) a $C_{1-6}$ alkyl group optionally substituted by 1 to 3 halogen atoms,
   (b) a hydroxy group,
   (c) a $C_{1-6}$ alkoxy group, and
   (d) a halogen atom;
and the like. When the number of the substituents is two or more, the respective substituents may be the same or different.

The "optionally substituted 3- to 11-membered cyclic group" for $R^3$ is preferably a $C_{3-10}$ cycloalkyl group (e.g., cyclohexyl) optionally substituted by 1 to 3 halogen atoms (e.g., a fluorine atom), or the like.

$R^3$ is preferably
(1) a $C_{1-6}$ alkyl group (e.g., methyl, ethyl, propyl, isopropyl) optionally substituted by 1 to 3 substituents selected from
   (A) a $C_{1-6}$ alkylsulfonyl group (e.g., methylsulfonyl),
   (B) a hydroxy group,
   (C) a $C_{1-6}$ alkoxy group (e.g., methoxy), and
   (D) a halogen atom (e.g., a fluorine atom, a chlorine atom, a bromine atom);
(2) a $C_{3-10}$ cycloalkyl group (e.g., cyclohexyl) optionally substituted by 1 to 3 halogen atoms (e.g., a fluorine atom); or the like.

$R^3$ is more preferably
(1) a $C_{1-6}$ alkyl group (e.g., ethyl, propyl) optionally substituted by 1 to 3 halogen atoms (e.g., a fluorine atom);
(2) a $C_{3-10}$ cycloalkyl group (e.g., cyclohexyl) optionally substituted by 1 to 3 halogen atoms (e.g., a fluorine atom); or the like.

$R^4$ is an optionally substituted $C_{1-6}$ alkyl group or an optionally substituted 3- to 11-membered cyclic group.

The "$C_{1-6}$ alkyl group" of the "optionally substituted $C_{1-6}$ alkyl group" for $R^4$ optionally has 1 to 3 substituents at substitutable positions. Examples of the substituent include those similar to the substituent that the "$C_{1-6}$ alkoxy group" of the "optionally substituted $C_{1-6}$ alkoxy group" for $R^1$ optionally has. When the number of the substituents is two or more, the respective substituents may be the same or different.

The "optionally substituted $C_{1-6}$ alkyl group" for $R^4$ is preferably a $C_{1-6}$ alkyl group optionally substituted by 1 to 3 halogen atoms.

Examples of the "optionally substituted 3- to 11-membered cyclic group" for $R^4$ include those similar to the "optionally substituted 3- to 11-membered cyclic group" for $R^3$.

$R^4$ is preferably a $C_{1-6}$ alkyl group (e.g., ethyl) optionally substituted by 1 to 3 halogen atoms (e.g., a fluorine atom).

Preferable examples of compound (I) include the following compounds.

[Compound A]
   Compound (1) wherein
ring A is a ring represented by the formula:

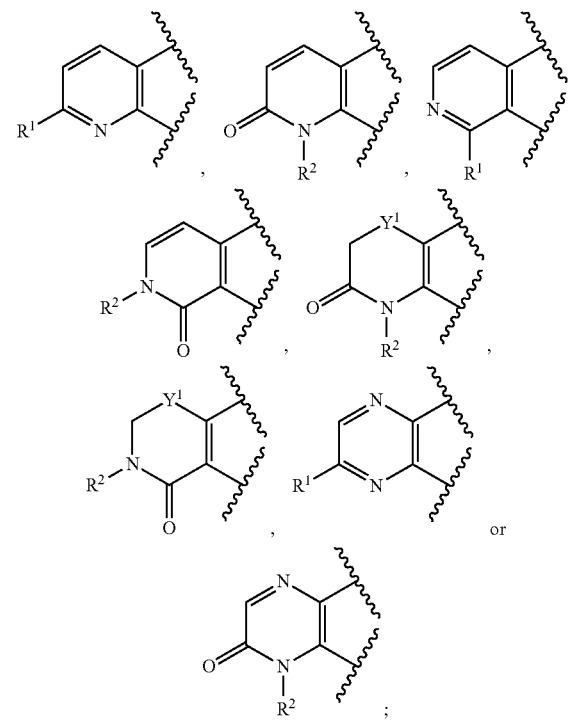

ring B is benzene;
$X^1$ is S, O or $NR^5$;
$X^2$ is O;
$Y^1$ is $CR^8R^9$ or S;
$R^1$ is
(1) a $C_{1-6}$ alkoxy group (e.g., methoxy, ethoxy) optionally substituted by 1 to 3 $C_{1-6}$ alkoxy groups (e.g., methoxy);
(2) amino; or
(3) carbamoyl;

$R^2$ is a hydrogen atom or a $C_{1-6}$ alkyl group (e.g., methyl);
$R^3$ is
(1) a $C_{1-6}$ alkyl group (e.g., methyl, ethyl, propyl, isopropyl) optionally substituted by 1 to 3 substituents selected from
   (A) a $C_{1-6}$ alkylsulfonyl group (e.g., methylsulfonyl),
   (B) a hydroxy group,
   (C) a $C_{1-6}$ alkoxy group (e.g., methoxy), and
   (D) a halogen atom (e.g., a fluorine atom, a chlorine atom, a bromine atom), or
(2) a $C_{3-10}$ cycloalkyl group (e.g., cyclohexyl) optionally substituted by 1 to 3 halogen atoms (e.g., a fluorine atom);

$R^4$ is a $C_{1-6}$ alkyl group (e.g., ethyl) optionally substituted by 1 to 3 halogen atoms (e.g., a fluorine atom);
$R^5$ is a hydrogen atom;
$R^8$ is a hydrogen atom; and
$R^9$ is a hydrogen atom.

[Compound B]
Compound (I) wherein
ring A is a ring represented by the formula:

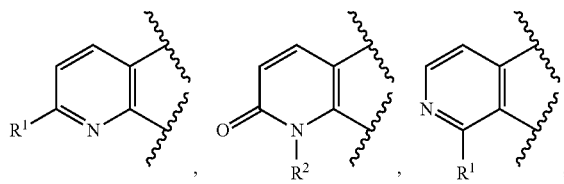
,
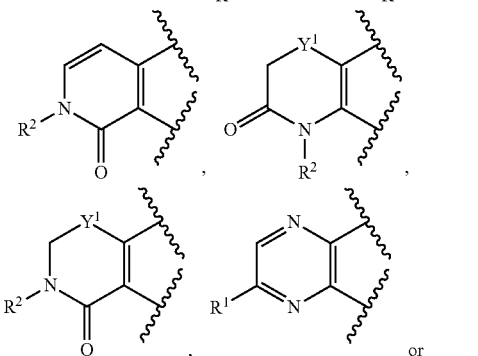
,
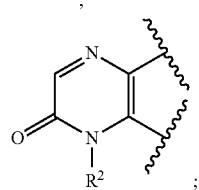
or ring B is benzene;
$X^1$ is a bond, S, O or $NR^5$;
$X^2$ is O;
$Y^1$ is $CR^8R^9$ or S;
$R^1$ is
(1) a $C_{1-6}$ alkoxy group (e.g., methoxy, ethoxy) optionally substituted by 1 to 3 $C_{1-6}$ alkoxy groups (e.g., methoxy);
(2) amino; or
(3) carbamoyl;
$R^2$ is a hydrogen atom or a $C_{1-6}$ alkyl group (e.g., methyl);
$R^3$ is
(1) a $C_{1-6}$ alkyl group (e.g., methyl, ethyl, propyl, isopropyl) optionally substituted by 1 to 3 substituents selected from
    (A) a $C_{1-6}$ alkylsulfonyl group (e.g., methylsulfonyl),
    (B) a hydroxy group,
    (C) a $C_{1-6}$ alkoxy group (e.g., methoxy), and
    (D) a halogen atom (e.g., a fluorine atom, a chlorine atom, a bromine atom), or
(2) a $C_{3-10}$ cycloalkyl group (e.g., cyclohexyl) optionally substituted by 1 to 3 halogen atoms (e.g., a fluorine atom);
$R^4$ is a $C_{1-6}$ alkyl group (e.g., ethyl) optionally substituted by 1 to 3 halogen atoms (e.g., a fluorine atom);
$R^5$ is a hydrogen atom;
$R^8$ is a hydrogen atom; and
$R^9$ is a hydrogen atom.
[Compound C]
Compound (I) wherein
ring A is a ring represented by the formula:

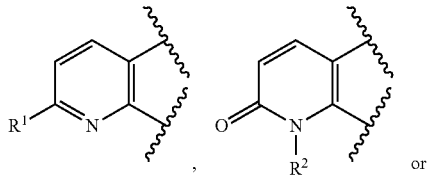
,
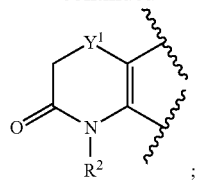
;

ring B is benzene;
$X^1$ is a bond, S or O;
$X^2$ is O;
$Y^1$ is $CH_2$;
$R^1$ is a $C_{1-6}$ alkoxy group (e.g., methoxy);
$R^2$ is a hydrogen atom;
$R^3$ is
(1) a $C_{1-6}$ alkyl group (e.g., ethyl, propyl) optionally substituted by 1 to 3 halogen atoms (e.g., a fluorine atom), or
(2) a $C_{3-10}$ cycloalkyl group (e.g., cyclohexyl) optionally substituted by 1 to 3 halogen atoms (e.g., a fluorine atom); and
$R^4$ is a $C_{1-6}$ alkyl group (e.g., ethyl) optionally substituted by 1 to 3 halogen atoms (e.g., a fluorine atom).
[Compound D]
Compound (I) wherein
ring A is a ring represented by the formula:

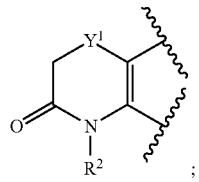
;

ring B is benzene;
$X^1$ is a bond, S or O;
$X^2$ is O;
$Y^1$ is $CH_2$;
$R^2$ is a hydrogen atom;
$R^3$ is
(1) a $C_{1-6}$ alkyl group (e.g., ethyl, propyl) optionally substituted by 1 to 3 halogen atoms (e.g., a fluorine atom), or
(2) a $C_{3-10}$ cycloalkyl group (e.g., cyclohexyl) optionally substituted by 1 to 3 halogen atoms (e.g., a fluorine atom); and
$R^4$ is a $C_{1-6}$ alkyl group (e.g., ethyl) optionally substituted by 1 to 3 halogen atoms (e.g., a fluorine atom).
[Compound E]
2-(2,2,2-trifluoroethoxy)-3-[4-(2,2,2-trifluoroethoxy)phenyl]-5,6-dihydropyrido[2,3-d]pyrimidine-4,7(3H,8H)-dione; 2-ethoxy-3-[4-(2,2,2-trifluoroethoxy)phenyl]-5,6-dihydropyrido[2,3-d]pyrimidine-4,7(3H,8H)-dione; or 3-[4-(2,2,2-trifluoroethoxy)phenyl]-2-(3,3,3-trifluoropropyl)-5,6-dihydropyrido[2,3-d]pyrimidine-4,7(3H,8H)-dione;
or a salt thereof.

As a salt of the compound represented by the formula (I), a pharmacologically acceptable salt is preferable. Examples of such salt include salts with inorganic bases, salts with organic bases, salts with inorganic acids, salts with organic acids, salts with basic or acidic amino acids, and the like.

Preferable examples of the salts with inorganic bases include alkali metal salts such as sodium salt, potassium salt and the like; alkaline earth metal salts such as calcium salts, magnesium salts and the like; aluminum salt; ammonium salts, and the like.

Preferable examples of the salts with organic bases include salts with trimethylamine, triethylamine, pyridine, picoline, ethanolamine, diethanolamine, triethanolamine, tromethamine[tris(hydroxymethyl)methylamine], tert-butylamine, cyclohexylamine, benzylamine, dicyclohexylamine, N,N-dibenzylethylenediamine and the like.

Preferable examples of the salts with inorganic acids include salts with hydrochloric acid, hydrobromic acid, nitric acid, sulfuric acid, phosphoric acid and the like.

Preferable examples of the salts with organic acids include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like.

Preferable examples of the salts with basic amino acids include salts with arginine, lysine, ornithine and the like.

Preferable examples of the salts with acidic amino acids include salts with aspartic acid, glutamic acid and the like.

Compound (I) may be labeled with an isotope (e.g., $^{3}H$, $^{11}C$, $^{14}C$, $^{18}F$, $^{35}S$, $^{125}I$) and the like.

Compound (I) may be a non-solvate (e.g., anhydrate) or a solvate (e.g., hydrate).

Furthermore, a deuterated form wherein $^{1}H$ is converted to $^{2}H(D)$ is also encompassed in compound (I).

Compound (I) may also be a crystal or amorphous. When compound (I) is a crystal, compound (I) encompasses a single crystal form and a mixture of crystal forms.

The crystal of compound (I) can be produced by crystallizing compound (I) by applying a crystallization method known per se.

In the present specification, the melting point means, for example, a melting point measured by a trace melting point measurement device (YANACO, MP-500D type or Buchi, B-545 type) or DSC (Differential scanning calorimetry) apparatus (SEIKO, EXSTAR6000) and the like.

Generally, the melting point sometimes varies depending on the measurement device, measurement condition and the like. The crystal in the present specification may be a crystal showing a melting point different from the values described in the present specification as long as the difference is within a general error range.

Compound (I) may be a pharmaceutically acceptable cocrystal or cocrystal salt. Here, the cocrystal or cocrystal salt means a crystalline substance constituted by two or more kinds of special solids each having different physical properties (e.g., structure, melting point, melting heat and the like) at room temperature. The cocrystal or cocrystal salt can be produced by a cocrystallization method known per se.

The crystal of the present invention is superior in the physicochemical properties (e.g., melting point, solubility, stability) and biological properties (e.g., pharmacokinetics (absorbability, distribution, metabolism, excretion), efficacy expression) and extremely useful as a medicament.

Compound (I) may be a prodrug. A prodrug of compound (I) means a compound which is converted to compound (I) with a reaction due to an enzyme or an gastric acid, etc. under the physiological condition in the living body, that is, a compound which is converted to compound (I) with enzymatic oxidation, reduction, hydrolysis and the like; a compound which is converted to compound (I) by hydrolysis and the like due to gastric acid and the like.

A prodrug of compound (I) may be a compound obtained by subjecting an amino group in compound (I) to an acylation, alkylation or phosphorylation (e.g., a compound obtained by subjecting an amino group in compound (I) to an eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation or tert-butylation);

a compound obtained by subjecting a hydroxy group in compound (I) to an acylation, alkylation, phosphorylation or boration (e.g., a compound obtained by subjecting an hydroxy group in compound (I) to an acetylation, palmitoylation, propanoylation, pivaloylation, succinylation, fumarylation, alanylation or dimethylaminomethylcarbonylation);

a compound obtained by subjecting a carboxy group in compound (I) to an esterification or amidation (e.g., a compound obtained by subjecting a carboxy group in compound (I) to an ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification or methylamidation) and the like. These compounds can be produced from compound (I) according to a method known per se.

A prodrug of compound (I) may also be one which is converted into compound (I) under a physiological condition, such as those described in IYAKUHIN NO KAIHATSU (Development of Pharmaceuticals), Vol. 7, Design of Molecules, pp. 163-198, Published by HIROKAWA SHOTEN (1990).

The production methods of compound (I) are explained in the following.

Compound (I) can be produced, for example, by the method shown in the following method or a method analogous thereto. In the following reaction schemes, each starting compound may form a salt as long as it does not inhibit the reaction, and examples of the salt include those exemplified as the salts of the compound represented by the aforementioned formula (I) can be used.

In the following reaction schemes, the starting compounds without indication of specific production method are easily commercially available, or can be produced according to a method known per se or a method analogous thereto.

While the solvent used for the reaction in each scheme is not particularly limited as long as it does not inhibit the reaction and dissolves a starting material to some extent, examples thereof include aromatic hydrocarbons such as benzene, toluene, xylene and the like; aliphatic hydrocarbons such as hexane, heptane and the like; ethers such as diethyl ether, diisopropyl ether, tert-butyl methyl ether, tetrahydrofuran, dioxane, 1,2-dimethoxyethane and the like; ketones such as acetone, 2-butanone and the like; nitriles such as acetonitrile, propionitrile and the like; esters such as ethyl acetate, isopropyl acetate, tert-butyl acetate and the like; amides such as N,N-dimethylformamide, N,N-dimethylacetamide, 1-methyl-2-pyrrolidinone and the like; imides such as 1,3-dimethyl-2-imidazolidinone and the like; alcohols such as methanol, ethanol, isopropanol, tert-butanol and the like; halogenated hydrocarbons such as chloroform, dichloromethane, 1,2-dichloroethane, carbon tetrachloride and the like; sulfoxides such as dimethyl sulfoxide and the like; water and the like. These solvents may be used in a mixture thereof in an appropriate ratio. The reaction temperature is generally −100-250° C. which is the temperature of not more than the boiling point of the above-mentioned solvent. Where necessary, the reaction can be carried out at the temperature of not less than the boiling point of the solvent under pressure-resistant reaction conditions and the like. The reaction time generally 0.5 hr-100 hr.

Scheme 1

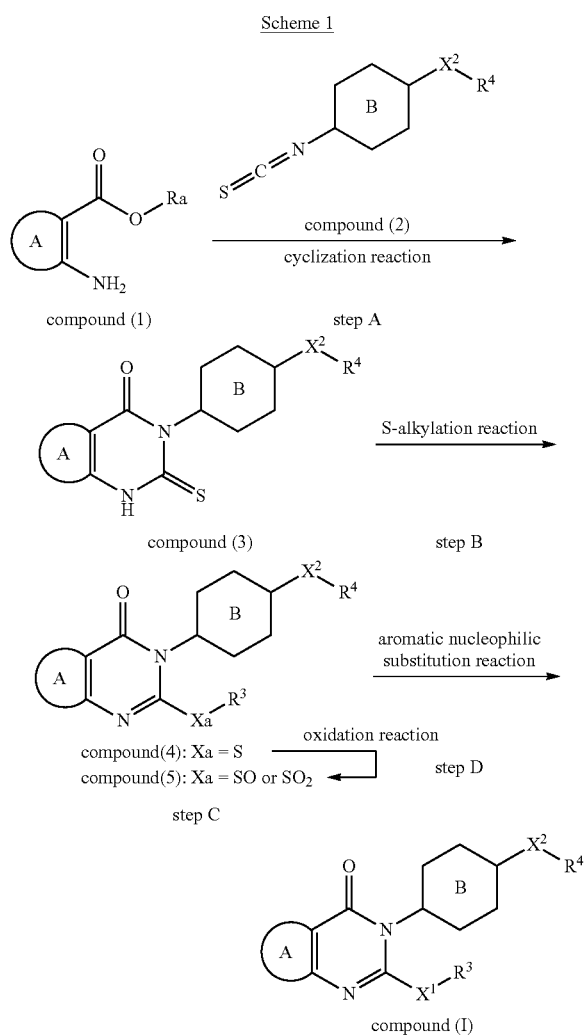

wherein each symbol is as defined above, Ra is a $C_{1-6}$ alkyl group, and Xa is S, SO or $SO_2$.

Compound (I) can be produced according to the route shown in Scheme 1. To be specific, compound (I) can be produced by subjecting compound (4) or (5) to an aromatic nucleophilic substitution reaction, from compound (I) as a starting material via compound (3).

Compound (1) may be commercially available product, or can be produced according to a method known per se or a method analogous thereto.

Step A (Cyclization Reaction)

Compound (3) can be produced by subjecting compound (1) to a ring closure reaction with compound (2) under basic conditions. To be specific, the reaction is carried out using compound (2) in an amount of about 1.0-5.0 mol, preferably about 1.0-2.0 mol, per 1 mol of compound (1). Examples of the base include inorganic bases such as sodium hydroxide, potassium hydroxide, barium hydroxide, sodium carbonate, potassium carbonate and the like, metal alkoxides such as sodium methoxide, sodium ethoxide, potassium tert-butoxide and the like, metal hydrides such as sodium hydride, potassium hydride and the like, organic bases such as triethylamine, N,N-diisopropylethylamine and the like, and the like, and the base is used in an amount of about 1.0-10.0 mol, preferably about 1.0-5.0 mol, per 1.0 mol of compound (1).

This reaction is preferably carried out in a solvent inert to the reaction. While the solvent is not particularly limited as long as the reaction proceeds, preferable examples thereof include aromatic hydrocarbons such as benzene, toluene and the like, ethers such as tetrahydrofuran, dioxane, 1,2-dimethoxyethane and the like, amides such as N,N-dimethylformamide, N,N-dimethylacetamide and the like, nitriles such as acetonitrile, propionitrile and the like, sulfoxides such as dimethyl sulfoxide and the like, mixed solvents thereof and the like. The reaction time is generally 1 hr-60 hr, preferably 1 hr-24 hr. The reaction temperature is generally -10-200° C., preferably 0-100° C. Compound (3) can be used directly as the reaction mixture or as a crude product for the next reaction, or can be also isolated from the reaction mixture according to a conventional method, and can be easily purified according to separation means such as washing, recrystallization, distillation, chromatography and the like.

Step B (S-Alkylation Reaction)

Compound (4) can be produced by subjecting compound (3) to an S-alkylation reaction with a base and an alkylating agent corresponding to $R^3$. To be specific, the reaction is carried out using a base in an amount of 1.0-10.0 mol, preferably 1.0-5.0 mol and an alkylating agent corresponding to $R^3$ in an amount of 1.0-20.0 mol, preferably 1.0-10.0 mol, per 1 mol of compound (3). Examples of the base include inorganic bases such as sodium hydroxide, potassium hydroxide, barium hydroxide, sodium hydrogen carbonate, sodium carbonate, potassium carbonate and the like, metal alkoxides such as sodium methoxide, sodium ethoxide, potassium tert-butoxide and the like, metal hydrides such as sodium hydride, potassium hydride and the like, organic bases such as triethylamine, N,N-diisopropylethylamine and the like, and the like. Examples of the alkylating agent corresponding to $R^3$ include various alkyl halides such as alkyl chlorides, alkyl bromides, alkyl iodides and the like and derivatives thereof, sulfonates such as p-toluenesulfonate, methylsulfonate and the like, sulfates such as dimethyl sulfate and the like, and the like. This reaction is preferably carried out in a solvent inert to the reaction. While the solvent is not particularly limited as long as the reaction proceeds, preferable examples thereof include alcohols such as methanol, ethanol, propanol, 1,1-dimethylethanol and the like, aromatic hydrocarbons such as benzene, toluene and the like, ethers such as tetrahydrofuran, dioxane, 1,2-dimethoxyethane and the like, amides such as N,N-dimethylformamide, N,N-dimethylacetamide and the like, nitriles such as acetonitrile, propionitrile and the like, sulfoxides such as dimethyl sulfoxide and the like, water, mixed solvents thereof and the like. The reaction time is generally 15 min-60 hr, preferably 15 min-24 hr. The reaction temperature is generally -10-200° C., preferably 0-150° C. Compound (4) can be used directly as the reaction mixture or as a crude product for the next reaction, or can be also isolated from the reaction mixture according to a conventional method, and can be easily purified according to separation means such as washing, recrystallization, distillation, chromatography and the like.

Step C (Oxidation Reaction)

Compound (5) can be produced by subjecting compound (4) to an oxidation reaction. To be specific, the reaction is carried out using an oxidant in an amount of 1.0-30.0 mol, preferably 1.0-3.0 mol, per 1 mol of compound (4). Examples of the oxidant include peracids such as hydrogen peroxide, oxone (registered mark), acetic peracid, perbenzoic acid, m-chloroperbenzoic acid and the like, oxoacids such as hypochlorous acid, periodic acid and the like and salts thereof, metal oxoacids such as chromic acid and the like and salts thereof, other oxidants and the like. This reaction is preferably carried out in a solvent inert to the reaction. While the solvent is not particularly limited as long as the reaction proceeds, preferable examples thereof include alcohols such as methanol, ethanol, propanol, 1,1-dimethylethanol and the like, aromatic hydrocarbons such as benzene, toluene and the like, amides such as N,N-dimethylformamide, N,N-dimethylacetamide and the like, nitriles such as acetonitrile, propionitrile and the like, sulfoxides such as dimethyl sulfoxide and the like, carboxylic acids such as acetic acid, formic acid and the like, water, mixed solvents thereof and the like. The reaction time is generally 10 min-60 hr, preferably 30 min-5 hr. The reaction temperature is generally -10-200° C., preferably 0-150° C. Compound (5) can be used directly as the reaction mixture or as a crude product for the next reaction, or can be also isolated from the reaction mixture according to a conventional method, and can be easily purified according to separation means such as washing, recrystallization, distillation, chromatography and the like.

Step D (Aromatic Nucleophilic Substitution Reaction)

Compound (I) can be produced by subjecting compound (4) or (5) to a substitution reaction with a base and a nucleophilic reagent corresponding to $X^1$—$R^3$. To be specific, the reaction is carried out using a base in an amount of 1.0-20.0 mol, preferably 1.0-10.0 mol and a nucleophilic reagent corresponding to $X^1$—$R^3$ in an amount of 1.0-100.0 mol, preferably 1.0-10.0 mol, per 1 mol of compound (4) or (5). Examples of the base include inorganic bases such as sodium hydroxide, potassium hydroxide, barium hydroxide, sodium carbonate, potassium carbonate and the like, metal alkoxides such as sodium methoxide, sodium ethoxide, potassium tert-butoxide and the like, metal hydrides such as sodium hydride, potassium hydride and the like, and the like. Examples of the nucleophilic reagent corresponding to $X^1$—$R^3$ include alcohols such as methanol, ethanol, propanol, 1,1-dimethylethanol, 2,2,2-trifluoroethanol, 2,2,3,3,3-pentafluoropropanol and the like, various phenol derivatives having an aromatic hydroxyl group, organic thiols such as ethanethiol, thioglycolamide and the like, various aromatic thiol derivatives such as thiophenol and the like, organic bases such as methylamine, ethylamine and the like, various aromatic amines such as aniline and the like, organic metal reagents such as organic Grignard reagents (n-propylmagnesium bromide, n-butylmagnesium bromide), organic lithium reagents (n-propyllithium, n-butyllithium) and the like, and the like. Where necessary, the base can be used as a nucleophilic reagent. This reaction is preferably carried out without solvent or in a solvent inert to the reaction. While the solvent is not particularly limited as long as the reaction proceeds, preferable examples thereof include alcohols such as methanol, ethanol, propanol and the like, aromatic hydrocarbons such as benzene, toluene and the like, saturated hydrocarbons such as cyclohexane, hexane and the like, ethers such as tetrahydrofuran, dioxane, 1,2-dimethoxyethane and the like, amides such as N,N-dimethylformamide, N,N-dimethylacetamide and the like, nitriles such as acetonitrile, propionitrile and the like, ketones such as acetone, methyl ethyl ketone and the like, sulfoxides such as dimethyl sulfoxide and the like, water, mixed solvents thereof and the like. The reaction time is generally 10 min-24 hr, preferably 15 min-12 hr. The reaction temperature is generally -10-200° C., preferably 0-100° C. Compound (I) can be used directly as the reaction mixture or as a crude product for the next reaction, or can be also isolated from the reaction mixture according to a conventional method, and can be easily purified according to separation means such as washing, recrystallization, distillation, chromatography and the like.

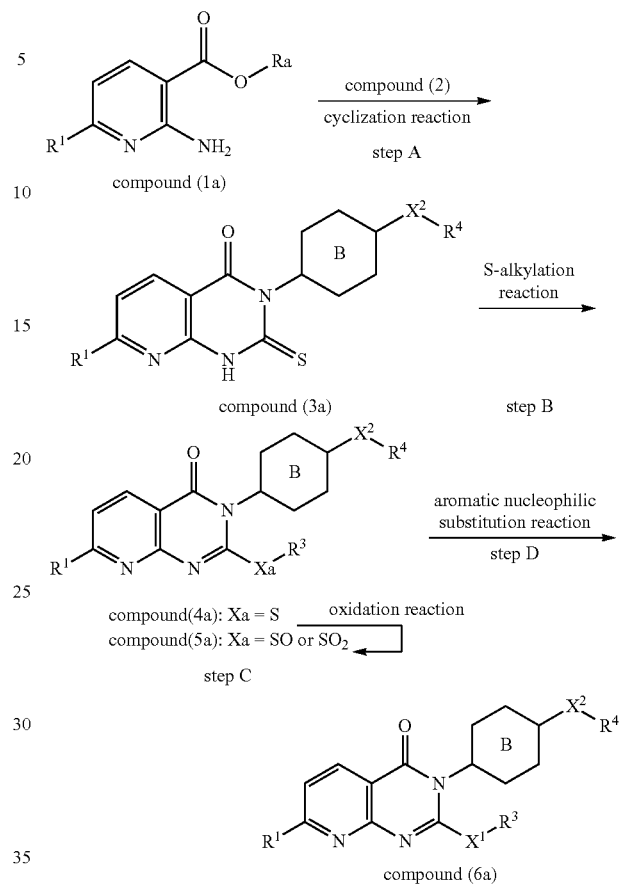

wherein each symbol is as defined above.

Compound (6a) can be produced according to the route similar to Steps A-D of Scheme 1, as shown in Scheme 2. To be specific, compound (1a) as a starting material is subjected to cyclization reaction to produce compound (3a), compound (3a) is converted to compound (4a), and compound (4a) or (5a) is subjected to an aromatic substitution reaction to produce compound (6a).

Compound (1a) can be produced according to the method shown in the below-mentioned Scheme 4.

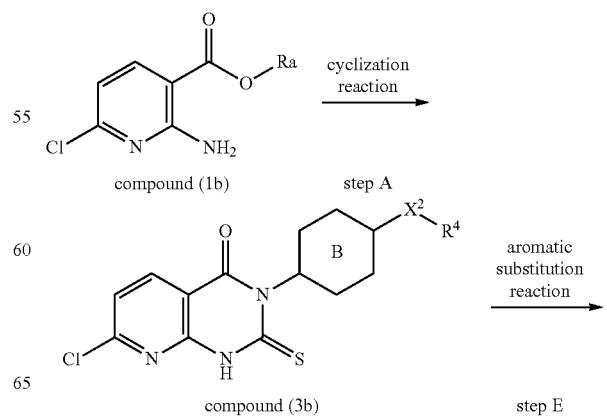

-continued

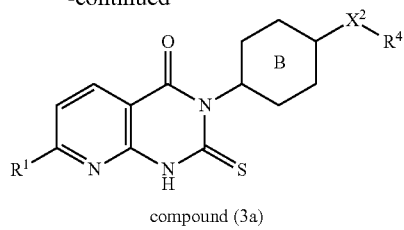

compound (3a)

wherein each symbol is as defined above.

Alternatively, compound (3a) can be produced by subjecting compound (3b) to an aromatic nucleophilic substitution reaction (Step E), as shown in Scheme 3. Compound (3b) is produced from compound (1b) according to the method similar to Step A (Scheme 1).

Compound (1b) can be produced according to the method similar to the below-mentioned Scheme 4.

Step E (Aromatic Nucleophilic Substitution Reaction)

The reaction is carried out using a nucleophilic reagent corresponding to $R^1$ in an amount of 1.0-10 mol, preferably 1.0-5.0 mol, per 1 mol of compound (3b). Examples of the nucleophilic reagent corresponding to $R^1$ include alcohols such as methanol, ethanol, propanol, ethylene glycol and the like, metal alkoxides such as sodium methoxide, sodium ethoxide and the like, organic amines such as methylamine, ethylamine, benzylamine, 4-methoxybenzylamine and the like, and the like. Where necessary, a base can be used. The base is used in an amount of 1.0-10 mol, preferably 1.0-5.0 mol, per 1 mol of compound (3b). Examples of the base include inorganic bases such as sodium hydroxide, potassium hydroxide, barium hydroxide, sodium carbonate, potassium carbonate and the like, metal alkoxides such as sodium methoxide, sodium ethoxide, potassium tert-butoxide and the like, metal hydrides such as sodium hydride, potassium hydride and the like, and the like. Examples of the metal catalyst include copper iodide, copper bromide, palladium acetate, palladium chloride and the like, and the metal catalyst can be used in an amount of 0.01-1.0 mol, preferably 0.1-0.5 mol, per 1 mol of compound (3b). This reaction is preferably carried out without solvent or in a solvent inert to the reaction. While the solvent is not particularly limited as long as the reaction proceeds, preferable examples thereof include alcohols such as methanol, ethanol, propanol, ethylene glycol and the like, amides such as N,N-dimethylformamide, N,N-dimethylacetamide, N-methylpyrrolidone and the like, nitriles such as acetonitrile, propionitrile and the like, sulfoxides such as dimethyl sulfoxide and the like, water, mixed solvents thereof and the like. The reaction time is generally 10 min-60 hr, preferably 15 min-24 hr. The reaction temperature is generally −10-200° C., preferably 0-180° C. Compound (3a) can be used directly as the reaction mixture or as a crude product for the next reaction, or can be also isolated from the reaction mixture according to a conventional method, and can be easily purified according to separation means such as washing, recrystallization, distillation, chromatography and the like.

Scheme 4

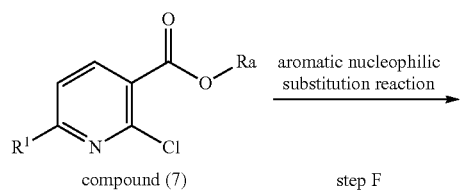

compound (7)       step F

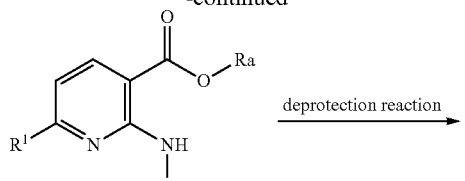

compound (8)        step G

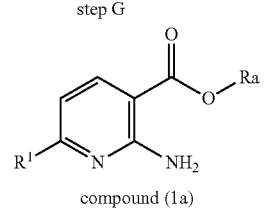

compound (1a)

wherein each symbol is as defined above, and Rb is a 4-methoxybenzyl group or a 2,4-dimethoxybenzyl group.

Compound (1a) can be produced according to the route shown in Scheme 4. To be specific, compound (1a) can be produced by subjecting compound (7) to an aromatic nucleophilic substitution reaction (Step F) and subsequent deprotection (Step G).

Compound (7) may be commercially available product, or can be produced according to a method known per se or a method analogous thereto.

Step F (Aromatic Nucleophilic Substitution Reaction)

Compound (8) can be produced by subjecting compound (7) to a nucleophilic substitution reaction with an amine derivative corresponding to Rb in the presence of a base. To be specific, the reaction is carried out using an amine derivative corresponding to Rb in an amount of 1.0-5.0 mol, preferably 1.0-3.0 mol, per 1 mol of compound (7). Examples of the amine derivative corresponding to Rb include 4-methoxybenzylamine and 2,4-dimethoxybenzylamine. Examples of the base include inorganic bases such as sodium hydroxide, potassium hydroxide, barium hydroxide, sodium carbonate, potassium carbonate and the like, metal alkoxides such as sodium methoxide, sodium ethoxide, potassium tert-butoxide and the like, metal hydrides such as sodium hydride, potassium hydride and the like, and the like. In addition, a metal catalyst such as copper iodide, copper bromide, palladium acetate, palladium chloride and the like can be used in an amount of 0.01-1.0 mol, preferably 0.1-0.5 mol, per 1 mol of compound (7). This reaction is preferably carried out without solvent or in a solvent inert to the reaction. While the solvent is not particularly limited as long as the reaction proceeds, preferable examples thereof include amides such as N,N-dimethylformamide, N,N-dimethylacetamide, N-methylpyrrolidone and the like, nitriles such as acetonitrile, propionitrile and the like, sulfoxides such as dimethyl sulfoxide and the like, water, mixed solvents thereof and the like. The reaction time is generally 10 min-60 hr, preferably 15 min-24 hr. The reaction temperature is generally −10-200° C., preferably 0-180° C. Compound (8) can be used directly as the reaction mixture or as a crude product for the next reaction, or can be also isolated from the reaction mixture according to a conventional method, and can be easily purified according to separation means such as washing, recrystallization, distillation, chromatography and the like.

Step G (Deprotection)

Compound (1a) can be produced by subjecting compound (8) to deprotection under acidic conditions. To be specific, the reaction is carried out using an acid in an amount of 1.0-50 mol, preferably 1.0-10 mol, per 1 mol of compound (8). Examples of the acid include organic acids such as p-toluenesulfonic acid, pyridinium p-toluenesulfonate, trifluoroacetic acid, formic acid, acetic acid and the like, and inorganic acids such as hydrochloric acid, hydrobromic acid and the like. This reaction is preferably carried out without solvent or in a solvent inert to the reaction. While the solvent is not particularly limited as long as the reaction proceeds, preferable examples thereof include alcohols such as methanol, ethanol, isopropylalcohol and the like, amides such as N,N-dimethylformamide, N,N-dimethylacetamide, N-methylpyrrolidone and the like, organic acids such as acetic acid, formic acid, trifluoroacetic acid and the like, sulfoxides such as dimethyl sulfoxide and the like, acetone, water, mixed solvents thereof and the like. The reaction time is generally 10 min-60 hr, preferably 15 min-24 hr. The reaction temperature is generally -10-200° C., preferably 0-180° C. Where necessary, anisole can be added to the reaction system, and can be used in an amount of 0.5-20 mol, preferably 1.0-10 mol, per 1 mol of compound (8). Compound (1a) can be used directly as the reaction mixture or as a crude product for the next reaction, or can be also isolated from the reaction mixture according to a conventional method, and can be easily purified according to separation means such as washing, recrystallization, distillation, chromatography and the like.

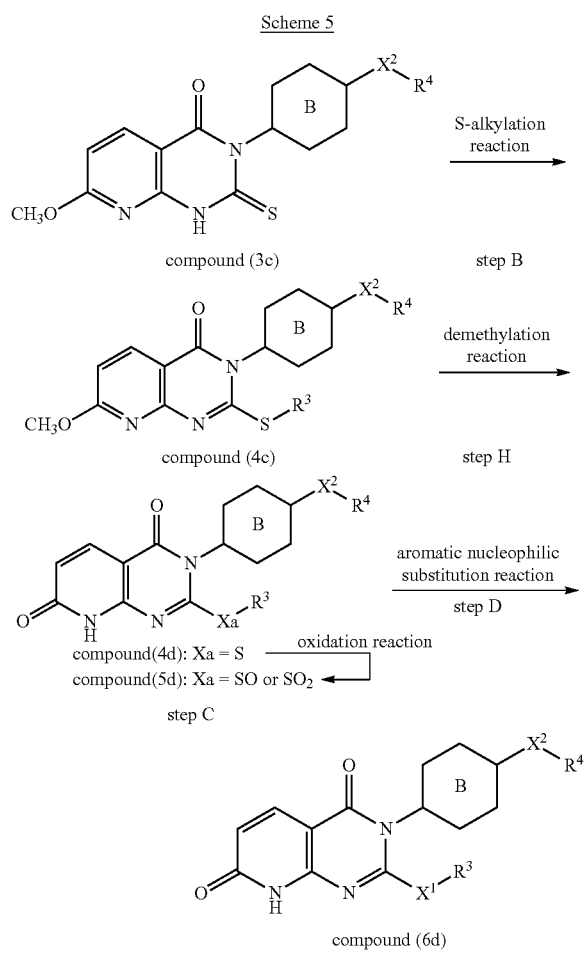

wherein each symbol is as defined above.

Compound (6d) can be produced according to the route shown in Scheme 5. Compound (6d) can be produced from compound (4d) or (5d) according to the method similar to Step D of Scheme 1. Compound (4d) can be produced from compound (4c) which is obtained from compound (3c) according to the method similar to Step B of Scheme 1, according to Step H. Compound (3c) can be produced according to the method similar to Step E of Scheme 3.

Step H (Demethylation Reaction)

Compound (4d) can be produced by subjecting compound (4c) to a demethylation reaction. To be specific, the reaction is carried out using pyridine hydrochloride in an amount of 1.0-100 mol, preferably 1.0-20.0 mol, per 1 mol of compound (4c). This reaction is preferably carried out without solvent or in a solvent inert to the reaction. While the solvent is not particularly limited as long as the reaction proceeds, preferable examples thereof include amides such as N,N-dimethylformamide, N,N-dimethylacetamide, N-methylpyrrolidone and the like, nitriles such as acetonitrile, propionitrile and the like, sulfoxides such as dimethyl sulfoxide and the like, carboxylic acids such as acetic acid, formic acid and the like, water, mixed solvents thereof and the like. The reaction time is generally 15 min-60 hr, preferably 30 min-24 hr. The reaction temperature is generally 30-250° C., preferably 50-180° C. Compound (4d) can be used directly as the reaction mixture or as a crude product for the next reaction, or can be also isolated from the reaction mixture according to a conventional method, and can be easily purified according to separation means such as washing, recrystallization, distillation, chromatography and the like.

Alternatively, a demethylation reaction can also be carried out using a Lewis acid. To be specific, the reaction is carried out using a Lewis acid in an amount of 1.0 mol-10 mol, preferably 1.0-5.0 mol, per 1 mol of compound (4c). Examples of the Lewis acid include borons such as boron tribromide, boron trichloride, boron trifluoride diethyl ether complex and the like, aluminum salts such as aluminum bromide, aluminum chloride and the like, and the like. This reaction is preferably carried out in a solvent inert to the reaction. While the solvent is not particularly limited as long as the reaction proceeds, examples thereof include halogenated hydrocarbons such as dichloromethane, 1,2-dichloroethane and the like, aromatic hydrocarbons such as toluene, xylene and the like, and the like. Where necessary, an additive can be used for this reaction, and examples thereof include sulfur compounds such as dimethylsulfide, ethanethiol and the like. The reaction time is generally 10 min-60 hr, preferably 30 min-24 hr. The reaction temperature is generally -30-150° C., preferably 0-100° C. Compound (4d) can be used directly as the reaction mixture or as a crude product for the next reaction, or can be also isolated from the reaction mixture according to a conventional method, and can be easily purified according to separation means such as washing, recrystallization, distillation, chromatography and the like.

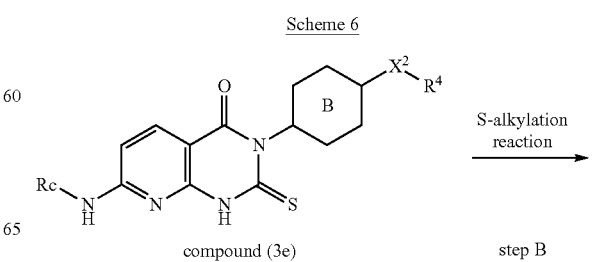

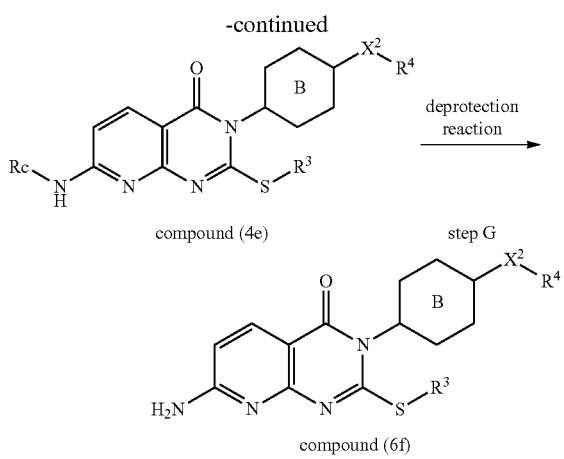

compound (4e)

deprotection reaction step G compound (6f)

wherein each symbol is as defined above, and Rc is a 4-methoxybenzyl group or a 2,4-dimethoxybenzyl group.

Compound (6f) can be produced according to the route shown in Scheme 6. To be specific, compound (6f) can be produced from compound (3e) according to the method similar to Step B (Scheme 1) to obtain compound (4e), and then subjecting compound (4e) according to the deprotection reaction similar to Step G (Scheme 4). Compound (3e) can be produced by reacting compound (3b) with an amine corresponding Rc according to the method similar to Step E (Scheme 3).

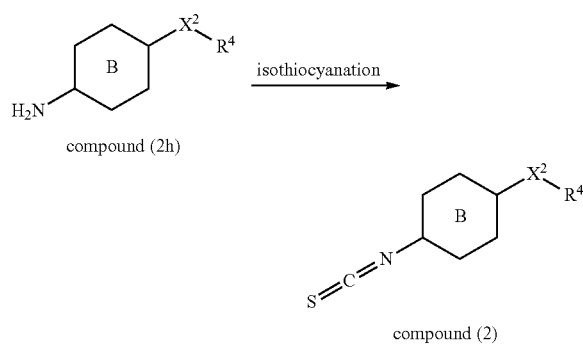

Compound (2) can be produced according to the route shown in Scheme 7, that is, by subjecting compound (2h) to an isothiocyanation reaction. To be specific, the reaction is carried out using an isothiocyanating agent in an amount of about 1.0-5.0 mol, preferably about 1.0-2.0 mol, per 1 mol of compound (2h). Examples of the isothiocyanating agent include thiophosgene, 1,1'-thiocarbonyldi-2(1H)-pyridone, di-2-pyridyl thionocarbonate, 1,1'-thiocarbonyldiimidazole and the like. When thiophosgene is used for this reaction, the reaction can be carried out in the presence of a base in order to remove the released halogenated hydrogen from the reaction system. Preferable examples of the base include inorganic bases such as sodium carbonate, potassium carbonate, sodium hydrogen carbonate and the like, aromatic amines such as pyridine, lutidine and the like, tertiary amines such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine and the like, and the like. This reaction is preferably carried out in a solvent inert to the reaction. While the solvent is not particularly limited as long as the reaction proceeds, preferable examples thereof include halogenated hydrocarbons such as dichloromethane, chloroform, carbon tetrachloride, 1,2-dichloroethane and the like, alcohols such as methanol, ethanol, propanol, 1,1-dimethylethanol and the like, aromatic hydrocarbons such as benzene, toluene and the like, saturated hydrocarbons such as cyclohexane, hexane and the like, ethers such as tetrahydrofuran, dioxane, 1,2-dimethoxyethane and the like, amides such as N,N-dimethylformamide, N,N-dimethylacetamide and the like, nitriles such as acetonitrile, propionitrile and the like, ketones such as acetone, methyl ethyl ketone and the like, sulfoxides such as dimethyl sulfoxide and the like, water, mixed solvents thereof and the like. The reaction time is generally 10 min-60 hr, preferably 15 min-12 hr. The reaction temperature is generally -10-200° C., preferably 0-120° C. Compound (2) can be used directly as the reaction mixture or as a crude product for the next reaction, or can be also isolated from the reaction mixture according to a conventional method, and can be easily purified according to separation means such as recrystallization, distillation, chromatography and the like.

Compound (2h) may be commercially available product, or can be produced according to a method known per se or a method analogous thereto.

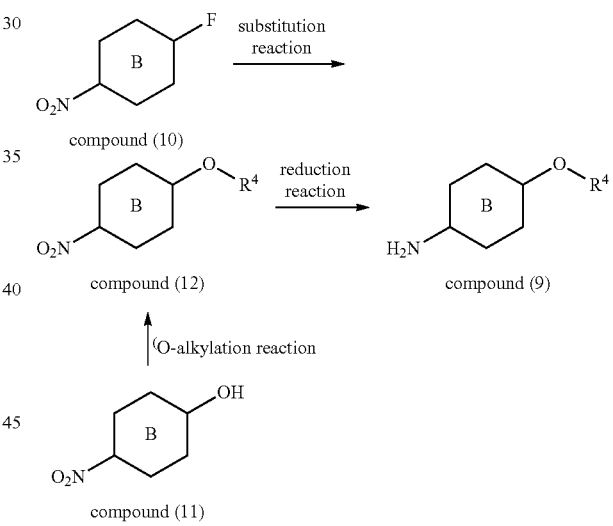

wherein each symbol is as defined above.

Compound (9) can be produced from compound (10) or compound (11) via compound (12) according to the route shown in Scheme 8.

Compound (12) can be produced by subjecting compound (10) to a substitution reaction with a base and an alcohol corresponding to $R^4$. To be specific, the reaction is carried out using an base in an amount of about 1.0-10.0 mol, preferably about 1.0-5.0 mol and an alcohol corresponding to $R^4$ in an amount of about 1.0-100.0 mol, preferably 1.0-2.0 mol, per 1 mol of compound (10). Examples of the base include inorganic bases such as sodium carbonate, potassium carbonate and the like, metal hydrides such as sodium hydride, potassium hydride and the like, and the like. Examples of the alcohol include ethanol, 2,2,2-trifluoroethanol, cyclopropylmethanol, 2-propanol, 2-methylpropanol, 2,2,3,3,3-pentafluoropropanol and the like. This reaction is preferably carried out without solvent or in a solvent inert to the reaction. While the solvent is not particularly limited as long as the reaction proceeds, preferable examples thereof include aromatic hydrocarbons such as benzene, toluene and the like, ethers such as tetrahydrofuran, dioxane, 1,2-dimethoxyethane and the like, amides such as N,N-dimethylformamide, N,N-dimethylacetamide and the like, sulfoxides such as dimethyl sulfoxide and the like, mixed solvents thereof and the like. The reaction time is generally 1 hr-60 hr, preferably 5 hr-12 hr. The reaction temperature is generally-10-200° C., preferably 0-150° C.

Alternatively, compound (12) can also be produced by subjecting compound (11) to an O-alkylation with a base and an alkylating agent corresponding to $R^4$. To be specific, the reaction is carried out using a base in an amount of about 1.0-5.0 mol, preferably about 1.0-2.0 mol and an alkylating agent corresponding to $R^4$ in an amount of about 1.0-10.0 mol, preferably about 1.0-3.0 mol, per 1 mol of compound (11). Examples of the base include inorganic bases such as sodium hydroxide, potassium hydroxide, barium hydroxide, sodium carbonate, potassium carbonate and the like, metal alkoxides such as sodium methoxide, sodium ethoxide, potassium tert-butoxide and the like, metal hydrides such as sodium hydride, potassium hydride and the like, and the like. Examples of the alkylating agent include various alkyl halides such as alkyl chlorides, alkyl bromides, alkyl iodides and the like and derivatives thereof, sulfonates such as p-toluenesulfonate, methylsulfonate and the like, sulfates such as dimethyl sulfate and the like, and the like. This reaction is preferably carried out in a solvent inert to the reaction. While the solvent is not particularly limited as long as the reaction proceeds, preferable examples thereof include alcohols such as methanol, ethanol, propanol, 1,1-dimethylethanol and the like, aromatic hydrocarbons such as benzene, toluene and the like, ethers such as tetrahydrofuran, dioxane, 1,2-dimethoxyethane and the like, amides such as N,N-dimethylformamide, N,N-dimethylacetamide and the like, sulfoxides such as dimethyl sulfoxide and the like, mixed solvents thereof and the like. The reaction time is generally 1 hr-60 hr, preferably 5 hr-24 hr. The reaction temperature is generally-10-200° C., preferably 0-150° C. Compound (12) can be used directly as the reaction mixture or as a crude product for the next reaction, or can be also isolated from the reaction mixture according to a conventional method, and can be easily purified according to separation means such as washing, recrystallization, distillation, chromatography and the like.

Compound (9) can be synthesized by subjecting compound (12) to a reduction reaction. To be specific, compound (9) can be produced by subjecting compound (12) to a reduction reaction using a metal catalyst in an amount of about 0.01-5.0 mol, preferably about 0.01-2.0 mol, per 1 mol of compound (12) under a hydrogen atmosphere. Examples of the metal catalyst include palladium-carbon, palladium hydroxide-carbon, platinum oxide, platinum and the like. This reaction is preferably carried out in a solvent inert to the reaction. While the solvent is not particularly limited as long as the reaction proceeds, preferable examples thereof include alcohols such as methanol, ethanol, propanol and the like, aromatic hydrocarbons such as benzene, toluene and the like, saturated hydrocarbons such as cyclohexane, hexane and the like, ethers such as tetrahydrofuran, dioxane, 1,2-dimethoxyethane and the like, amides such as N,N-dimethylformamide, N,N-dimethylacetamide and the like, sulfoxides such as dimethyl sulfoxide and the like, water, mixed solvents thereof and the like. The reaction time is generally 1 hr-60 hr, preferably 5 hr-36 hr. The reaction temperature is generally –10-200° C., preferably 0-150° C. The reaction is carried out under the pressure of about 1-10 atm, preferably about 1-5 atom. Alternatively, the reduction can also be carried out using a reduced metal. To be specific, the reduction is carried out using a reduced metal in an amount of about 5.0-20.0 mol, preferably about 5.0-10.0 mol, per 1 mol of compound (12). Examples of the reduced metal include reduced iron, tin, zinc and the like. Hydrochloric acid or a hydrochloride such as ammonium chloride, calcium chloride and the like may be added to the reaction system in order to prompt the reaction. This reaction is preferably carried out in a solvent inert to the reaction. While the solvent is not particularly limited as long as the reaction proceeds, preferable examples thereof include alcohols such as methanol, ethanol, propanol and the like, aromatic hydrocarbons such as benzene, toluene and the like, saturated hydrocarbons such as cyclohexane, hexane and the like, ethers such as tetrahydrofuran, dioxane, 1,2-dimethoxyethane and the like, amides such as N,N-dimethylformamide, N,N-dimethylacetamide and the like, ketones such as acetone, methyl ethyl ketone and the like, sulfoxides such as dimethyl sulfoxide and the like, aqueous ammonia solution, water, mixed solvents thereof and the like. The reaction time is generally 1 hr-60 hr, preferably 5 hr-36 hr. The reaction temperature is generally-10-200° C., preferably 0-150° C. Compound (9) can be used directly as the reaction mixture or as a crude product for the next reaction, or can be also isolated from the reaction mixture according to a conventional method, and can be easily purified according to separation means such as washing, recrystallization, distillation, chromatography and the like.

Compound (10) and compound (11) may be commercially available product, or can be produced according to a method known per se or a method analogous thereto.

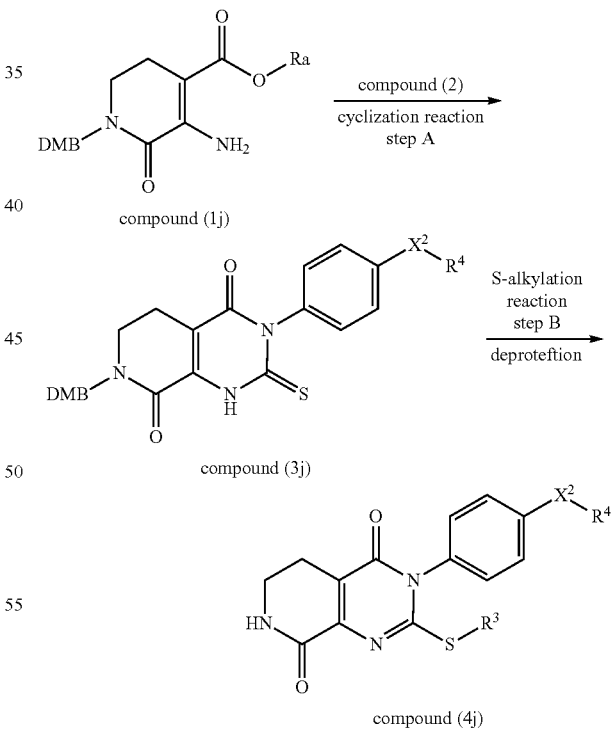

wherein each symbol is as defined above, and DMB is a 2,4-dimethoxybenzyl group.

Compound (4j) can be produced according to the route shown in Scheme 9. To be specific, compound (4j) can be produced according to the method similar to Step A and Step B (Scheme 1), and then the method similar to Step G (Scheme 4).

Scheme 10

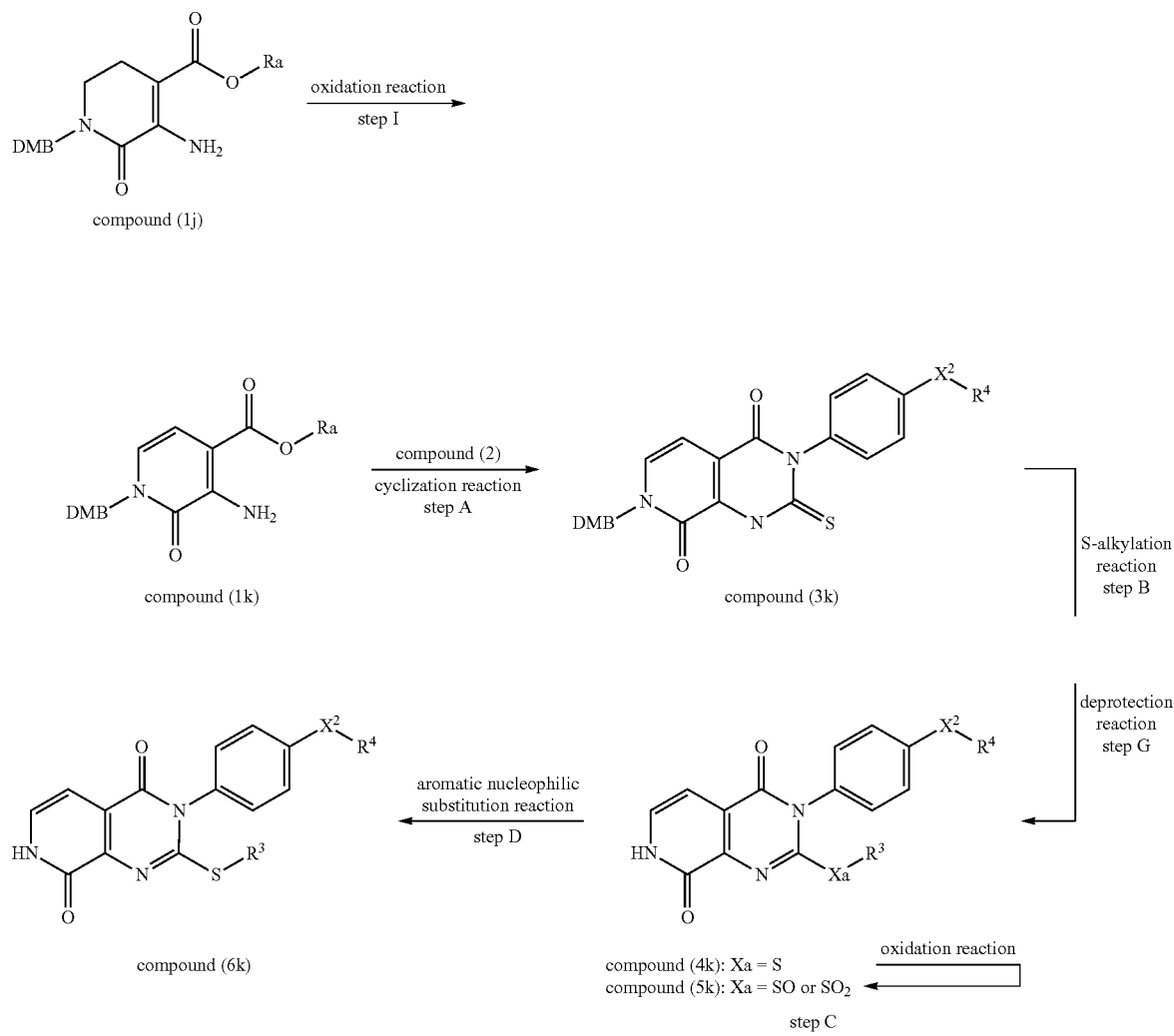

wherein each symbol is as defined above.

Compound (4k) can be produced according to the route shown in Scheme 10. To be specific, compound (4k) can be produced according to the method similar to Step A (Scheme 1), Step B (Scheme 1) and Step G (Scheme 4). Compound (6k) can be produced from compound (4k) or compound (5k) which is produced according to the method similar to Step C (Scheme 1), according to the method similar to Step D (Scheme 1).

Compound (1k) is produced by subjecting compound (1j) to an oxidation reaction (Step I).

Step I (Oxidation Reaction)

The reaction is carried out using an oxidant in an amount of 0.1-10.0 mol, preferably 0.5-5.0 mol, per 1 mol of compound (1j). Examples of the oxidant include 2,3-dichloro-5,6-dicyano-1,4-benzoquinone, 2,3,5,6-tetrachloro-1,4-benzoquinone, palladium-carbon and the like. This reaction is preferably carried out in a solvent inert to the reaction. While the solvent is not particularly limited as long as the reaction proceeds, preferable examples thereof include alcohols such as methanol, ethanol, propanol and the like, aromatic hydrocarbons such as benzene, toluene, xylene and the like, saturated hydrocarbons such as cyclohexane, hexane and the like, amides such as N,N-dimethylformamide, N,N-dimethylacetamide and the like, sulfoxides such as dimethyl sulfoxide and the like, water, mixed solvents thereof and the like. The reaction time is generally 5 min-60 hr, preferably 10 min-12 hr. The reaction temperature is generally −10-200° C., preferably 0-150° C. Compound (1k) can be used directly as the reaction mixture or as a crude product for the next reaction, or can be also isolated from the reaction mixture according to a conventional method, and can be easily purified according to separation means such as washing, recrystallization, distillation, chromatography and the like.

Scheme 11

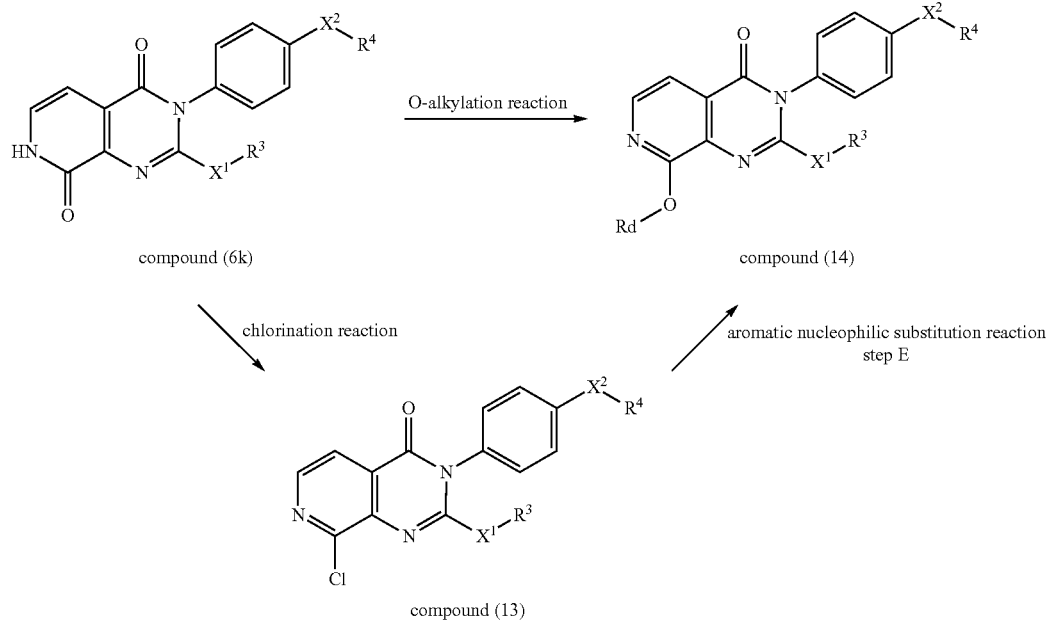

compound (6k)     compound (14)

compound (13)

wherein each symbol is as defined above, and Rd is an optionally substituted $C_{1-6}$ alkyl group.

Compound (14) can be produced by subjecting compound (6k) to an O-alkylation as shown in Scheme 11. To be specific, the reaction is carried out using an alkylating agent corresponding to Rd in an amount of 1.0-5.0 mol, preferably 1.5-3.0 mol, per 1 mol of compound (6k). Examples of the alkylating agent corresponding to Rd include borate complexes such as trimethyloxonium tetrafluoroborate, triethyloxonium tetrafluoroborate and the like, various alkyl halides such as alkyl chlorides, alkyl bromides, alkyl iodides and the like and derivatives thereof, sulfonates such as p-toluenesulfonate, methylsulfonate and the like, sulfates such as dimethyl sulfate and the like, and the like. Where necessary, the reaction is carried out using a base in an amount of 1.0-5.0 mol, preferably 1.1-3.0 mol, per 1 mol of compound (6k). Examples of the base include inorganic bases such as sodium hydroxide, potassium hydroxide, barium hydroxide, sodium hydrogen carbonate, sodium carbonate, potassium carbonate and the like, metal alkoxides such as sodium methoxide, sodium ethoxide, potassium tert-butoxide and the like, metal hydrides such as sodium hydride, potassium hydride and the like, organic bases such as triethylamine, N,N-diisopropylethylamine and the like, and the like. This reaction is preferably carried out in a solvent inert to the reaction. While the solvent is not particularly limited as long as the reaction proceeds, preferable examples thereof include alcohols such as methanol, ethanol, propanol and the like, aromatic hydrocarbons such as benzene, toluene and the like, halogenated hydrocarbons such as dichloromethane, 1,2-dichloroethane and the like, ethers such as tetrahydrofuran, dioxane, 1,2-dimethoxyethane and the like, amides such as N,N-dimethylformamide, N,N-dimethylacetamide and the like, sulfoxides such as dimethyl sulfoxide and the like, water, mixed solvents thereof and the like. The reaction time is generally 1 hr-60 hr, preferably 5 hr-36 hr. The reaction temperature is generally-10-200° C., preferably 0-150° C. Compound (14) can be used directly as the reaction mixture or as a crude product for the next reaction, or can be also isolated from the reaction mixture according to a conventional method, and can be easily purified according to separation means such as washing, recrystallization, distillation, chromatography and the like.

Alternatively, compound (14) can be produced from compound (13) according to the method similar to Step E (Scheme 3). Compound (13) can be produced by subjecting compound (6k) to a chlorination reaction. To be specific, the reaction is carried out using a chlorinating agent in an amount of 1.0-50 mol, preferably 1.0-10 mol, per 1 mol of compound (6k). Examples of the chlorinating agent include acid chlorides such as phosphorus oxychloride, thionyl chloride, oxalyl chloride and the like. This reaction is preferably carried out using a chlorinating agent as a solvent, or in other solvent inert to the reaction. While the solvent is not particularly limited as long as the reaction proceeds, preferable examples thereof include aromatic hydrocarbons such as benzene, toluene and the like, halogenated hydrocarbons such as dichloromethane, 1,2-dichloroethane and the like, ethers such as tetrahydrofuran, dioxane, 1,2-dimethoxyethane and the like, mixed solvents thereof and the like. The reaction time is generally 1 hr-60 hr, preferably 5 hr-36 hr. The reaction temperature is generally-10-200° C., preferably 0-150° C. Compound (13) can be used directly as the reaction mixture or as a crude product for the next reaction, or can be also isolated from the reaction mixture according to a conventional method, and can be easily purified according to separation means such as washing, recrystallization, distillation, chromatography and the like.

Scheme 12

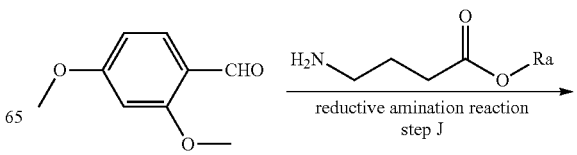

reductive amination reaction
step J

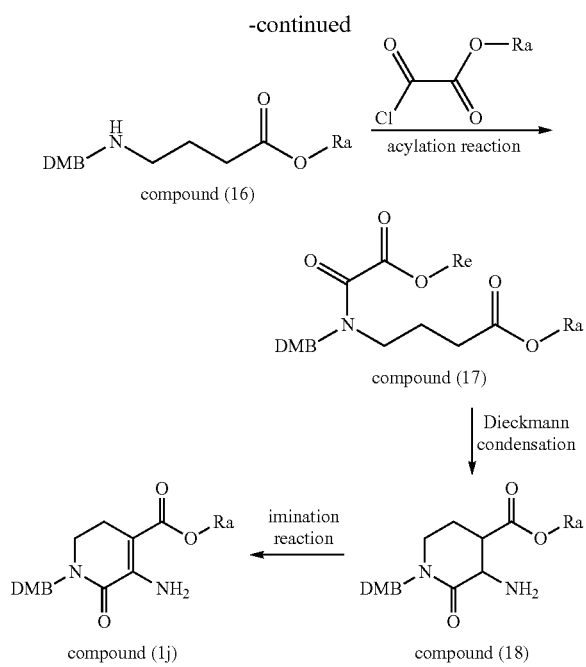

wherein each symbol is as defined above, and Re is a $C_{1-6}$ alkyl group.

Compound (1j) can be produced according to the route shown in Scheme 12. To be specific, compound (16) is produced by reductive amination reaction, compound (17) is produced by subjecting compound (16) to an acylation reaction, compound (18) is produced by subjecting compound (17) to a cyclization reaction, and compound (1j) is produced by subjecting compound (18) to an imination reaction to obtain compound (1j).

Step J (Reductive Amination Reaction)

Compound (16) can be produced by subjecting 2,4-dimethoxybenzaldehyde to a reductive amination reaction with compound (15) using a reducing agent. To be specific, the reaction is carried out using 2,4-dimethoxybenzaldehyde in an amount of 1.0-3.0 mol, preferably 1.0-1.5 mol and a reducing agent in an amount of 1.0-5.0 mol, preferably 1.0-2.0 mol, per 1 mol of compound (15). Examples of the reducing agent include sodium borohydride, lithium borohydride, sodium triacetoxyborohydride and the like. This reaction is preferably carried out in a solvent inert to the reaction. While the solvent is not particularly limited as long as the reaction proceeds, preferable examples thereof include alcohols such as methanol, ethanol, propanol and the like, halogenated hydrocarbons such as dichloromethane, 1,2-dichloroethane and the like, ethers such as tetrahydrofuran, dioxane, 1,2-dimethoxyethane and the like, amides such as N,N-dimethylformamide, N,N-dimethylacetamide and the like, sulfoxides such as dimethyl sulfoxide and the like, nitriles such as acetonitrile, propionitrile and the like, acetic acid, water, mixed solvents thereof and the like. The reaction time is generally 30 min-60 hr, preferably 1 hr-36 hr. The reaction temperature is generally-10-200° C., preferably 0-150° C. Compound (16) can be used directly as the reaction mixture or as a crude product for the next reaction, or can be also isolated from the reaction mixture according to a conventional method, and can be easily purified according to separation means such as washing, recrystallization, distillation, chromatography and the like.

Compound (17) can be produced by subjecting compound (16) to an acylation reaction. To be specific, the reaction is carried out using a $C_{1-6}$ alkyl chloroglyoxylate in an amount of 1.0-3.0 mol, preferably 1.0-1.5 mol, per 1 mol of compound (16). This reaction can be carried out in the presence of a base in order to remove the release halogenated hydrogen from the reaction system. The base is used in an amount of 1.0-5.0, preferably 1.0-3.0 mol, relative to compound (16). Preferable examples of the base include inorganic bases such as sodium carbonate, potassium carbonate, sodium hydrogen carbonate and the like, aromatic amines such as pyridine, lutidine and the like, tertiary amines such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine and the like, and the like. This reaction is preferably carried out in a solvent inert to the reaction. While the solvent is not particularly limited as long as the reaction proceeds, preferable examples thereof include halogenated hydrocarbons such as dichloromethane, 1,2-dichloroethane and the like, ethers such as tetrahydrofuran, dioxane, 1,2-dimethoxyethane and the like, amides such as N,N-dimethylformamide, N,N-dimethylacetamide and the like, sulfoxides such as dimethyl sulfoxide and the like, nitriles such as acetonitrile, propionitrile and the like, mixed solvents thereof and the like. The reaction time is generally 30 min-60 hr, preferably 1 hr-36 hr. The reaction temperature is generally-10-200° C., preferably 0-150° C. Compound (17) can be used directly as the reaction mixture or as a crude product for the next reaction, or can be also isolated from the reaction mixture according to a conventional method, and can be easily purified according to separation means such as washing, recrystallization, distillation, chromatography and the like.

Compound (18) can be produced by subjecting compound (17) to Dieckmann condensation under basic conditions. To be specific, the reaction is carried out using a base in an amount of 1.0-10 mol, preferably 2.0-5.0 mol, per 1 mol of compound (17). Examples of the base include inorganic bases such as sodium hydroxide, potassium hydroxide, barium hydroxide, sodium carbonate, potassium carbonate and the like, metal alkoxides such as sodium methoxide, sodium ethoxide, potassium tert-butoxide and the like, metal hydrides such as sodium hydride, potassium hydride and the like, and the like. This reaction is preferably carried out in a solvent inert to the reaction. While the solvent is not particularly limited as long as the reaction proceeds, preferable examples thereof include alcohols such as methanol, ethanol, propanol and the like, ethers such as tetrahydrofuran, dioxane, 1,2-dimethoxyethane and the like, amides such as N,N-dimethylformamide, N,N-dimethylacetamide and the like, sulfoxides such as dimethyl sulfoxide and the like, nitriles such as acetonitrile, propionitrile and the like, mixed solvents thereof and the like. The reaction time is generally 30 min-60 hr, preferably 1 hr-36 hr. The reaction temperature is generally −10-200° C., preferably 0-150° C. Compound (18) can be used directly as the reaction mixture or as a crude product for the next reaction, or can be also isolated from the reaction mixture according to a conventional method, and can be easily purified according to separation means such as washing, recrystallization, distillation, chromatography and the like.

Compound (1j) can be produced by subjecting compound (18) to an amination reaction. To be specific, the reaction is carried out using an ammonium salt in an amount of 1.0-30 mol, preferably 1.0-20 mol, per 1 mol of compound (18). Examples of the ammonium salt include ammonium chloride, ammonium acetate, ammonium formate and the like. This reaction is preferably carried out in a solvent inert to the reaction, While the solvent is not particularly limited as long as the reaction proceeds, preferable examples thereof include alcohols such as methanol, ethanol, propanol and the like, ethers such as tetrahydrofuran, dioxane, 1,2-dimethoxyethane and the like, amides such as N,N-dimethylformamide, N,N-dimethylacetamide and the like, sulfoxides such as dimethyl sulfoxide and the like, nitriles such as acetonitrile, propionitrile and the like, organic acids such as acetic acid, formic acid and the like, mixed solvents thereof and the like.

The reaction time is generally 30 min-60 hr, preferably 1 hr-36 hr. The reaction temperature is generally −10-200° C., preferably 0-150° C. Compound (1j) can be used directly as the reaction mixture or as a crude product for the next reaction, or can be also isolated from the reaction mixture according to a conventional method, and can be easily purified according to separation means such as washing, recrystallization, distillation, chromatography and the like.

Scheme 13

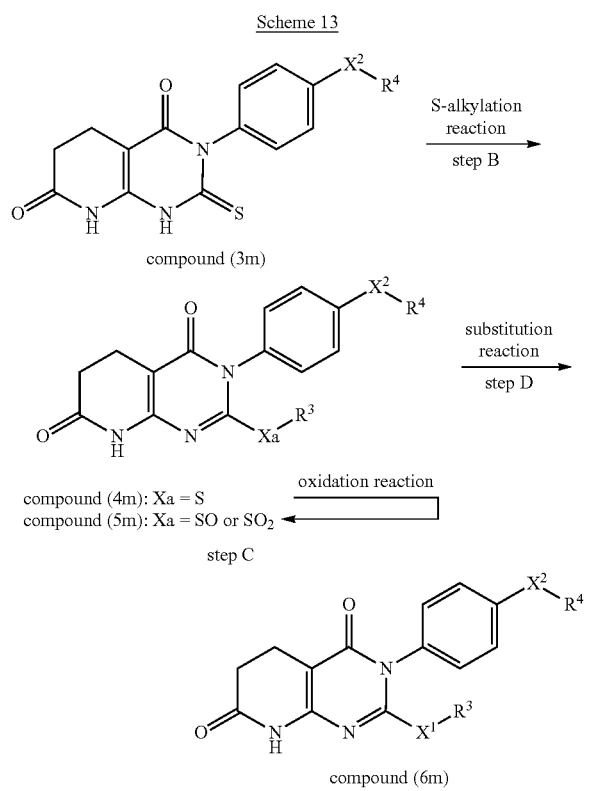

wherein each symbol is as defined above.

Compound (6m) can be produced according to the route shown in Scheme 13. To be specific, compound (4m) can be produced from compound (3m) according to the method similar to Step B (Scheme 1). Compound (6m) can be produced from compound (4m) or compound (5m) which is produced according to the method similar to Step C (Scheme 1), according to the method similar to Step D (Scheme 1).

Scheme 14

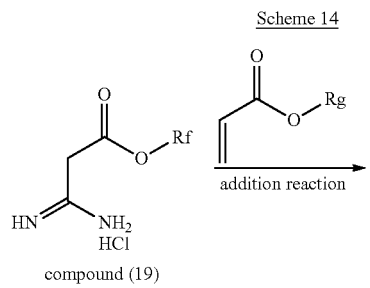

compound (19)

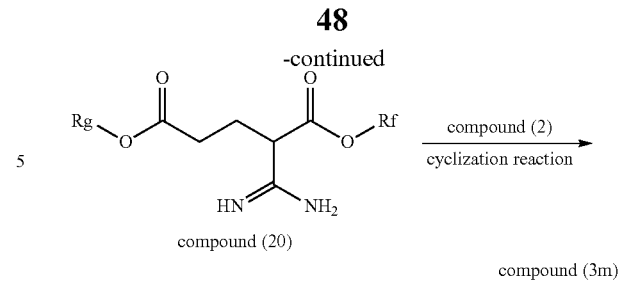

compound (20)

compound (3m)

wherein each symbol is as defined above, Rf is a $C_{1-6}$ alkyl group, and Rg is a $C_{1-6}$ alkyl group.

Compound (3m) can be produced according to the route shown in Scheme 14. To be specific, compound (20) can be produced by subjecting compound (19) to Michael addition with an acrylate, and compound (3m) can be produced by subjecting compound (20) to a cyclization reaction with compound (2) under basic conditions.

Compound (20) can be produced by subjecting compound (19) to Michael addition with an acrylate corresponding to Rg in the presence of a base. To be specific, the reaction is carried out using an acrylate corresponding to Rg in an amount of 1.0-5.0 mol, preferably 1.0-2.0 mol and a base in an amount of 2.0-5.0 mol, preferably 2.0-3.0 mol, per 1 mol of compound (19). Examples of the base include inorganic bases such as sodium hydrogen carbonate, sodium carbonate, potassium carbonate and the like, metal alkoxides such as sodium methoxide, sodium ethoxide, potassium tert-butoxide and the like, metal hydrides such as sodium hydride, potassium hydride and the like, organic bases such as triethylamine, N,N-diisopropylethylamine and the like, and the like. This reaction is preferably carried out in a solvent inert to the reaction. While the solvent is not particularly limited as long as the reaction proceeds, preferable examples thereof include halogenated hydrocarbons such as dichloromethane, chloroform, carbon tetrachloride, 1,2-dichloroethane and the like, alcohols such as methanol, ethanol, propanol, 1,1-dimethylethanol and the like, aromatic hydrocarbons such as benzene, toluene and the like, ethers such as tetrahydrofuran, dioxane, 1,2-dimethoxyethane and the like, amides such as N,N-dimethylformamide, N,N-dimethylacetamide and the like, sulfoxides such as dimethyl sulfoxide and the like, water, mixed solvents thereof and the like. The reaction time is generally 30 min-30 hr, preferably 45 min-24 hr. The reaction temperature is generally -10-200° C., preferably 0-40° C. Compound (20) can be used directly as the reaction mixture or as a crude product for the next reaction, or can be also isolated from the reaction mixture according to a conventional method, and can be purified according to separation means such as washing, recrystallization, distillation, chromatography and the like. Compound (19) can be produced according to a method known per se, for example, the method described in Chemical and Pharmaceutical Bulletin, vol. 43, page 788 (1995) or a method analogous thereto.

Compound (3m) can be produced by subjecting compound (20) to an addition reaction with compound (2) in the presence of a base and a cyclization reaction. To be specific, the reaction is carried out using compound (2) in an amount of 1.0-3.0 mol, preferably 1.0-1.5 mol and a base in an amount of 1.0-10 mol, preferably 2.0-5.0 mol, per 1 mol of compound (20). Examples of the base include inorganic bases such as sodium carbonate, potassium carbonate and the like, metal alkoxides such as sodium methoxide, sodium ethoxide, potassium tert-butoxide and the like, metal hydrides such as sodium hydride, potassium hydride and the like, and the like.

This reaction is preferably carried out in a solvent inert to the reaction. While the solvent is not particularly limited as long as the reaction proceeds, preferable examples thereof include alcohols such as methanol, ethanol, propanol, 1,1-dimethylethanol and the like, aromatic hydrocarbons such as benzene, toluene and the like, ethers such as tetrahydrofuran, dioxane, 1,2-dimethoxyethane and the like, amides such as N,N-dimethylformamide, N,N-dimethylacetamide and the like, sulfoxides such as dimethyl sulfoxide and the like, nitriles such as acetonitrile, propionitrile and the like, water, mixed solvents thereof and the like. The reaction time is generally 30 min-30 hr, preferably 45 min-24 hr. The reaction temperature is generally −10-200° C., preferably 0-100° C. Compound (3m) can be used directly as the reaction mixture or as a crude product for the next reaction, or can be also isolated from the reaction mixture according to a conventional method, and can be purified according to separation means such as washing, recrystallization, distillation, chromatography and the like.

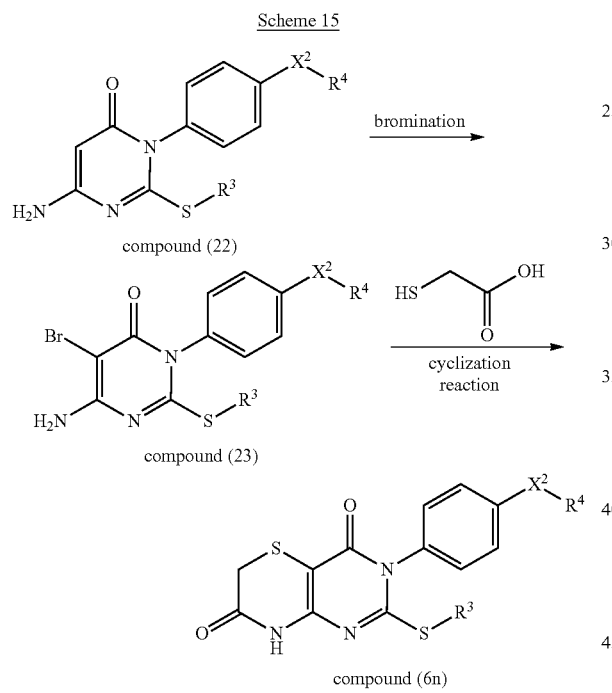

wherein each symbol is as defined above.

Compound (6n) can be produced according to the route shown in Scheme 15. To be specific, compound (23) can be produced by compound (22) to a bromination reaction, and then compound (6n) can be produced by subjecting compound (23) to a cyclization reaction with mercaptoacetic acid.

Compound (23) can be produced by subjecting compound (22) to a bromination reaction. To be specific, the reaction is carried out using a brominating reagent in an amount of 1.0 mol-3.0 mol, preferably 1.0-1.5 mol, per 1 mol of compound (22). Examples of the brominating reagent include bromine, N-bromosuccinimide, pyridinium bromide perbromide and the like. An additive such as sodium acetate and the like can be added to the reaction system in order to adjust the reactive. This reaction is preferably carried out in a solvent inert to the reaction. While the solvent is not particularly limited as long as the reaction proceeds, preferable examples thereof include halogenated hydrocarbons such as dichloromethane, chloroform, carbon tetrachloride, 1,2-dichloroethane and the like, methanol, acetic acid, mixed solvents thereof and the like. The reaction time is generally 30 min-30 hr, preferably 45 min-5 hr. The reaction temperature is generally −10-100° C., preferably 0-40° C. Compound (23) can be used directly as the reaction mixture or as a crude product for the next reaction, or can be also isolated from the reaction mixture according to a conventional method, and can be purified according to separation means such as washing, recrystallization, distillation, chromatography and the like.

Compound (6n) can be produced by subjecting compound (23) to a cyclization reaction with mercaptoacetic acid. To be specific, the reaction is carried out using mercaptoacetic acid in an amount of 1.0 mol-10 mol, preferably 1.0-2.0 mol, per 1 mol of compound (23). This reaction is preferably carried out in a solvent inert to the reaction. While the solvent is not particularly limited as long as the reaction proceeds, preferable examples thereof include halogenated hydrocarbons such as carbon tetrachloride, 1,2-dichloroethane and the like, aromatic hydrocarbons such as benzene, toluene and the like, methanol, acetic acid, mixed solvents thereof and the like. The reaction time is generally 30 min-30 hr, preferably 45 min-5 hr. The reaction temperature is generally 0-300° C., preferably 10-190° C. The reaction can also be carried out with microwave irradiation while heating. compound (6n) can be used directly as the reaction mixture or as a crude product for the next reaction, or can be also isolated from the reaction mixture according to a conventional method, and can be purified according to separation means such as washing, recrystallization, distillation, chromatography and the like.

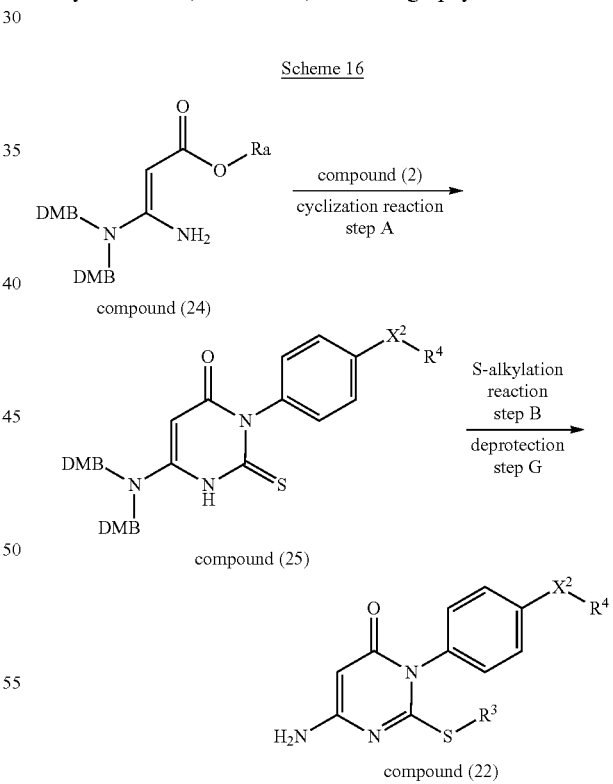

wherein each symbol is as defined above.

Compound (22) can be produced according to the route shown in Scheme 16. To be specific, compound (25) is produced by subjecting compound (24) to a cyclization reaction according to the method similar to Step A (Scheme 1), and compound (22) can be produced by subjecting compound (25) to an S-alkylation according to the method similar to Step B (Scheme 1) and a deprotection according to the method similar to Step G (Scheme 4).

Scheme 17

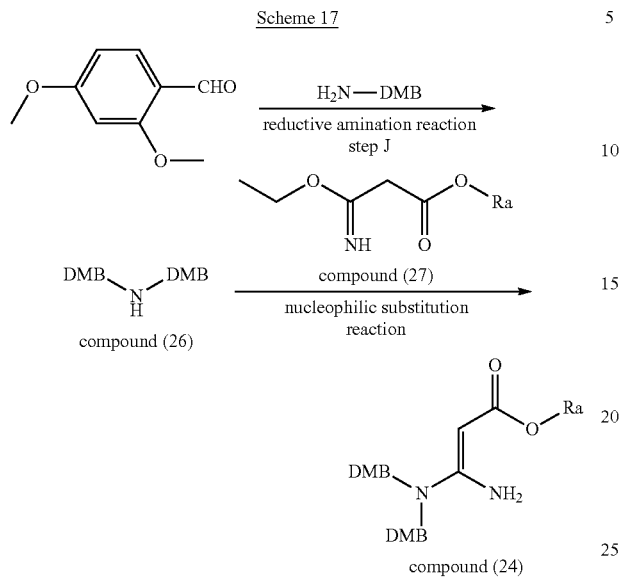

compound (24)

wherein each symbol is as defined above.

Compound (24) can be produced by subjecting compound (26) to a nucleophilic substitution with compound (27). To be specific, the reaction is carried out using compound (27) in an amount of 1.0-5.0 mol, preferably 1.0-3.0 mol, per 1 mol of compound (26). Acetic acid can also be used in an amount of 1.0-5.0 mol, preferably 1.0-2.0 mol in order to promote the reaction. This reaction is preferably carried out in a solvent inert to the reaction. While the solvent is not particularly limited as long as the reaction proceeds, preferable examples thereof include alcohols such as methanol, ethanol, propanol, 1,1-dimethylethanol and the like, aromatic hydrocarbons such as benzene, toluene and the like, ethers such as tetrahydrofuran, dioxane, 1,2-dimethoxyethane and the like, amides such as N,N-dimethylformamide, N,N-dimethylacetamide and the like, sulfoxides such as dimethyl sulfoxide and the like, nitriles such as acetonitrile, propionitrile and the like, mixed solvents thereof and the like. The reaction time is generally 30 min-30 hr, preferably 1 hr-24 hr. The reaction temperature is generally −10-200° C., preferably 0-100° C. Compound (24) can be used directly as the reaction mixture or as a crude product for the next reaction, or can be also isolated from the reaction mixture according to a conventional method, and can be purified according to separation means such as washing, recrystallization, distillation, chromatography and the like.

Compound (26) can be produced according to the reductive amination reaction similar to Step J (Scheme 12).

Scheme 18

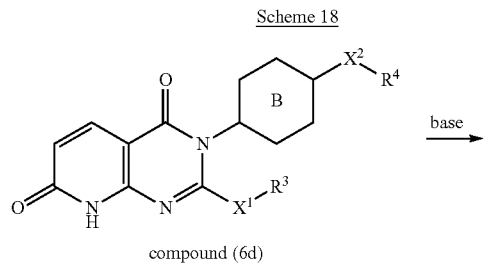

compound (6d)

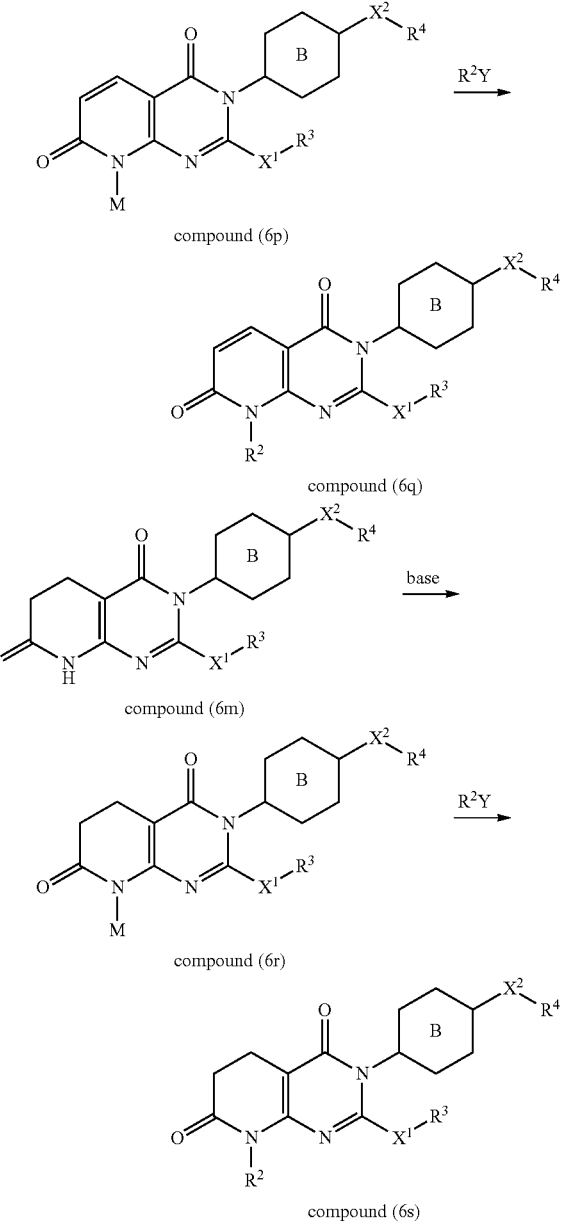

wherein each symbol is as defined above, M is a metal (e.g., potassium, sodium, lithium, magnesium, calcium, copper, mercury, zinc and the like, each of which is optionally complexed), and Y is a leaving group (e.g., a halogen atom, —OSO$_2$Me, —OSO$_2$ (4-tolyl) etc.).

Compound (6p) or (6r) can be produced by subjecting compound (6d) or (6m) to a base treatment, respectively (Scheme 18). To be specific, the base is used in an amount of 1.0-10 mol, preferably 2.0-5.0 mol, per 1 mol of compound (6d) or (6m). Examples of the base include inorganic bases such as sodium carbonate, potassium carbonate and the like, metal alkoxides such as sodium methoxide, sodium ethoxide, potassium tert-butoxide and the like, metal hydrides such as sodium hydride, potassium hydride and the like, and the like. This reaction is preferably carried out in a solvent inert to the reaction. While the solvent is not particularly limited as long as the reaction proceeds, preferable examples thereof include alcohols such as methanol, ethanol, propanol, 1,1-dimethylethanol and the like, aromatic hydrocarbons such as benzene, toluene and the like, ethers such as tetrahydrofuran, dioxane, 1,2-dimethoxyethane and the like, amides such as N,N-dimethylformamide, N,N-dimethylacetamide and the like, sulfoxides such as dimethyl sulfoxide and the like, nitriles such as acetonitrile, propionitrile and the like, water, mixed solvents thereof and the like. The reaction time is generally 1 min-30 hr, preferably 3 min-30 min. The reaction temperature is generally -10-200° C., preferably 0-60° C. Compounds (6p) and (6r) can be used directly as the reaction mixture or as a crude product for the next reaction, or can be also isolated from the reaction mixture according to a conventional method, and can be purified according to separation means such as washing, recrystallization, distillation, chromatography and the like.

nol and the like, aromatic hydrocarbons such as benzene, toluene and the like, ethers such as tetrahydrofuran, dioxane, 1,2-dimethoxyethane and the like, amides such as N,N-dimethylformamide, N,N-dimethylacetamide and the like, nitriles such as acetonitrile, propionitrile and the like, sulfoxides such as dimethyl sulfoxide and the like, water, mixed solvents thereof and the like. The reaction time is generally 15 min-60 hr, preferably 15 min-24 hr. The reaction temperature is generally -10-200° C., preferably 0-150° C. Compound (6q) or (6s) can be used directly as the reaction mixture or as a crude product for the next reaction, or can be also isolated from the reaction mixture according to a conventional method, and can be easily purified according to separation means such as washing, recrystallization, distillation, chromatography and the like.

Scheme 19

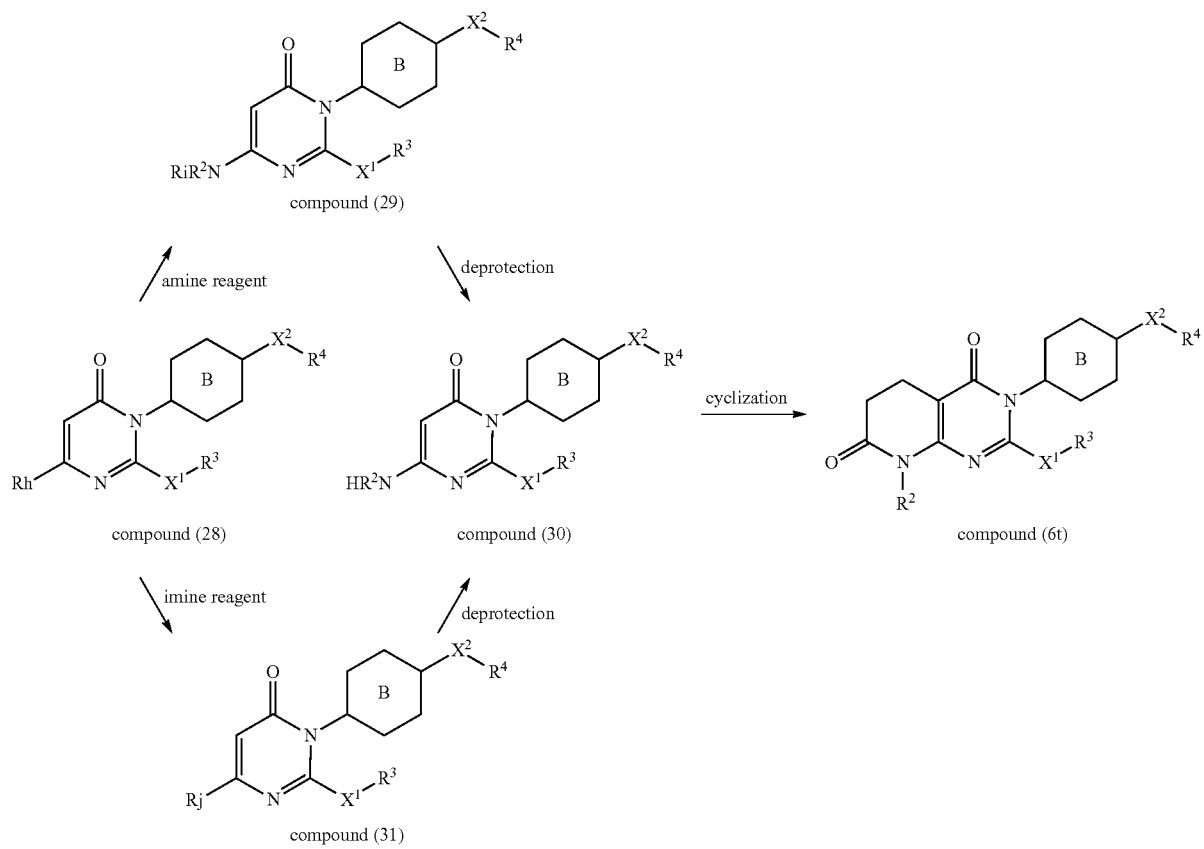

Compound (6q) or (6s) can be produced by treating compound (6p) or (6r) with an alkylating agent corresponding to $R^2$ (Scheme 18). To be specific, the alkylating agent corresponding to $R^2$ is used in an amount of 1.0-10 mol, preferably 1.0-3.0 mol, per 1 mol of compound (6p) and (6r). Examples of the alkylating agent corresponding to $R^2$ include various alkyl halides such as alkyl chlorides, alkyl bromides, alkyl iodides and the like and derivatives thereof, sulfonates such as p-toluenesulfonate, methylsulfonate and the like, sulfates such as dimethyl sulfate and the like, and the like. This reaction is preferably carried out in a solvent inert to the reaction. While the solvent is not particularly limited as long as the reaction proceeds, preferable examples thereof include alcohols such as methanol, ethanol, propanol, 1,1-dimethylethawherein each symbol is as defined above, Rh is a halogen atom or a trifluoromethanesulfonyloxy group, Ri is a benzyl group optionally substituted by an alkyl group or an alkoxy group, and Rj is a benzophenonimino group optionally substituted by an alkyl group or an alkoxy group.

In Scheme 19, compound (6t) is produced by converting compound (28) obtained in below-mentioned Scheme 20 to compound (29) or compound (31), and subjecting compound (29) or compound (31) to a deprotection to obtain compound (30), and then subjecting compound (30) to a cyclization reaction.

Compound (29) or compound (31) is produced by subjecting compound (28) to a coupling reaction with a corresponding nitrogen-containing reagent. To be specific, the reaction is carried out using an amine reagent or imine reagent in an amount of 1.0-10.0 mol, preferably 1.0-3.0 mol, an organic metal reagent in an amount of 0.01-1 mol, preferably 0.05-0.2 mol, a phosphine ligand in an amount of 0.01-1 mol, preferably 0.1-0.5 mol and a base in an amount of 1.0-10.0 mol, preferably 2.0-6.0 mol, per 1 mol of compound (28). Where necessary, the reaction may be carried out without a phosphine ligand.

Examples of the amine reagent include benzylamine, dibenzylamine, 2-methoxybenzylamine, 3-methoxybenzylamine, 4-methoxybenzylamine, 2,3-dimethoxybenzylamine, 2,4-dimethoxybenzylamine, 3,4-dimethoxybenzylamine, 2,4,6-trimethoxybenzylamine, 3,4,5-trimethoxybenzylamine, 2,3,4-trimethoxybenzylamine, 2,4,5-trimethoxybenzylamine, 2-methylbenzylamine, 3-methylbenzylamine, 4-methylbenzylamine, 2,3-dimethylbenzylamine, 2,4-dimethylbenzylamine, 3,4-dimethylbenzylamine, 2,4,6-trimethylbenzylamine, 2,4,5-trimethylbenzylamine and the like. Examples of the imine reagent include benzophenonimine, 1,1-bis(4-methoxyphenyl)methanimine, 9-iminofluorene and the like.

Examples of the organic metal reagent include tris(dibenzylideneacetone)dipalladium(0), tetrakis(triphenylphosphine)palladium, [1,1'-bis(diphenylphosphino)ferrocene]palladium(II)dichloride dichloromethane complex, palladium acetate and the like.

Examples of the phosphine ligand include 2-dicyclohexylphosphino-2',4',6'-triisopropylbiphenyl, (9,9-dimethyl-9H-xanthene-4,5-diyl)bis(diphenylphosphane), 2,2'-bis(diphenylphosphino)-1,1'-binaphthyl and the like.

Examples of the base include basic salts such as sodium hydroxide, potassium hydroxide, barium hydroxide, sodium hydrogen carbonate, sodium carbonate, potassium carbonate, to sodium acetate, potassium acetate, cesium carbonate and the like, metal alkoxides such as sodium methoxide, sodium ethoxide, potassium tert-butoxide and the like, metal hydrides such as sodium hydride, potassium hydride and the like, and the like.

This reaction is preferably carried out in a solvent inert to the reaction. While the solvent is not particularly limited as long as the reaction proceeds, examples thereof include ethers (e.g., diethyl ether, tetrahydrofuran, 1,2-dimethoxyethane etc.), alcohols (e.g., methanol, ethanol etc.), esters (e.g., ethyl acetate etc.), aromatic hydrocarbons (e.g., benzene, toluene etc.), aliphatic hydrocarbons (e.g., hexane etc.), amides (e.g., N,N-dimethylformamide, N,N-dimethylacetamide etc.), halogenated hydrocarbons (e.g., dichloromethane, chloroform, carbon tetrachloride, 1,2-dichloroethane etc.), nitriles (e.g., acetonitrile, propionitrile etc.), sulfoxides (e.g., dimethyl sulfoxide etc.), organic acids (e.g., acetic acid etc.), water and mixtures of two or more kinds thereof.

The reaction time is generally 10 min-50 hr, preferably 30 min-12 hr. The reaction temperature is generally 0° C.-300° C., preferably 20° C.-200° C.

The product is obtained as a single compound or mixture, and can be used directly as the reaction mixture or as a crude product for the next reaction, or can be also isolated from the reaction mixture according to a conventional method, and can be easily purified according to separation means such as washing, recrystallization, distillation, chromatography and the like.

Compound (30) is produced by subjecting compound (29) to an acid treatment or hydrogenation.

The acid treatment is carried out using an acid reagent in an amount of 1.0-200 mol, preferably 3.0-20.0 mol, per 1 mol of compound (29). Examples of the acid reagent include Lewis acids such as aluminum chloride and the like, organic acids such as acetic acid, trifluoroacetic acid and the like, and mineral acids such as hydrochloric acid and the like.

The hydrogenation is carried out using a metal reagent in an amount of 5 wt %-1000 wt %, preferably 10 wt %-300 wt %, relative to compound (29). Examples of the metal reagent include palladium carbon, palladium hydroxide, platinum oxide, Raney-nickel, Raneycobalt and the like. The hydrogen pressure is generally 1 atom-100 atom.

This reaction is preferably carried out in the absent or presence of an appropriate solvent. While the solvent is not particularly limited as long as the reaction proceeds, examples thereof include ethers (e.g., diethyl ether, tetrahydrofuran, 1,2-dimethoxyethane etc.), alcohols (e.g., methanol, ethanol etc.), esters (e.g., ethyl acetate etc.), aromatic hydrocarbons (e.g., benzene, toluene etc.), aliphatic hydrocarbons (e.g., hexane etc.), amides (e.g., N,N-dimethylformamide, N,N-dimethylacetamide etc.), halogenated hydrocarbons (e.g., dichloromethane, chloroform, carbon tetrachloride, 1,2-dichloroethane etc.), nitriles (e.g., acetonitrile, propionitrile etc.), sulfoxides (e.g., dimethyl sulfoxide etc.), organic acids (e.g., acetic acid etc.), water and mixtures of two or more kinds thereof.

The reaction time is generally 10 min-50 hr, preferably 30 min-12 hr. The reaction temperature is generally 25° C.-300° C., preferably 50° C.-200° C.

The product is obtained as a single compound or mixture, and can be used directly as the reaction mixture or as a crude product for the next reaction, or can be also isolated from the reaction mixture according to a conventional method, and can be easily purified according to separation means such as washing, recrystallization, distillation, chromatography and the like.

Compound (30) can be produced by subjecting compound (31) to an acid treatment. To be specific, the reaction is carried out using an acid reagent in an amount of 1.0-200 mol, preferably 3.0-20.0 mol, per 1 mol of compound (31).

Examples of the acid reagent include Lewis acids such as aluminum chloride and the like, organic acids such as acetic acid, trifluoroacetic acid and the like, and mineral acids such as hydrochloric acid and the like.

This reaction is preferably carried out in the absent or presence of an appropriate solvent. While the solvent is not particularly limited as long as the reaction proceeds, examples thereof include ethers (e.g., diethyl ether, tetrahydrofuran, 1,2-dimethoxyethane etc.), alcohols (e.g., methanol, ethanol etc.), esters (e.g., ethyl acetate etc.), aromatic hydrocarbons (e.g., benzene, toluene etc.), aliphatic hydrocarbons (e.g., hexane etc.), amides (e.g., N,N-dimethylformamide, N,N-dimethylacetamide etc.), halogenated hydrocarbons (e.g., dichloromethane, chloroform, carbon tetrachloride, 1,2-dichloroethane etc.), nitriles (e.g., acetonitrile, propionitrile etc.), sulfoxides (e.g., dimethyl sulfoxide etc.), organic acids (e.g., acetic acid etc.), water and mixtures of two or more kinds thereof.

The reaction time is generally about 10 min-about 50 hr, preferably about 30 min-about 12 hr. The reaction temperature is generally 25° C.-300° C., preferably 50° C.-200° C.

The product is obtained as a single compound or mixture, and can be used directly as the reaction mixture or as a crude product for the next reaction, or can be also isolated from the reaction mixture according to a conventional method, and can be easily purified according to separation means such as washing, recrystallization, distillation, chromatography and the like.

Compound (6t) can be produced by subjecting compound (30) to a substitution reaction with a corresponding electrophile reagent and subsequent cyclization reaction. To be specific, the reaction is carried out using an electrophile reagent in an amount of 1.0-20.0 mol, preferably 1.0-5.0 mol, per 1 mol of compound (30).

Examples of the electrophile reagent include prop-2-enoyl chloride, 2-methylprop-2-enoyl chloride, (2E)-but-2-enoyl chloride, (2Z)-but-2-enoyl chloride, (2E)-2-methylbut-2-enoyl chloride, (2Z)-2-methylbut-2-enoyl chloride and the like.

This reaction is preferably carried out in the absence or presence of a solvent inert to the reaction. While the solvent is not particularly limited as long as the reaction proceeds, examples thereof include ethers (e.g., diethyl ether, tetrahydrofuran, 1,2-dimethoxyethane etc.), alcohols (e.g., methanol, ethanol etc.), esters (e.g., ethyl acetate etc.), aromatic hydrocarbons (e.g., benzene, toluene etc.), aliphatic hydrocarbons (e.g., hexane etc.), amides (e.g., N,N-dimethylformamide, N,N-dimethylacetamide etc.), halogenated hydrocarbons (e.g., dichloromethane, chloroform, carbon tetrachloride, 1,2-dichloroethane etc.), nitriles (e.g., acetonitrile, propionitrile etc.), sulfoxides (e.g., dimethyl sulfoxide etc.), organic acids (e.g., acetic acid etc.), water and mixtures of two or more kinds thereof.

The reaction time is generally about 1 min-about 100 hr, preferably about 5 min-about 4 hr. The reaction temperature is generally about 0° C.-about 200° C., preferably about 0° C.-about 100° C.

The product is obtained as a single compound or mixture, and can be used directly as the reaction mixture or as a crude product for the next reaction, or can be also isolated from the reaction mixture according to a conventional method, and can be easily purified according to separation means such as washing, recrystallization, distillation, chromatography and the like.

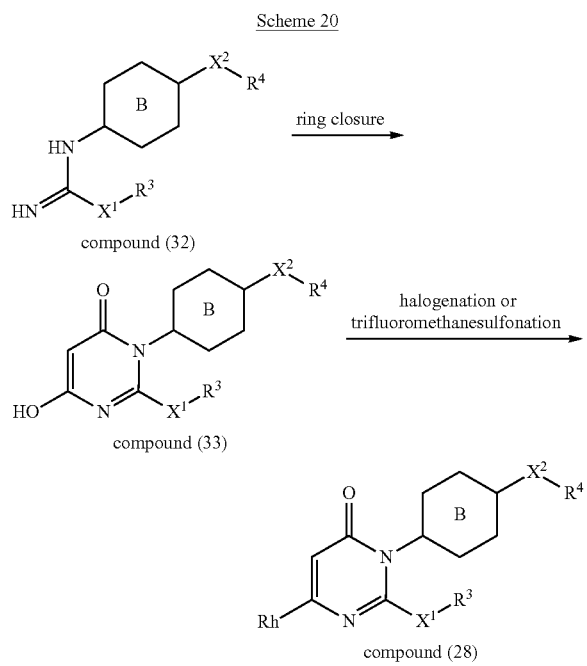

Scheme 20 wherein each symbol is as defined above.

In Scheme 20, compound (28), which is a starting material compound in Scheme 19 is obtained, is produced from compound (32) obtained in below-mentioned Scheme 21 via compound (33).

Compound (33) is produced by subjecting compound (32) to a cyclization reaction with a dialkyl malonate under basic conditions. To be specific, the reaction is carried out using a dialkyl malonate in an amount of 1.0-10.0 mol, preferably 1.0-3.0 mol and a base in an amount of 1.0-100.0 mol, preferably 2.0-10.0 mol, per 1 mol of compound (32).

Examples of the base include inorganic bases such as sodium hydroxide, potassium hydroxide, barium hydroxide, sodium carbonate, potassium carbonate and the like, metal alkoxides such as sodium methoxide, sodium ethoxide, potassium tert-butoxide and the like, metal hydrides such as sodium hydride, potassium hydride and the like, organic amines such as triethylamine, pyridine, diisopropylethylamine, 1,8-diazabicyclo[5.4.0]undec-7-ene and the like, and the like.

This reaction is preferably carried out in a solvent inert to the reaction. While the solvent is not particularly limited as long as the reaction proceeds, examples thereof include ethers (e.g., diethyl ether, tetrahydrofuran, 1,2-dimethoxyethane etc.), alcohols (e.g., methanol, ethanol etc.), esters (e.g., ethyl acetate etc.), aromatic hydrocarbons (e.g., benzene, toluene etc.), aliphatic hydrocarbons (e.g., hexane etc.), amides (e.g., N,N-dimethylformamide, N,N-dimethylacetamide etc.), halogenated hydrocarbons (e.g., dichloromethane, chloroform, carbon tetrachloride, 1,2-dichloroethane etc.), nitriles (e.g., acetonitrile, propionitrile etc.), sulfoxides (e.g., dimethyl sulfoxide etc.), organic acids (e.g., acetic acid etc.), water and mixtures of two or more kinds thereof.

The reaction time is generally 10 min-72 hr, preferably 15 min-24 hr. The reaction temperature is generally 0° C.-150° C., preferably 0° C.-100° C.

The product is obtained as a single compound or mixture, and can be used directly as the reaction mixture or as a crude product for the next reaction, or can be also isolated from the reaction mixture according to a conventional method, and can be easily purified according to separation means such as washing, recrystallization, distillation, chromatography and the like.

Compound (28) is produced by subjecting compound (33) to a substitution reaction. To be specific, the reaction is carried out using phosphorus oxychloride or phosphorus oxybromide in an amount of 1.0-100.0 mol, preferably 3.0-10.0 mol, per 1 mol of compound (33).

This reaction is advantageously carried out the absence or presence of a solvent inert to the reaction. While the solvent is not particularly limited as long as the reaction proceeds, examples thereof include ethers (e.g., diethyl ether, tetrahydrofuran, 1,2-dimethoxyethane etc.), esters (e.g., ethyl acetate etc.), aromatic hydrocarbons (e.g., benzene, toluene etc.), aliphatic hydrocarbons (e.g., hexane etc.), amides (e.g., N,N-dimethylformamide, N,N-dimethylacetamide etc.), halogenated hydrocarbons (e.g., dichloromethane, chloroform, carbon tetrachloride, 1,2-dichloroethane etc.), nitriles (e.g., acetonitrile, propionitrile etc.), sulfoxides (e.g., dimethyl sulfoxide etc.), mixtures of two or more kinds thereof and the like.

The reaction time is generally 10 min-72 hr, preferably 30 min-3 hr. The reaction temperature is generally 0° C.-150° C., preferably 0° C.-100° C.

The product is obtained as a single compound or mixture, and can be used directly as the reaction mixture or as a crude product for the next reaction, or can be also isolated from the reaction mixture according to a conventional method, and can be easily purified according to separation means such as washing, recrystallization, distillation, chromatography and the like.

Alternatively, the reaction is carried out using a trifluoromethylsulfonating reagent in an amount of 1.0-10.0 mol, preferably 1.0-3.0 mol and a base in an amount of 1.0-20.0 mol, preferably 1.0-10.0 mol, per 1 mol of compound (33).

Examples of the trifluoromethylsulfonating reagent include 1,1,1-trifluoro-N-phenyl-N-[(trifluoromethyl)sulfonyl]methanesulfonamide, 2-[N,N-bis(trifluoromethylsulfonyl)amine]-5-chloropyridine, trifluoromethanesulfonic anhydride and the like.

Examples of the base include inorganic bases such as sodium hydroxide, potassium hydroxide, barium hydroxide, sodium carbonate, potassium carbonate and the like, metal alkoxides such as sodium methoxide, sodium ethoxide, potassium tert-butoxide and the like, metal hydrides such as sodium hydride, potassium hydride and the like, organic amines such as triethylamine, pyridine, diisopropylethylamine, 1,8-diazabicyclo[5.4.0]undec-7-ene and the like.

This reaction is preferably carried out in a solvent inert to the reaction. While the solvent is not particularly limited as long as the reaction proceeds, examples thereof include ethers (e.g., diethyl ether, tetrahydrofuran, 1,2-dimethoxyethane etc.), esters (e.g., ethyl acetate etc.), aromatic hydrocarbons (e.g., benzene, toluene etc.), aliphatic hydrocarbons (e.g., hexane etc.), amides (e.g., N,N-dimethylformamide, N,N-dimethylacetamide etc.), halogenated hydrocarbons (e.g., dichloromethane, chloroform, carbon tetrachloride, 1,2-dichloroethane etc.), nitriles (e.g., acetonitrile, propionitrile etc.), sulfoxides (e.g., dimethyl sulfoxide etc.), mixtures of two or more kinds thereof and the like.

The reaction time is generally 10 min-72 hr, preferably 15 min-24 hr. The reaction temperature is generally −78° C.-100° C., preferably 0° C.-50° C.

The product is obtained as a single compound or mixture, and can be used directly as the reaction mixture or as a crude product for the next reaction, or can be also isolated from the reaction mixture according to a conventional method, and can be easily purified according to separation means such as washing, recrystallization, distillation, chromatography and the like.

wherein each symbol is as defined above, and Rk is an optionally substituted $C_{1-6}$ alkyl group.

In Scheme 21, compound (32) which is a starting material compound in Scheme 20 is obtained from compound (34).

Compound (34) may be commercially available product, or can be produced according to a method known per se or a method analogous thereto.

Compound (35) is obtained by subjecting compound (34) to a substitution reaction. To be specific, the reaction is carried out using a chlorinating agent in an amount of 1.0-10.0 mol, preferably 1.0-3.0 mol and 28% aqueous ammonia solution in an amount of 1.0-20.0 mol, preferably 1.0-3.0 mol, per 1 mol of compound (34). Where necessary, the chlorination may be carried out using pyridine, dicyclohexylamine, N,N-dimethylformamide, a phase-transfer catalyst and the like in an amount of 0.001-10.0 mol, preferably 0.001-3.0 mol.

Examples of the chlorinating agent include oxalyl chloride, thionyl chloride, phosphorus oxychloride and the like.

This reaction is preferably carried out in a solvent inert to the reaction. While the solvent is not particularly limited as long as the reaction proceeds, examples thereof include ethers (e.g., diethyl ether, tetrahydrofuran, 1,2-dimethoxyethane etc.), esters (e.g., ethyl acetate etc.), aromatic hydrocarbons (e.g., benzene, toluene etc.), aliphatic hydrocarbons (e.g., hexane etc.), amides (e.g., N,N-dimethylformamide, N,N-dimethylacetamide etc.), halogenated hydrocarbons (e.g., dichloromethane, chloroform, carbon tetrachloride, 1,2-dichloroethane etc.), nitriles (e.g., acetonitrile, propionitrile etc.), sulfoxides (e.g., dimethyl sulfoxide etc.), mixtures of two or more kinds thereof and the like.

The reaction time is generally 10 min-72 hr, preferably 30 min-24 hr. The reaction temperature is generally −78° C.-100° C., preferably −10° C.-25° C.

The product is obtained as a single compound or mixture, and can be used directly as the reaction mixture or as a crude

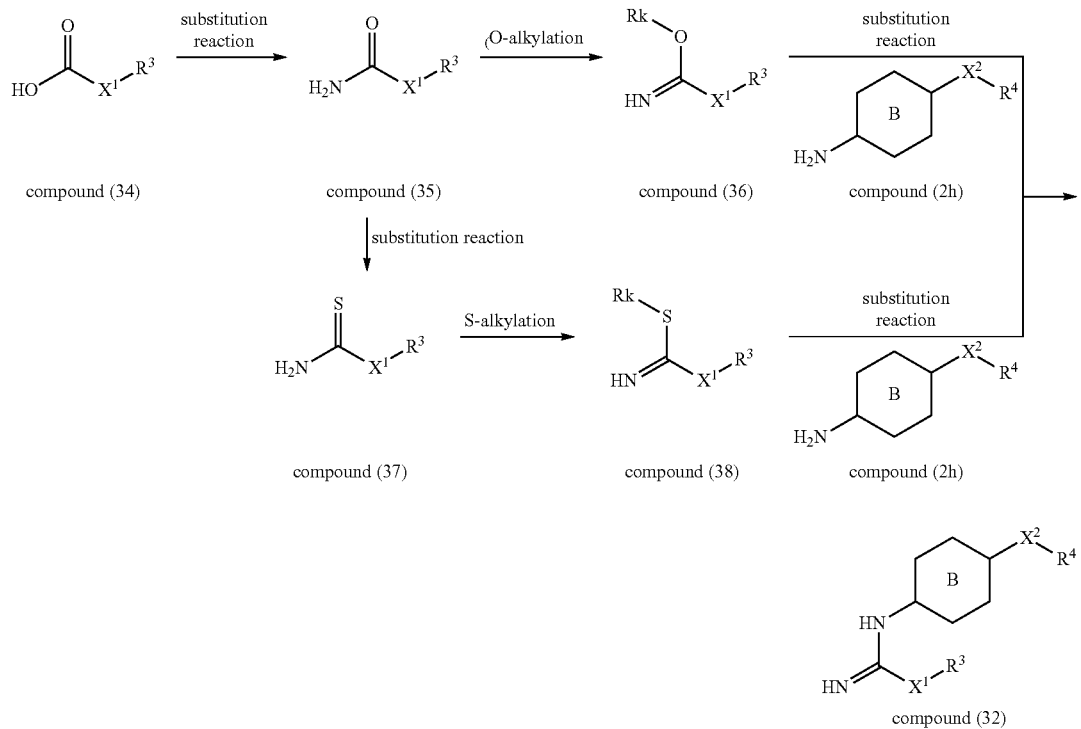

product for the next reaction, or can be also isolated from the reaction mixture according to a conventional method, and can be easily purified according to separation means such as washing, recrystallization, distillation, chromatography and the like.

Compound (36) may be commercially available product, or can be produced according to the method described in Examples, a method known per se or a method analogous thereto. For example, compound (36) is produced by subjecting compound (35) to an O-alkylation reaction. To be specific, the reaction is carried out using a corresponding alkylating agent in an amount of 1.0-50.0 mol, preferably 1.0-10.0 mol and a base in an amount of 1.0-100.0 mol, preferably 3.0-10.0 mol, per 1 mol of compound (35).

Examples of the alkylating agent include trimethyloxonium tetrafluoroborate, dimethylsulfate, methyl trifluoromethanesulfonate, methyl fluorosulfonate and the like.

Examples of the base include inorganic bases such as sodium hydroxide, potassium hydroxide, barium hydroxide, sodium carbonate, potassium carbonate, cesium carbonate, sodium hydrogenphosphate, sodium phosphate and the like, metal alkoxides such as sodium methoxide, sodium ethoxide, potassium tert-butoxide and the like, and the like.

This reaction is preferably carried out in a solvent inert to the reaction. While the solvent is not particularly limited as long as the reaction proceeds, examples thereof include ethers (e.g., diethyl ether, tetrahydrofuran, 1,2-dimethoxyethane etc.), esters (e.g., ethyl acetate etc.), aromatic hydrocarbons (e.g., benzene, toluene etc.), aliphatic hydrocarbons (e.g., hexane etc.), amides (e.g., N,N-dimethylformamide, N,N-dimethylacetamide etc.), halogenated hydrocarbons (e.g., dichloromethane, chloroform, carbon tetrachloride, 1,2-dichloroethane etc.), nitriles (e.g., acetonitrile, propionitrile etc.), sulfoxides (e.g., dimethyl sulfoxide etc.), mixtures of two or more kinds thereof and the like.

The reaction time is generally 10 min-72 hr, preferably 30 min-24 hr. The reaction temperature is generally −78° C.-100° C., preferably −10° C.-25° C.

The product is obtained as a single compound or mixture, and can be used directly as the reaction mixture or as a crude product for the next reaction, or can be also isolated from the reaction mixture according to a conventional method, and can be easily purified according to separation means such as washing, recrystallization, distillation, chromatography and the like.

Compound (37) is produced by subjecting compound (35) to a substitution reaction. To be specific, the reaction is carried out using a nucleophilic reagent in an amount of 1.0-3.0 mol, preferably 1.0-1.30 mol, per 1 mol of compound (35).

Examples of the nucleophilic reagent include Lawesson reagents, phosphorus pentasulfide, diphosphorus pentasulfide and the like.

This reaction is preferably carried out in a solvent inert to the reaction. While the solvent is not particularly limited as long as the reaction proceeds, examples thereof include ethers (e.g., diethyl ether, tetrahydrofuran, 1,2-dimethoxyethane etc.), alcohols (e.g., methanol, ethanol etc.), esters (e.g., ethyl acetate etc.), aromatic hydrocarbons (e.g., benzene, toluene etc.), aliphatic hydrocarbons (e.g., hexane etc.), amides (e.g., N,N-dimethylformamide, N,N-dimethylacetamide etc.), halogenated hydrocarbons (e.g., dichloromethane, chloroform, carbon tetrachloride, 1,2-dichloroethane etc.), nitriles (e.g., acetonitrile, propionitrile etc.), sulfoxides (e.g., dimethyl sulfoxide etc.), organic acids (e.g., acetic acid etc.), water and mixtures of two or more kinds thereof.

The reaction time is generally 10 min-72 hr, preferably 1 hr-24 hr. The reaction temperature is generally 0° C.-150° C., preferably 25° C.-100° C.

The product is obtained as a single compound or mixture, and can be used directly as the reaction mixture or as a crude product for the next reaction, or can be also isolated from the reaction mixture according to a conventional method, and can be easily purified according to separation means such as washing, recrystallization, distillation, chromatography and the like.

Compound (38) is produced by subjecting compound (37) to an S-alkylation reaction with a corresponding alkylating agent. To be specific, the reaction is carried out using an alkylating agent in an amount of 1.0-10.0 mol, preferably 1.0-5.0 mol, per 1 mol of compound (37).

Examples of the alkylating agent include various alkyl halides such as alkyl chlorides, alkyl bromides, alkyl iodides and the like and derivatives thereof, sulfonates such as p-toluenesulfonate, methylsulfonate and the like, sulfates such as dimethyl sulfate and the like, and the like.

This reaction is preferably carried out in a solvent inert to the reaction. While the solvent is not particularly limited as long as the reaction proceeds, examples thereof include ethers (e.g., diethyl ether, tetrahydrofuran, 1,2-dimethoxyethane etc.), alcohols (e.g., methanol, ethanol etc.), esters (e.g., ethyl acetate etc.), aromatic hydrocarbons (e.g., benzene, toluene etc.), aliphatic hydrocarbons (e.g., hexane etc.), amides (e.g., N,N-dimethylformamide, N,N-dimethylacetamide etc.), halogenated hydrocarbons (e.g., dichloromethane, chloroform, carbon tetrachloride, 1,2-dichloroethane etc.), nitriles (e.g., acetonitrile, propionitrile etc.), sulfoxides (e.g., dimethyl sulfoxide etc.), organic acids (e.g., acetic acid etc.), water and mixtures of two or more kinds thereof.

The reaction time is generally 15 min-60 hr, preferably 30 min-24 hr. The reaction temperature is generally 0° C.-150° C., preferably 25° C.-100° C.

The product is obtained as a single compound or mixture, and can be used directly as the reaction mixture or as a crude product for the next reaction, or can be also isolated from the reaction mixture according to a conventional method, and can be easily purified according to separation means such as washing, recrystallization, distillation, chromatography and the like.

Compound (32) is obtained by subjecting compound (36) or compound (38) to a substitution reaction. To be specific, the reaction is carried out using compound (2h) in an amount of 1.0-20.0 mol, preferably 1.0-2.0 mol and a base in an amount of 1.0-20.0 mol, preferably 1.0-10.0 mol, per 1 mol of compound (36) or compound (38).

Examples of the base include inorganic bases such as sodium hydroxide, potassium hydroxide, barium hydroxide, sodium carbonate, potassium carbonate and the like, metal alkoxides such as sodium methoxide, sodium ethoxide, potassium tert-butoxide and the like, metal hydrides such as sodium hydride, potassium hydride and the like, organic amines such as triethylamine, pyridine, diisopropylethylamine, 1,8-diazabicyclo[5.4.0]undec-7-ene and the like. Where necessary, the reaction is carried out without a base.

This reaction is preferably carried out in a solvent inert to the reaction. While the solvent is not particularly limited as long as the reaction proceeds, examples thereof include ethers (e.g., diethyl ether, tetrahydrofuran, 1,2-dimethoxyethane etc.), alcohols (e.g., methanol, ethanol etc.), esters (e.g., ethyl acetate etc.), aromatic hydrocarbons (e.g., benzene, toluene etc.), aliphatic hydrocarbons (e.g., hexane etc.), amides (e.g., N,N-dimethylformamide, N,N-dimethylacetamide etc.), halogenated hydrocarbons (e.g., dichloromethane, chloroform, carbon tetrachloride, 1,2-dichloroethane etc.), nitriles (e.g., acetonitrile, propionitrile etc.), sulfoxides (e.g., dimethyl sulfoxide etc.), organic acids (e.g., acetic acid etc.), water and mixtures of two or more kinds thereof.

The reaction time is generally 30 min-100 hr, preferably 1 hr-72 hr. The reaction temperature is generally 0° C.-150° C., preferably 25° C.-100° C.

The product is obtained as a single compound or mixture, and can be used directly as the reaction mixture or as a crude product for the next reaction, or can be also isolated from the reaction mixture according to a conventional method, and can be easily purified according to separation means such as washing, recrystallization, distillation, chromatography and the like.

Scheme 22

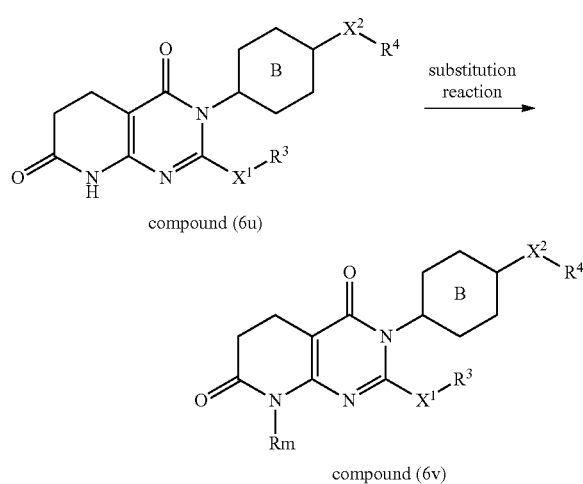

compound (6u)

compound (6v)

wherein each symbol is as defined above, and Rm is an optionally substituted $C_{1-6}$ alkyl group.

In Scheme 22, compound (6v) is obtained from compound (6u).

Compound (6v) can be produced by subjecting compound (6u) to an alkylation reaction. To be specific, the reaction is carried out using an corresponding alkylating agent in an amount of 1.0-50.0 mol, preferably 1.0-3.0 mol and a base in an amount of 1.0-100.0 mol, preferably 2.0-20.0 mol, per 1 mol of compound (6u).

Examples of the alkylating agent include various alkyl halides such as alkyl chlorides, alkyl bromides, alkyl iodides and the like and derivatives thereof, sulfonates such as p-toluenesulfonate, methylsulfonate and the like, sulfates such as dimethyl sulfate and the like, and the like.

Examples of the base include inorganic bases such as sodium carbonate, potassium carbonate and the like, metal alkoxides such as sodium methoxide, sodium ethoxide, potassium tert-butoxide and the like, metal hydrides such as sodium hydride, potassium hydride and the like, and the like.

This reaction is carried out in a solvent inert to the reaction.

While the solvent is not particularly limited as long as the reaction proceeds, this reaction is preferably carried out in a solvent inert to the reaction. While the solvent is not particularly limited as long as the reaction proceeds, examples thereof include ethers (e.g., diethyl ether, tetrahydrofuran, 1,2-dimethoxyethane etc.), alcohols (e.g., methanol, ethanol etc.), esters (e.g., ethyl acetate etc.), aromatic hydrocarbons (e.g., benzene, toluene etc.), aliphatic hydrocarbons (e.g., hexane etc.), amides (e.g., N,N-dimethylformamide, N,N-dimethylacetamide etc.), halogenated hydrocarbons (e.g., dichloromethane, chloroform, carbon tetrachloride, 1,2-dichloroethane etc.), nitriles (e.g., acetonitrile, propionitrile etc.), sulfoxides (e.g., dimethyl sulfoxide etc.), organic acids (e.g., acetic acid etc.), water and mixtures of two or more kinds thereof.

The reaction time is generally 15 min-100 hr, preferably 30 min-12 hr. The reaction temperature is generally −10° C.-200° C., preferably 0° C.-100° C.

The product is obtained as a single compound or mixture, and can be used directly as the reaction mixture or as a crude product for the next reaction, or can be also isolated from the reaction mixture according to a conventional method, and can be easily purified according to separation means such as washing, recrystallization, distillation, chromatography and the like.

In the above-mentioned reactions, when the starting compound has amino (including —NH—, —NH$_2$—), carboxy, hydroxy, carbonyl or mercapto, a protecting group generally used in peptide chemistry and the like may be introduced into these groups. By removing the protecting group as necessary after the reaction, the objective compound can be obtained.

Examples of the amino-protecting group include a formyl group, a $C_{1-6}$ alkyl-carbonyl group, a $C_{1-6}$ alkoxy-carbonyl group, a benzoyl group, a $C_{7-10}$ aralkyl-carbonyl group (e.g., benzylcarbonyl), a $C_{7-14}$ aralkyloxy-carbonyl group (e.g., benzyloxycarbonyl, a 9-fluorenylmethoxycarbonyl), a trityl group, a phthaloyl group, an N,N-dimethylaminomethylene group, a substituted silyl group (e.g., trimethylsilyl, triethylsilyl, dimethylphenylsilyl, tert-butyldimethylsilyl, tert-butyldiethylsilyl), a $C_{2-6}$ alkenyl group (e.g., 1-allyl), a substituted $C_{7-10}$ aralkyl group (e.g., 2,4-dimethylbenzyl) and the like. These protecting groups are optionally substituted by 1 to 3 substituents selected from a halogen atom, a $C_{1-6}$ alkoxy group and a nitro group.

Examples of the carboxy-protecting group include a $C_{1-6}$ alkyl group, a $C_{7-11}$ aralkyl group (e.g., benzyl), a phenyl group, a trityl group, a substituted silyl group (e.g., trimethylsilyl, triethylsilyl, dimethylphenylsilyl, tert-butyldimethylsilyl, tert-butyldiethylsilyl), a $C_{2-6}$ alkenyl group (e.g., 1-allyl) and the like. These protecting groups are optionally substituted by 1 to 3 substituents selected from a halogen atom, a $C_{1-6}$ alkoxy group and a nitro group.

Examples of the hydroxy-protecting group include a $C_{1-6}$ alkyl group, a phenyl group, a trityl group, a $C_{7-10}$ aralkyl group (e.g., benzyl), a formyl group, a $C_{1-6}$ alkyl-carbonyl group, a benzoyl group, a $C_{7-10}$ aralkyl-carbonyl group (e.g., benzylcarbonyl), a 2-tetrahydropyranyl group, a 2-tetrahydrofuranyl group, a substituted silyl group (e.g., trimethylsilyl, triethylsilyl, dimethylphenylsilyl, tert-butyldimethylsilyl, tert-butyldiethylsilyl), a $C_{2-6}$ alkenyl group (e.g., 1-allyl) and the like. These protecting-groups are optionally substituted by 1 to 3 substituents selected from a halogen atom, a $C_{1-6}$ alkyl group, a $C_{1-6}$ alkoxy group and a nitro group.

Examples of the protected carbonyl group include a cyclic acetal (e.g., 1,3-dioxane), an acyclic acetal (e.g., di-$C_{1-6}$ alkyl acetal) and the like.

Examples of the mercapto-protecting group include a $C_{1-6}$ alkyl group, a phenyl group, a trityl group, a $C_{7-10}$ aralkyl group (e.g., benzyl), a $C_{1-6}$ alkyl-carbonyl group, a benzoyl group, a $C_{7-10}$ aralkyl-carbonyl group (e.g., benzylcarbonyl), a $C_{1-6}$ alkoxy-carbonyl group, a $C_{6-14}$ aryloxy-carbonyl group (e.g., phenyloxycarbonyl), a $C_{7-14}$ aralkyloxy-carbonyl group (e.g., benzyloxycarbonyl, 9-fluorenylmethoxycarbonyl), a 2-tetrahydropyranyl group, a $C_{1-6}$ alkylamino-carbonyl group (e.g., methylaminocarbonyl, ethylaminocarbonyl) and the like. These protecting groups are optionally substituted by 1 to 3 substituents selected from a halogen atom, a $C_{1-6}$ alkyl group, a $C_{1-6}$ alkoxy group and a nitro group.

Examples of the method for removing the above-mentioned protecting group include a method known per se, for example, the method described in Protective Groups in Organic Synthesis, John Wiley and Sons (1980) and the like. Specifically, a method using acid, base, ultraviolet rays, hydrazine, phenylhydrazine, sodium N-methyldithiocarbamate, tetrabutylammonium fluoride, palladium acetate, trialkylsilyl halide (e.g., trimethylsilyl iodide, trimethylsilyl bromide) and the like, a reduction method and the like.

Compound (I) obtained by each of the above-mentioned production methods can be isolated and purified by a known means such as concentration, concentration under reduced pressure, solvent extraction, crystallization, recrystallization, phase transfer, chromatography and the like. Each starting compound obtained by each of the above-mentioned production methods can be isolated and purified by a known means similar to those mentioned above. In addition, these starting compounds may be used without isolation as a reaction mixture and as a starting material of the next reaction.

When compound (I) contains isomers such as optical isomer, stereoisomer, positional isomer, rotamer and the like, such isomers and a mixture thereof are also encompassed in compound (I). For example, when compound (I) contains an optical isomer, an optical isomer resolved from the compound is also encompassed in compound (I). These isomers are can be obtained as a single product by a synthesis method or separation method known per se (e.g., concentration, solvent extraction, recrystallization, chromatography etc.).

Compound (I) or a prodrug thereof (hereinafter sometimes to be abbreviated as the compound of the present invention) shows low toxicity and can be used as an agent for the prophylaxis or treatment of various diseases to be mentioned later for mammals (e.g., humans, mice, rats, rabbits, dogs, cats, bovines, horses, pigs, monkeys) as they are or by admixing with a pharmacologically acceptable carrier and the like to give a pharmaceutical composition.

Here, various organic or inorganic carriers conventionally used as materials for pharmaceutical preparations are used as a pharmacologically acceptable carrier, which are added as excipient, lubricant, binder and disintegrant for solid preparations; solvent, solubilizing agent, suspending agent, isotonicity agent, buffer and soothing agent for liquid preparations, and the like. Where necessary, an additive for pharmaceutical preparations such as preservative, antioxidant, colorant, sweetening agent and the like can be used.

Preferable examples of the excipient include lactose, sucrose, D-mannitol, D-sorbitol, starch, pregelatinized starch, dextrin, microcrystalline cellulose, low-substituted hydroxypropyl cellulose, sodium carboxymethylcellulose, gum arabic, pullulan, light anhydrous silicic acid, synthetic aluminum silicate and magnesium aluminate metasilicate.

Preferred examples of the lubricant include magnesium stearate, calcium stearate, talc and colloidal silica.

Preferable examples of the binder include pregelatinized starch, saccharose, gelatin, gum arabic, methylcellulose, carboxymethylcellulose, sodium carboxymethylcellulose, microcrystalline cellulose, sucrose, D-mannitol, trehalose, dextrin, pullulan, hydroxypropyl cellulose, hydroxypropylmethylcellulose and polyvinylpyrrolidone.

Preferable examples of the disintegrant include lactose, sucrose, starch, carboxymethylcellulose, calcium carboxymethylcellulose, croscarmellose sodium, sodium carboxymethyl starch, light anhydrous silicic acid and low-substituted hydroxypropyl cellulose.

Preferable examples of the solvent include water for injection, physiological saline, Ringer's solution, alcohol, propylene glycol, polyethylene glycol, sesame oil, corn oil, olive oil and cottonseed oil.

Preferable examples of the solubilizing agent include polyethylene glycol, propylene glycol, D-mannitol, trehalose, benzyl benzoate, ethanol, trisaminomethane, cholesterol, triethanolamine, sodium carbonate, sodium citrate, sodium salicylate and sodium acetate.

Preferable examples of the suspending agent include surfactants such as stearyltriethanolamine, sodium lauryl sulfate, laurylaminopropionic acid, lecithin, benzalkonium chloride, benzethonium chloride, glyceryl monostearate and the like; hydrophilic polymers such as polyvinyl alcohol, polyvinylpyrrolidone, sodium carboxymethylcellulose, methylcellulose, hydroxymethylcellulose, hydroxyethylcellulose, hydroxypropylcellulose and the like; polysorbates; and polyoxyethylene hydrogenated castor oil.

Preferable examples of the isotonicity agent include sodium chloride, glycerol, D-mannitol, D-sorbitol and glucose.

Preferable examples of the buffer include buffers such as phosphates, acetates, carbonates and citrates.

Preferable examples of the soothing agent include benzyl alcohol.

Preferable examples of the preservative include p-hydroxybenzoate, chlorobutanol, benzyl alcohol, phenethyl alcohol, dehydroacetic acid and sorbic acid.

Preferable examples of the antioxidant include sulfites and ascorbates.

Preferable examples of the colorant include water-soluble edible tar pigments (e.g., foodcolors such as Food Color Red Nos. 2 and 3, Food Color Yellow Nos. 4 and 5, Food Color Blue Nos. 1 and 2 and the like), water insoluble lake pigments (e.g., aluminum salts of the aforementioned water-soluble edible tar pigment), and natural pigments (e.g., beta-carotene, chlorophyll, red iron oxide).

Preferable examples of the sweetening agent include saccharin sodium, dipotassium glycyrrhizinate, aspartame and stevia.

The medicament containing the compound of the present invention can be safely administered solely or by mixing with a pharmacologically acceptable carrier according to a method known per se (e.g., the method described in the Japanese Pharmacopoeia etc.) as a production method of a pharmaceutical preparation, and in the form of, for example, tablet (including sugar-coated tablet, film-coated tablet, sublingual tablet, orally disintegrating tablet, buccal and the like), pill, powder, granule, capsule (including soft capsule, microcapsule), troche, syrup, liquid, emulsion, suspension, release control preparation (e.g., immediate-release preparation, sustained-release preparation, sustained-release microcapsule), aerosol, film (e.g., orally disintegrating film, oral mucosa-adhesive film), injection (e.g., subcutaneous injection, intravenous injection, intramuscular injection, intraperitoneal injection), drip infusion, transdermal absorption preparation, ointment, lotion, adhesive preparation, suppository (e.g., rectal suppository, vaginal suppository), pellet, nasal preparation, pulmonary preparation (inhalation), eye drop and the like, orally or parenterally (e.g., intravenous, intramuscular, subcutaneous, intraorgan, intranasal, intradermal, instillation, intracerebral, intrarectal, intravaginal, intraperitoneal and intratumor administrations, administration to the vicinity of tumor, and direct administration to the lesion).

The pharmaceutical compositions can be manufactured by the commonly-used methods in the field of formulation technology, for example, methods listed in the Japanese pharmacopoeia, etc.

The content of the compound of the present invention in the pharmaceutical compositions varies based on the dosage forms, dosages of the compound of the present invention, etc. For example, the content approximately ranges from about 0.1 to 100 wt %.

During production of an oral preparation, coating may be applied as necessary for the purpose of masking of taste, enteric property or durability.

Examples of the coating base to be used for coating include sugar coating base, water-soluble film coating base, enteric film coating base and sustained-release film coating base.

As the sugar coating base, sucrose is used. Moreover, one or more kinds selected from talc, precipitated calcium carbonate, gelatin, gum arabic, pullulan, carnauba wax and the like may be used in combination.

Examples of the water-soluble film coating base include cellulose polymers such as hydroxypropyl cellulose, hydroxypropylmethyl cellulose, hydroxyethyl cellulose, methylhydroxyethyl cellulose and the like; synthetic polymers such as polyvinylacetal diethylaminoacetate, aminoalkyl methacrylate copolymer E [Eudragit E (trade name)], polyvinylpyrrolidone and the like; and polysaccharides such as pullulan and the like.

Examples of the enteric film coating base include cellulose polymers such as hydroxypropyl methyl cellulose phthalate, hydroxypropyl methyl cellulose acetate succinate, carboxymethylethyl cellulose, cellulose acetate phthalate and the like; acrylic polymers such as methacrylic acid copolymer L [Eudragit L (trade name)], methacrylic acid copolymer LD [Eudragit L-30D55 (trade name)], methacrylic acid copolymer S [Eudragit S (trade name)] and the like; and naturally occurring substances such as shellac and the like.

Examples of the sustained-release film coating base include cellulose polymers such as ethyl cellulose and the like; and acrylic polymers such as aminoalkyl methacrylate copolymer RS [Eudragit RS (trade name)], ethyl acrylate-methyl methacrylate copolymer suspension [Eudragit NE (trade name)] and the like.

The above-mentioned coating bases may be used after mixing with two or more kinds thereof at appropriate ratios. For coating, for example, a light shielding agent such as titanium oxide, red ferric oxide and the like can be used.

The compound of the present invention shows low toxicity (e.g., acute toxicity, chronic toxicity, genetic toxicity, reproductive toxicity, cardiotoxicity, carcinogenicity) and a few side effects. Therefore, it can be used as an agent for the prophylaxis or treatment or a diagnostic of various diseases in a mammal (e.g., human, bovine, horse, dog, cat, monkey, mouse, rat).

Since the compound of the present invention has a strong delta-5-desaturase inhibitory action, it is useful as an agent for the prophylaxis or treatment of a disease developed by the involvement of eicosanoid produced via delta-5-desaturase (or a disease whose onset is promoted).

Examples of the disease include cardiac diseases (cardiac hypertrophy, acute heart failure and chronic heart failure including congestive heart failure, cardiomyopathy, angina, myocarditis, arrhythmia, tachycardia, myocardial infarction, etc.), myocardial ischemia, venous insufficiency, post-myocardial infarction transition to heart failure, hypertension, cor pulmonale, arteriosclerosis including atherosclerosis (aneurysm, coronary arterial sclerosis, cerebral arterial sclerosis, peripheral arterial sclerosis, etc.), ascular thickening, intervention (percutaneous coronary angioplasty, stent placement, coronary angioscopy, intravascular ultrasound, coronary thrombolytic therapy, etc.)—and heart transplantation-related vascular thickening/occlusion/organ damages, vascular reocclusion/restenosis after bypass surgery, respiratory diseases (cold syndrome, pneumonia, asthma, pulmonary hypertension, pulmonary thrombus/pulmonary embolism, etc.), bone disorders (nonmetabolic bone disorders such as bone fracture, refracture, bone malformation/spondylosis deformans, osteosarcoma, myeloma, dysostosis and scoliosis, bone defect, osteoporosis, osteomalacia, rickets, osteitis fibrosis, renal osteodystrophy, Paget's disease of bone, myelitis with rigidity, chronic rheumatoid arthritis, gonarthrosis and articular tissue destruction in similar disorders thereof, etc.), inflammatory diseases (retinopathy, nephropathy, nerve damage, arthritis such as chronic rheumatoid arthritis, osteoarthritis, rheumatoid myelitis and periostitis, inflammation after surgery/trauma, reduction of swelling, pharyngitis, cystitis, atopic dermatitis, inflammatory enteric diseases such as Crohn's disease and ulcerative colitis, meningitis, inflammatory eye diseases, inflammatory pulmonary diseases such as pneumonia, silicosis, pulmonary sarcoidosis and pulmonary tuberculosis, etc.), allergic diseases (allergic rhinitis, conjunctivitis, gastrointestinal allergy, pollen allergy, anaphylaxis, etc.), drug dependence, neurodegenerative diseases (Alzheimer's disease, Parkinson's disease, amyotrophic lateral sclerosis, AIDS encephalopathy, etc.), central nervous system damage (disorders such as cerebral hemorrhage and cerebral infarction and aftereffects and complications thereof, head injury, spinal damage, cerebral edema, etc.), dementia, disturbed memory, disturbed consciousness, amnesia, anxiety symptoms, nervous symptoms, unpleasant condition, mental disorders (depression, epilepsy, alcohol dependency, etc.), ischemic peripheral circulatory disorder, deep-vein thrombosis, occlusive peripheral circulatory disorder, arteriosclerosis obliterans (ASO), occlusive thromboangiitis, diabetes (type 1 diabetes, type 2 diabetes, type 1.5 diabetes (LADA (Latent Autoimmune Diabetes in Adults)), pregnancy diabetes, diabetes with impaired insulin secretion, obese diabetes, impaired glucose tolerance (IGT), IFG (Impaired Fasting Glucose), IFG (Impaired Fasting Glycaemia), etc.), diabetic complications (nerve damage, nephropathy, retinopathy, cataract, macroangiopathy, osteopenia, diabetic hyperosmolar diabetic coma, infectious diseases (respiratory infection; urinary infection, digestive tract infection, skin and soft tissue infection, lower limb infection, etc.), diabetic gangrene, xerostomia, deterioration in hearing, cerebrovascular damage, peripheral circulatory disorder, etc.), urinary incontinence, metabolic/nutritional disorders (obesity (e.g., malignant mastocytosis, exogenous obesity, hyperinsulinar obesity, hyperplasmic obesity, hypophyseal adiposity, hypoplasmic obesity, hypothyroid obesity, hypothalamic obesity, symptomatic obesity, infantile obesity, upper body obesity, alimentary obesity, hypogonadal obesity, systemic mastocytosis, simple obesity, central obesity, etc.), hyperphagia, hyperlipidemia, hypercholesterolemia, impaired glucose tolerance, etc.), insulin resistant syndrome, syndrome X, vesceral obesity syndrome, male or female sexual dysfunction, cerebrovascular damage (asymptomatic cerebrovascular damage, transient cerebral ischemia attack, stroke, cerebrovascular dementia, hypertensive encephalopathy, cerebral infarction, etc.), cerebral edema, cerebral circulatory disturbance, recurrence and aftereffects of cerebrovascular damages (neurological symptoms, mental symptoms, subjective symptoms, impairment of activities of daily living, etc.), kidney diseases (nephritis, glomerulonephritis, glomerulosclerosis, renal failure, thrombotic microangiopathy, diabetic nephropathy, nephrotic syndrome, hypertensive nephrosclerosis, complications of dialysis, organ damage including nephropathy by irradiation, etc.), ocular disorders (glaucoma, ocular hypertension, etc.), thrombosis, multiple organ failure, endothelial dysfunction, other circulatory diseases (ischemic cerebral circulatory disturbance, Raynaud's disease, Buerger's disease, etc.), chronic occlusive pulmonary diseases, interstitial pneumonia, carinii pneumonia, connective tissue disorders (e.g., systemic erythematosus, scleroderma, polyarteritis, etc.), liver disorders (hepatitis and cirrhosis including chronic types, etc.), digestive disorders (gastritis, gastric ulcer, gastric cancer, disorder after gastric surgery, poor digestion, esophageal ulcer, pancreatitis, colon polyp, cholelithiasis, hemorrhoidal problem, esophageal and gastric variceal rupture, etc.), hematological/hematopoietic disorders (erythrocytosis, vascular purpura, autoimmune hemolytic anemia, disseminated intravascular coagulation syndrome, multiple myelosis, etc.), solid tumor, tumors (malignant melanoma, malignant lymphoma, digestive organs (e.g., stomach, intestine, etc.) cancers, etc.), cancers and cachexia associated therewith, cancer metastases, endocrine disorders (Addison's disease, Cushing's syndrome, pheochromocytoma, primary aldosteronism, etc.), urological/male genital diseases (cystitis, prostatic enlargement, prostate cancer, sexually transmitted diseases, etc.), gynecological disorders (menopausal disorders, pregnancy toxemia, endometriosis, uterine fibroid, ovarian diseases, mammary gland diseases, sexually transmitted diseases, etc.), infectious diseases (viral infectious diseases of, for example, cytomegalovirus, influenza virus and herpesvirus, rickettsial infectious diseases, bacterial infectious diseases, etc.), toxemia (septicemia, septic shock, endotoxic shock, gram-negative septicemia, toxin shock syndrome, etc.), cutaneous diseases (keloid, hemangioma, psoriasis, etc.). In particular, the compound is preferably used for preventing or treating atherosclerosis, diabetes or obesity. Herein, the concept of preventing or treating atherosclerosis include: preventing and delaying further progression of severity of so-called atherothrombosis such as ischemic cardiac diseases resulting from atherosclerotic plaque rupture (unstable angina, acute myocardial infarction, acute heart failure, cardiac death) or strokes (including transient cerebral ischemia); preventing occurrence of cardiovascular events of patients having a high risk of developing cardiovascular events (patients with acute coronary artery disease, stroke patients, patients with metabolic disorder, patients with hypertension/obesity/diabetes/hyperlipidemia, etc.) based on anti-atherosclerotic effects; preventing recurrence of ischemic cardiac diseases; preventing primary onset of cardiovascular event; preventing or treating peripheral arterial angiopathy; and the like.

For diagnostic criteria of diabetes, Japan Diabetes Society reported new diagnostic criteria in 1999.

According to this report, diabetes is a condition showing any of a fasting blood glucose level (glucose concentration of intravenous plasma) of not less than 126 mg/dl, a 75 g oral glucose tolerance test (75 g OGTT) 2 h level (glucose concentration of intravenous plasma) of not less than 200 mg/dl, and a non-fasting blood glucose level (glucose concentration of intravenous plasma) of not less than 200 mg/dl. A condition not falling under the above-mentioned diabetes and different from "a condition showing a fasting blood glucose level (glucose concentration of intravenous plasma) of less than 110 mg/dl or a 75 g oral glucose tolerance test (75 g OGTT) 2 h level (glucose concentration of intravenous plasma) of less than 140 mg/dl" (normal type) is called a "borderline type".

In addition, ADA (American Diabetes Association) in 1997 and WHO in 1998 reported diagnostic criteria of diabetes.

According to these reports, diabetes is a condition showing a fasting blood glucose level (glucose concentration of intravenous plasma) of not less than 126 mg/dl, or a 75 g oral glucose tolerance test 2 h level (glucose concentration of intravenous plasma) of not less than 200 mg/dl.

According to the above-mentioned reports, impaired glucose tolerance is a condition showing a fasting blood glucose level (glucose concentration of intravenous plasma) of less than 126 mg/dl, and a 75 g oral glucose tolerance test 2 h level (glucose concentration of intravenous plasma) of not less than 140 mg/dl and less than 200 mg/dl. According to the report of ADA, a condition showing a fasting blood glucose level (glucose concentration of intravenous plasma) of not less than 110 mg/dl and less than 126 mg/dl is called IFG (Impaired Fasting Glucose). According to the report of WHO, among the IFG (Impaired Fasting Glucose), a condition showing a 75 g oral glucose tolerance test 2 h level (glucose concentration of intravenous plasma) of not less than 110 mg/dl and less than 140 mg/dl is called IFG (Impaired Fasting Glycemia).

The compound of the present invention can also be used as an agent for the prophylaxis or treatment of diabetes, borderline type, impaired glucose tolerance, IFG (Impaired Fasting Glucose) and IFG (Impaired Fasting Glycemia), as determined according to the above-mentioned diagnostic criteria. Moreover, the compound of the present invention can prevent progress of borderline type, impaired glucose tolerance, IFG (Impaired Fasting Glucose) or IFG (Impaired Fasting Glycemia) into diabetes.

The compound of the present invention may also be used for secondary prevention and delaying the progression of the above-mentioned various diseases (e.g., cardiovascular events such as myocardial infarction).

By continuously suppressing eicosanoid production for a prolonged time period, the compound of the prevent invention may also be used for preventing or treating inflammatory diseases suggestively associated with prophlogistic eicosanoid, such as asthma, allergic airway hyperresponsiveness, fever, pain production, thrombosis, cerebral infarction, myocardial infarction, cancer, autoimmune encephalomyelitis, pain, renal failure, rheumatism, osteoarthritis, pruritus, atopic dermatitis, rhinitis, inflammatory enteric diseases and Crohn's disease. Furthermore, the compound may improve or suppress enhancement of disorder or abnormality of biological function or physiological action that is causative of various diseases associated with inflammatory reaction, and may be used for primary or secondary prevention and delaying the progression of a disease or a pathological condition resulting therefrom. Examples of such disorders or abnormalities of biological functions and physiological actions include facial flush, pain and itch of skin (including those associated with administration of nicotinic acid derivative preparation, prostacyclin preparation or the like), overactive bladder, disorder or abnormality of cerebral circulatory/renal circulatory autoregulation, circulatory disorder (e.g., peripheral circulation, cerebral circulation, microcirculation, etc.), disorder of blood-brain barrier, salt sensitivity, abnormality of coagulation or fibrinolytic system, abnormality of blood/hemocyte component property (e.g., sickle cell disease, enhanced platelet aggregation, abnormality of erythrocyte deformability, enhanced leukocyte viscosity, increase in blood viscosity, etc.), generation and increased activities of growth factors and cytokines (e.g., PDGF, VEGF, FGF, interleukin, TNF-$\alpha$, MCP-1, etc.), production and increased invasion of inflammatory cells, increase in free radical generation, acceleration of fatty deposition, endothelial dysfunction, endothelial, cellular and organ damages, edema, morphology alteration of cell such as smooth muscle (morphology alteration into proliferative form or the like), production and enhanced functions of vasoactive substances and thrombus-inducing substances (e.g., catecholamine, endothelin, thromboxane A2, etc.), abnormal contraction of blood vessel or the like, metabolic abnormality (e.g., serum lipid abnormality, blood glucose abnormality, etc.), overgrowth of cell or the like, and angiogenesis (including abnormal angiopoiesis upon abnormal capillary net formation of outer membrane of atherosclerotic plaque).

Since the compound of the prevent invention has an analgetic effect, it may also be used as an analgesic or a prophylactic/therapeutic drug for pain. Examples of painful diseases include acute pain caused by inflammation, pain associated with chronic inflammation, pain associated with acute inflammation, postoperative pain (pain at an incisional wound, deep pain, vesceral pain, postoperative chronic pain, etc.), muscular ache (muscular ache associated with chronic painful diseases, stiff shoulder, etc.), joint pain, toothache, jaw joint pain, headache (migraine, tension-type headache, headache associated with fever, headache associated with hypertension), vesceral pain (cardiac pain, anginal pain, stomach ache, pain in the kidney, pain in the urinary duct, pain in the bladder), obstetric and gynecologic pain (intermenstrual pain, dysmenorrhea, labor pain), neuralgia (disc herniation, radicular pain, postherpetic neuralgia, trigeminal neuralgia), cancerous pain, reflex sympathetic atrophy and complex regional pain syndrome. The compound of the invention is effective in directly and immediately relieving various pain such as neurogenic pain, cancerous pain and inflammatory pain, and exhibits particularly excellent analgetic effect for patients with low pain threshold and clinical conditions (e.g., hypertension or the like, and complications thereof, etc.).

The content of the compound of the present invention in a pharmaceutical composition is generally about 0.01 to about 99.9% by weight, preferably about 0.1 to about 50% by weight of the whole preparation.

A dosage of the compound of the present invention is determined by considering age, weight, general health condition, sex, diet, administration time, administration method, excretion rate, combination of drugs, and the condition of the patient's disease under treatment, and/or other factors.

The compound of the invention may be used in combination, for example, with a drug such as an anti-atherosclerotic agent, an anti-thrombotic agent, an anti-heart failure agent, an anti-arrhythmia agent, an anti-hypertensive agent, an agent for treating diabetes, an agent for treating diabetic complications, an HDL-raising agent, an anti-hyperlipidemia agent, an anti-obesity agent, a diuretic, an anti-inflammatory agent, an antigout agent, a chemotherapeutic agent, an immunotherapeutic agent, an osteoporosis drug, an anti-dementia agent, an erectile dysfunction-improving agent, an agent for treating urinary incontinence and an agent for treating urination difficulty (hereinafter, abbreviated as concomitant drugs). These concomitant drugs may be low-molecular compounds, or high-molecular proteins, polypeptides, antibodies, vaccines or the like.

Examples of the above-mentioned "anti-atherosclerotic agent" include Lp-PL A2 inhibitors (e.g., darapladib, rilapladib, etc.), FLAP inhibitors (e.g., AM-103, AM-803, DG-031, etc.), sPLA2 inhibitors (e.g., varespladib), 5-lipoxygenase inhibitors (e.g., VIA-2291, etc.), acyl-coenzyme A: cholesterol acyltransferase (ACAT) inhibitors (e.g., melinamide, avasimibe, eflucimibe, etc.), lipid-rich plaque regression drugs (e.g., compounds described in WO 02/06264, WO 03/059900, etc.), reconstituted HDL (e.g., CSL-111, etc.), CTEP inhibitors (e.g., torcetrapib, anacetrapib, dalcetrapib, etc.), MMP inhibitors, chymase inhibitors, SPT inhibitors, ApoA-1 and related molecules thereof (e.g., ApoA-1 Milano, D-4F, L-4F, etc.).

Examples of the above-mentioned "anti-thrombotic agent" include blood coagulation inhibitors (e.g., heparin sodium, heparin calcium, warfarin calcium (warfarin), antithrombin drugs (e.g., argatroban, dabigatran), activated blood coagulation Factor Xa inhibitors (e.g., rivaroxaban, apixaban, edoxaban, YM-150, compounds described in WO 02/06234, WO 2004/048363, WO 2005/030740, WO 2005/058823, WO 2005/113504 and WO 2004/048363), etc.), thrombolytic drugs (e.g., tPA, urokinase, tisokinase, alteplase, nateplase, monteplase, pamiteplase), antiplatelet drugs (e.g., aspirin, sulfinpyrazone (Anturan), dipyridamole (Persantin), ticlopidine (Panaldine), cilostazol (Pletal), GPIIb/IIIa antagonists (e.g., ReoPro, etc.), clopidogrel, prasugrel, ticagrelor, E5555, SHC530348, ethyl icosapentate, beraprost sodium, sarpogrelate hydrochloride, etc.) and the like.

Examples of the above-mentioned "anti-heart failure agent" include inotropic agents (e.g., digitoxin, digoxin, methyldigoxin, lanatoside C, proscillaridin, etc.), [alpha], [beta] stimulants (e.g., epinephrine, norepinephrine, isoproterenol, dopamine, docarpamine, dobutamine, denopamine, etc.), phosphodiesterase inhibitors (e.g., aminone, milrinone, olprinone hydrochloride, etc.), calcium channel sensitivity augmenting agents (e.g., pimobendan, etc.), nitrate drugs (e.g., nitroglycerin, isosorbide nitrate, etc.), angiotensin-converting enzyme inhibitors (e.g., an angiotensin-converting enzyme inhibitor mentioned below, etc.), angiotensin II antagonist (e.g., an angiotensin II antagonist mentioned below, etc.), [beta]-blockers (e.g., [beta]-blocker mentioned below, etc.), diuretics (e.g., diuretic mentioned below, etc.), ANPs, sGC-activating agents, myosin sensitivity augmenting agents, carperitide, ubidecarenone, vesnarinone, aminophylline and the like.

Examples of the above-mentioned "anti-arrhythmia agents" include sodium channel blockers (e.g., quinidine, procainamide, disopyramide, ajmaline, cibenzoline, lidocaine, diphenylhydantoin, mexiletine, propafenone, flecamide, pilsicamide, phenyloin, etc.), [beta]-blockers (e.g., propranolol, alprenolol, bufetolol, oxprenolol, atenolol, acebutolol, metoprolol, bisoprolol, pindolol, carteolol, arotinolol, etc.), potassium channel blockers (e.g., amiodarone, etc.), calcium channel blockers (e.g., verapamil, diltiazem, etc.) and the like.

Examples of the above-mentioned "anti-hypertensive agent" include angiotensin-converting enzyme inhibitors (e.g., captopril, enalapril, delapril, etc.), angiotensin II antagonists (e.g., candesartan cilexetil, candesartan, azilsartan, azilsartan medoxomil, losartan, losartan potassium, eprosartan, valsartan, telmisartan, irbesartan, tasosartan, olmesartan, olmesartan medoxomil, etc.), calcium antagonists (e.g., manidipine, nifedipine, amlodipine, efonidipine, nicardipine, etc.), β-blockers (e.g., propranolol, nadolol, timolol, nipradilol, bunitrolol, indenolol, penbutolol, carteolol, carvedilol, pindolol, acebutolol, atenolol, bisoprolol, metoprolol, labetalol, amosulalol, arotinolol, etc.), clonidine and the like. Examples of the above-mentioned "diuretics" include xanthine derivatives (e.g., theobromine sodium salicylate, theobromine calcium salicylate, etc.), thiazide preparations (e.g., ethiazide, cyclopenthiazide, trichloromethiazide, hydrochlorothiazide, hydroflumethiazide, bentyl hydrochlorothiazide, penfluthiazide, poly 5 thiazide, methychlothiazide, etc.), anti-aldosterone preparations (e.g., spironolactone, eplerenone, triamterene, etc.), carbonate dehydratase inhibitors (e.g., acetazolamide, etc.), chlorobenzenesulfonamide preparations (e.g., chlortalidone, mefruside, indapamide, etc.), azosemide, isosorbide, ethacrynic acid, piretanide, bumetanide, furosemide and the like.

Examples of the above-mentioned "agent for treating diabetes" include insulin preparations (e.g., animal insulin preparations extracted from bovine or swine pancreas; human insulin preparations synthesized by genetic engineering using *E. coli* or yeast; insulin zinc; protamine insulin zinc; insulin fragments or derivatives (e.g., INS-1), oral insulin preparation), insulin-resistance improving agents (e.g., pioglitazone or salts thereof (preferably, hydrochloride salt), rosiglitazone or salts thereof (preferably, maleate salt), Netoglitazone (MCC-555), Rivoglitazone (CS-011), FK-614, compounds described in WO01/38325, Tesaglitazar (AZ-242), Ragaglitazar (N,N-622), Muraglitazar (BMS-298585), Edaglitazone (BM-13-1258), Metaglidasen (MBX-102), Naveglitazar (LY-519818), MX-6054, LY-510929, AMG131(T-131) or salts thereof, THR-0921), [alpha]-glucosidase inhibitor (e.g., voglibose, acarbose, miglitol, emiglitate), biguanides (e.g., phenformin, metformin, buformin or salts thereof (e.g., hydrochloride salt, fumarate salt, succinate salt)), insulin secretion promoters (sulphonylurea agents (e.g., tolbutamide, glibenclamide, gliclazide, chlorpropamide, tolazamide, acetohexamide, glyclopyramide, glimepiride, glipizide, glybuzole), repaglinide, nateglinide, mitiglinide or calcium salt hydrates thereof), dipeptidyl peptidase-IV inhibitors (e.g., Vildagliptin (LAF237), P32/98, Sitagliptin (MK-431), alogliptin, P93/01, PT-100, Saxagliptin (BMS-477118), BI1356, GRC8200, MP-513, PF-00734200, PHX1149, SK-0403, ALS2-0426, TA-6666, TS-021, KRP-104, 2-[[6-[(3R)-3-amino-1-piperidinyl]-3,4-dihydro-3-methyl-2,4-dioxo-1(2H)-pyrimidinyl]methyl]-4-fluorobenzonitrile or salts thereof), β3-agonists (e.g., AJ-9677), GPR40 agonists, GLP-1 receptor agonists (e.g., GLP-1, GLP-1MR agent, N,N-2211, AC-2993 (exendin-4), BIM-51077, Aib(8,35)hGLP-1(7,37)NH2, CJC-1131], amylin agonists (e.g., pramlintide), phosphotyrosine phosphatase inhibitors (e.g., sodium vanadate), gluconeogenesis inhibitors (e.g., glycogen phosphorylase inhibitors, glucose-6-phosphatase inhibitors, glucagon antagonists), SGLUT (sodium-glucose cotransporter) inhibitors (e.g., T-1095, dapagliflozin, remogliflozin), 11β-hydroxysteroid dehydrogenase inhibitors (e.g., BVT-3498), adiponectin or agonists thereof, IKK inhibitors (e.g., AS-2868), leptin-resistant improving drugs, somatostatin receptor agonists (e.g., compounds described in WO 01/25228, WO 03/42204, WO 98/44921, WO 98/45285, WO 99/22735, etc.), glucokinase activators (e.g., Ro-28-1675), ACC2 (acetyl-CoA carboxylase 2) inhibitors and the like.

Examples of the above-mentioned "agent for treating diabetic complications" include aldose reductase inhibitors (e.g., tolrestat, epalrestat, zenarestat, zopolrestat, minalrestat, fidarestat, CT-112, ranirestat (AS-3201)), neurotrophic factors and augmenting agents thereof (e.g., NGF, NT-3, BDNF, neurotrophin production/secretion promoters described in WO 01/14372 (e.g., 4-(4-chlorophenyl)-2-(2-methyl-1-imidazolyl)-5-(3-(2-methylphenoxy)propyl)oxazole)), PKC inhibitors (e.g., ruboxistaurin mesylate), AGE inhibitors (e.g., ALT946, pimagedine, N-phenacylthiazolium bromide (ALT766), EXO-226, Pyridorin, pyridoxamine), active oxygen scavenging agents (e.g., thioctic acid), cerebral vasodilators (e.g., tiapride, mexiletine), somatostatin receptor agonists (e.g., BIM23190), and apoptosis signal-regulating kinase-1(ASK-1) inhibitors.

Examples of the above-mentioned "HDL-raising agent" include squalene synthetase inhibitors, CETP inhibitors (e.g., torcetrapib, anacetrapib, dalcetrapib, etc.), LPL activators, nicotinic drugs (e.g., nicomol, niceritrol), endothelial lipase inhibitors and the like.

Examples of the above-mentioned "anti-hyperlipidemia agent" include statin compounds as cholesterol synthesis inhibitors (e.g., cerivastatin, pravastatin, simvastatin, lovastatin, rosuvastatin, atorvastatin, fluvastatin, pitavastatin or salts thereof (e.g., sodium salt, etc.) etc.), squalene synthetase inhibitors or fibrate compounds with hypotriglyceride action (e.g., bezafibrate, clofibrate, simfibrate, clinofibrate, etc.), cholesterol absorption inhibitors (e.g., zetia), anion-exchange resins (e.g., cholestyramine), probucol, nicotinic drugs (e.g., nicomol, niceritrol), phytosterols (e.g., soysterol, [gamma]-oryzanol)), fish oil preparations (EPA, DHA, omacor, etc.), PPAR α-agonists, PPAR γ-agonists, PPAR [delta]-agonists, LXR agonists, FXR antagonists, FXR agonists, DGAT inhibitors, MGAT inhibitors, MTP inhibitors (e.g., lomitapide), nucleic acid drugs including ApoB antisense (e.g., mipomersen) or PCSK9 siRNA antisense oligonucleotides, and the like.

Examples of the above-mentioned "anti-obesity agent" include monoamine uptake inhibitors (e.g., phentermine, sibutramine, mazindol, fluoxetine, tesofensine), serotonin 2C receptor agonists (e.g., lorcaserin), serotonin 6 receptor antagonists, histamine H3 receptors, GABA modulators (e.g., topiramate), neuropeptide Y antagonists (e.g., velneperit), cannabinoid receptor antagonists (e.g., rimonabant, taranabant), ghrelin antagonists, ghrelin receptor antagonists, ghrelin-acylating enzyme inhibitors, opioid receptor antagonists (e.g., GSK-1521498), orexin receptor antagonists, melanocortin 4 receptor agonists, 11β-hydroxysteroid dehydrogenase inhibitors (e.g., AZD-4017), pancreatic lipase inhibitors (e.g., orlistat, cetilistat), [beta]3-agonists (e.g., N-5984), diacylglycerol acyltransferase1 (DGAT1) inhibitors, acetyl CoA carboxylase (ACC) inhibitors, stearate CoA desaturase inhibitors, microsome triglyceride transfer protein inhibitors (e.g., R-256918), Na-glucose cotransport carrier inhibitors (e.g., JNJ-28431754, remogliflozin, NF[kappa] inhibitors (e.g., HE-3286), PPAR agonists (e.g., GFT-505, DRF-11605), phosphotyrosine phosphatase inhibitors (e.g., sodium vanadate, Trodusquemin), GPR119 agonists (e.g., PSN-821), glucokinase activators (e.g., AZD-1656), leptin, leptin derivatives (e.g., metreleptin), CNTFs (ciliary neurotrophic factors), BDNFs (brain-derived neurotrophic factors), cholecystokinin agonists, glucagon-like peptide-1 (GLP-1) preparations (e.g., animal GLP-1 preparations extracted from bovine or swine pancreas; human GLP-1 preparations synthesized by genetic engineering using *E. coli* or yeast; GLP-1 fragments or derivatives (e.g., exenatide, liraglutide)), amylin preparations (e.g., pramlintide, AC-2307), neuropeptide Y agonists (e.g., PYY3-36, PYY3-36 derivatives, obinepitide, TM-30339, TM-30335), oxyntomodulin preparations: FGF21 preparations (e.g., animal FGF21 preparations extracted from bovine or swine pancreas; human FGF21 preparations synthesized by genetic engineering using *E. coli* or yeast; FGF21 fragments or derivatives)), appetite suppressors (e.g., P-57) and the like.

Examples of the above-mentioned "diuretics" include xanthine derivatives (e.g., theobromine sodium salicylate, theobromine calcium salicylate, etc.), thiazide preparations (e.g., ethiazide, cyclopenthiazide, trichloromethiazide, hydrochlorothiazide, hydroflumethiazide, bentyl hydrochlorothiazide, penfluthiazide, poly 5 thiazide, methychlothiazide, etc.), antialdosterone preparations (e.g., spironolactone, eplerenone, triamterene, etc.), carbonate dehydratase inhibitors (e.g., acetazolamide, etc.), chlorobenzenesulfonamide preparations (e.g., chlortalidone, mefruside, indapamide, etc.), azosemide, isosorbide, ethacrynic acid, piretanide, bumetanide, furosemide and the like.

Examples of the above-mentioned "anti-inflammatory agent" include nonsteroidal anti-inflammatory agents such as acetaminophen, phenacetin, ethenzamide, sulpyrine, antipyrine, migrenin, aspirin, mefenamic acid, flufenamic acid, diclofenac sodium, loxoprofen sodium, phenylbutazone, indomethacin, ibuprofen, ketoprofen, naproxen, oxaprozin, flurbiprofen, fenbufen, pranoprofen, floctafenine, epirizole, tiaramide hydrochloride, zaltoprofen, gabexate mesilate, camostat mesylate, ulinastatin, colchicine, probenecid, sulfinpyrazone, benzbromarone, allopurinol, sodium aurothiomalate, sodium hyaluronate, sodium salicylate, morphine hydrochloride, salicylic acid, atropine, scopolamine, morphine, pethidine, levorphanol, ketoprofen, naproxen, oxymorphone and salts thereof, and the like.

Examples of the above-mentioned "antigout agent" include febuxostat, allopurinol, probenecid, colchicine, benzbromarone, febuxostat, citric salt and the like.

Examples of the above-mentioned "chemotherapeutic agent" include alkylating agents (e.g., cyclophosphamide, ifosfamide, etc.), metabolic antagonists (e.g., methotrexate, 5-fluorouracil, etc.), anticancerous antibiotics (e.g., mitomycin, adriamycin, etc.), plant-derived anticancer agents (e.g., vincristine, vindesine, taxol, etc.), cisplatin, carboplatin, etoposide and the like. In particular, 5-fluorouracil derivatives furtulon, neofurtulon and the like are preferable.

Examples of the above-mentioned "immunotherapeutic agent" include microbial or bacterial components (e.g., muramyldipeptide derivatives, picibanil, etc.), polysaccharides with immunological-enhancing activity (e.g., lentinan, schizophyllan, krestin, etc.), cytokines obtained through genetic engineering procedure (e.g., interferon, interleukin (IL), etc.), colony-stimulating factors (e.g., granulocyte colony-stimulating factors, erythropoietin, etc.) and the like. In particular, IL-1, IL-2, IL-12 and the like are preferable.

Examples of the above-mentioned "osteoporosis drug" include alfacalcidol, calcitriol, elcaltonin, calcitonin salmon, estriol, ipriflavone, pamidronate disodium, alendronate sodium hydrate, incadronate disodium and the like.

Examples of the above-mentioned "an antidementia agent" include tacrine, donepezil, rivastigmine, galantamine and the like.

Examples of the above-mentioned "erectile dysfunction improving agent" include apomorphine, PDE5 (phosphodiesterase5) inhibitors (e.g., sildenafil citrate) and the like.

Examples of the above-mentioned "agent for treating urinary incontinence" include flavoxate hydrochloride, oxybutynin hydrochloride, propiverine hydrochloride and the like.

Examples of the above-mentioned "agent for treating urination difficulty" include acetylcholinesterase inhibitors (e.g., distigmine) and the like.

Moreover, examples of concomitant drugs include prostacyclin preparations/derivatives (e.g., beraprost, epoprostenol, iloprost, treprostinil, etc.), prostaglandin preparations/derivatives (e.g., enprostil, alprostadil, limaprost, misoprostol, ornoprostil, etc.), anti-asthma drugs (e.g., salmeterol, fluticasone, montelukast), rheumatoid arthritis agents (e.g., etanercept, infliximab, adalimumab), nerve regeneration promoters (e.g., Y-128, VX-853, prosaptide), antidepressants (e.g., desipramine, amitriptyline, imipramine), antiepilepsy drugs (e.g., lamotrigine), antiarrhythmic drugs (e.g., mexiletine), acetylcholine receptor ligands (e.g., ABT-594), endothelin receptor antagonists (e.g., bosentan, ABT-627), monoamine uptake inhibitors (e.g., tramadol), narcotic analgesics (e.g., morphine), GABA receptor agonists (e.g., gabapentin), α2 receptor agonists (e.g., clonidine), local analgesics (e.g., capsaicin), antianxiety drugs (e.g., benzodiazepine), dopamine agonists (e.g., apomorphine), midazolam, ketoconazole and the like.

The time of administration of the compound of the present invention and that of the concomitant drug are not limited, and they may be administered simultaneously or in a staggered manner to the administration subject. The dose of the concomitant drug can be appropriately determined based on the dose employed in clinical situations, and it can be appropriately determined depending on the administration subject, administration route, target disease, symptom, combination and the like.

These concomitant drugs may be used in a mixture of two or more thereof in an appropriate ratio. In this case, the administration period of the compound of the present invention and the concomitant drugs is not limited as long as the compound of the present invention is combined with the concomitant drugs upon administration.

Examples of such administration mode include the following:

(1) administration of a single preparation obtained by simultaneously processing the compound of the present invention and the concomitant drug, (2) simultaneous administration of two kinds of preparations of the compound of the present invention and the concomitant drug, which have been separately produced, by the same administration route, (3) administration of two kinds of preparations of the compound of the present invention and the concomitant drug, which have been separately produced, by the same administration route in a staggered manner, (4) simultaneous administration of two kinds of preparations of the compound of the present invention and the concomitant drug, which have been separately produced, by different administration routes, (5) administration of two kinds of preparations of the compound of the present invention and the concomitant drug, which have been separately produced, by different administration routes in a staggered manner (e.g., administration in the order of the compound of the present invention and the concomitant drug, or in the reverse order) and the like.

The dose of the combination drug can be determined as appropriate based on the dose clinically employed. The proportion of the compound of the present invention and the concomitant drug can be appropriately determined depending on the administration subject, administration route, target disease, condition, combination and the like. When, for example, the administration subject is human, the concomitant drug is used in an amount of 0.01-100 parts by weight per 1 part by weight of the compound of the present invention.

By combining the compound of the present invention and a concomitant drug, a superior effect such as (1) the dose can be reduced as compared to single administration of the compound of the present invention or a concomitant drug, (2) the period of treatment can be set longer by selecting a concomitant drug having different action and mechanism from the compound of the present invention, (3) a sustained treatment effect can be designed by selecting a concomitant drug having different action and mechanism from the compound of the present invention, (4) a synergistic effect can be afforded by a combined use of the compound of the present invention and a concomitant drug, and the like, can be achieved.

EXAMPLES

The present invention is explained in more detail by referring to the following Examples, Experimental Examples and Formulation Examples, which do not limit the present invention and may be changed as long as they do not deviate from the scope of the present invention.

In the following Examples, the "room temperature" generally shows about 10° C. to about 35° C. The ratios indicated for mixed solvents are volume mixing ratios, unless otherwise specified. % means wt %, unless otherwise specified.

In silica gel column chromatography, NH means use of aminopropylsilane-bound silica gel. In HPLC (high performance liquid chromatography), C18 means use of octadecyl-bound silica gel. The ratios of elution solvents are volume mixing ratios, unless otherwise specified.

$^1$H NMR (protone nuclear magnetic resonance spectrum) was measured by Fourier-transform type NMR. For the analysis, ACD/SpecManager (trade name) and the like were used. Peaks with very mild protons such as a hydroxy group, an amino group and the like are note described.

MS (mass spectrum) was measured by LC/MS (liquid chromatography mass spectrometer).

As the ionization method, ESI (ElectroSpray Ionization) method, or APCI (Atomospheric Pressure Chemical Ionization) method was used. The data indicates those found. In the case of a salt, a molecular ion peak or fragment ion peak of free form is generally observed.

The abbreviations used in Examples mean the following.
s: singlet
d: doublet
t: triplet
q: quartet
dd: double doublet
ddd: double double doublet
dt: double triplet
td: triple doublet
tt: triple triplet
tq: triple quartet
spt: septet
sxt: sextet
br. s.: broad singlet
m: multiplet
J: coupling constant
Hz: hertz
CHLOROFORM-d: deuterated chloroform
DMSO-$d_6$: deuterated dimethyl sulfoxide
$^1$H NMR: proton nuclear magnetic resonance In the following Examples, HPLC-mass spectrum (LC-MS) was measured by following conditions.
measurement device: Waters Micromass ZQ-Alliance HT
column: CAPCELL PAK C18UG120, S-3 μm, 1.5×35 mm
solvent: SOLUTION A; 0.05% trifluoroacetic acid-containing water, SOLUTION B; 0.04% trifluoroacetic acid-containing acetonitrile
gradient cycle: 0.00 min (SOLUTION A/SOLUTION B=90/10), 2.00 min (SOLUTION A/SOLUTION B=5/95), 2.75 min (SOLUTION A/SOLUTION B=5/95), 2.76 min (SOLUTION A/SOLUTION B=90/10), 3.45 min (SOLUTION A/SOLUTION B=90/10)
injection volume: 2 μl, flow rate: 0.5 ml/min, detection method: UV 220 nm
ionization method: electron impact ionization method (Electron Spray Ionization: ESI)

Example 1

2-(ethylsulfanyl)-7-methoxy-3-[4-(2,2,2-trifluoroethoxy)phenyl]pyrido[2,3-d]pyrimidin-4(3H)-one A) methyl 6-chloro-2-[(4-methoxybenzyl)amino] pyridine-3-carboxylate A mixture of methyl 2,6-dichloropyridine-3-carboxylate (2.06 g), sodium hydrogen carbonate (1.26 g), 4-methoxybenzylamine (1.50 ml), copper(I) iodide (190 mg) and N,N-dimethylformamide (20 ml) was heated to 80° C., and the mixture was stirred for 1 hr and 30 min. The reaction mixture was concentrated under reduced pressure, the obtained residue was diluted with ethyl acetate (150 ml), and the insoluble solid was removed by filtration. To the filtrate was 28% aqueous ammonia (5 ml), and the mixture was washed successively with water and saturated brine, dried over anhydrous magnesium sulfate, and concentrated under reduced pressure. The obtained yellow oil residue was purified by silica gel column chromatography (ethyl acetate/hexane) to give the title compound (1.58 g).

$^1$H NMR (300 MHz, DMSO-$d_6$) δ3.73 (3H, s), 3.81 (3H, s), 4.55 (2H, d, J=5.7 Hz), 6.68 (1H, d, J=8.3 Hz), 6.89 (2H, d, J=8.7 Hz), 7.29 (2H, d, J=8.7 Hz), 8.08 (1H, d, J=8.3 Hz), 8.43 (1H, t, J=5.7 Hz).

B) methyl 2-amino-6-chloropyridine-3-carboxylate

To a solution of methyl 6-chloro-2-[(4-methoxybenzyl) amino]pyridine-3-carboxylate (1.0 g) in trifluoroacetic acid (5 ml) was added anisole (0.5 ml), and the mixture was stirred at room temperature for 2 hr. The reaction mixture was concentrated under reduced pressure, and the residue was subjected to azeotropic distillation with toluene. The obtained oil residue was diluted with ethyl acetate (80 ml), and the mixture was washed with saturated aqueous sodium hydrogen carbonate solution and saturated brine, dried over anhydrous magnesium sulfate, and concentrated under reduced pressure. The residue was purified by silica gel column chromatography (ethyl acetate/hexane) to give the title compound (596 mg).

$^1$H NMR (300 MHz, DMSO-$d_6$) δ3.81 (3H, s), 6.66 (1H, d, J=8.3 Hz), 7.54 (2H, brs), 8.05 (1H, d, J=8.3 Hz).

C) 1-nitro-4-(2,2,2-trifluoroethoxy)benzene

1-Fluoro-4-nitrobenzene (10.6 g) and 2,2,2-trifluoroethanol (12.0 g) were dissolved in N,N-dimethylformamide (80 ml), and potassium carbonate (15.5 g) was added thereto. The mixture was stirred at 80° C. for 2 hr, and allowed to be cooled. To the reaction mixture was added ethyl acetate (100 ml), and the white precipitate was removed by filtration. The filtrate was concentrated under reduced pressure to give an orange residue. The obtained residue was again dissolved in ethyl acetate (400 ml), and the solution was washed with water and saturated brine, dried over anhydrous magnesium sulfate, and concentrated under reduced pressure to give an orange crude solid. The obtained solid was washed with a mixed solvent of 10% diethyl ether/hexane to give the title compound (15.8 g) as yellow-white needle crystals.

$^1$H NMR (400 MHz, DMSO-$d_6$) δ4.99 (2H, q, J=8.8 Hz), 7.30 (2H, d, J=9.3 Hz), 8.26 (2H, d, J=9.3 Hz).

D) 4-(2,2,2-trifluoroethoxy)aniline

1-Nitro-4-(2,2,2-trifluoroethoxy)benzene (5.5 g) was dissolved in methanol (100 ml), 10% palladium/activated carbon (50% in water, 2.5 g) was added thereto, and the mixture was stirred at room temperature for 24 hr under a hydrogen atmosphere. The palladium/activated carbon was removed by filtration, and the filtrate was concentrated under reduced pressure to give a dark orange oil residue. The obtained residue was dissolved in ethyl acetate (200 ml), and the solution was washed with saturated brine, dried over anhydrous magnesium sulfate, and concentrated under reduced pressure. The obtained dark orange oil residue was purified by silica gel column chromatography (ethyl acetate/hexane) to give the title compound (4.5 g) as an orange oil.

$^1$H NMR (400 MHz, DMSO-$d_6$) δ4.53 (2H, q, J=9.0 Hz), 4.76 (2H, s), 6.52 (2H, d, J=8.9 Hz), 6.75 (2H, d, J=8.9 Hz).

E) 1-isothiocyanato-4-(2,2,2-trifluoroethoxy)benzene 4-(2,2,2-Trifluoroethoxy)aniline (10 g) was dissolved in tetrahydrofuran (100 ml), 6M hydrochloric acid (9 ml) was added thereto, and the mixture was cooled to −5° C. A solution of thiophosgene (4.01 ml) in tetrahydrofuran (20 ml) was added dropwise thereto over 5 min, and the mixture was stirred at −5° C. for 10 min. Saturated aqueous sodium hydrogen carbonate solution (125 ml) was poured into the mixture, and the mixture was extracted twice with ethyl acetate (200 ml). The extracted layers were combined, washed with saturated brine, and dried over anhydrous magnesium sulfate. The solvent was evaporated under reduced pressure, the obtained brown crude product was purified by silica gel column chromatography, and the obtained pale-yellow solid was washed with hexane to give the title compound (10.7 g) as white crystals.

$^1$H NMR (300 MHz, DMSO-$d_6$) δ4.81 (2H, q, J=8.8 Hz), 7.13 (2H, d, J=9.1 Hz), 7.45 (2H, d, J=9.1 Hz).

F) 7-methoxy-2-thioxo-3-[4-(2,2,2-trifluoroethoxy)phenyl]-2,3-dihydropyrido[2,3-d]pyrimidin-4(1H)-one 1-Isothiocyanato-4-(2,2,2-trifluoroethoxy)benzene (725 mg) was dissolved in N,N-dimethylformamide (10 ml), and sodium hydride (60% in oil, 274 mg) was added thereto under ice-cooling. Methyl 2-amino-6-chloropyridine-3-carboxylate (580 mg) was dissolved in N,N-dimethylformamide (5 ml), and to the reaction mixture was added dropwise the solution under ice-cooling, and the mixture was stirred for additional 20 min. To the reaction mixture was poured into 0.2M hydrochloric acid (35 ml), and the white precipitate was collected by filtration. The precipitate was dissolved in tetrahydrofuran (50 ml), and the solution was diluted with ethyl acetate (100 ml), washed with saturated brine, and dried over anhydrous magnesium sulfate. The solvent was evaporated under reduced pressure to give a white residue (1.2 g). The obtained residue was dissolved in methanol (20 ml), and sodium methoxide (28% methanol solution, 3.0 g) was added thereto. The mixture was heated under reflux for 30 min, allowed to be cooled, and poured into 0.2M hydrochloric acid solution (100 ml) under ice-cooling. The white precipitate was collected by filtration. The obtained precipitate was dissolved in tetrahydrofuran (100 ml), and the solution was diluted with ethyl acetate (200 ml), washed with saturated brine, and dried over anhydrous magnesium sulfate. The solvent was evaporated under reduced pressure, and the obtained residue was washed with diethyl ether to give the title compound (861 mg) as a white solid.

$^1$H NMR (300 MHz, DMSO-$d_6$) δ3.99 (3H, s), 4.82 (2H, q, J=8.9 Hz), 6.77 (1H, d, J=8.7 Hz), 7.12 (2H, d, J=9.1 Hz), 7.21 (2H, d, J=9.1 Hz), 8.16 (1H d, J=8.7 Hz), 13.34 (1H, s).

G) 2-(ethylsulfanyl)-7-methoxy-3-[4-(2,2,2-trifluoroethoxy)phenyl]pyrido[2,3-d]pyrimidin-4(3H)-one A mixture of 7-methoxy-2-thioxo-3-[4-(2,2,2-trifluoroethoxy)phenyl]-2,3-dihydropyrido[2,3-d]pyrimidin-4(1H)-one (383 mg), 1M aqueous sodium hydrogen carbonate solution (1.0 ml), iodoethane (0.4 ml) and acetonitrile (10 ml) was stirred at 100° C. for 1 hr. The reaction mixture was allowed to be cooled, diluted with ethyl acetate (80 ml), washed with water and saturated brine, and dried over anhydrous magnesium sulfate. The solvent was evaporated under reduced pressure, and the obtained residue was purified by silica gel column chromatography (NH, ethyl acetate/hexane) to give the title compound (375 mg).

$^1$H NMR (300 MHz, DMSO-$d_6$) δ1.27 (3H, t), 3.14 (2H, q, J=7.4 Hz), 4.00 (3H, s), 4.88 (2H, q, J=8.9 Hz), 6.88 (1H, d, J=8.7 Hz), 7.22 (2H, d, J=9.0 Hz), 7.42 (2H, d, J=9.0 Hz), 8.27 (1H, d, J=8.7 Hz).

Example 2

7-methoxy-2-(methylsulfanyl)-3-[4-(2,2,2-trifluoroethoxy)phenyl]pyrido[2,3-d]pyrimidin-4(3H)-one A mixture of 7-methoxy-2-thioxo-3-[4-(2,2,2-trifluoroethoxy)phenyl]-2,3-dihydropyrido[2,3-d]pyrimidin-4(1H)-one (1.2 g), 1M aqueous sodium hydrogen carbonate solution (3.1 ml), iodomethane (0.98 ml) and N,N-dimethylformamide (10 ml) was stirred at 60° C. for 1 hr. The reaction mixture was allowed to be cooled, diluted with ethyl acetate (100 ml), washed with water and saturated brine, and dried over anhydrous magnesium sulfate. The solvent was evaporated under reduced pressure, and the obtained residue was purified by silica gel column chromatography (NH, ethyl acetate/hexane) to give the title compound (1.24 g).

$^1$H NMR (300 MHz, DMSO-$d_6$) δ2.51 (3H, s), 4.00 (3H, s), 4.88 (2H, q, J=8.9 Hz), 6.89 (1H, d, J=8.5 Hz), 7.22 (2H, d, J=9.0 Hz), 7.43 (2H, d, J=9.0 Hz), 8.28 (1H, d, J=8.7 Hz).

Example 3

7-methoxy-2-(propylsulfanyl)-3-[4-(2,2,2-trifluoroethoxy)phenyl]pyrido[2,3-d]pyrimidin-4(3H)-one A mixture of 7-methoxy-2-thioxo-3-[4-(2,2,2-trifluoroethoxy)phenyl]-2,3-dihydropyrido[2,3-d]pyrimidin-4(1H)-one (153 mg), 1M aqueous sodium hydrogen carbonate solution (439 μl), 1-iodopropane (117 μl) and N,N-dimethylformamide (3 ml) was stirred at 80° C. for 10 min. The reaction mixture was allowed to be cooled, and water (20 ml) was added thereto. The white precipitate was collected by filtration, washed with water, and dissolved in tetrahydrofuran (10 ml). The solution was diluted with ethyl acetate (20 ml), washed with water and saturated brine, and dried over anhydrous magnesium sulfate. The solvent was evaporated under reduced pressure, and the obtained residue was recrystallized from a mixed solvent of ethyl acetate/heptane to give the title compound (114 mg) as cotton-like needle crystals.

$^1$H NMR (300 MHz, DMSO-$d_6$) δ0.94 (3H, t, J=7.4 Hz), 1.65 (2H, qt, J=7.4, 7.2 Hz), 3.14 (2H, t, J=7.2 Hz), 4.00 (3H, s), 4.88 (2H, q, J=8.9 Hz), 6.89 (1H, d, J=8.7 Hz), 7.22 (2H, d, J=9.1 Hz), 7.42 (2H, d, J=9.1 Hz), 8.28 (1H, d, J=8.7 Hz).

Example 4

2-ethoxy-7-methoxy-3-[4-(2,2,2-trifluoroethoxy)phenyl]pyrido[2,3-d]pyrimidin-4(3H)-one 7-Methoxy-2-(propylsulfanyl)-3-[4-(2,2,2-trifluoroethoxy)phenyl]pyrido[2,3-d]pyrimidin-4(3H)-one (200 mg)

was dissolved in ethanol (15 ml), sodium ethoxide (20% ethanol solution, 850 mg) was added thereto, and the mixture was stirred at 60° C. for 1 hr. The reaction mixture was poured into 0.2M hydrochloric acid (15 ml), and the precipitated precipitate was collected by filtration, and dissolved in tetrahydrofuran (15 ml). The solution was diluted with ethyl acetate (30 ml), and dried over anhydrous magnesium sulfate. The solvent was evaporated under reduced pressure, and the obtained residue was purified by silica gel column chromatography (ethyl acetate/hexane) to give the title compound (95 mg).

$^1$H NMR (300 MHz, DMSO-$d_6$) δ1.18 (3H, t, J=7.1 Hz), 3.98 (3H, s), 4.43 (2H, q, J=7.1 Hz), 4.85 (2H, q, J=8.9 Hz), 6.81 (1H, d, J=8.7 Hz), 7.17 (2H, d, J=9.0 Hz), 7.35 (2H, d, J=9.0 Hz), 8.24 (1H, d, J=8.7 Hz).

Example 5

7-methoxy-2-(2,2,2-trifluoroethoxy)-3-[4-(2,2,2-trifluoroethoxy)phenyl]pyrido[2,3-d]pyrimidin-4(3H)-one 7-Methoxy-2-(propylsulfanyl)-3-[4-(2,2,2-trifluoroethoxy)phenyl]pyrido[2,3-d]pyrimidin-4(3H)-one (350 mg) and 2,2,2-trifluoroethanol (592 μl) were dissolved in tetrahydrofuran (3 ml), and sodium hydride (60% in oil, 165 mg) was added thereto at room temperature. The reaction mixture was heated under reflux for 3 days, and allowed to be cooled to room temperature, and poured into 0.5M hydrochloric acid (10 ml). The mixture was extracted with ethyl acetate, and the extract was washed with saturated brine, dried over anhydrous magnesium sulfate, and concentrated under reduced pressure. The obtained white solid was purified by silica gel column chromatography (ethyl acetate/hexane) and then (NH, ethyl acetate/hexane) to give the white title compound (63 mg).

$^1$H NMR (300 MHz, DMSO-$d_6$) δ3.99 (3H, s), 4.85 (2H, q, J=8.9 Hz), 5.10 (2H, q, J=8.8 Hz), 6.89 (1H, d, J=8.7 Hz), 7.19 (2H, d, J=9.0 Hz), 7.38 (2H, d, J=9.0 Hz), 8.28 (1H, d, J=8.7 Hz).

Example 6

2-(ethylsulfanyl)-3-[4-(2,2,2-trifluoroethoxy)phenyl]pyrido[2,3-d]pyrimidine-4,7(3H,8H)-dione A mixture of 2-(ethylsulfanyl)-7-methoxy-3-[4-(2,2,2-trifluoroethoxy)phenyl]pyrido[2,3-d]pyrimidin-4(3H)-one (150 mg), pyridine hydrochloride (1156 mg) and N,N-dimethylformamide (1 ml) was stirred at 120° C. for 15 min. The reaction mixture was poured into 0.2M hydrochloric acid (10 ml), and the precipitated white solid was collected by filtration, and washed with water. The obtained solid was dissolved in tetrahydrofuran (5 ml), and the solution was diluted with ethyl acetate (70 ml), washed with saturated brine, and dried over anhydrous magnesium sulfate. The solvent was evaporated under reduced pressure, and the obtained residue was purified by silica gel column chromatography (ethyl acetate/hexane) to give the title compound (137 mg) as a white solid.

$^1$H NMR (300 MHz, DMSO-$d_6$) δ1.26 (3H, t, J=7.4 Hz), 3.10 (2H, q, J=7.3 Hz), 4.86 (2H, q, J=8.9 Hz), 6.28 (1H, d, J=9.5 Hz), 7.20 (2H, d, J=9.1 Hz), 7.38 (2H, d, J=9.1 Hz), 7.83 (1H, d, J=9.5 Hz), 12.29 (1H, brs).

Example 7

2-(ethylsulfanyl)-3-[4-(2,2,2-trifluoroethoxy)phenyl]pyrido[2,3-d]pyrimidine-4,7(3H,8H)-dione sodium salt 2-(Ethylsulfanyl)-3-[4-(2,2,2-trifluoroethoxy)phenyl]pyrido[2,3-d]pyrimidine-4,7(3H,8H)-dione (100 mg) was suspended in methanol (2 ml), sodium methoxide (28% methanol solution, 53.4 mg) was added thereto at room temperature, and the mixture was heated to 30-40° C. to give a transparent solution. The solvent was evaporated under reduced pressure, and the obtained white solid was recrystallized from ethanol/diethyl ether to give the title compound (79 mg) as cotton-like white needle crystals.

$^1$H NMR (300 MHz, DMSO-$d_6$) δ1.22 (3H, t, J=7.3 Hz), 3.02 (2H, q, J=7.3 Hz), 4.85 (2H, q, J=8.9 Hz), 5.88 (1H, d, J=8.8 Hz), 7.14 (2H, d, J=9.0 Hz), 7.25 (2H, d, J=9.0 Hz), 7.52 (1H, d, J=8.9 Hz).

Example 8

2-(ethylsulfanyl)-8-methyl-3-[4-(2,2,2-trifluoroethoxy)phenyl]pyrido[2,3-d]pyrimidine-4,7(3H,8H)-dione 2-(Ethylsulfanyl)-3-[4-(2,2,2-trifluoroethoxy)phenyl]pyrido[2,3-d]pyrimidine-4,7(3H,8H)-dione (120 mg) and iodomethane (37.8 μl) were dissolved in N,N-dimethylformamide (2 ml), sodium hydride (60% in oil, 86 mg) was added thereto under ice-cooling, and the mixture was stirred for 45 min. 0.5M Hydrochloric acid (6 ml) was added thereto under ice-cooling, and the mixture was extracted with ethyl acetate. The extract was washed with water and saturated brine, dried over anhydrous magnesium sulfate, and concentrated under reduced pressure. The obtained white solid residue was purified by silica gel column chromatography (ethyl acetate/hexane) to give the title compound (123 mg) as a white solid.

$^1$H NMR (300 MHz, DMSO-$d_6$) δ1.31 (3H, t, J=7.4 Hz), 3.16 (2H, q, J=7.4 Hz), 3.64 (3H, s), 4.87 (2H, q, J=8.9 Hz), 6.43 (1H, d, J=9.4 Hz), 7.22 (2H, d, J=9.1 Hz), 7.40 (2H, d, J=9.1 Hz), 7.88 (1H, d, J=9.4 Hz).

Example 9

2-ethoxy-3-[4-(2,2,2-trifluoroethoxy)phenyl]pyrido[2,3-d]pyrimidine-4,7(3H,8H)-dione A) 2-(methylsulfanyl)-3-[4-(2,2,2-trifluoroethoxy)phenyl]pyrido[2,3-d]pyrimidine-4,7(3H,8H)-dione 7-Methoxy-2-(methylsulfanyl)-3-[4-(2,2,2-trifluoroethoxy)phenyl]pyrido[2,3-d]pyrimidin-4(3H)-one (1.55 g) and pyridine hydrochloride (3.1 g) were added to N,N-dimethylformamide (20 ml), and the mixture was stirred at 120° C. for 2 hr, and allowed to be cooled. The reaction mixture was poured into 0.5M hydrochloric acid (22 ml), and the white precipitate was collected by filtration, washed with water, and dissolved in tetrahydrofuran (30 ml). The solution was diluted with ethyl acetate (60 ml), dried over anhydrous magnesium sulfate, and concentrated under reduced pressure. The obtained residue was washed with ethyl acetate to give the title compound (1.33 g) as a white solid.

$^1$H NMR (300 MHz, DMSO-$d_6$) δ2.47 (3H, s), 4.87 (2H, q, J=8.9 Hz), 6.29 (1H, d, J=9.4 Hz), 7.21 (2H, d, J=9.1 Hz), 7.40 (2H, d, J=9.1 Hz), 7.84 (1H, d, J=9.4 Hz), 12.31 (1H, s).

B) 2-ethoxy-3-[4-(2,2,2-trifluoroethoxy)phenyl]pyrido[2,3-d]pyrimidine-4,7(3H,8H)-dione 2-(Methylsulfanyl)-3-[4-(2,2,2-trifluoroethoxy)phenyl]pyrido[2,3-d]pyrimidine-4,7(3H,8H)-dione (300 mg) was suspended in ethanol (9 ml), sodium ethoxide (20% ethanol solution, 1.33 g) was added thereto at room temperature, and the mixture was heated under reflux for 3 hr, and allowed to be cooled. The reaction mixture was poured into 0.5M hydrochloric acid (9 ml) under ice-cooling, and the brown precipitate was collected by filtration, washed with water, and dissolved in tetrahydrofuran (100 ml). The solution was diluted with ethyl acetate (150 ml), and dried over anhydrous magnesium sulfate. The solvent was evaporated under reduced pressure, and the obtained brown residue was purified by silica gel column chromatography (ethyl acetate/hexane) and then silica gel column chromatography (NH, methanol/ethyl acetate) to give the title compound (251 mg) as a white solid.

$^1$H NMR (300 MHz, DMSO-$d_6$) δ1.17 (3H, t, J=7.1 Hz), 4.40 (2H, q, J=7.1 Hz), 4.84 (2H, q, J=8.9 Hz), 6.21 (1H, d, J=9.4 Hz), 7.15 (2H, d, J=9.1 Hz), 7.32 (2H, d, J=9.1 Hz), 7.80 (1H, d, J=9.4 Hz), 12.23 (1H, s).

Example 10

2-ethoxy-3-[4-(2,2,2-trifluoroethoxy)phenyl]pyrido[2,3-d]pyrimidine-4,7(3H,8H)-dione sodium salt 2-ethoxy-3-[4-(2,2,2-trifluoroethoxy)phenyl]pyrido[2,3-d]pyrimidine-4,7(3H,8H)-dione (100 mg) was suspended in methanol (3 ml), sodium methoxide (28% methanol solution, 55.7 mg) was added thereto at room temperature, and the mixture was heated to 30-40° C. to give a transparent solution. The solvent was evaporated under reduced pressure, and the obtained white solid was recrystallized from ethanol/diethyl ether to give the title compound (100 mg) as a white powder.

$^1$H NMR (300 MHz, DMSO-$d_6$) δ1.16 (3H, t, J=7.1 Hz), 4.35 (2H, q, J=7.1 Hz), 4.83 (2H, q, J=8.9 Hz), 6.05 (1H, d, J=9.2 Hz), 7.13 (2H, d, J=9.1 Hz), 7.26 (2H, d, J=9.1 Hz), 7.68 (1H, d, J=9.2 Hz).

Example 11

2-(2,2,2-trifluoroethoxy)-3-[4-(2,2,2-trifluoroethoxy)phenyl]pyrido[2,3-d]pyrimidine-4,7(3H,8H)-dione A) 2-(methylsulfinyl)-3-[4-(2,2,2-trifluoroethoxy)phenyl]pyrido[2,3-d]pyrimidine-4,7(3H,8H)-dione 2-(Methylsulfanyl)-3-[4-(2,2,2-trifluoroethoxy)phenyl]pyrido[2,3-d]pyrimidine-4,7(3H,8H)-dione (505 mg) was dissolved in acetic acid (12 ml), and a solution of oxoso (registered mark) (1.05 g) in water (3 ml) was added thereto, and the mixture was stirred at room temperature for 1 hr. To the reaction mixture was added water (50 ml), and the white precipitate was collected by filtration, and washed with diisopropyl ether. The obtained solid was dried under reduced pressure, and subjected to azeotropic distillation with acetonitrile to give the title compound (528 mg) as a white solid.

$^1$H NMR (300 MHz, DMSO-$d_6$) δ2.72 (3H, s), 4.87 (2H, q, J=8.9 Hz), 6.48 (1H, d, J=9.4 Hz), 7.18-7.29 (2H, m), 7.44-7.53 (1H, m), 7.58-7.67 (1H, m), 7.93 (1H, d, J=9.4 Hz), 12.83 (1H, brs).

B) 2-(2,2,2-trifluoroethoxy)-3-[4-(2,2,2-trifluoroethoxy)phenyl]pyrido[2,3-d]pyrimidine-4,7(3H,8H)-dione 2-(Methylsulfinyl)-3-[4-(2,2,2-trifluoroethoxy)phenyl]pyrido[2,3-d]pyrimidine-4,7(3H,8H)-dione (150 mg) was suspended in tetrahydrofuran (5 ml), 2,2,2-trifluoroethanol (108 μl) was added thereto, and then sodium hydride (60% in oil, 37.6 mg) was added thereto under ice-cooling, and the mixture was stirred for 10 min. To the reaction mixture was added 0.5M hydrochloric acid (4 ml), and the mixture was extracted with ethyl acetate. The extract was washed with saturated brine, dried over anhydrous magnesium sulfate, and concentrated under reduced pressure. The obtained white residue was purified by silica gel column chromatography (ethyl acetate/hexane) to give the title compound (128 mg) as a white solid.

$^1$H NMR (300 MHz, DMSO-$d_6$) δ4.85 (2H, q, J=8.9 Hz), 5.03 (2H, q, J=8.7 Hz), 6.28 (1H, d, J=9.4 Hz), 7.18 (2H, d, J=9.1 Hz), 7.35 (2H, d, J=9.1 Hz), 7.84 (1H, d, J=9.4 Hz), 12.39 (1H, s).

Example 12

2-(2,2,2-trifluoroethoxy)-3-[4-(2,2,2-trifluoroethoxy)phenyl]pyrido[2,3-d]pyrimidine-4,7(3H,8H)-dione sodium salt 2-(2,2,2-Trifluoroethoxy)-3-[4-(2,2,2-trifluoroethoxy)phenyl]pyrido[2,3-d]pyrimidine-4,7(3H,8H)-dione (93 mg) was suspended in methanol (3 ml), sodium methoxide (28% methanol solution, 41.2 mg) was added thereto at room temperature, and the mixture was heated to 30-40° C. to give a transparent solution. The solvent was evaporated under reduced pressure, and the obtained white solid was recrystallized from methanol/diethyl ether to give the title compound (84 mg) as a white powder.

$^1$H NMR (300 MHz, DMSO-$d_6$) δ4.83 (2H, q, J=8.9 Hz), 4.97 (2H, q, J=8.9 Hz), 5.89 (1H, d, J=8.9 Hz), 7.13 (2H, d, J=9.1 Hz), 7.23 (2H, d, J=9.1 Hz), 7.53 (1H, d, J=8.9 Hz).

Example 13

2-[3-(methylsulfonyl)propoxy]-3-[4-(2,2,2-trifluoroethoxy)phenyl]pyrido[2,3-d]pyrimidine-4,7(3H,8H)-dione A) 2-(propylsulfanyl)-3-[4-(2,2,2-trifluoroethoxy)phenyl]pyrido[2,3-d]pyrimidine-4,7(3H,8H)-dione A mixture of 7-methoxy-2-(propylsulfanyl)-3-[4-(2,2,2-trifluoroethoxy)phenyl]pyrido[2,3-d]pyrimidin-4(3H)-one (213 mg), pyridine hydrochloride (1156 mg) and N,N-dimethylformamide (10 ml) was stirred at 120° C. for 3 hr. The mixture was allowed to be cooled to room temperature, and to the reaction mixture was added water thereto, and the mixture was extracted with ethyl acetate. The extract was washed with aqueous sodium hydrogen carbonate solution and saturated brine, and dried over anhydrous magnesium sulfate. The solvent was evaporated under reduced pressure. The residue was purified by silica gel column chromatography (ethyl acetate/hexane) to give the title compound (183 mg).

MS (ESI+): [M+H]$^+$ 412.3.

B) 2-[3-(methylsulfanyl)propoxy]-3-[4-(2,2,2-trifluoroethoxy)phenyl]pyrido[2,3-d]pyrimidine-4,7(3H,8H)-dione To a suspension of sodium hydride (60% in oil, 48 mg) in tetrahydrofuran (5 ml) was added 3-(methylsulfanyl)propan- 1-ol (0.206 ml) at room temperature, and the mixture was stirred at room temperature for 10 min. To the reaction mixture was added 2-(propylsulfanyl)-3-[4-(2,2,2-trifluoroethoxy)phenyl]pyrido[2,3-d]pyrimidine-4,7(3H,8H)-dione (165 mg), and the mixture was stirred at room temperature for 5 hr. The reaction mixture was poured into water, and the mixture was extracted with ethyl acetate. The extract was washed with saturated brine, and dried over anhydrous magnesium sulfate. The solvent was evaporated under reduced pressure. The residue was purified by silica gel column chromatography (acetic acid ethyl/hexane) to give the title compound (96 mg).

MS (ESI+): [M+H]$^+$ 442.0.

C) 2-[3-(methylsulfonyl)propoxy]-3-[4-(2,2,2-trifluoroethoxy)phenyl]pyrido[2,3-d]pyrimidine-4,7(3H,8H)-dione To a solution of 2-[3-(methylsulfanyl)propoxy]-3-[4-(2,2,2-trifluoroethoxy)phenyl]pyrido[2,3-d]pyrimidine-4,7(3H,8H)-dione (90 mg) in ethyl acetate was added 3-chloroperbenzoic acid (135 mg) at 0° C., and the mixture was stirred at room temperature for 2 hr. To the reaction mixture was added saturated aqueous sodium hydrogen carbonate solution, and the mixture was extracted with ethyl acetate. The extract was washed with saturated brine, and dried over anhydrous magnesium sulfate. The solvent was evaporated under reduced pressure. The residue was purified by silica gel column chromatography (ethyl acetate/methanol) to give the title compound (70 mg).

Example 14

2-(2,2-difluoro-3-methoxypropoxy)-3-[4-(2,2,2-trifluoroethoxy)phenyl]pyrido[2,3-d]pyrimidine-4,7(3H,8H)-dione A) 2,2-difluoro-3-methoxypropan-1-ol To a solution of 2,2-difluoropropane-1,3-diol (1121 mg) in tetrahydrofuran (20 ml) was added sodium hydride (60% in oil, 320 mg) at room temperature, and the mixture was stirred at room temperature for 10 min. To the reaction mixture was added iodomethane (0.934 ml), and the mixture was stirred at room temperature overnight. To the reaction mixture was added saturated brine, and the mixture was extracted with ethyl acetate. The extract was washed with saturated brine, and dried over anhydrous magnesium sulfate. The solvent was evaporated under reduced pressure. The residue was purified by silica gel column chromatography (ethyl acetate/hexane) to give the title compound (191 mg).

$^1$H NMR (300 MHz, DMSO-d$_6$) δ3.34 (3H, s), 3.53-3.68 (4H, m), 5.50 (1H, t, J=6.2 Hz).

B) 2-(2,2-difluoro-3-methoxypropoxy)-3-[4-(2,2,2-trifluoroethoxy)phenyl]pyrido[2,3-d]pyrimidine-4,7(3H,8H)-dione To a suspension of sodium hydride (60% in oil, 29 mg) in tetrahydrofuran (5 ml) was added 2,2-difluoro-3-methoxypropan-1-ol (151 mg) at room temperature, and the mixture was stirred at room temperature for 10 min. To the reaction mixture was added 2-(propylsulfanyl)-3-[4-(2,2,2-trifluoroethoxy)phenyl]pyrido[2,3-d]pyrimidine-4,7(3H,8H)-dione (165 mg), and the mixture was stirred at room temperature for 5 hr. The reaction mixture was added to water, and the mixture was extracted with ethyl acetate. The extract was washed with saturated brine, and dried over anhydrous magnesium sulfate. The solvent was evaporated under reduced pressure. The residue was purified by silica gel column chromatography (ethyl acetate/hexane), and recrystallized from a mixed solvent of hexane/ethyl acetate to give the title compound (8 mg).

$^1$H NMR (300 MHz, CDCl$_3$) δ3.26-3.43 (5H, m), 4.42 (2H, q, J=8.0 Hz), 4.66 (2H, t, J=12.1 Hz), 6.47 (1H, d, J=9.4 Hz), 7.02-7.14 (2H, m), 7.16-7.24 (2H, m), 8.02 (1H, d, J=9.4 Hz), 10.32 (1H, brs).

Example 15

2-[(4,4-difluorocyclohexyl)oxy]-3-[4-(2,2,2-trifluoroethoxy)phenyl]pyrido[2,3-d]pyrimidine-4,7(3H,8H)-dione To a suspension of sodium hydride (60% in oil, 19 mg) in tetrahydrofuran (5 ml) was added 4,4-difluorocyclohexanol (109 mg) at room temperature, and the mixture was stirred at room temperature for 10 min. To the reaction mixture was added 2-(propylsulfanyl)-3-[4-(2,2,2-trifluoroethoxy)phenyl]pyrido[2,3-d]pyrimidine-4,7(3H,8H)-dione (165 mg), and the mixture was stirred at room temperature for 5 hr. The reaction mixture was added to water, and the mixture was extracted with ethyl acetate. The extract was washed with saturated brine, and dried over anhydrous magnesium sulfate. The solvent was evaporated under reduced pressure. The residue was purified by silica gel column chromatography (ethyl acetate/hexane), and recrystallized from a mixed solvent of hexane/ethyl acetate to give the title compound (75 mg).

$^1$H NMR (300 MHz, DMSO-d$_6$) δ1.43 (2H, brs), 1.78 (6H, brs), 4.84 (2H, q, J=8.7 Hz), 5.19-5.34 (1H, m), 6.21 (1H, d, J=9.4 Hz), 7.10-7.25 (2H, m), 7.30-7.43 (2H, m), 7.82 (1H, d, J=9.4 Hz), 12.24 (1H, s).

Example 16

2-(2,2-difluoroethoxy)-3-[4-(2,2,2-trifluoroethoxy)phenyl]pyrido[2,3-d]pyrimidine-4,7(3H,8H)-dione To a suspension of sodium hydride (60% in oil, 36 mg) in tetrahydrofuran (5 ml) was added 2,2-difluoroethanol (0.095 ml) at room temperature, and the mixture was stirred at room temperature for 10 min. To the reaction mixture was added 2-(propylsulfanyl)-3-[4-(2,2,2-trifluoroethoxy)phenyl]pyrido[2,3-d]pyrimidine-4,7(3H,8H)-dione (123 mg), and the mixture was stirred at room temperature for 5 hr. The reaction mixture was added to water, and the mixture was extracted with ethyl acetate. The extract was washed with saturated brine, and dried over anhydrous magnesium sulfate. The solvent was evaporated under reduced pressure. The residue was purified by silica gel column chromatography (ethyl acetate/hexane), and recrystallized from a mixed solvent of hexane/ethyl acetate to give the title compound (73 mg).

$^1$H NMR (300 MHz, DMSO-d$_6$) δ4.63 (2H, td, J=14.5, 3.4 Hz), 4.84 (2H, q, J=9.0 Hz), 6.08-6.52 (2H, m), 7.12-7.22 (2H, m), 7.27-7.40 (2H, m), 7.83 (1H, d, J=9.4 Hz), 12.33 (1H, s).

Example 17

2-(2,2-difluoro-3-hydroxypropoxy)-3-[4-(2,2,2-trifluoroethoxy)phenyl]pyrido[2,3-d]pyrimidine-4,7(3H,8H)-dione The title compound was obtained in the same manner as in B) of Example 13 and using 2-(propylsulfanyl)-3-[4-(2,2,2-

Example 18

2-methoxy-3-[4-(2,2,2-trifluoroethoxy)phenyl]pyrido[2,3-d]pyrimidine-4,7(3H,8H)-dione 2-(Methylsulfinyl)-3-[4-(2,2,2-trifluoroethoxy)phenyl]pyrido[2,3-d]pyrimidine-4,7(3H,8H)-dione (60 mg) was suspended in tetrahydrofuran (2 ml), sodium methoxide (28% methanol solution, 200 mg) was added thereto under ice-cooling, and the mixture was stirred for 10 min. To the reaction mixture was added 1M hydrochloric acid (3 ml), and the mixture was extracted with ethyl acetate. The extract was washed with saturated brine, dried over anhydrous magnesium sulfate, and concentrated under reduced pressure. The obtained white residue was purified by silica gel column chromatography (ethyl acetate/hexane) to give the title compound (39 mg) as a white solid.

$^1$H NMR (300 MHz, DMSO-d$_6$) δ3.89 (3H, s), 4.83 (2H, q, J=8.9 Hz), 6.22 (1H, d, J=9.4 Hz), 7.16 (2H, d, J=9.1 Hz), 7.32 (2H, d, J=9.1 Hz), 7.81 (1H, d, J=9.4 Hz), 12.28 (1H, s).

Example 19

2-(ethylamino)-3-[4-(2,2,2-trifluoroethoxy)phenyl]pyrido[2,3-d]pyrimidine-4,7(3H,8H)-dione Ethylamine tetrahydrofuran solution (2M, 2 ml) was diluted with tetrahydrofuran (2 ml), 2-(methylsulfinyl)-3-[4-(2,2,2-trifluoroethoxy)phenyl]pyrido[2,3-d]pyrimidine-4,7(3H,8H)-dione (100 mg) was added thereto at room temperature, and the mixture was stirred at room temperature for 10 min. The pH of the reaction mixture was adjusted to about 7 with 0.5M hydrochloric acid (about 4 ml), and the mixture was extracted with ethyl acetate. The extract was washed with saturated brine, dried over anhydrous magnesium sulfate, and concentrated under reduced pressure. The obtained white residue was purified by silica gel column chromatography (ethyl acetate/hexane) to give the title compound (52 mg) as a white solid.

$^1$H NMR (300 MHz, DMSO-d$_6$) δ1.04 (3H, t, J=7.1 Hz), 3.25-3.35 (2H, m), 4.84 (2H, q, J=8.9 Hz), 5.95 (1H, d, J=9.4 Hz), 6.52 (1H, t, J=5.8 Hz), 7.22 (2H, d, J=9.0 Hz), 7.29 (2H, d, J=9.0 Hz), 7.68 (1H, d, J=9.4 Hz), 11.63 (1H, s).

Example 20

2-(1-methylethoxy)-3-[4-(2,2,2-trifluoroethoxy)phenyl]pyrido[2,3-d]pyrimidine-4,7(3H,8H)-dione 2-(Methylsulfinyl)-3-[4-(2,2,2-trifluoroethoxy)phenyl]pyrido[2,3-d]pyrimidine-4,7(3H,8H)-dione (100 mg) was suspended in tetrahydrofuran (4 ml), 2-propanol (77 µl) was added thereto, and then sodium hydride (25.0 mg) was added thereto under ice-cooling, and the mixture was stirred for 10 min, and then at room temperature for 15 min. To the reaction mixture was added 0.5M hydrochloric acid (3 ml), and the mixture was extracted with ethyl acetate. The extract was washed with water and saturated brine, dried over anhydrous magnesium sulfate, and concentrated under reduced pressure. The obtained white residue was purified by silica gel column chromatography (ethyl acetate/hexane) to give the title compound (35.4 mg) as a white solid.

MS (ESI+): [M+H]$^+$ 396.4.

Example 21

2-(methylsulfanyl)-3-[4-(2,2,2-trifluoroethoxy)phenyl]-5,6-dihydropyrido[2,3-d]pyrimidine-4,7(3H,8H)-dione A) diethyl 2-carbamimidoylpentane-1,5-dioate To a solution of ethyl 3-amino-3-iminopropionoate hydrochloride (10 g) and triethylamine (18.4 mL) in ethanol (100 mL) was added ethyl acrylate (7.15 mL), and the mixture was stirred overnight at room temperature. To the reaction mixture was added saturated aqueous sodium hydrogen carbonate solution, and the mixture was extracted with ethyl acetate. The extract was washed with saturated brine, and dried over anhydrous sodium sulfate. The solvent was evaporated under reduced pressure. The residue was purified by silica gel column chromatography (ethyl acetate/hexane) to give the title compound (2.5 g).

$^1$H NMR (300 MHz, DMSO-d$_6$) δ1.11 (3H, t, J=7.2 Hz), 1.17 (3H, t, J=7.2 Hz), 2.15-2.40 (3H, m), 3.91 (2H, q, J=7.2 Hz), 4.02 (2H, q, J=7.2 Hz), 5.66 (2H, s).

B) 2-thioxo-3-[4-(2,2,2-trifluoroethoxy)phenyl]-2,3,5,6-tetrahydropyrido[2,3-d]pyrimidine-4,7(1H,8H)-dione To a solution of 1-isothiocyanato-4-(2,2,2-trifluoroethoxy)benzene (1.77 g) in N,N-dimethylformamide (25 mL) was added sodium hydride (60% in oil, 0.478 g) under ice-cooling. The reaction mixture was stirred for 5 min under ice-cooling, diethyl 2-carbamimidoylpentane-1,5-dioate (2.5 g) was added thereto, and the mixture was stirred for 30 min under ice-cooling. To the reaction mixture was added 1M hydrochloric acid, and the mixture was extracted with ethyl acetate. The extract was washed with saturated brine, and dried over anhydrous sodium sulfate. The solvent was evaporated under reduced pressure. The residue was dissolved in ethanol (25 mL), sodium ethoxide (20% ethanol solution, 10.6 mL) was added thereto, and the mixture was stirred for 30 min. To the reaction mixture was added 1M hydrochloric acid, and the mixture was extracted with ethyl acetate. The extract was washed with saturated brine, and dried over anhydrous sodium sulfate. The solvent was evaporated under reduced pressure. The residue was purified by silica gel column chromatography (ethyl acetate/hexane) to give the title compound (0.75 g).

$^1$H NMR (300 MHz, DMSO-d$_6$) δ2.54-2.62 (4H, m), 4.81 (2H, q, J=9.1 Hz), 7.00-7.20 (4H, m), 9.16 (1H, s), 12.00 (1H, brs).

C) 2-(methylsulfanyl)-3-[4-(2,2,2-trifluoroethoxy)phenyl]-5,6-dihydropyrido[2,3-d]pyrimidine-4,7(3H,8H)-dione To a solution of 2-thioxo-3-[4-(2,2,2-trifluoroethoxy)phenyl]-2,3,5,6-tetrahydropyrido[2,3-d]pyrimidine-4,7(1H,8H)-dione (2.05 g) in acetonitrile (40 mL) were added 1M aqueous sodium hydrogen carbonate solution (5.52 mL) and iodomethane (1.73 mL), and the mixture was stirred at 50° C. for 30 min. To the reaction mixture was added water, and the mixture was extracted with ethyl acetate. The extract was washed with saturated brine, and dried over anhydrous sodium sulfate. The solvent was evaporated under reduced pressure. The residue was purified by silica gel column chromatography (ethyl acetate/hexane) to give the title compound (2.1 g).

¹H NMR (300 MHz, DMSO-$d_6$) δ2.40 (3H, s), 2.45-2.67 (4H, m), 4.86 (2H, q, J=9.1 Hz), 7.13-7.38 (4H, m), 10.45 (1H, s).

Example 22

2-(2,2,2-trifluoroethoxy)-3-[4-(2,2,2-trifluoroethoxy) phenyl]-5,6-dihydropyrido[2,3-d]pyrimidine-4,7(3H, 8H)-dione A) 2-(methylsulfinyl)-3-[4-(2,2,2-trifluoroethoxy) phenyl]-5,6-dihydropyrido[2,3-d]pyrimidine-4,7(3H, 8H)-dione To a solution of 2-(methylsulfanyl)-3-[4-(2,2,2-trifluoroethoxy)phenyl]-5,6-dihydropyrido[2,3-d]pyrimidine-4,7 (3H,8H)-dione (2.1 g) in acetic acid (40 mL) was added a solution of oxone (registered mark) (4.02 g) in water (8 mL). The reaction mixture was stirred at room temperature for 2 hr, water was added thereto, and the precipitate was collected by filtration to give the title compound (1.68 g).

¹H NMR (300 MHz, DMSO-$d_6$) δ2.41-2.80 (7H, m), 4.86 (2H, q, J=9.0 Hz), 7.08-7.59 (4H, m), 10.87 (1H, s).

B) 2-(2,2,2-trifluoroethoxy)-3-[4-(2,2,2-trifluoroethoxy)phenyl]-5,6-dihydropyrido[2,3-d]pyrimidine-4, 7(3H,8H)-dione To a solution of 2,2,2-trifluoroethanol (0.472 mL) in tetrahydrofuran (20 mL) was added sodium hydride (60% in oil, 0.184 g). The reaction mixture was stirred for 5 min, 2-(methylsulfinyl)-3-[4-(2,2,2-trifluoroethoxy)phenyl]-5,6-dihydropyrido[2,3-d]pyrimidine-4,7(3H,8H)-dione (0.88 g) was added thereto, and the mixture was stirred at room temperature for 1 hr. To the reaction mixture was added water, and the mixture was extracted with ethyl acetate. The extract was washed with saturated brine, and dried over anhydrous sodium sulfate. The solvent was evaporated under reduced pressure. The residue was purified by silica gel column chromatography (ethyl acetate/hexane), and recrystallized from ethyl acetate/hexane to give the title compound (0.80 g).

¹H NMR (300 MHz, DMSO-$d_6$) δ2.44-2.68 (4H, m), 4.84 (2H, q, J=8.7 Hz), 4.96 (2H, q, J=8.8 Hz), 7.08-7.36 (4H, m), 10.49 (1H, s).

Example 23

2-ethoxy-3-[4-(2,2,2-trifluoroethoxy)phenyl]-5,6-dihydropyrido[2,3-d]pyrimidine-4,7(3H,8H)-dione To a solution of 2-(methylsulfinyl)-3-[4-(2,2,2-trifluoroethoxy)phenyl]-5,6-dihydropyrido[2,3-d]pyrimidine-4,7(3H, 8H)-dione (0.64 g) in tetrahydrofuran (10 mL) was added sodium ethoxide (20% ethanol solution, 1.56 mL), and the mixture was stirred at room temperature for 1 hr. To the reaction mixture was added water, and the mixture was extracted with ethyl acetate. The extract was washed with saturated brine, and dried over anhydrous sodium sulfate. The solvent was evaporated under reduced pressure. The residue was purified by silica gel column chromatography (ethyl acetate/hexane), and recrystallized from a mixed solvent of ethyl acetate/hexane to give the title compound (0.40 g).

¹H NMR (300 MHz, DMSO-$d_6$) δ1.14 (3H, t, J=7.2 Hz), 2.41-2.64 (4H, m), 4.31 (2H, q, J=7.1 Hz), 4.83 (2H, q, J=8.7 Hz), 7.03-7.34 (4H, m), 10.37 (1H, s).

Example 24

2-(ethylsulfanyl)-3-[4-(2,2,2-trifluoroethoxy)phenyl]-5,6-dihydropyrido[2,3-d]pyrimidine-4,7(3H, 8H)-dione To a solution of 2-thioxo-3-[4-(2,2,2-trifluoroethoxy)phenyl]-2,3,5,6-tetrahydropyrido[2,3-d]pyrimidine-4,7(1H, 8H)-dione (0.1 g) in acetonitrile (2 mL) were added 1M aqueous sodium hydrogen carbonate solution (0.269 mL) and iodoethane (0.109 mL), and the mixture was stirred at 70° C. for 2 hr. The solvent was evaporated under reduced pressure, and the residue was purified by silica gel column chromatography (ethyl acetate/hexane) to give the title compound (0.08 g).

¹H NMR (300 MHz, DMSO-$d_6$) δ1.22 (3H, t, J=7.4 Hz) 2.44-2.67 (4H, m) 3.02 (2H, q, J=7.3 Hz) 4.86 (2H, q, J=8.7 Hz) 7.12-7.37 (4H, m) 10.46 (1H, s).

Example 25

2-(ethylsulfanyl)-3-[4-(2,2,2-trifluoroethoxy)phenyl]-3H-pyrimido[5,4-b][1,4]thiazine-4,7(6H,8H)-dione A) bis(2,4-dimethoxybenzyl)amine A solution of 2,4-dimethoxybenzylamine (8.98 mL) and 2,4-dimethoxybenzaldehyde (9.94 g) in ethanol (200 mL) was stirred at room temperature for 2 hr. To the reaction mixture was added sodium triacetoxyborohydride (20.3 g), and the mixture was stirred at room temperature for 1 hr. To the reaction mixture was added water, the solvent was evaporated under reduced pressure, and the residue was purified by silica gel column chromatography (ethyl acetate/hexane) to give the title compound (8 g).

¹H NMR (300 MHz, DMSO-$d_6$) δ2.01 (1H, brs) 3.55 (4H, s) 3.74 (6H, s) 3.75 (6H, s) 6.46 (2H, dd, J=8.1, 2.3 Hz) 6.51 (2H, d, J=2.3 Hz) 7.18 (2H, d, J=8.1 Hz).

B) ethyl (2E)-3-amino-3-[bis(2,4-dimethoxybenzyl) amino]prop-2-enoate

A mixture of bis(2,4-dimethoxybenzyl)amine (8 g), ethyl 3-ethoxy-3-iminopropanoate (8.02 g), acetic acid (1.44 mL) and ethanol (420 mL) was refluxed overnight. The solvent was evaporated under reduced pressure, and the residue was purified by silica gel column chromatography (ethyl acetate/hexane) to give the title compound (17 g).

¹H NMR (300 MHz, DMSO-$d_6$) δ1.07 (3H, t, J=7.0 Hz) 3.75 (12H, s) 3.85 (2H, q, J=7.2 Hz) 4.26 (4H, s) 6.51 (2H, dd, J=8.3, 2.3 Hz) 6.56 (2H, d, J=2.3 Hz) 6.90 (2H, d, J=8.3 Hz) 7.32 (2H, brs).

C) 6-[bis(2,4-dimethoxybenzyl)amino]-2-thioxo-3-[4-(2,2,2-trifluoroethoxy)phenyl]-2,3-dihydropyrimidin-4(1H)-one To a solution of 1-isothiocyanato-4-(2,2,2-trifluoroethoxy) benzene (3.96 g) in N,N-dimethylformamide (120 mL) was added sodium hydride (60% in oil, 0.68 g) under ice-cooling. The reaction mixture was stirred for 5 min under ice-cooling, ethyl (2E)-3-amino-3-[bis(2,4-dimethoxybenzyl)amino]

prop-2-enoate (7.3 g) was added thereto, and the mixture was stirred for 30 min under ice-cooling. To the reaction mixture was added 1M hydrochloric acid, and the mixture was extracted with ethyl acetate. The extract was washed with saturated brine, and dried over anhydrous sodium sulfate. The solvent was evaporated under reduced pressure. The residue was dissolved in ethanol (120 mL), sodium ethoxide (20% ethanol solution, 14.5 mL) was added thereto, and the mixture was stirred for 1 hr. To the reaction mixture was added 1M hydrochloric acid, and the precipitated solid was collected by filtration to give the title compound (2.8 g).

$^1$H NMR (300 MHz, DMSO-d$_6$) δ3.77 (6H, s) 3.86 (6H, s) 4.51 (4H, s) 4.70-4.91 (3H, m) 6.53 (2H, dd, J=8.3, 2.3 Hz) 6.62 (2H, d, J=2.3 Hz) 7.03-7.15 (6H, m) 11.23 (1H, s).

D) 6-[bis(2,4-dimethoxybenzyl)amino]-2-(ethylsulfanyl)-3-[4-(2,2,2-trifluoroethoxy)phenyl]pyrimidin-4(3H)-one To a solution of 6-[bis(2,4-dimethoxybenzyl)amino]-2-thioxo-3-[4-(2,2,2-trifluoroethoxy)phenyl]-2,3-dihydropyrimidin-4(1H)-one (0.65 g) in acetonitrile (7 mL) were added 1M aqueous sodium hydrogen carbonate solution (1.05 mL) and iodoethane (0.425 mL), and the mixture was stirred at 70° C. for 2 hr. The solvent was evaporated under reduced pressure, and the residue was purified by silica gel column chromatography (ethyl acetate/hexane) to give the title compound (0.68 g).

$^1$H NMR (300 MHz, DMSO-d$_6$) δ1.02 (3H, t, J=7.4 Hz) 2.82 (2H, q, J=7.3 Hz) 3.75 (6H, s) 3.77 (6H, s) 4.83 (2H, q, J=8.7 Hz) 4.96 (1H, s) 6.46-6.64 (4H, m) 6.99 (2H, d, J=8.3 Hz) 7.06-7.28 (4H, m).

E) 6-amino-2-(ethylsulfanyl)-3-[4-(2,2,2-trifluoroethoxy)phenyl]pyrimidin-4(3H)-one A mixture of 6-[bis(2,4-dimethoxybenzyl)amino]-2-(ethylsulfanyl)-3-[4-(2,2,2-trifluoroethoxy)phenyl]pyrimidin-4(3H)-one (0.68 g), anisole (0.459 mL) and trifluoroacetic acid (7 mL) was stirred at room temperature for 1 hr. The solvent was evaporated under reduced pressure, and the residue was purified by silica gel column chromatography (ethyl acetate/hexane) to give the title compound (0.19 g).

$^1$H NMR (300 MHz, DMSO-d$_5$) 51.20 (3H, t, J=7.4 Hz) 2.97 (2H, q, J=7.2 Hz) 4.83 (2H, q, J=8.7 Hz) 4.95 (1H, s) 6.57 (2H, brs) 7.09-7.24 (4H, m).

F) 6-amino-5-bromo-2-(ethylsulfanyl)-3-[4-(2,2,2-trifluoroethoxy)phenyl]pyrimidin-4(3H)-one To a solution of 6-amino-2-(ethylsulfanyl)-3-[4-(2,2,2-trifluoroethoxy)phenyl]pyrimidin-4(3H)-one (0.5 g) and sodium acetate (0.143 g) in acetic acid (10 mL) was added dropwise bromine (0.09 mL), and the mixture was stirred at room temperature for 2 hr. To the reaction mixture was added water, and the precipitated crystals were collected by filtration to give the title compound (0.1 g).

$^1$H NMR (300 MHz, DMSO-d$_6$) δ1.21 (3H, t, J=7.3 Hz) 3.00 (2H, q, J=7.3 Hz) 4.85 (2H, q, J=9.0 Hz) 6.95 (2H, brs) 7.10-7.34 (4H, m).

G) 2-(ethylsulfanyl)-3-[4-(2,2,2-trifluoroethoxy)phenyl]-3H-pyrimido[5,4-b][1,4]thiazine-4,7(6H,8H)-dione A solution of 6-amino-5-bromo-2-(ethylsulfanyl)-3-[4-(2,2,2-trifluoroethoxy)phenyl]pyrimidin-4(3H)-one (0.1 g) and mercaptoacetic acid (0.168 mL) in toluene (2 mL) was stirred at 170° C. for 2 hr under microwave irradiation. To the reaction mixture was added saturated aqueous sodium hydrogen carbonate solution, and the mixture was extracted with ethyl acetate. The extract was washed with saturated brine, and the solvent was evaporated under reduced pressure. The residue was purified by silica gel column chromatography (ethyl acetate/hexane) to give the title compound (0.04 g).

$^1$H NMR (300 MHz, DMSO-d$_6$) δ1.23 (3H, t, J=7.3 Hz) 3.03 (2H, q, J=7.3 Hz) 3.50 (2H, s) 4.86 (2H, q, J=9.0 Hz) 7.19 (2H, d, J=9.0 Hz) 7.34 (2H, d, J=9.0 Hz) 11.06 (1H, s).

Example 26

7-amino-2-(ethylsulfanyl)-3-[4-(2,2,2-trifluoroethoxy)phenyl]pyrido[2,3-d]pyrimidin-4(3H)-one

A) 7-chloro-2-thioxo-3-[4-(2,2,2-trifluoroethoxy)phenyl]pyrido[2,3-d]pyrimidin-4(3H)-one 1-Isothiocyanato-4-(2,2,2-trifluoroethoxy)benzene (4.06 g) was dissolved in N,N-dimethylformamide (50 ml), and sodium hydride (60% in oil, 1.39 g) was added thereto under ice-cooling. Methyl 2-amino-6-chloropyridine-3-carboxylate (2.95 g) was dissolved in N,N-dimethylformamide (25 ml), the solution was added dropwise to the reaction mixture under ice-cooling, and the mixture was stirred for 20 min, and then at room temperature for 1 hr and 30 min. The reaction mixture was poured into 0.5M hydrochloric acid (80 ml), and the white precipitate was collected by filtration. The precipitate was dissolved in tetrahydrofuran (100 ml), and the solution was diluted with ethyl acetate (200 ml), washed with saturated brine, and dried over anhydrous magnesium sulfate. The solvent was evaporated under reduced pressure to give a white residue. The residue was suspended in diethyl ether (100 ml), and the filtrate was concentrated under reduced pressure. The obtained residue was purified by silica gel column chromatography (ethyl acetate/hexane), and washed with diethyl ether to give the white title compound (1.1 g).

$^1$H NMR (300 MHz, DMSO-d$_6$) δ4.83 (2H, q), 7.14 (2H, d, J=9.1 Hz), 7.23 (2H, d, J=9.1 Hz), 7.44 (1H, d, J=8.3 Hz), 8.32 (1H, d, J=8.3 Hz), 13.65 (1H, s).

B) 7-[(4-methoxybenzyl)amino]-2-thioxo-3-[4-(2,2,2-trifluoroethoxy)phenyl]-2,3-dihydropyrido[2,3-d]pyrimidin-4(1H)-one A mixture of 7-chloro-2-thioxo-3-[4-(2,2,2-trifluoroethoxy)phenyl]pyrido[2,3-d]pyrimidin-4(3H)-one (200 mg), 4-methoxybenzylamine (181 µl), copper(I) iodide (57 mg), potassium carbonate (166 mg) and N,N-dimethylformamide (3 ml) was stirred at 130° C. for 2 hr. To the reaction mixture were added saturated aqueous ammonium chloride solution and water, and the precipitate was collected by filtration, and dissolved in tetrahydrofuran. The solution was filtered through celite, and concentrated under reduced pressure. The residue was dissolved in a mixed solvent of ethyl acetate/tetrahydrofuran, and the solution was washed with aqueous ammonia solution and saturated brine, dried over anhydrous magnesium sulfate, and concentrated under reduced pressure. The obtained residue was purified by silica gel column chromatography (ethyl acetate/hexane) to give the white title compound (108 mg).

$^1$H NMR (300 MHz, DMSO-d$_6$) δ3.73 (3H, s), 4.52 (2H, d, J=5.3 Hz), 4.82 (2H, q, J=9.0 Hz), 6.45 (1H, d, J=8.7 Hz), 6.90 (2H, d, J=8.7 Hz), 7.10 (2H, d, J=9.1 Hz), 7.17 (2H, d, J=9.1 Hz), 7.37 (2H, d, J=8.3 Hz), 7.77 (1H, d, J=8.7 Hz), 8.35 (1H, brs), 12.89 (1H, s).

C) 2-(ethylsulfanyl)-7-[(4-methoxybenzyl)amino]-3-[4-(2,2,2-trifluoroethoxy)phenyl]pyrido[2,3-d]pyrimidin-4(3H)-one 7-[(4-Methoxybenzyl)amino]-2-thioxo-3-[4-(2,2,2-trifluoroethoxy)phenyl]-2,3-dihydropyrido[2,3-d]pyrimidin-4(1H)-one (108 mg), iodoethane (53 μl) and 1M aqueous sodium hydroxide solution (220 μl) were added to N,N-dimethylformamide (2 ml), and the mixture was stirred at 50° C. for 1 hr. To the reaction mixture were added 1M hydrochloric acid and water, and the mixture was extracted with ethyl acetate. The extract was washed with water and saturated brine, dried over anhydrous magnesium sulfate, and concentrated under reduced pressure. The obtained residue was purified by silica gel column chromatography (NH, ethyl acetate/hexane) to give the white title compound (63 mg).
$^1$H NMR (300 MHz, DMSO-$d_6$) δ1.24 (3H, t, J=7.3 Hz), 3.09 (2H, q, J=7.5 Hz), 3.73 (3H, s), 4.46-4.66 (2H, m), 4.87 (2H, q, J=8.7 Hz), 6.60 (1H, d, J=8.7 Hz), 6.91 (2H, d, J=8.7 Hz), 7.18 (2H, d, J=9.0 Hz), 7.30 (2H, d, J=8.7 Hz), 7.35 (2H, d, J=9.0 Hz), 7.93 (1H, d, J=8.7 Hz), 8.07 (1H, brs).

D) 7-amino-2-(ethylsulfanyl)-3-[4-(2,2,2-trifluoroethoxy)phenyl]pyrido[2,3-d]pyrimidin-4(3H)-one 2-(Ethylsulfanyl)-7-[(4-methoxybenzyl)amino]-3-[4-(2,2,2-trifluoroethoxy)phenyl]pyrido[2,3-d]pyrimidin-4(3H)-one (63 mg) and anisole (26 μl) were added to trifluoroacetic acid (1 ml), and the mixture was heated under reflux for 1 hr and 30 min. The reaction mixture was basified with saturated aqueous sodium hydrogen carbonate solution, and extracted with ethyl acetate. The extract was washed with water and saturated brine, dried over anhydrous magnesium sulfate, and concentrated under reduced pressure. The obtained residue was purified by silica gel column chromatography (ethyl acetate/hexane) to give the title compound (29 mg) as a white solid.
$^1$H NMR (300 MHz, DMSO-$d_6$) δ1.25 (3H, t, J=7.4 Hz), 3.05 (2H, q, J=7.2 Hz), 4.86 (2H, q, J=8.7 Hz), 6.50 (1H, d, J=8.7 Hz), 7.12 (2H, s), 7.18 (2H, d, J=9.1 Hz), 7.35 (2H, d, J=9.1 Hz), 7.94 (1H, d, J=8.7 Hz).

Example 27

2-(ethylsulfanyl)-4-oxo-3-[4-(2,2,2-trifluoroethoxy)phenyl]-3,4-dihydropyrido[2,3-d]pyrimidine-7-carboxamide A) dimethyl 6-[(4-methoxybenzyl)amino]pyridine-2,5-dicarboxylate The title compound (943 mg) was obtained as a pale-yellow oil in the same manner as in A) of Example 1 and using dimethyl 6-chloropyridine-2,5-dicarboxylate (1.61 g), sodium hydrogen carbonate (882 mg), 4-methoxybenzylamine (1.37 ml), copper(I) iodide (133 mg) and N,N-dimethylformamide (20 ml) and stirring at 80° C. for 3 hr.
$^1$H NMR (300 MHz, DMSO-$d_6$) δ3.72 (3H, s), 3.84 (3H, s), 3.87 (3H, s), 4.62 (2H, s), 6.88 (2H, d, J=8.7 Hz), 7.26 (1H, d, J=7.9 Hz), 7.37 (2H, d, J=8.7), 8.25 (1H, d, J=7.9 Hz), 8.26-8.34 (1H, m).

B) dimethyl 6-aminopyridine-2,5-dicarboxylate

The title compound (491 mg) was obtained as a pale-yellow solid in the same manner as in B) of Example 1 and using dimethyl 6-[(4-methoxybenzyl)amino]pyridine-2,5-dicarboxylate (943 mg), anisole (311 μl) and trifluoroacetic acid (3 ml) and heating under reflux for 1 hr.
$^1$H NMR (300 MHz, DMSO-$d_6$) δ3.84 (6H, s), 7.25 (1H, d, J=7.9 Hz), 7.44 (2H, brs), 8.23 (1H, d, J=7.9 Hz).

C) methyl 2-amino-6-(hydroxymethyl)pyridine-3-carboxylate

Dimethyl 6-aminopyridine-2,5-dicarboxylate (395 mg) was suspended in a mixed solvent (16 ml) of tetrahydrofuran/ethanol (1/1), calcium chloride (834 mg) and sodium borohydride (85.5 mg) were added thereto under ice-cooling, and the mixture was stirred for 2 hr. The reaction mixture was acidified with 1M hydrochloric acid, basified with saturated aqueous potassium carbonate solution, and extracted with ethyl acetate. The extract was washed with water and saturated brine, dried over anhydrous magnesium sulfate, and concentrated under reduced pressure to give the title compound (296 mg) as a white solid.
$^1$H NMR (300 MHz, DMSO-$d_6$) δ3.80 (3H, s), 4.38 (2H, d, J=6.1 Hz), 5.36 (1H, t, J=5.9 Hz), 6.75 (1H, d, J=8.0 Hz), 7.12 (2H, brs), 8.07 (1H, d, J=8.0 Hz).

D) 7-({[tert-butyl(dimethyl)silyl]oxy}methyl)-2-thioxo-3-[4-(2,2,2-trifluoroethoxy)phenyl]-2,3-dihydropyrido[2,3-d]pyrimidin-4(1H)-one A mixture of methyl 2-amino-6-(hydroxymethyl)pyridine-3-carboxylate (296 mg), tert-butyl(chloro)dimethylsilane (298 mg), imidazole (218 mg) and N,N-dimethylformamide (8 ml) was stirred at room temperature for 15 min. To the reaction solution was added water, and the mixture was extracted with ethyl acetate. The extract was washed with water and saturated brine, and dried over anhydrous magnesium sulfate. The solvent was evaporated under reduced pressure to give a white solid. The white solid was added to a mixture of 1-isothiocyanato-4-(2,2,2-trifluoroethoxy)benzene (670 mg), sodium hydride (60% in oil, 132 mg) and N,N-dimethylformamide (15 ml) under ice-cooling, and the mixture was stirred for 30 min. The reaction mixture was acidified with 1M hydrochloric acid, and extracted with ethyl acetate. The extract was washed with water and saturated brine, dried over anhydrous magnesium sulfate, and concentrated under reduced pressure. The obtained residue was purified by silica gel column chromatography (ethyl acetate/hexane) to give the title compound (547 mg) as a white solid.
$^1$H NMR (300 MHz, DMSO-$d_6$) δ-0.14 (6H, s), 0.80 (9H, s), 4.57-4.84 (4H, m), 6.99 (2H, d, J=9.1 Hz), 7.10 (2H, d, J=9.1 Hz), 7.30 (1H, d, J=8.0 Hz), 8.23 (1H, d, J=8.0 Hz), 13.27 (1H, s).

E) 2-(ethylsulfanyl)-7-(hydroxymethyl)-3-[4-(2,2,2-trifluoroethoxy)phenyl]pyrido[2,3-d]pyrimidin-4(3H)-one 7-({[tert-Butyl(dimethyl)silyl]oxy}methyl)-2-thioxo-3-[4-(2,2,2-trifluoroethoxy)phenyl]-2,3-dihydropyrido[2,3-d]pyrimidin-4(1H)-one (498 mg) was suspended in tetrahydrofuran (15 ml), a tetrahydrofuran solution (1M, 3 ml) of tetrabutylammonium fluoride was added thereto, and the mixture was stirred at room temperature for 1 hr. To the reaction mixture was added water, and the mixture was extracted with ethyl acetate. The extract was washed with water and saturated brine, dried over anhydrous magnesium sulfate, and concentrated under reduced pressure. The obtained residue was dissolved in N,N-dimethylformamide (15 ml), iodoethane (0.24 ml) and 1M aqueous sodium hydrogen carbonate solution (1 ml) were added thereto, and the mixture was stirred at room temperature for 1 hr. To the reaction mixture were added 1M hydrochloric acid and water, and the precipitate was collected by filtration, washed with water, and dissolved in tetrahydrofuran. The solution was dried over anhydrous magnesium sulfate, and concentrated under reduced pressure. The residue was recrystallized from a mixed solvent of ethyl acetate/hexane to give the title compound (373 mg) as a white solid.

$^1$H NMR (300 MHz, DMSO-$d_5$) 51.28 (3H, t, J=7.4 Hz), 3.13 (2H, q, J=7.2 Hz), 4.69 (2H, d, J=5.7 Hz), 4.88 (2H, q, J=9.1 Hz), 5.70 (1H, t, J=5.9 Hz), 7.22 (2H, d, J=8.7 Hz), 7.44 (2H, d, J=8.7 Hz), 7.59 (1H, d, J=7.9 Hz), 8.46 (1H, d, J=8.3 Hz).

F) 2-(ethylsulfanyl)-4-oxo-3-[4-(2,2,2-trifluoroethoxy)phenyl]-3,4-dihydropyrido[2,3-d]pyrimidine-7-carbaldehyde 2-(Ethylsulfanyl)-7-(hydroxymethyl)-3-[4-(2,2,2-trifluoroethoxy)phenyl]pyrido[2,3-d]pyrimidin-4(3H)-one (373 mg) and triethylamine (6 ml) were dissolved in dimethyl sulfoxide (18 ml), sulfur trioxide pyridine complex (1.16 g) was added thereto by several portions, and the mixture was stirred at room temperature for 1 hr. To the reaction mixture was added water, and the mixture was extracted with ethyl acetate. The extract was washed with water, 1M hydrochloric acid and saturated brine, dried over anhydrous magnesium sulfate, and concentrated under reduced pressure. The obtained residue was purified by silica gel column chromatography (ethyl acetate/hexane) to give the title compound (299 mg) as a orange solid.

$^1$H NMR (300 MHz, DMSO-$d_6$) δ1.31 (3H, t, J=7.2 Hz), 3.18 (2H, q, J=7.4 Hz), 4.88 (2H, q, J=8.7 Hz), 7.24 (2H, d, J=9.1 Hz), 7.47 (2H, d, J=9.1 Hz), 7.91 (1H, d, J=7.9 Hz), 8.66 (1H, d, J=7.9 Hz), 10.11 (1H, s).

G) 2-(ethylsulfanyl)-4-oxo-3-[4-(2,2,2-trifluoroethoxy)phenyl]-3,4-dihydropyrido[2,3-d]pyrimidine-7-carboxamide To a mixture of 2-(ethylsulfanyl)-4-oxo-3-[4-(2,2,2-trifluoroethoxy)phenyl]-3,4-dihydropyrido[2,3-d]pyrimidine-7-carbaldehyde (299 mg), 2-methylbut-2-ene (387 mg), potassium dihydrogen phosphate (88 mg) and 2-methyl-2-propanol/water (4/1, 70 ml) was added sodium chlorite (232 mg) by small portions, and the mixture was stirred at room temperature for 1 hr. To the reaction mixture were added 1M hydrochloric acid and water under ice-cooling, and the mixture was extracted with tetrahydrofuran. The extract was washed with saturated brine, dried over anhydrous magnesium sulfate, and concentrated under reduced pressure to give a pale-yellow residue. The residue (117 mg) and 1-hydroxybenzotriazole ammonium (40 mg) were dissolved in N,N-dimethylformamide (2 ml), 1-ethyl-3-(3-dimethylaminopropyl)carbodiimide hydrochloride (56 mg) was added thereto, and the mixture was stirred at room temperature for 16 hr. To the reaction mixture was added water, and the mixture was extracted with ethyl acetate. The extract was washed with water, saturated aqueous sodium hydrogen carbonate solution and saturated brine, and dried over anhydrous magnesium sulfate, and the solvent was evaporated under reduced pressure. The obtained residue was purified by silica gel column chromatography (ethyl acetate/hexane) and then (NH, ethyl acetate/hexane), and recrystallized from a mixed solvent of ethyl acetate/hexane to give the white title compound (28 mg).

$^1$H NMR (300 MHz, DMSO-$d_6$) δ1.29 (3H, t, J=7.3 Hz), 3.17 (2H, q, J=7.2 Hz), 4.88 (2H, q, J=8.5 Hz), 7.23 (2H, d, J=9.0 Hz), 7.46 ((2H, d, J=9.0 Hz), 7.87 (1H, s), 8.06 (1H, d, J=7.9 Hz), 8.19 (1H, s), 8.62 (1H, d, J=8.3 Hz).

Example 28

2-(ethylsulfanyl)-3-[4-(2,2,2-trifluoroethoxy)phenyl]-3,5,6,7-tetrahydropyrido[3,4-d]pyrimidine-4,8-dione A) ethyl 4-[(2,4-dimethoxybenzyl)amino]butanoate Ethyl 4-aminobutanoate hydrochloride (1.77 g) and 2,4-dimethoxybenzaldehyde (1.75 g) were dissolved in ethanol (50 ml), and the solution was heated under reflux for 1 hr. The mixture was allowed to be cooled to room temperature, sodium triacetoxyborohydride (2.2 g) was added thereto, and the mixture was stirred for 1 hr, and concentrated under reduced pressure. To the residue was added saturated aqueous sodium hydrogen carbonate solution (40 ml), and the mixture was extracted with ethyl acetate. The extract was washed with saturated brine, and dried over anhydrous magnesium sulfate, and the solvent was evaporated under reduced pressure to give the title compound (2.77 g) as a yellow oil.

$^1$H NMR (300 MHz, DMSO-$d_6$) δ1.16 (3H, t, J=7.2 Hz), 1.66 (2H, tt, J=7.4, 7.0 Hz), 2.31 (2H, t, J=7.4 Hz), 2.47 (2H, t, J=7.0 Hz), 3.57 (2H, s), 3.74 (3H, s), 3.76 (3H, s), 4.03 (2H, q, J=7.2 Hz), 6.46 (1H, dd, J=8.3, 2.5 Hz), 6.52 (1H, d, J=2.5 Hz), 7.16 (1H, d, J=8.3 Hz).

B) ethyl 5-amino-1-(2,4-dimethoxybenzyl)-6-oxo-1,2,3,6-tetrahydropyridine-4-carboxylate To a solution of ethyl 4-[(2,4-dimethoxybenzyl)amino]butanoate (2.77 g) in tetrahydrofuran (40 ml) was added triethylamine (1.78 ml), a solution of methyloxalyl chloride (998 µl) in tetrahydrofuran (5 ml) was added dropwise over 5 min under water bath, and the mixture was stirred at room temperature for 10 min. To the reaction mixture was added ethyl acetate (50 ml), and the white precipitate was removed by filtration, and washed with ethyl acetate (50 ml). The filtrate was washed with saturated aqueous sodium hydrogen carbonate solution and saturated brine, dried over anhydrous magnesium sulfate, and concentrated under reduced pressure. The obtained yellow oil was purified by silica gel column chromatography (ethyl acetate/hexane) to give a yellow oil (2.53 g). The yellow oil (2.14 g) was dissolved in ethanol (15 ml), sodium ethoxide (20% ethanol solution, 4.95 g) was added thereto at room temperature, and the mixture was heated under reflux for 30 min, allowed to be cooled, and concentrated under reduced pressure. The obtained solid residue was dissolved in water (5 ml), and the solution was acidified with 1M hydrochloric acid (16 ml), and extracted with ethyl acetate. The extract was washed with water and saturated brine, dried over anhydrous magnesium sulfate, and concentrated under reduced pressure to give an orange oil. The oil (1.95 g) and ammonium formate (1.8 g) were added to ethanol (20 ml), and the mixture was heated under reflux for 30 min, allowed to be cooled, and concentrated under reduced pressure. The obtained residue was basified with water (10 ml) and saturated aqueous sodium hydrogen carbonate solution (25 ml), and the mixture was extracted with ethyl acetate. The extract was washed with saturated brine, dried over anhydrous magnesium sulfate, and concentrated under reduced pressure. The obtained dark orange oil was purified by silica gel column chromatography (ethyl acetate/hexane) to give the title compound (650 mg) as a colorless oil.

$^1$H NMR (300 MHz, DMSO-d$_6$) δ1.21 (3H, t, J=7.2 Hz), 2.41 (2H, t, J=6.9 Hz), 3.28 (2H, t, J=6.9 Hz), 3.75 (3H, s), 3.78 (3H, s), 4.11 (2H, q, J=7.1 Hz), 4.47 (2H, s), 6.49 (1H, dd, J=8.3, 2.5 Hz), 6.57 (1H, d, J=2.5 Hz), 6.93 (2H, brs), 7.06 (1H, J=8.3 Hz).

C) 7-(2,4-dimethoxybenzyl)-2-thioxo-3-[4-(2,2,2-trifluoroethoxy)phenyl]-1,2,3,5,6,7-hexahydropyrido[3,4-d]pyrimidine-4,8-dione To a solution of 1-isothiocyanato-4-(2,2,2-trifluoroethoxy) benzene (115 mg) in N,N-dimethylformamide (2 ml) was added sodium hydride (60% in oil, 45 mg), and a solution of ethyl 5-amino-1-(2,4-dimethoxybenzyl)-6-oxo-1,2,3,6-tetrahydropyridine-4-carboxylate (150 mg) in N,N-dimethylformamide (2 ml) was added dropwise thereto over 5 min under ice-cooling. The mixture was stirred for 10 min, allowed to be warmed to room temperature, and stirred for 30 min. The reaction mixture was poured into 0.5M hydrochloric acid (4 ml) under ice-cooling, and the mixture was extracted with ethyl acetate. The extract was washed with water and saturated brine, dried over anhydrous magnesium sulfate, and concentrated under reduced pressure. The obtained yellow solid was washed with diethyl ether to give the title compound (70 mg) as beige fine needle crystals.

$^1$H NMR (300 MHz, DMSO-d$_6$) δ2.57 (2H, t), 3.49 (2H, t, J=7.0 Hz), 3.76 (3H, s), 3.81 (3H, s), 4.55 (2H, s), 4.82 (2H, q, J=8.9 Hz), 6.51 (1H, dd, J=8.3, 2.3 Hz), 6.60 (1H, d, J=2.3 Hz), 7.15 (2H, d, J=8.3 Hz), 11.74 (1H, s).

D) 7-(2,4-dimethoxybenzyl)-2-(ethylsulfanyl)-3-[4-(2,2,2-trifluoroethoxy)phenyl]-3,5,6,7-tetrahydropyrido[3,4-d]pyrimidine-4,8-dione To a solution of 7-(2,4-dimethoxybenzyl)-2-thioxo-3-[4-(2,2,2-trifluoroethoxy)phenyl]-1,2,3,5,6,7-hexahydropyrido[3,4-d]pyrimidine-4,8-dione (68 mg) in N,N-dimethylformamide (2 ml) were added 1M aqueous sodium hydroxide solution (140 μl) and iodoethane (11 μl), and the mixture was stirred at room temperature for 30 min. The reaction mixture was poured into 0.5M hydrochloric acid (4 ml), and the mixture was extracted with ethyl acetate. The extract was washed with water and saturated brine, and dried over anhydrous magnesium sulfate. The solvent was evaporated under reduced pressure to give the colorless title compound (72 mg).

$^1$H NMR (300 MHz, DMSO-d$_6$) δ1.24 (3H, t, J=7.3 Hz), 2.66 (2H, t, J=6.9 Hz), 3.08 (2H, q, J=7.3 Hz), 3.49 (2H, t, J=6.9 Hz), 3.76 (3H, s), 3.81 (3H, s), 4.55 (2H, s), 4.86 (2H, q, J=8.9 Hz), 6.51 (1H, dd, J=8.4, 2.4 Hz), 6.59 (1H, d, J=2.4 Hz), 7.13 (1H, d, J=8.4 Hz), 7.20 (2H, d, J=9.1 Hz), 7.34 (2H, d, J=9.1 Hz).

E) 2-(ethylsulfanyl)-3-[4-(2,2,2-trifluoroethoxy)phenyl]-3,5,6,7-tetrahydropyrido[3,4-d]pyrimidine-4,8-dione 7-(2,4-Dimethoxybenzyl)-2-(ethylsulfanyl)-3-[4-(2,2,2-trifluoroethoxy)phenyl]-3,5,6,7-tetrahydropyrido[3,4-d]pyrimidine-4,8-dione (71 mg) was dissolved in formic acid (3 ml), and the solution was stirred at 100° C. for 1 hr, allowed to be cooled to room temperature, and concentrated under reduced pressure. The residue was subjected to azeotropic distillation with toluene. The obtained white solid was purified by silica gel column chromatography (methanol/ethyl acetate) to give the title compound (38 mg) as a white solid.

$^1$H NMR (300 MHz, DMSO-d$_6$) δ1.23 (3H, t, J=7.3 Hz), 2.64 (2H, t, J=6.8 Hz), 3.07 (2H, q, J=7.3 Hz), 3.36 (2H, td, J=6.8, 2.7 Hz), 4.87 (2H, q, J=8.9 Hz), 7.20 (2H, d, J=9.1 Hz), 7.35 (2H, d, J=9.1 Hz), 8.21 (1H, t, J=2.7 Hz).

Example 29

2-(ethylsulfanyl)-3-[4-(2,2,2-trifluoroethoxy)phenyl]-3,7-dihydropyrido[3,4-d]pyrimidine-4,8-dione

A) ethyl 3-amino-1-(2,4-dimethoxybenzyl)-2-oxo-1,2-dihydropyridine-4-carboxylate To a solution of ethyl 5-amino-1-(2,4-dimethoxybenzyl)-6-oxo-1,2,3,6-tetrahydropyridine-4-carboxylate (890 mg) in toluene (20 ml) was added 2,3-dichloro-5,6-dicyano-1,4-benzoquinone (785 mg) at room temperature, and the mixture was heated under reflux for 30 min, allowed to be cooled to room temperature, and diluted with ethyl acetate. The insoluble material was filtered, and the filtrate was concentrated under reduced pressure. The residue was purified by silica gel column chromatography (ethyl acetate/hexane) to give the title compound (535 mg).

$^1$H NMR (300 MHz, DMSO-d$_6$) δ1.28 (3H, t, J=7.2 Hz), 3.74 (3H, s), 3.80 (3H, s), 4.24 (2H, q, J=7.2 Hz), 4.95 (2H, s), 6.41 (1H, d, J=7.6 Hz), 6.47 (1H, dd, J=8.3, 2.6 Hz), 6.58 (1H, d, J=2.3 Hz), 6.75 (1H, d, J=7.6 Hz), 6.88 (2H, brs), 6.98 (1H, d, J=8.3 Hz).

B) 7-(2,4-dimethoxybenzyl)-2-thioxo-3-[4-(2,2,2-trifluoroethoxy)phenyl]-1,2,3,7-tetrahydropyrido[3,4-d]pyrimidine-4,8-dione To a solution of 1-isothiocyanato-4-(2,2,2-trifluoroethoxy) benzene (375 mg) in N,N-dimethylformamide (5 ml) was added sodium hydride (60% in oil, 193 mg) under ice-cooling, and the mixture was cooled to 0° C. A solution of ethyl 3-amino-1-(2,4-dimethoxybenzyl)-2-oxo-1,2-dihydropyridine-4-carboxylate (535 mg) in N,N-dimethylformamide (5 ml) was added dropwise thereto, and the mixture was stirred at 0° C. for 15 min. The reaction mixture was poured into 0.3M hydrochloric acid (15 ml), and the precipitate was collected by filtration. The obtained solid was suspended in toluene, and the suspension was concentrated under reduced pressure. The residue was washed with diisopropyl ether to give the title compound (527 mg).

MS (ESI+): [M+H]$^+$ 520.3.

C) 7-(2,4-dimethoxybenzyl)-2-(ethylsulfanyl)-3-[4-(2,2,2-trifluoroethoxy)phenyl]-3,7-dihydropyrido[3,4-d]pyrimidine-4,8-dione

MS (ESI+): [M+H]$^+$ 548.1.

D) 2-(ethylsulfanyl)-3-[4-(2,2,2-trifluoroethoxy)phenyl]-3,7-dihydropyrido[3,4-d]pyrimidine-4,8-dione 7-(2,4-Dimethoxybenzyl)-2-(ethylsulfanyl)-3-[4-(2,2,2-trifluoroethoxy)phenyl]-3,7-dihydropyrido[3,4-d]pyrimidine-4,8-dione (219 mg) was dissolved in formic acid (5 ml), and the solution was stirred at 100° C. for 3 hr, allowed to be cooled to room temperature, and concentrated under reduced pressure. To the residue was added toluene, and the mixture was again concentrated under reduced pressure. The residue was purified by silica gel column chromatography (NH, methanol/ethyl acetate), and recrystallized from a mixed solvent of ethyl acetate/hexane/methanol to give the title compound (132 mg).

Example 30

2-(propylsulfanyl)-3-[4-(2,2,2-trifluoroethoxy)phenyl]-3,7-dihydropyrido[3,4-d]pyrimidine-4,8-dione The title compound was obtained in the same manner as in C) and D) of Example 29 and using 7-(2,4-dimethoxybenzyl)-2-thioxo-3-[4-(2,2,2-trifluoroethoxy)phenyl]-1,2,3,7-tetrahydropyrido[3,4-d]pyrimidine-4,8-dione and 1-iodopropane.

Example 31

2-(2,2,2-trifluoroethoxy)-3-[4-(2,2,2-trifluoroethoxy)phenyl]-3,7-dihydropyrido[3,4-d]pyrimidine-4,8-dione To a solution of 2,2,2-trifluoroethanol (0.052 ml) in N,N-dimethylformamide (3 ml) was added sodium hydride (60% in oil, 24 mg) at room temperature, and the mixture was stirred for 5 min. A solution of 2-(propylsulfanyl)-3-[4-(2,2,2-trifluoroethoxy)phenyl]-3,7-dihydropyrido[3,4-d]pyrimidine-4,8-dione (535 mg) in N,N-dimethylformamide (3 ml) was added to the reaction mixture, and the mixture was stirred at 60° C. for 4 hr. The reaction mixture was allowed to be cooled to room temperature, saturated brine was added thereto, and the mixture was extracted with ethyl acetate. The extract was washed with saturated brine, and dried over anhydrous magnesium sulfate. The solvent was evaporated under reduced pressure. The residue was purified by silica gel column chromatography (NH, methanol/ethyl acetate), and recrystallized from a mixed solvent of ethyl acetate/hexane to give the title compound (8 mg).

Example 32

2-ethoxy-3-[4-(2,2,2-trifluoroethoxy)phenyl]-3,7-dihydropyrido[3,4-d]pyrimidine-4,8-dione To a solution of 2-(propylsulfanyl)-3-[4-(2,2,2-trifluoroethoxy)phenyl]-3,7-dihydropyrido[3,4-d]pyrimidine-4,8-dione (535 mg) in N,N-dimethylformamide (5 ml) was added sodium ethoxide (20% ethanol solution, 0.863 ml), and the mixture was stirred at 60° C. for 4 hr. The reaction mixture was allowed to be cooled to room temperature, saturated brine was added thereto, and the mixture was extracted with ethyl acetate. The extract was washed with saturated brine, and dried over anhydrous magnesium sulfate. The solvent was evaporated under reduced pressure. The residue was purified by silica gel column chromatography (NH, methanol/ethyl acetate) to give the title compound (140 mg).

Example 33

2-(ethylsulfanyl)-8-methoxy-3-[4-(2,2,2-trifluoroethoxy)phenyl]pyrido[3,4-d]pyrimidin-4(3H)-one To a mixture of 2-(ethylsulfanyl)-3-[4-(2,2,2-trifluoroethoxy)phenyl]-3,7-dihydropyrido[3,4-d]pyrimidine-4,8-dione (40 mg) and (trifluoromethyl)benzene (10 ml) was added trimethyloxonium tetrafluoroborate (22 mg) at room temperature, and the reaction mixture was heated under reflux for 3 hr, allowed to be cooled to room temperature, and diluted with ethyl acetate. The reaction mixture was washed successively with water and saturated brine, and dried over anhydrous magnesium sulfate. The solvent was evaporated under reduced pressure. The residue was purified by silica gel column chromatography (ethyl acetate/hexane), and recrystallized from a mixed solvent of ethyl acetate/hexane to give the title compound (16 mg).

Example 34

2-ethoxy-8-(2-methoxyethoxy)-3-[4-(2,2,2-trifluoroethoxy)phenyl]pyrido[3,4-d]pyrimidin-4(3H)-one A) 8-chloro-3-[4-(2,2,2-trifluoroethoxy)phenyl]pyrido[3,4-d]pyrimidine-2,4(1H,3H)-dione A mixture of 2-ethoxy-3-[4-(2,2,2-trifluoroethoxy)phenyl]-3,7-dihydropyrido[3,4-d]pyrimidine-4,8-dione (763 mg) and phosphorus oxychloride (10 ml) was stirred at 100° C. for 5 hr, allowed to be cooled to room temperature, and concentrated under reduced pressure. To the residue was added toluene, and the mixture was again concentrated under reduced pressure. The residue was purified by silica gel column chromatography (hexane/ethyl acetate) to give the title compound (437 mg).
$^1$H NMR (300 MHz, DMSO-d$_6$) δ4.75-4.90 (2H, m), 7.17 (2H, d, J=9.0 Hz), 7.30 (2H, d, J=9.0 Hz), 7.85 (1H, d, J=5.3 Hz), 8.24 (1H, d, J=4.9 Hz), 11.43 (1H, s).

B) 8-chloro-2-ethoxy-3-[4-(2,2,2-trifluoroethoxy)phenyl]pyrido[3,4-d]pyrimidin-4(3H)-one To a mixture of 8-chloro-3-[4-(2,2,2-trifluoroethoxy)phenyl]pyrido[3,4-d]pyrimidine-2,4(1H,3H)-dione (437 mg), iodoethane (0.19 ml) and N,N-dimethylformamide (10 ml) was added potassium carbonate (326 mg) at room temperature, and the mixture was stirred at 80° C. for 15 hr, and allowed to be cooled to room temperature. To the reaction mixture was added water, and the mixture was extracted with ethyl acetate. The extract was washed with saturated brine, and dried over anhydrous magnesium sulfate. The solvent was evaporated under reduced pressure. The residue was purified by silica gel column chromatography (methanol/ethyl acetate) to give the title compound (116 mg).
MS (ESI+): [M+H]$^+$ 400.0.

C) 2-ethoxy-8-(2-methoxyethoxy)-3-[4-(2,2,2-trifluoroethoxy)phenyl]pyrido[3,4-d]pyrimidin-4(3H)-one To a solution of 2-methoxyethanol (0.019 ml) in N,N-dimethylformamide (3 ml) was added sodium hydride (60% in oil, 9 mg) at room temperature, and the mixture was stirred for 30 min. 8-Chloro-2-ethoxy-3-[4-(2,2,2-trifluoroethoxy)phenyl]pyrido[3,4-d]pyrimidin-4(3H)-one (80 mg) was added to reaction mixture, and the mixture was stirred at 60° C., for 5 hr, and allowed to be cooled to room temperature. To the reaction mixture was added water, and the mixture was extracted with ethyl acetate. The extract was washed with saturated brine, and dried over anhydrous magnesium sulfate. The solvent was evaporated under reduced pressure. The residue was purified by silica gel column chromatography (ethyl acetate/hexane). The obtained residue was suspended in a mixed solvent of ethyl acetate/hexane, and the resulting solid was collected by filtration to give the title compound (21 mg).

Example 35

2,8-bis(2-methoxyethoxy)-3-[4-(2,2,2-trifluoroethoxy)phenyl]pyrido[3,4-d]pyrimidin-4(3H)-one The title compound (6 mg) was obtained as a by-product in C) of Example 34.

Example 36

2-(ethylsulfanyl)-7-methyl-3-[4-(2,2,2-trifluoroethoxy)phenyl]-3,7-dihydropyrido[3,4-d]pyrimidine-4,8-dione To a solution of 2-(ethylsulfanyl)-3-[4-(2,2,2-trifluoroethoxy)phenyl]-3,7-dihydropyrido[3,4-d]pyrimidine-4,8-dione (40 mg) in N,N-dimethylformamide (5 ml) was added sodium hydride (60% in oil, 193 mg) at room temperature, and the mixture was stirred for 10 min. To the reaction mixture was added iodomethane (0.009 ml), and the mixture was stirred at room temperature for 3 hr. To the reaction mixture was added water, and the precipitate was collected by filtration. The obtained solid was suspended in toluene, and the suspension was concentrated under reduced pressure. The residue was recrystallized from a mixed solvent of hexane/ethyl acetate/methanol to give the title compound (33 mg).

Example 37

2-(ethylsulfanyl)-7-methoxy-3-[4-(2,2,2-trifluoroethoxy)phenyl]pteridin-4(3H)-one A) 7-methoxy-2-thioxo-3-[4-(2,2,2-trifluoroethoxy)phenyl]-2,3-dihydropteridinee-4(1H)-one The title compound (122 mg) was obtained as a beige solid in the same manner as in F) of Example 1 and using 1-isothiocyanato-4-(2,2,2-trifluoroethoxy)benzene (88 mg), sodium hydride (60% in oil, 37.7 mg) and methyl 3-amino-5-methoxypyrazine-2-carboxylate (68 mg).
$^1$H NMR (300 MHz, DMSO-$d_6$) δ 4.05 (3H, s), 4.83 (2H, q, J=8.9 Hz), 7.14 (2H, d, J=9.0 Hz), 7.22 (2H, d, J=9.0 Hz), 8.26 (1H, s), 13.56 (1H, s).

B) 2-(ethylsulfanyl)-7-methoxy-3-[4-(2,2,2-trifluoroethoxy)phenyl]pteridin-4(3H)-one The title compound (110 mg) was was obtained as a white solid in the same manner as in G) of Example 1 and using 7-methoxy-2-thioxo-3-[4-(2,2,2-trifluoroethoxy)phenyl]-2,3-dihydropteridinee-4(1H)-one (135 mg), 1M aqueous sodium hydrogen carbonate solution (351 μl), iodoethane (142 μl) and acetonitrile (6 ml).
$^1$H NMR (300 MHz, DMSO-$d_6$) δ 1.27 (3H, t, J=7.4 Hz), 3.15 (2H, q, J=7.4 Hz), 4.06 (3H, s), 4.88 (2H, q, J=8.9 Hz), 7.23 (2H, d, J=9.0 Hz), 7.44 (2H, d, J=9.0 Hz), 8.38 (1H, s).

Example 38

2-(ethylsulfanyl)-3-[4-(2,2,2-trifluoroethoxy)phenyl]pteridine-4,7(3H,8H)-dione

A mixture of 2-(ethylsulfanyl)-7-methoxy-3-[4-(2,2,2-trifluoroethoxy)phenyl]pteridin-4(3H)-one (92 mg), pyridine hydrochloride (640 mg) and N,N-dimethylformamide (3 ml) was stirred at 120° C. for 10 hr, and in the same manner as in Example 6, the title compound (50 mg) was obtained as a white powder.
$^1$H NMR (300 MHz, DMSO-$d_6$) δ 1.26 (3H, t, J=7.4 Hz), 3.10 (2H, q, J=7.4 Hz), 4.87 (2H, q, J=8.8 Hz), 7.22 (2H, d, J=9.0 Hz), 7.39 (2H, d, J=9.0 Hz), 7.89 (1H, s), 13.04 (1H, s).

Example 39

3-[4-(2,2,2-trifluoroethoxy)phenyl]-2-(3,3,3-trifluoropropyl)-5,6-dihydropyrido[2,3-d]pyrimidine-4,7(3H,8H)-dione A) 4,4,4-trifluorobutanamide To a solution of 4,4,4-trifluorobutanoic acid (19.9 g) in THF (200 mL) were added oxalyl chloride (30.5 mL) and DMF (0.54 mL) at 0° C., and the mixture was stirred for 4 hr. The obtained reaction mixture was added to 28% aqueous ammonia (150 mL) at 0° C., and the mixture was stirred for 1 hr. The reaction mixture was filtration, and the filtrate was extracted with ethyl acetate. The extract was washed with saturated brine, dried over magnesium sulfate, and concentrated under reduced pressure. The obtained solid was suspended in diisopropyl ether. The precipitate was collected by filtration, washed with diisopropyl ether, and dried to give the title compound (17.9 g) as a solid.
$^1$H NMR (300 MHz, DMSO-$d_6$) δ 2.27-2.35 (2H, m), 2.37-2.55 (2H, m), 6.96 (1H, brs), 7.44 (1H, brs).

B) 4,4,4-trifluorobutanethioamide

A mixture of 4,4,4-trifluorobutanamide (17.9 g), 2,4-bis(4-methoxyphenyl)-1,3,2,4-dithiadiphosphetane 2,4-disulfide (51.3 g) and toluene (400 mL) was stirred at 80° C. for 3 hr. The reaction mixture was purified by aminopropylsilane-bonded silica gel column chromatography (ethyl acetate), and again purified by aminopropylsilane-bonded silica gel column chromatography (ethyl acetate/hexane) to give the title compound (14.6 g) as a solid.
$^1$H NMR (300 MHz, DMSO-$d_6$) δ 2.59-2.79 (4H, m), 9.37 (1H, brs), 9.60 (1H, brs).

C) methyl 4,4,4-trifluorobutanimidethioate iodate

To a solution of 4,4,4-trifluorobutanethioamide (8.27 g) in acetone (160 mL) was added iodomethane (16.4 mL) at room temperature, and the mixture was stirred at 40° C. for 3 hr. The reaction mixture was concentrated under reduced pressure to give the title compound (15.4 g) as a solid.
$^1$H NMR (300 MHz, DMSO-$d_6$) δ 2.68 (3H, s), 2.72-2.87 (2H, m), 3.02-3.10 (2H, m), 11.64 (2H, brs).

D) 4,4,4-trifluoro-N-[4-(2,2,2-trifluoroethoxy)phenyl]butanimidamide

A mixture of methyl 4,4,4-trifluorobutanimidethioate iodate (15.3 g), 4-(2,2,2-trifluoroethoxy)aniline (8.90 g) and ethanol (150 mL) was stirred at room temperature for 2 hr. To the reaction mixture were added ethyl acetate and saturated aqueous sodium hydrogen carbonate solution, and the mixture was extracted with ethyl acetate. The extract was washed with saturated brine, dried over magnesium sulfate, and concentrated under reduced pressure. The residue was subjected to aminopropylsilane-bonded silica gel column chromatography (ethyl acetate/hexane) to give the title compound (10.9 g) as a solid.

MS (ESI+): [M+H]$^+$ 315.1.

E) 6-hydroxy-3-[4-(2,2,2-trifluoroethoxy)phenyl]-2-(3,3,3-trifluoropropyl)pyrimidin-4(3H)-one A mixture of 4,4,4-trifluoro-N-[4-(2,2,2-trifluoroethoxy)phenyl]butanimidamide (20.9 g), diethyl malonate (20.2 mL), sodium methoxide (10.8 g) and 2-methoxyethanol (400 mL) was heated under reflux overnight, and the reaction mixture was concentrated under reduced pressure. Similarly, a mixture of 4,4,4-trifluoro-N-[4-(2,2,2-trifluoroethoxy)phenyl]butanimidamide (22.6 g), diethyl malonate (21.8 mL), sodium methoxide (11.7 g) and 2-methoxyethanol (400 mL) was heated under reflux overnight, and the reaction mixture was concentrated under reduced pressure. The obtained residues were combined, and partitioned between diethyl ether and water. The aqueous layer was separated, to the organic layer was added 1N hydrochloric acid, and the mixture was extracted with ethyl acetate. The extract was washed with saturated brine, dried over magnesium sulfate, and concentrated under reduced pressure. The obtained solid was suspended in diisopropyl ether. The precipitate was collected by filtration, washed with diisopropyl ether, and dried to give the title compound (41.6 g) as a solid.

MS (ESI+): [M+H]$^+$ 383.1.

F) 6-oxo-1-[4-(2,2,2-trifluoroethoxy)phenyl]-2-(3,3,3-trifluoropropyl)-1,6-dihydropyrimidin-4-yl trifluoromethanesulfonate To a solution of 6-hydroxy-3-[4-(2,2,2-trifluoroethoxy)phenyl]-2-(3,3,3-trifluoropropyl)pyrimidin-4(3H)-one (2.63 g) and triethylamine (1.44 mL) in THF (50 mL) was added 1,1,1-trifluoro-N-phenyl-N-[(trifluoromethyl)sulfonyl]methanesulfonamide (2.46 g) at 0° C., and the mixture was stirred at room temperature overnight. To the reaction mixture was added ice-cooled saturated brine, and the mixture was extracted with ethyl acetate. The extract was washed with saturated brine, dried over magnesium sulfate, and concentrated under reduced pressure. The residue was purified by silica gel column chromatography (ethyl acetate/hexane) to give the title compound (3.21 g) as a solid.

MS (ESI+): [M+H]$^+$ 515.2.

G) 6-amino-3-[4-(2,2,2-trifluoroethoxy)phenyl]-2-(3,3,3-trifluoropropyl)pyrimidin-4(3H)-one To a solution of tris(dibenzylideneacetone)dipalladium(0) (537 mg), 4,5-bis(diphenylphosphino)-9,9-dimethylxanthene (679 mg) in toluene (50 mL) were added 6-oxo-1-[4-(2,2,2-trifluoroethoxy)phenyl]-2-(3,3,3-trifluoropropyl)-1,6-dihydropyrimidin-4-yl trifluoromethanesulfonate (5.03 g), 1,1-diphenylmethanimine (1.97 mL) and cesium carbonate (7.97 g) at room temperature, and the mixture was stirred overnight at 100° C. The reaction mixture was concentrated under reduced pressure. To the residue was added THF, and the insoluble material was removed by filtration. The filtrate was concentrated under reduced pressure. To a solution of the obtained residue in THF (100 mL) was added 1N hydrochloric acid (100 mL) at 0° C., and the mixture was stirred for 2 hr. The reaction mixture was extracted with ethyl acetate, and the extract was washed with saturated brine, dried over magnesium sulfate, and concentrated under reduced pressure. The residue was subjected to aminopropylsilane-bonded silica gel column chromatography (ethyl acetate/hexane) and then silica gel column chromatography (ethyl acetate/hexane) to give the title compound (2.64 g) as a solid.

MS (ESI+): [M+H]$^+$ 382.1.

H) 3-[4-(2,2,2-trifluoroethoxy)phenyl]-2-(3,3,3-trifluoropropyl)-5,6-dihydropyrido[2,3-d]pyrimidine-4,7(3H,8H)-dione A solution of 6-amino-3-(4-(2,2,2-trifluoroethoxy)phenyl)-2-(3,3,3-trifluoropropyl)pyrimidin-4(3H)-one (1.0 g) in N,N-dimethylacetamide (30 mL) was heated to 60° C., acryloyl chloride (0.85 mL) was added thereto, and the mixture was stirred for 10 min. To the reaction mixture was added water under ice-cooling, and the mixture was extracted with ethyl acetate. The extract was dried over magnesium sulfate, and concentrated under reduced pressure. The residue was purified by silica gel column chromatography (ethyl acetate/hexane), diolpropylsilane-bonded silica gel column chromatography (ethyl acetate/hexane) and then silica gel column chromatography (ethyl acetate/hexane). The obtained solid was recrystallized from ethyl acetate-hexane to give the title compound (0.72 g) as a solid. The solid (487 mg) was recrystallized from ethyl acetate to give the title compound (300 mg) as a solid.

$^1$H NMR (300 MHz, CDCl$_3$) δ 2.45-2.62 (4H, m), 2.62-2.73 (2H, m), 2.79-2.93 (2H, m), 4.42 (2H, q, J=7.9 Hz), 7.03-7.20 (4H, m), 7.42 (1H, s).

Example 40

2-propyl-3-[4-(2,2,2-trifluoroethoxy)phenyl]-5,6-dihydropyrido[2,3-d]pyrimidine-4,7(3H,8H)-dione A)
N-[4-(2,2,2-trifluoroethoxy)phenyl]butanimidamide A mixture of ethyl butylimidate hydrochloride (10.0 g), 4-(2,2,2-trifluoroethoxy)aniline (12.6 g), triethylamine (6.67 g) and THF (250 mL) was stirred at 70° C. for 2 days. To the reaction mixture were added ethyl acetate and water, and the mixture was extracted with ethyl acetate. The extract was washed with saturated brine, dried over magnesium sulfate, and concentrated under reduced pressure. The residue was subjected to aminopropylsilane-bonded silica gel column chromatography (ethyl acetate/hexane) to give the title compound (4.80 g) as a solid.

MS (ESI+): [M+H]$^+$ 261.4.

B) 6-hydroxy-2-propyl-3-[4-(2,2,2-trifluoroethoxy)phenyl]pyrimidin-4(3H)-one

In the same manner as in Step E of Example, the title compound was obtained. MS (ESI+): [M+H]$^+$ 329.3.

C) 6-oxo-2-propyl-1-[4-(2,2,2-trifluoroethoxy)phenyl]-1,6-dihydropyrimidin-4-yl trifluoromethanesulfonate In the same manner as in Step F of Example, the title compound was obtained.

$^1$H NMR (300 MHz, DMSO-d$_6$) δ 0.80 (3H, t, J=7.3 Hz), 1.40-1.70 (2H, m), 2.31 (2H, t, J=7.3 Hz), 4.86 (2H, q, J=9.0 Hz), 6.62 (1H, s), 7.23 (2H, d, J=9.0 Hz), 7.43 (2H, d, J=9.0 Hz).

D) 6-[(4-methoxybenzyl)amino]-2-propyl-3-[4-(2,2,2-trifluoroethoxy)phenyl]pyrimidin-4(3H)-one To a solution of palladium(II) acetate (49.0 mg) and 4,5-bis(diphenylphosphino)-9,9-dimethylxanthene (189 mg) in toluene (20 mL) were added 6-oxo-2-propyl-1-[4-(2,2,2-trifluoroethoxy)phenyl]-1,6-dihydropyrimidin-4-yl trifluoromethanesulfonate (1.0 g), 4-methoxybenzylamine (0.43 mL) and cesium carbonate (1.77 g) at room temperature, and the mixture was stirred at 100° C. for 3 hr. To the reaction mixture were added ethyl acetate and water, and the mixture was extracted with ethyl acetate. The extract was washed with saturated brine, dried over magnesium sulfate, and concentrated under reduced pressure. The residue was subjected to aminopropylsilane-bonded silica gel column chromatography (ethyl acetate/hexane) to give the title compound (462 mg) as a solid.

MS (ESI+): [M+H]$^+$ 448.3.

E) 6-amino-2-propyl-3-[4-(2,2,2-trifluoroethoxy)phenyl]pyrimidin-4(3H)-one

A solution (3 mL) of 6-[(4-methoxybenzyl)amino]-2-propyl-3-[4-(2,2,2-trifluoroethoxy)phenyl]pyrimidin-4(3H)-one (400 mg) in trifluoroacetic acid was stirred with microwave irradiation at 100° C. for 30 min. The reaction mixture was concentrated under reduced pressure, and the residue was subjected to aminopropylsilane-bonded silica gel column chromatography (ethyl acetate/hexane) to give the title compound (270 mg) as a solid.

MS (ESI+): [M+H]$^+$ 328.1.

F) 2-propyl-3-[4-(2,2,2-trifluoroethoxy)phenyl]-5,6-dihydropyrido[2,3-d]pyrimidine-4,7(3H,8H)-dione To a solution of 6-amino-2-propyl-3-[4-(2,2,2-trifluoroethoxy)phenyl]pyrimidin-4(3H)-one (270 mg) in N,N-dimethylacetamide (15 mL) was added acryloyl chloride (0.20 mL) at 0° C., and the mixture was stirred for 30 min, and then at room temperature overnight. To the reaction mixture was added potassium carbonate (570 mg) at room temperature, and the mixture was stirred for 1 hr. To the reaction mixture was added saturated aqueous ammonium chloride solution under ice-cooling, and the mixture was extracted with a mixed solvent of ethyl acetate and THF. The extract was dried over magnesium sulfate, and concentrated under reduced pressure. The residue was purified by silica gel column chromatography (ethyl acetate/hexane) to give the title compound (59.6 mg) as a solid.

The chemical name, structural formula and MS of the compounds of Examples are shown in Table 1 to Table 4.

TABLE 1

| Example No. | IUPAC Name | Structure | Salt | MS (ESI+) |
|---|---|---|---|---|
| 1 | 2-(ethylsulfanyl)-7-methoxy-3-[4-(2,2,2-trifluoroethoxy)phenyl]pyrido[2,3-d]pyrimidin-4(3H)-one | 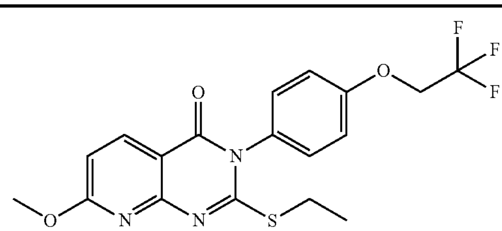 | — | 412.1 |
| 2 | 7-methoxy-2-(methylsulfanyl)-3-[4-(2,2,2-trifluoroethoxy)phenyl]pyrido[2,3-d]pyrimidin-4(3H)-one | 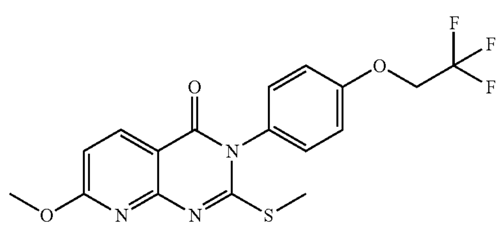 [SMILES: COc1ccc2c(=O)n(-c3ccc(OCC(F)(F)F)cc3)c(SC)nc2n1] | — | 397.9 |
| 3 | 7-methoxy-2-(propylsulfanyl)-3-[4-(2,2,2-trifluoroethoxy)phenyl]pyrido[2,3-d]pyrimidin-4(3H)-one | 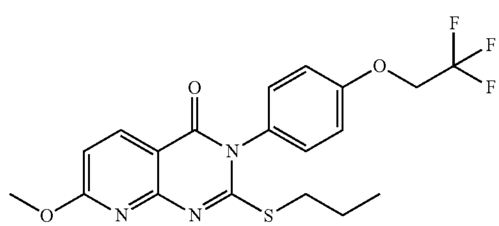 [SMILES: CCCSc1nc2nc(OC)ccc2c(=O)n1-c1ccc(OCC(F)(F)F)cc1] | — | 425.9 |
| 4 | 2-ethoxy-7-methoxy-3-[4-(2,2,2-trifluoroethoxy)phenyl]pyrido[2,3-d]pyrimidin-4(3H)-one | 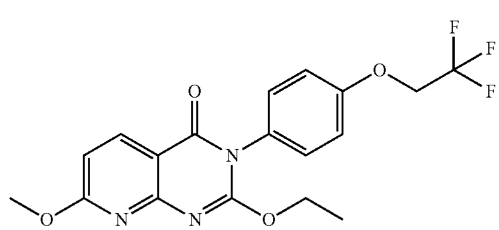 [SMILES: CCOc1nc2nc(OC)ccc2c(=O)n1-c1ccc(OCC(F)(F)F)cc1] | — | 396.1 |

TABLE 1-continued

| Example No. | IUPAC Name | Structure | Salt | MS (ESI+) |
|---|---|---|---|---|
| 5 | 7-methoxy-2-(2,2,2-trifluoroethoxy)-3-[4-(2,2,2-trifluoroethoxy)phenyl]pyrido[2,3-d]pyrimidin-4(3H)-one | 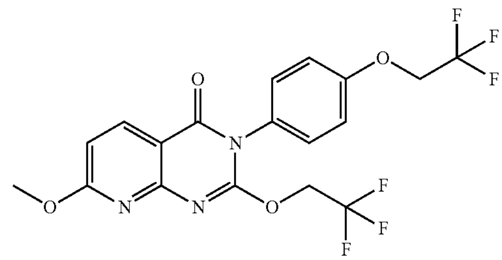 [SMILES: COc1ccc2c(=O)n(-c3ccc(OCC(F)(F)F)cc3)c(OCC(F)(F)F)nc2n1] | — | 450.2 |
| 6 | 2-(ethylsulfanyl)-3-[4-(2,2,2-trifluoroethoxy)phenyl]pyrido[2,3-d]pyrimidine-4,7(3H,8H)-dione | 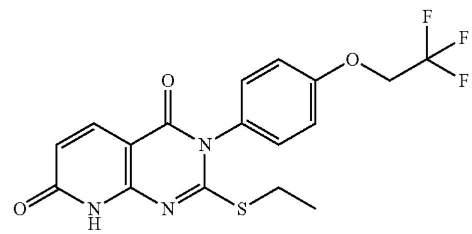 | — | 398.0 |
| 7 | 2-(ethylsulfanyl)-3-[4-(2,2,2-trifluoroethoxy)phenyl]pyrido[2,3-d]pyrimidine-4,7(3H,8H)-dione | 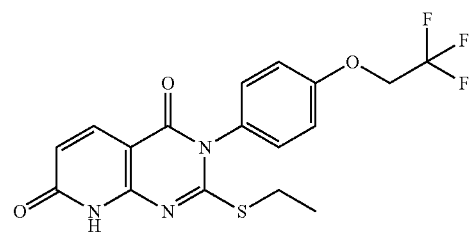 | Na-salt | 398.2 |
| 8 | 2-(ethylsulfanyl)-8-methyl-3-[4-(2,2,2-trifluoroethoxy)phenyl]pyrido[2,3-d]pyrimidine-4,7(3H,8H)-dione | 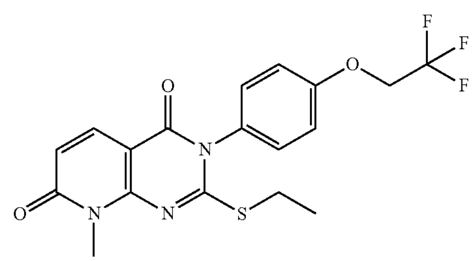 [SMILES: CCSc1nc2c(ccc(=O)n2C)c(=O)n1-c1ccc(OCC(F)(F)F)cc1] | — | 412.3 |
| 9 | 2-ethoxy-3-[4-(2,2,2-trifluoroethoxy)phenyl]pyrido[2,3-d]pyrimidine-4,7(3H,8H)-dione | 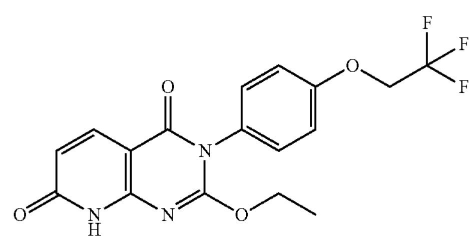 [SMILES: CCOc1nc2[nH]c(=O)ccc2c(=O)n1-c1ccc(OCC(F)(F)F)cc1] | — | 382.2 |
| 10 | 2-ethoxy-3-[4-(2,2,2-trifluoroethoxy)phenyl]pyrido[2,3-d]pyrimidine-4,7(3H,8H)-dione | 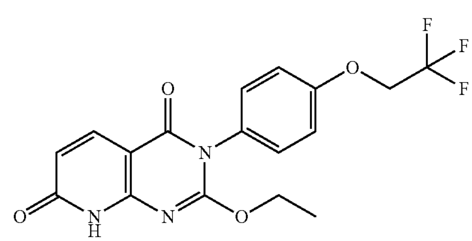 | Na-salt | 382.2 |

TABLE 2

| Example No. | IUPAC Name | Structure | Salt | MS (ESI+) |
|---|---|---|---|---|
| 11 | 2-(2,2,2-trifluoroethoxy)-3-[4-(2,2,2-trifluoroethoxy)phenyl]pyrido[2,3-d]pyrimidine-4,7(3H,8H)-dione | 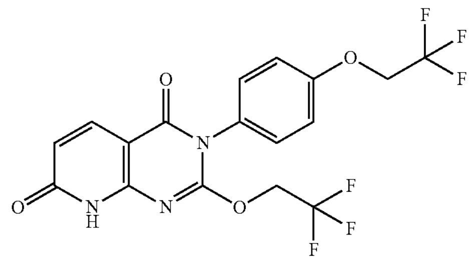 [SMILES: O=c1ccc2c(=O)n(-c3ccc(OCC(F)(F)F)cc3)c(OCC(F)(F)F)nc2[nH]1] | — | 436.3 |
| 12 | 2-(2,2,2-trifluoroethoxy)-3-[4-(2,2,2-trifluoroethoxy)phenyl]pyrido[2,3-d]pyrimidine-4,7(3H,8H)-dione | 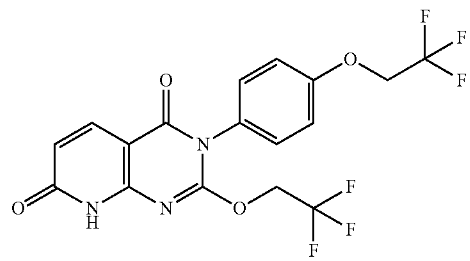 [SMILES: O=c1ccc2c(=O)n(-c3ccc(OCC(F)(F)F)cc3)c(OCC(F)(F)F)nc2[nH]1] | Na-salt | 436.4 |
| 13 | 2-[3-(methylsulfonyl)propoxy]-3-[4-(2,2,2-trifluoroethoxy)phenyl]pyrido[2,3-d]pyrimidine-4,7(3H,8H)-dione | 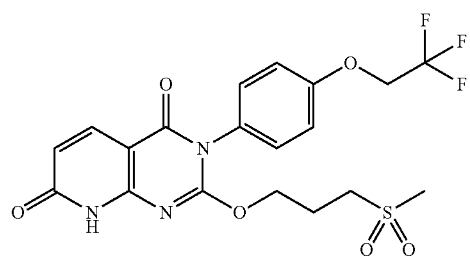 [SMILES: CS(=O)(=O)CCCOc1nc2[nH]c(=O)ccc2c(=O)n1-c1ccc(OCC(F)(F)F)cc1] | — | 474.3 |
| 14 | 2-(2,2-difluoro-3-methoxypropoxy)-3-[4-(2,2,2-trifluoroethoxy)phenyl]pyrido[2,3-d]pyrimidine-4,7(3H,8H)-dione | 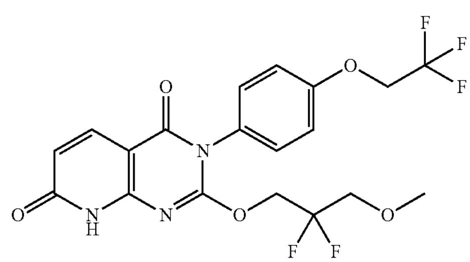 [SMILES: COCC(F)(F)COc1nc2[nH]c(=O)ccc2c(=O)n1-c1ccc(OCC(F)(F)F)cc1] | — | 462.1 |
| 15 | 2-[(4,4-difluorocyclohexyl)oxy]-3-[4-(2,2,2-trifluoroethoxy)phenyl]pyrido[2,3-d]pyrimidine-4,7(3H,8H)-dione | 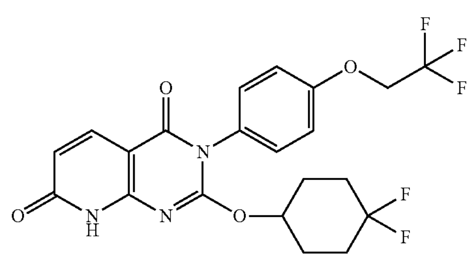 [SMILES: O=c1ccc2c(=O)n(-c3ccc(OCC(F)(F)F)cc3)c(OC3CCC(F)(F)CC3)nc2[nH]1] | — | 472.1 |
| 16 | 2-(2,2-difluoroethoxy)-3-[4-(2,2,2-trifluoroethoxy)phenyl]pyrido[2,3-d]pyrimidine-4,7(3H,8H)-dione | 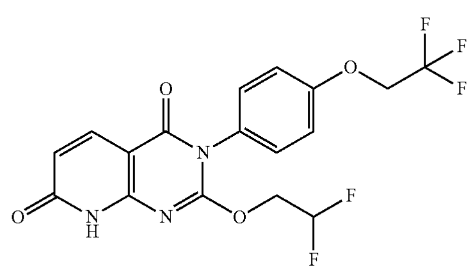 [SMILES: O=c1ccc2c(=O)n(-c3ccc(OCC(F)(F)F)cc3)c(OCC(F)F)nc2[nH]1] | — | 418.3 |

TABLE 2-continued

| Example No. | IUPAC Name | Structure | Salt | MS (ESI+) |
|---|---|---|---|---|
| 17 | 2-(2,2-difluoro-3-hydroxypropoxy)-3-[4-(2,2,2-trifluoroethoxy)phenyl]pyrido[2,3-d]pyrimidine-4,7(3H,8H)-dione | 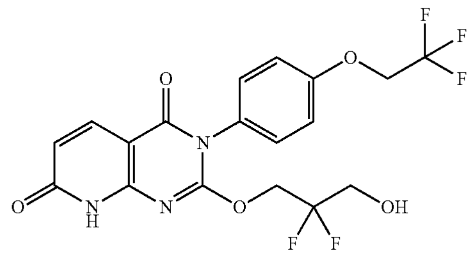 [SMILES: O=c1ccc2c(=O)n(-c3ccc(OCC(F)(F)F)cc3)c(OCC(F)(F)CO)nc2[nH]1] | — | 448.3 |
| 18 | 2-methoxy-3-[4-(2,2,2-trifluoroethoxy)phenyl]pyrido[2,3-d]pyrimidine-4,7(3H,8H)-dione | 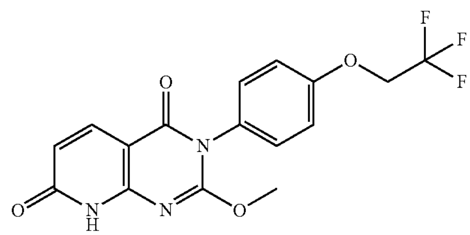 [SMILES: COc1nc2[nH]c(=O)ccc2c(=O)n1-c1ccc(OCC(F)(F)F)cc1] | — | 368.3 |
| 19 | 2-(ethylamino)-3-[4-(2,2,2-trifluoroethoxy)phenyl]pyrido[2,3-d]pyrimidine-4,7(3H,8H)-dione | 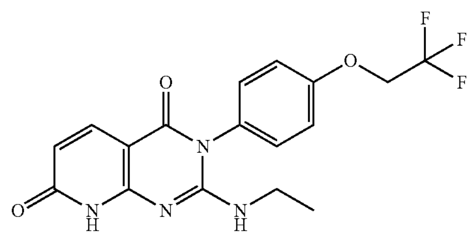 [SMILES: CCNc1nc2[nH]c(=O)ccc2c(=O)n1-c1ccc(OCC(F)(F)F)cc1] | — | 381.3 |
| 20 | 2-(1-methylethoxy)-3-[4-(2,2,2-trifluoroethoxy)phenyl]pyrido[2,3-d]pyrimidine-4,7(3H,8H)-dione | 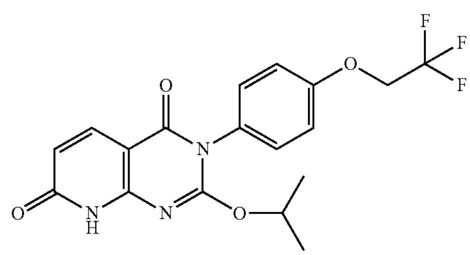 [SMILES: CC(C)Oc1nc2[nH]c(=O)ccc2c(=O)n1-c1ccc(OCC(F)(F)F)cc1] | — | 396.4 |

TABLE 3

| Example No. | IUPAC Name | Structure | Salt | MS (ESI+) |
|---|---|---|---|---|
| 21 | 2-(methylsulfanyl)-3-[4-(2,2,2-trifluoroethoxy)phenyl]-5,6-dihydropyrido[2,3-d]pyrimidine-4,7(3H,8H)-dione | 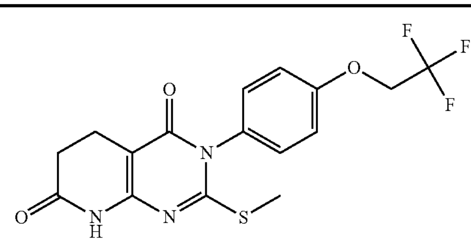 | — | — |

TABLE 3-continued

| Example No. | IUPAC Name | Structure | Salt | MS (ESI+) |
|---|---|---|---|---|
| 22 | 2-(2,2,2-trifluoroethoxy)-3-[4-(2,2,2-trifluoroethoxy)phenyl]-5,6-dihydropyrido[2,3-d]pyrimidine-4,7(3H,8H)-dione | 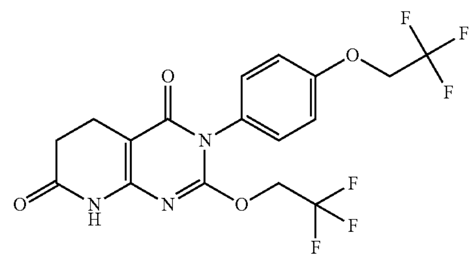 [SMILES: O=C1CCc2c(nc(OCC(F)(F)F)n(-c3ccc(OCC(F)(F)F)cc3)c2=O)N1] | — | 438.0 |
| 23 | 2-ethoxy-3-[4-(2,2,2-trifluoroethoxy)phenyl]-5,6-dihydropyrido[2,3-d]pyrimidine-4,7(3H,8H)-dione | 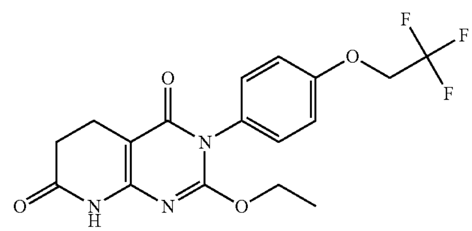 [SMILES: CCOc1nc2c(c(=O)n1-c1ccc(OCC(F)(F)F)cc1)CCC(=O)N2] | — | 384.1 |
| 24 | 2-(ethylsulfanyl)-3-[4-(2,2,2-trifluoroethoxy)phenyl]-5,6-dihydropyrido[2,3-d]pyrimidine-4,7(3H,8H)-dione | 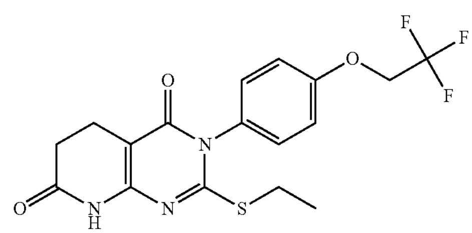 [SMILES: CCSc1nc2c(c(=O)n1-c1ccc(OCC(F)(F)F)cc1)CCC(=O)N2] | — | — |
| 25 | 2-(ethylsulfanyl)-3-[4-(2,2,2-trifluoroethoxy)phenyl]-3H-pyrimido[5,4-b][1,4]thiazine-4,7(6H,8H)-dione | 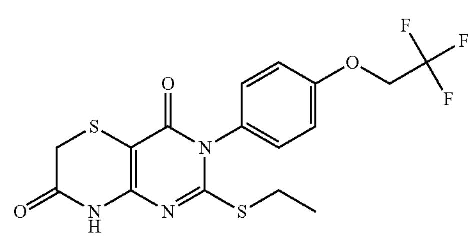 [SMILES: CCSc1nc2c(c(=O)n1-c1ccc(OCC(F)(F)F)cc1)SCC(=O)N2] | — | 418.2 |
| 26 | 7-amino-2-(ethylsulfanyl)-3-[4-(2,2,2-trifluoroethoxy)phenyl]pyrido[2,3-d]pyrimidin-4(3H)-one | 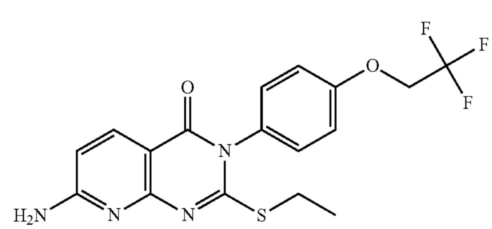 [SMILES: CCSc1nc2nc(N)ccc2c(=O)n1-c1ccc(OCC(F)(F)F)cc1] | — | 397.0 |
| 27 | 2-(ethylsulfanyl)-4-oxo-3-[4-(2,2,2-trifluoroethoxy)phenyl]-3,4-dihydropyrido[2,3-d]pyrimidine-7-carboxamide | 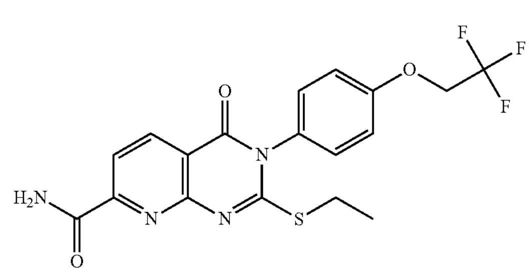 [SMILES: CCSc1nc2nc(C(N)=O)ccc2c(=O)n1-c1ccc(OCC(F)(F)F)cc1] | — | 425.3 |

TABLE 3-continued

| Example No. | IUPAC Name | Structure | Salt | MS (ESI+) |
|---|---|---|---|---|
| 28 | 2-(ethylsulfanyl)-3-[4-(2,2,2-trifluoroethoxy)phenyl]-3,5,6,7-tetrahydropyrido[3,4-d]pyrimidine-4,8-dione | 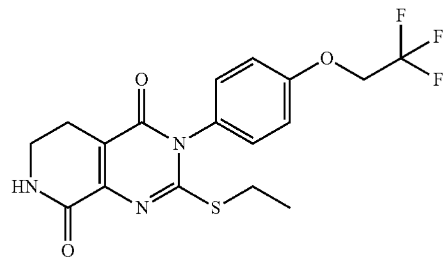 [SMILES: CCSc1nc2c(c(=O)n1-c1ccc(OCC(F)(F)F)cc1)CCNC2=O] | — | — |
| 29 | 2-(ethylsulfanyl)-3-[4-(2,2,2-trifluoroethoxy)phenyl]-3,7-dihydropyrido[3,4-d]pyrimidine-4,8-dione | 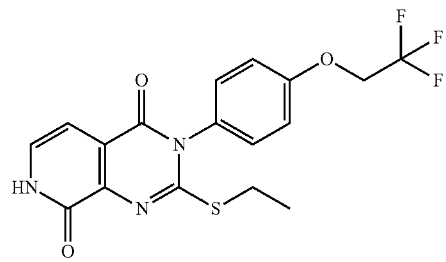 | — | 398.3 |
| 30 | 2-(propylsulfanyl)-3-[4-(2,2,2-trifluoroethoxy)phenyl]-3,7-dihydropyrido[3,4-d]pyrimidine-4,8-dione | 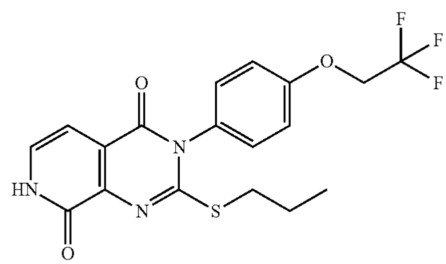 [SMILES: CCCSc1nc2c(=O)[nH]ccc2c(=O)n1-c1ccc(OCC(F)(F)F)cc1] | — | 412.1 |

TABLE 4

| Example No. | IUPAC Name | Structure | Salt | MS (ESI+) |
|---|---|---|---|---|
| 31 | 2-(2,2,2-trifluoroethoxy)-3-[4-(2,2,2-trifluoroethoxy)phenyl]-3,7-dihydropyrido[3,4-d]pyrimidine-4,8-dione | 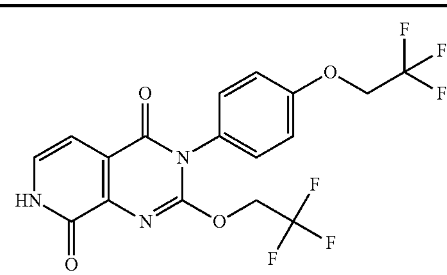 | — | 436.3 |
| 32 | 2-ethoxy-3-[4-(2,2,2-trifluoroethoxy)phenyl]-3,7-dihydropyrido[3,4-d]pyrimidine-4,8-dione | 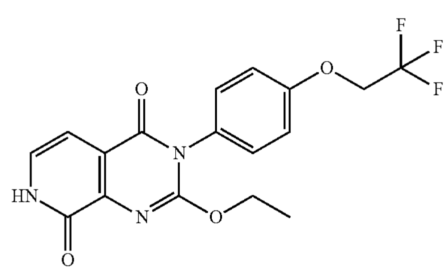 [SMILES: CCOc1nc2c(=O)[nH]ccc2c(=O)n1-c1ccc(OCC(F)(F)F)cc1] | — | 382.1 |

TABLE 4-continued

| Example No. | IUPAC Name | Structure | Salt | MS (ESI+) |
|---|---|---|---|---|
| 33 | 2-(ethylsulfanyl)-8-methoxy-3-[4-(2,2,2-trifluoroethoxy)phenyl]pyrido[3,4-d]pyrimidin-4(3H)-one | 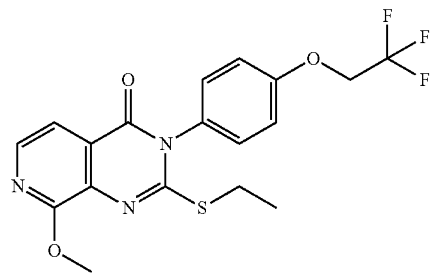 [SMILES: CCSc1nc2c(OC)nccc2c(=O)n1-c1ccc(OCC(F)(F)F)cc1] | — | 412.3 |
| 34 | 2-ethoxy-8-(2-methoxyethoxy)-3-[4-(2,2,2-trifluoroethoxy)phenyl]pyrido[3,4-d]pyrimidin-4(3H)-one | 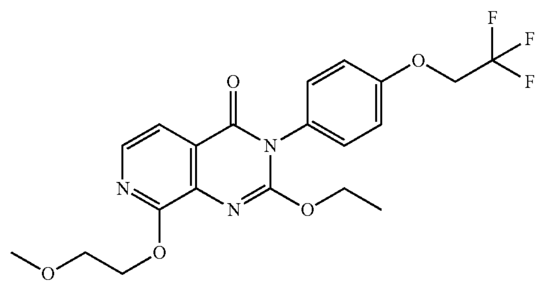 [SMILES: CCOc1nc2c(OCCOC)nccc2c(=O)n1-c1ccc(OCC(F)(F)F)cc1] | — | 440.3 |
| 35 | 2,8-bis(2-methoxyethoxy)-3-[4-(2,2,2-trifluoroethoxy)phenyl]pyrido[3,4-d]pyrimidin-4(3H)-one | 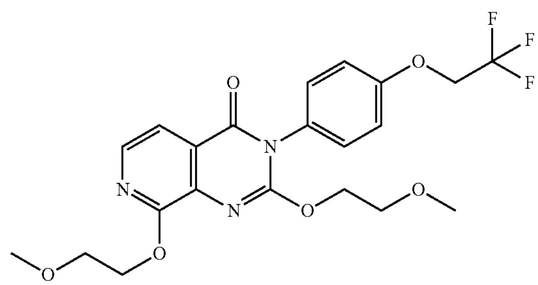 [SMILES: COCCOc1nccc2c(=O)n(-c3ccc(OCC(F)(F)F)cc3)c(OCCOC)nc12] | — | 470.3 |
| 36 | 2-(ethylsulfanyl)-7-methyl-3-[4-(2,2,2-trifluoroethoxy)phenyl]-3,7-dihydropyrido[3,4-d]pyrimidine-4,8-dione | 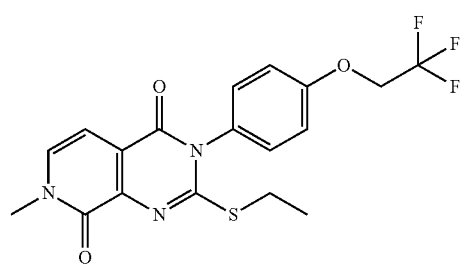 [SMILES: CCSc1nc2c(=O)n(C)ccc2c(=O)n1-c1ccc(OCC(F)(F)F)cc1] | — | 412.0 |
| 37 | 2-(ethylsulfanyl)-7-methoxy-3-[4-(2,2,2-trifluoroethoxy)phenyl]pteridin-4(3H)-one | 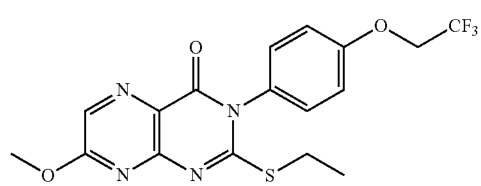 [SMILES: CCSc1nc2nc(OC)cnc2c(=O)n1-c1ccc(OCC(F)(F)F)cc1] | — | 413.0 |
| 38 | 2-(ethylsulfanyl)-3-[4-(2,2,2-trifluoroethoxy)phenyl]pteridine-4,7(3H,8H)-dione | 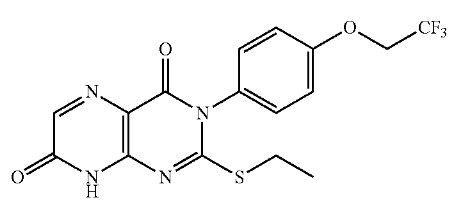 [SMILES: CCSc1nc2[nH]c(=O)cnc2c(=O)n1-c1ccc(OCC(F)(F)F)cc1] | — | 398.9 |

TABLE 4-continued

| Example No. | IUPAC Name | Structure | Salt | MS (ESI+) |
|---|---|---|---|---|
| 39 | 3-[4-(2,2,2-trifluoroethoxy)phenyl]-2-(3,3,3-trifluoropropyl)-5,6-dihydropyrido[2,3-d]pyrimidine-4,7(3H,8H)-dione | 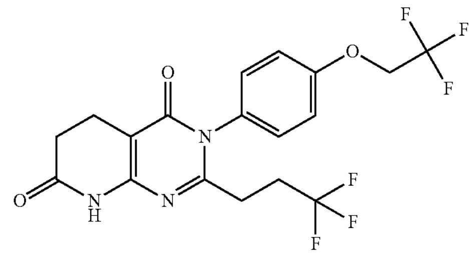 [SMILES: O=C1CCc2c(nc(CCC(F)(F)F)n(-c3ccc(OCC(F)(F)F)cc3)c2=O)N1] | — | 436.1 |
| 40 | 2-propyl-3-[4-(2,2,2-trifluoroethoxy)phenyl]-5,6-dihydropyrido[2,3-d]pyrimidine-4,7(3H,8H)-dione | 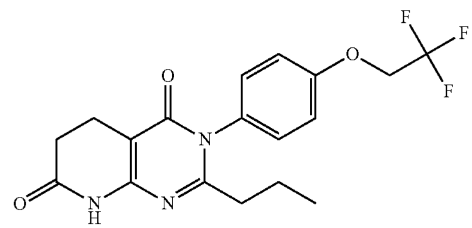 [SMILES: CCCc1nc2c(c(=O)n1-c1ccc(OCC(F)(F)F)cc1)CCC(=O)N2] | — | 382.1 |

Reference Example 1

N-[2-({4-oxo-3-[4-(2,2,2-trifluoroethoxy)[2,6-$^3$H$_2$]phenyl]-3,4-dihydrothieno[3,4-d]pyrimidin-2-yl}sulfanyl)ethyl]acetamide A) ethyl 4-isothiocyanatothiophene-3-carboxylate Ethyl 4-aminothiophene-3-carboxylate hydrochloride (69 g) was added to 1M aqueous sodium hydrogen carbonate solution (400 ml), and the mixture was extracted with ethyl acetate. The extract was washed with saturated brine, and dried over anhydrous sodium sulfate, and the solvent was evaporated under reduced pressure to give a brown oil (56 g). This brown oil was dissolved in chloroform (150 ml), and the solution was added to a solution of thiophosgene (12.5 ml) in chloroform (300 ml). The mixture was added dropwise to an aqueous solution (115 ml) of sodium hydrogen carbonate (18.5 g) at room temperature, and the mixture was stirred for 4 hr. The organic layer and aqueous layer were separated, and the aqueous layer was extracted with chloroform. The obtained organic layers were combined, washed with saturated brine, dried over anhydrous sodium sulfate, and concentrated under reduced pressure. The obtained crude product was purified by silica gel column chromatography (ethyl acetate/hexane) to give the title compound (15.6 g) as a pale-yellow solid.

$^1$H NMR (400 MHz, CDCl$_3$) δ1.39 (3H, t, J=7.2 Hz), 4.36 (2H, q, J=7.2 Hz), 7.14 (1H, d, J=3.6 Hz), 8.06 (1H, d, J=3.6 Hz).

B) 2-thioxo-3-[4-(2,2,2-trifluoroethoxy)phenyl]-2,3-dihydrothieno[3,4-d]pyrimidin-4(1H)-one Ethyl 4-isothiocyanatothiophene-3-carboxylate (1.1 g) and 4-(2,2,2-trifluoroethoxy)aniline (0.99 g) were dissolved in acetonitrile (40 ml), and the solution was heated under reflux for 1 hr, and allowed to be cooled. Potassium tert-butoxide (1.27 g) was dissolved in ethanol (15 ml) and the solution was poured into the reaction mixture at room temperature. The reaction mixture was heated under reflux for 10 min, allowed to be cooled, and concentrated under reduced pressure. The obtained brown residue was dissolved in ethanol (10 ml), and the solution was poured into 0.3M hydrochloric acid (35 ml) under ice-cooling. The resulting precipitate was collected by filtration, washed with water, and dissolved in tetrahydrofuran (40 ml). The solution was diluted with ethyl acetate (80 ml). This organic layer was dried over anhydrous magnesium sulfate, and the solvent was evaporated under reduced pressure to give a solid. This solid was washed with a mixed solvent of tetrahydrofuran/isopropyl ether (1/10) to give the title compound (1.59 g) as a solid.

$^1$H NMR (300 MHz, DMSO-d$_6$) δ4.82 (2H, q, J=8.9 Hz), 7.10 (2H, d, J=9.0 Hz), 7.12 (1H, d, J=3.3 Hz), 7.20 (2H, d, J=9.0 Hz), 8.51 (1H, d, J=3.3 Hz), 12.92 (1H, s).

C) tert-butyl [2-({4-oxo-3-[4-(2,2,2-trifluoroethoxy)phenyl]-3,4-dihydrothieno[3,4-d]pyrimidin-2-yl}sulfanyl)ethyl]carbamate 2-Thioxo-3-[4-(2,2,2-trifluoroethoxy)phenyl]-2,3-dihydrothieno[3,4-d]pyrimidin-4(1H)-one (1.59 g) was dissolved in N,N-dimethylformamide (20 ml), sodium hydride (60% in oil, 0.25 g) and tert-butyl(2-bromoethyl)carbamate (1.49 g) were added successively thereto under ice-cooling, and the mixture was stirred at room temperature for 1 hr. To the reaction mixture was poured into saturated aqueous ammonium chloride solution (30 ml), and the mixture was extracted with ethyl acetate. The organic layer was washed with water and saturated brine, dried over anhydrous magnesium sulfate, and concentrated under reduced pressure. The residue was purified by silica gel column chromatography (NH, ethyl acetate/hexane) to give the title compound (2.12 g) as a white solid.

$^1$H NMR (300 MHz, DMSO-d$_6$) δ1.35 (9H, s), 3.10 (2H, t, J=6.3 Hz), 3.23 (2H, td, J=6.3, 5.3 Hz), 4.86 (2H, q, J=8.9 Hz), 6.97 (1H, t, J=5.3 Hz), 7.18 (2H, d, J=9.0 Hz), 7.37 (2H, d, J=9.0 Hz), 7.66 (1H, d, J=3.3 Hz), 8.50 (1H, d, J=3.3 Hz).

D) 2-[(2-aminoethyl)sulfanyl]-3-[4-(2,2,2-trifluoroethoxy)phenyl]thieno[3,4-d]pyrimidin-4(3H)-one hydrochloride To a mixed solution of 4N hydrogen chloride ethyl acetate solution (20 ml) and methanol (10 ml) was added tert-butyl

[2-({4-oxo-3-[4-(2,2,2-trifluoroethoxy)phenyl]-3,4-dihydrothieno[3,4-d]pyrimidin-2-yl}sulfanyl)ethyl]carbamate (1.7 g), and the mixture was stirred at room temperature for 14 hr. The reaction mixture was concentrated under reduced pressure, and the residue was washed with a mixture of ethyl acetate/ether (1/1) to give the title compound (1.48 g) as a white solid.

$^1$H NMR (300 MHz, DMSO-$d_6$) δ3.03-3.21 (2H, m), 3.29 (2H, t, J=6.8 Hz), 4.87 (2H, q, J=8.8 Hz), 7.20 (2H, d, J=9.1 Hz), 7.43 (2H, d, J=9.1 Hz), 7.70 (1H, d, J=3.3 Hz), 8.17 (3H, br. s.), 8.53 (1H, d, J=3.3 Hz).

E) N-[2-({4-oxo-3-[4-(2,2,2-trifluoroethoxy)phenyl]-3,4-dihydrothieno[3,4-d]pyrimidin-2-yl}sulfanyl)ethyl]acetamide 2-[(2-Aminoethyl)sulfanyl]-3-[4-(2,2,2-trifluoroethoxy)phenyl]thieno[3,4-d]pyrimidin-4(3H)-one hydrochloride (0.33 g) was suspended in tetrahydrofuran (30 ml), triethylamine (0.31 ml), acetic anhydride (0.28 ml) and 4-dimethylaminopyridine (37 mg) were added successively thereto, and the mixture was stirred at room temperature for 18 hr. The reaction mixture was concentrated under reduced pressure, and the residue was diluted with ethyl acetate. The extract was washed successively with saturated aqueous citric acid solution, water and saturated aqueous sodium hydrogen carbonate solution, dried over anhydrous magnesium sulfate, and concentrated under reduced pressure. The obtained pale-yellow solid was purified by silica gel column chromatography (ethyl acetate/hexane) to give a colorless solid. This solid was recrystallized from ethyl acetate/hexane to give the title compound (0.22 g) as a colorless solid.

$^1$H NMR (300 MHz, DMSO-$d_6$) δ1.77 (3H, s), 3.01-3.20 (2H, m), 3.21-3.38 (2H, m), 4.86 (2H, q, J=8.7 Hz), 7.10-7.27 (2H, m), 7.31-7.45 (2H, m), 7.66 (1H, d, J=3.4 Hz), 8.01 (1H, t, J=5.3 Hz), 8.50 (1H, d, J=3.4 Hz).

MS (ESI+): [M+H]$^+$ 444.0.

F) N-[2-({4-oxo-3-[4-(2,2,2-trifluoroethoxy)[2,6-$^3$H$_2$]phenyl]-3,4-dihydrothieno[3,4-d]pyrimidin-2-yl}sulfanyl)ethyl]acetamide N-[2-({4-oxo-3-[4-(2,2,2-trifluoroethoxy)phenyl]-3,4-dihydrothieno[3,4-d]pyrimidin-2-yl}sulfanyl)ethyl]acetamide (3 mg) and Crabtree's catalyst: (1,5-cyclooctadiene)(pyridine)(tricyclohexylphosphine)iridium(I) hexafluorophosphate (6 mg) were dissolved in dichloromethane (1.5 ml), and the mixture was stirred for 4 hr under tritium gas (2Ci) atmosphere. The reaction mixture was concentrated under reduced pressure, to the residue was added ethanol, and the mixture was again concentrated under reduced pressure. The residue was purified by reverse layer high performance liquid is chromatography (C18 column, eluate: water/acetonitrile/trifluoroacetic acid) to give the title compound (44 Ci/mmol). The radiochemical purity of the title compound measured by high performance liquid chromatography was 99.9% (column: Spherisorb ODS2 5μ 150×4.6 mm, solvent: SOLUTION A; 0.1% trifluoroacetic acid-containing water, SOLUTION B; 0.1% trifluoroacetic acid-containing acetonitrile, gradient cycle: 0 min (SOLUTION A/SOLUTION B=80/20), 15 min (SOLUTION A/SOLUTION B=0/100), injection volume: 5 μl, flow rate: 1 ml/min).

MS (ESI+): [M+H]$^+$ 448.1.

Experimental Example 1

Delta-5-Desaturase Inhibitory Activity Using Rat Liver Microsome

The inhibitory activity of the test compound on delta-5-desaturase was measured by the method described below. To a solution of the test compound in DMSO prepared in advance was secondarily diluted with a buffer (300 mM NaH$_2$PO$_4$ [pH 7.4], 450 mM KCl, 30 mM NaF, 9 mM MgCl$_2$, 4.5 mM glutathione [reduced form], 0.3% BSA [fatty acid free, SIGMA]) to give an assay buffer. The assay buffer (10 μl) was dispensed to a polypropylene deep 96-well block, and a rat liver microsome fraction (10 μl) diluted to 3 mg/ml with a microsome buffer (10 mM Tris-HCl [pH 7.4], 1 mM EDTA, 250 mM sucrose) was added. The enzyme reaction was started by adding 9 mM NADH, 9 mM ATP, 0.9 mM CoA, 10 μCi/ml (8E,11E,14E)-(1-$^{14}$C)eicosa-8,11,14-trienoic acid (PerkinElmer Inc.) (10 μl). The enzyme reaction was performed for 120 min at room temperature, and discontinued by the addition of 10 μl of 2.5M NaOH. After discontinuation of the reaction, the plate was sealed and incubated overnight at 55° C. to allow saponification. The fatty acid was extracted with solvent based on the Bligh & Dyer method described in Can. J. Biochem. Physiol., vol. 37, page 911 (1959) by adding formic acid:methanol:chloroform (1:6:3) (200 μl), maintaining the single layer state, sufficiently stirring the mixture and adding pure water (120 μl) for separation into two layers. The lower chloroform layer (10 μl) was spotted on a reversed-phase TLC plate (RP-18, 1154230001, Merck Japan, Ltd.), developed with acetonitrile:pure water:acetic acid (95:4.5:0.5), and the dried TLC plate was transcribed on Imaging Plate (Fuji Photo Film Co., Ltd.) for 5 hr or longer. The detection was performed using BAS-5000 (Fuji Photo Film Co., Ltd.), and the obtained spot image was numerically converted by Multi Gauge Ver2.3 (Fuji Photo Film Co., Ltd.) and a delta-5-desaturase inhibitory rate (%) of 10 μM test compound was determined. The results are shown in Table 5.

As is clear from Table 5, the compound of the present invention showed a superior delta-5-desaturase inhibitory action.

Experimental Example 2

Inhibitory Activity on Binding of N-[2-({4-oxo-3-[4-(2,2,2-trifluoroethoxy)[2,6-$^3$H$_2$]phenyl]-3,4-dihydrothieno[3,4-d]pyrimidin-2-yl}sulfanyl)ethyl]acetamide (Reference Example 1) to delta-5-desaturase)

All tests were performed at room temperature at 200 μL/well. A rat liver microsome fraction (30 μg/well) was preincubated with a test compound at a final concentration of 10 μM for 15 min in an assay buffer (10 mM Tris-HCl (pH 7.5), 100 mM KCl, 10 mM NaF, 3 mM MgCl$_2$, 0.005% Tween20 and 1 mM GSH). N-[2-({4-oxo-3-[4-(2,2,2-trifluoroethoxy) [2,6-$^3$H$_2$]phenyl]-3,4-dihydrothieno[3,4-d]pyrimidin-2-yl}sulfanyl)ethyl]acetamide was added to a final concentration of 3 nM and the mixture was incubated for 150 min. For Bound/Free separation, the membrane fraction was added on a GF/C glass filter using a cell harvester. The GF/C glass filter was washed 5 times with 300 μl of ice-cooled assay buffer (without 0.005% Tween) to separate the ligand bound to delta-5-desaturase. 50 μl of MicroScinti 0 was added, and the radioactivity on the filter was measured by TopCount. To evaluate non-specific binding, 10 μM N-[2-({4-oxo-3-[4-(2, 2,2-trifluoroethoxy)phenyl]-3,4-dihydrothieno[3,4-d]pyrimidin-2-yl}sulfanyl)ethyl]acetamide was used. The inhibitory rate (%) of the test compound (10 μM) on the binding of N-[2-({4-oxo-3-[4-(2,2,2-trifluoroethoxy) [2,6-$^3$H$_2$]phenyl]-3,4-dihydrothieno[3,4-d]pyrimidin-2-yl}sulfanyl)ethyl]acetamide to delta-5-desaturase was determined. The results are shown in Table 5.

As is clear from Table 5, the compound of the present invention showed a superior inhibitory action on the binding of N-[2-({4-oxo-3-[4-(2,2,2-trifluoroethoxy)[2,6-$^3$H$_2$]phenyl]-3,4-dihydrothieno[3,4-d]pyrimidin-2-yl}sulfanyl)ethyl]acetamide to delta-5-desaturase.

Experimental Example 3

Delta-5-Desaturase Inhibitory Activity Using HepG2 Cell

HepG2 was plated on a 96-well plate at 1×10$^5$ cells/well, and cultured overnight in DMEM (Dulbecco's modified Eagle medium) containing 10% FBS (fetal bovine serum). After washing (200 μL×2) with PBS (phosphate buffered saline), 40 μL of a reaction medium (DMEM, penicillin/streptomycin, 0.3% BSA) containing the test compound was added, and the mixture was preincubated in a CO$_2$ incubator at 37° C. for 30 min. The reaction was started by adding a reaction medium (20 μL) containing 0.1 μCi [$^{14}$C]Eicosatrienoic acid, and the mixture was incubated in a CO$_2$ incubator at 37° C. Incubation was performed for 3 hr, the cells were washed twice with 200 μL of PBS, detached with 50 μL of trypsin-EDTA and placed on a 96-deep well block. Furthermore, 20 μL of 2.5N NaOH was added, the plate was sealed and incubated overnight at 55° C. to allow saponification. The fatty acid extraction included acidifying with 10 μL of formic acid, adding chloroform:methanol (1:4), stirring, and further adding 200 μL of pure water to separate into two layers. The operation after development with TLC followed the method of detection system using TLC in a system using a rat liver microsome. A delta-5-desaturase inhibitory rate (%) of 1 μM test compound was determined. The results are shown in Table 5.

As is clear from Table 5, the compound of the present invention showed a superior delta-5-desaturase inhibitory action.

TABLE 5

| Example | Binding inhibitory activity against compound bind to delta-5-desaturase Binding inhibition rate (%) at 10 μM | delta-5-desaturase inhibitory activity (at liver microsome) Inhibitory activity (%) at 10 μM | delta-5-desaturase inhibitory activity (HepG2 cell) Inhibitory activity (%) at 1 μM |
|---|---|---|---|
| 1 | 94 | 100 | 101 |
| 2 | 94 | 102 | 107 |
| 3 | 97 | 102 | no data |
| 4 | 99 | 102 | 96 |
| 5 | 93 | 101 | 95 |
| 6 | 97 | 99 | 101 |
| 7 | 96 | 98 | 101 |
| 8 | 96 | 99 | 103 |
| 9 | 96 | 99 | 97 |
| 10 | 94 | 98 | no data |
| 11 | 95 | 100 | 98 |
| 12 | 96 | 99 | no data |
| 13 | 89 | 97 | 88 |
| 14 | no data | 103 | 103 |
| 15 | 99 | 104 | 102 |
| 16 | 96 | 101 | 102 |
| 17 | 99 | 105 | 103 |
| 18 | 84 | 92 | 95 |
| 19 | 85 | 90 | no data |
| 20 | 97 | 104 | 97 |
| 21 | 93 | 97 | no data |
| 22 | 92 | 100 | 101 |
| 23 | 91 | 96 | 93 |
| 24 | 95 | 101 | 109 |
| 25 | 98 | 98 | 92 |
| 26 | 96 | 102 | 107 |
| 27 | 93 | 97 | 98 |
| 28 | 92 | 92 | 89 |
| 29 | 97 | 99 | 96 |
| 30 | 97 | 97 | 96 |
| 31 | 98 | 96 | 96 |
| 32 | 98 | 96 | 88 |
| 33 | 96 | 101 | 93 |
| 34 | 88 | 98 | 93 |
| 35 | 89 | 91 | 91 |
| 36 | 101 | 101 | 92 |
| 37 | 97 | 99 | 93 |
| 38 | 91 | 95 | 76 |
| 39 | 91 | no data | 98 |
| 40 | 89 | no data | 92 |

Experimental Example 4

Delta-5-Desaturase Inhibitory Action In Vivo

The delta-5-desaturase inhibitory action of the test compound in vivo was evaluated by the following method. A suspension of a test compound (3 mg/kg) in 0.5% methylcellulose was administered by gavage every morning at 10 mL/kg for 4 days to 7- to 9-week-old male normal mice (C57BL/6J, CLEA Japan, Inc.) acclimated with a normal chow feed (CE-2, CLEA Japan, Inc.) in individual cages. In the next morning of the final administration, the mice were anesthetized, and the liver was isolated. Total lipid was extracted from about 40 mg of a liver sample with hexane-propanol solution, and a phospholipid fraction was extracted using a solid phase extraction column (Sep-Pak Vac NH2, Waters) and labeled with an esterified long-chain and short-chain fatty acid labeling reagent (YMC). The arachidonic acid and dihomo-γ-linolenic acid contents of the sample after labeling were measured by high performance liquid chromatography (Agilent 1200, Agilent Technologies). The arachidonic acid (AA) content was divided by the content of dihomo-γ-linolenic acid (DGLA) to obtain an AA/DGLA ratio. The decrease rate of the test compound administration group was calculated based on the AA/DGLA ratio of the solvent administration group as 100%, which was used as an index of the liver delta-5-desaturase inhibitory action in vivo. The results are shown in Table 6.

TABLE 6

| Example No. | lowering rate (%) of arachidonic acid/dihomo-γ-linolenic acid ratio |
|---|---|
| 1 | 73 |
| 4 | 64 |
| 10 | 71 |
| 12 | 70 |
| 15 | 69 |
| 16 | 69 |
| 22 | 68 |

TABLE 6-continued

| Example No. | lowering rate (%) of arachidonic acid/dihomo-γ-linolenic acid ratio |
|---|---|
| 23 | 67 |
| 39 | 67 |

As is clear from Table 6, the compound of the present invention showed a superior delta-5-desaturase inhibitory action in vivo.

Formulation Example 1

| | |
|---|---|
| (1) compound of Example 1 | 10.0 g |
| (2) lactose | 70.0 g |
| (3) cornstarch | 50.0 g |
| (4) soluble starch | 7.0 g |
| (5) magnesium stearate | 3.0 g |

The compound of Example 1 (10.0 g) and magnesium stearate (3.0 g) are granulated with aqueous solution (70 ml) of soluble starch (7.0 g as soluble starch), dried and mixed with lactose (70.0 g) and cornstarch (50.0 g) (lactose, cornstarch, soluble starch and magnesium stearate are all products on the Japanese Pharmacopoeia 14th ed.). The mixture is compressed to give tablets.

INDUSTRIAL APPLICABILITY

The compound of the present invention has a delta-5-desaturase inhibitory action, and is useful for the prophylaxis or treatment of atherosclerosis, atherothrombosis, diabetes, obesity, asthma, fever, pain, cancer, rheumatism, osteoarthritis, atopic dermatitis and the like.

This application is based on patent application Nos. 2010-166475 and 2011-122796 filed in Japan, the contents of which are encompassed in full herein.

The invention claimed is:

1. A compound represented by the formula (I):

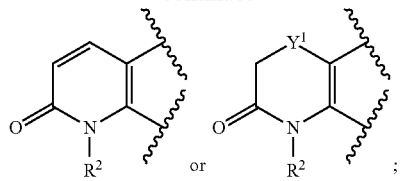

wherein
ring A is a ring represented by the formula:

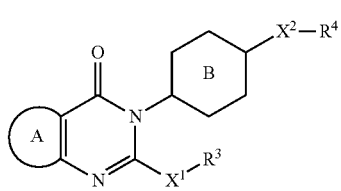

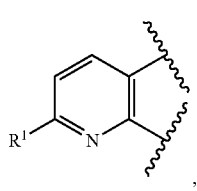

wherein each ring is optionally further substituted by substituent(s) selected from the group consisting of a halogen atom, a $C_{1-6}$ alkyl group and a $C_{1-6}$ alkoxy group, ring B is phenyl optionally further substituted by substituent(s) selected from the group consisting of a halogen atom, a $C_{1-6}$ alkyl group and a $C_{1-6}$ alkoxy group, $X^1$ is a bond, S, $SO_2$, O or $NR^5$, $X^2$ is $CR^6R^7$ or O, $Y^1$ is $CR^8R^9$, $R^1$ is (1) a $C_{1-6}$ alkoxy group optionally substituted by 1 to 3 $C_{1-6}$ alkoxy groups;

(2) amino; or (3) carbamoyl;

$R^2$ is a hydrogen atom or a $C_{1-6}$ alkyl group, $R^3$ is (1) a $C_{1-6}$ alkyl group optionally substituted by 1 to 3 substituents selected from the group consisting of
(A) a $C_{1-6}$ alkylsulfonyl group,
(B) a hydroxy group,
(C) a $C_{1-6}$ alkoxy group, and
(D) a halogen atom, or (2) a $C_{3-10}$ cycloalkyl group optionally substituted by 1 to 3 halogen atoms;

$R^4$ is a $C_{1-6}$ alkyl group optionally substituted by 1 to 3 halogen atoms, $R^5$ is a hydrogen atom, and $R^6$, $R^7$, $R^8$ and $R^9$ are each a hydrogen atom, a halogen atom, a $C_{1-6}$ alkyl group or a $C_{1-6}$ alkoxy group, or a pharmacologically acceptable salt thereof.

2. The compound or pharmacologically acceptable salt of claim 1, wherein $X^2$ is O.

3. The compound or pharmacologically acceptable salt of claim 1, wherein
ring A is a ring represented by the formula:

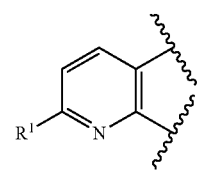

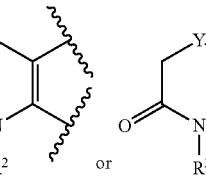

ring B is phenyl;
$X^1$ is a bond, S, O or NH;
$X^2$ is O; and
$Y^1$ is $CH_2$.

4. The compound or pharmacologically acceptable salt of claim 1, wherein
ring A is a ring represented by the formula:

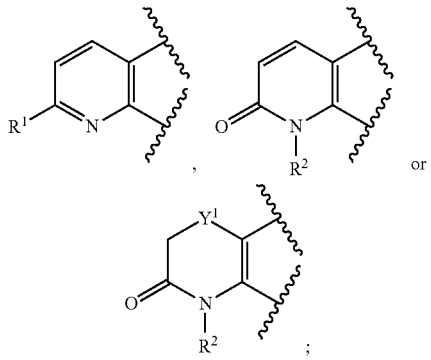

ring B is phenyl;
$X^1$ is a bond, S or O;
$X^2$ is O;
$Y^1$ is $CH_2$;
$R^1$ is a $C_{1-6}$ alkoxy group;
$R^2$ is a hydrogen atom; and
$R^3$ is
(1) a $C_{1-6}$ alkyl group optionally substituted by 1 to 3 halogen atoms, or
(2) a $C_{3-10}$ cycloalkyl group optionally substituted by 1 to 3 halogen atoms.

5. The compound or pharmacologically acceptable salt of claim 1, wherein
ring A is a ring represented by the formula:

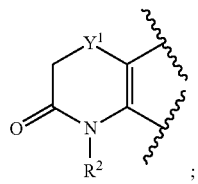

ring B is phenyl;
$X^1$ is a bond, S or O;
$X^2$ is O;
$Y^1$ is $CH_2$;
$R^2$ is a hydrogen atom; and
$R^3$ is
(1) a $C_{1-6}$ alkyl group optionally substituted by 1 to 3 halogen atoms, or
(2) a $C_{3-10}$ cycloalkyl group optionally substituted by 1 to 3 halogen atoms.

6. A pharmaceutical composition comprising the compound or pharmacologically acceptable salt of claim 1, and a pharmacologically acceptable carrier.

7. A method for the prophylaxis or treatment of arteriosclerosis in a mammal, comprising administering to said mammal an effective amount of the compound or pharmacologically acceptable salt of claim 1.

8. A method for the prophylaxis or treatment of diabetes or obesity in a mammal, comprising administering to said mammal an effective amount of the compound or pharmacologically acceptable salt of claim 1.

9. A method for inhibiting delta-5-desaturase activity in a mammal, comprising administering to said mammal an effective amount of the compound or pharmacologically acceptable salt of claim 1.

10. A compound of 2-(2,2,2-trifluoroethoxy)-3-[4-(2,2,2-trifluoroethoxy)phenyl]-5,6-dihydropyrido[2,3-d]pyrimidine-4,7(3H,8H)-dione or a pharmaceutically acceptable salt thereof.

11. A compound of 2-ethoxy-3-[4-(2,2,2-trifluoroethoxy)phenyl]-5,6-dihydropyrido[2,3-d]pyrimidine-4,7(3H,8H)-dione or a pharmacologically acceptable salt thereof.

12. A compound of 3-[4-(2,2,2-trifluoroethoxy)phenyl]-2-(3,3,3-trifluoropropyl)-5,6-dihydropyrido[2,3-d]pyrimidine-4,7(3H,8H)-dione or a pharmacologically acceptable salt thereof.

* * * * *